US009732385B2

(12) United States Patent
Barken et al.

(10) Patent No.: US 9,732,385 B2
(45) Date of Patent: Aug. 15, 2017

(54) METHOD FOR DETERMINING THE RISK OF CROHN'S DISEASE-RELATED COMPLICATIONS

(75) Inventors: Derren Barken, San Diego, CA (US); Fred Princen, La Jolla, CA (US); Leonard Eggleston, Seattle, WA (US); Sharat Singh, Rancho Santa Fe, CA (US)

(73) Assignee: NESTEC S.A., Vevey (CH)

( * ) Notice: Subject to any disclaimer, the term of this patent is extended or adjusted under 35 U.S.C. 154(b) by 420 days.

(21) Appl. No.: 12/851,517

(22) Filed: Aug. 5, 2010

(65) Prior Publication Data

US 2011/0045476 A1 Feb. 24, 2011

Related U.S. Application Data

(63) Continuation of application No. PCT/US2010/030934, filed on Apr. 13, 2010.

(60) Provisional application No. 61/302,066, filed on Feb. 5, 2010, provisional application No. 61/300,787, filed on Feb. 2, 2010, provisional application No. 61/286,356, filed on Dec. 14, 2009, provisional application No. 61/265,723, filed on Dec. 1, 2009, provisional application No. 61/265,324, filed on Nov. 30, 2009, provisional application No. 61/262,903, filed on Nov. 19, 2009, provisional application No. 61/255,066, filed on Oct. 26, 2009, provisional application No. 61/220,453, filed on Jun. 25, 2009, provisional application No. 61/178,454, filed on May 14, 2009, provisional application No. 61/169,230, filed on Apr. 14, 2009.

(51) Int. Cl.

| | |
|---|---|
| ***G01N 33/48*** | (2006.01) |
| ***C12Q 1/68*** | (2006.01) |
| ***G01N 33/564*** | (2006.01) |
| ***G01N 33/68*** | (2006.01) |

(52) U.S. Cl.

CPC ......... *C12Q 1/6883* (2013.01); *G01N 33/564* (2013.01); *G01N 33/6893* (2013.01); *C12Q 2600/106* (2013.01); *C12Q 2600/112* (2013.01); *C12Q 2600/118* (2013.01); *C12Q 2600/156* (2013.01); *G01N 2800/065* (2013.01); *G01N 2800/56* (2013.01); *Y10T 436/143333* (2015.01)

(58) Field of Classification Search

None

See application file for complete search history.

(56) References Cited

U.S. PATENT DOCUMENTS

| | | | | |
|---|---|---|---|---|
| 5,750,355 | A | 5/1998 | Targan et al. | |
| 5,916,748 | A | 6/1999 | Targan et al. | |
| 5,932,429 | A | 8/1999 | Targan et al. | |
| 6,033,864 | A | 3/2000 | Braun et al. | |
| 6,074,835 | A | 6/2000 | Braun et al. | |
| 6,218,129 | B1 | 4/2001 | Walsh et al. | |
| 6,309,643 | B1 | 10/2001 | Braun et al. | |
| 6,835,815 | B2 | 12/2004 | Nunez | |
| 6,858,391 | B2 | 2/2005 | Nunez | |
| 7,060,442 | B2 | 6/2006 | Nunez | |
| 7,060,493 | B2 | 6/2006 | Nunez | |
| 7,375,086 | B2 | 5/2008 | Nunez | |
| 7,592,437 | B2 | 9/2009 | Hugot et al. | |
| 7,873,479 | B2 * | 1/2011 | Lois et al. | 702/19 |
| 8,137,915 | B2 | 3/2012 | Hugot et al. | |
| 8,315,818 | B2 | 11/2012 | Lois et al. | |
| 8,715,943 | B2 | 5/2014 | Princen et al. | |
| 2002/0068313 | A1 | 6/2002 | Braun | |
| 2003/0204507 | A1 | 10/2003 | Li et al. | |
| 2004/0043931 | A1 | 3/2004 | Hersberg et al. | |
| 2004/0137536 | A1 | 7/2004 | Boon et al. | |
| 2004/0242972 | A1 | 12/2004 | Adak et al. | |
| 2005/0054021 | A1 | 3/2005 | Targan et al. | |
| 2005/0060295 | A1 | 3/2005 | Gould et al. | |
| 2005/0164929 | A1 | 7/2005 | Alvarez et al. | |
| 2006/0003392 | A1 | 1/2006 | Oh et al. | |
| 2006/0154276 | A1 | 7/2006 | Lois et al. | |
| 2008/0131439 | A1 | 6/2008 | Lois et al. | |
| 2008/0182280 | A1 | 7/2008 | Lois et al. | |
| 2011/0159521 | A1 | 6/2011 | Gong et al. | |
| 2011/0218956 | A1 | 9/2011 | Lois et al. | |
| 2011/0251100 | A1 | 10/2011 | Li et al. | |
| 2012/0171672 | A1 | 7/2012 | Barken et al. | |
| 2013/0225439 | A1 | 8/2013 | Princen et al. | |
| 2015/0072879 | A1 | 3/2015 | Princen et al. | |

FOREIGN PATENT DOCUMENTS

| | | |
|---|---|---|
| WO | WO 98/37415 | 8/1998 |
| WO | WO 01/89361 A2 | 11/2001 |
| WO | WO 03/053220 A2 | 7/2003 |
| WO | WO 2004/037073 | 5/2004 |

(Continued)

OTHER PUBLICATIONS

Ferrante et al. (Gut, 2007;56:1394-1403).*

Abreu, M. et al., "Use of serologic tests in Crohn's disease," Clin. Perspect. Gastroenterol., 2001, 155-164.

Arnott, I. et al., "Sero-reactivity to microbial components in Crohn's disease is associated with disease severity and progression, but not NOD2/CARD15 genotype," American Journal of Gastroenterology, 2004, 99:2376-2384.

Lois, Augusto et al., "Development of a hybrid algorithm based on learning classifiers that improves diagnosis of inflammatory bowel disease and differentiation between Crohn's and ulcerative colitis in a six-marker system," Gastroenterology, 2006, 130(4, Suppl. 2):A323.

(Continued)

*Primary Examiner* — Pablo S Whaley

(74) *Attorney, Agent, or Firm* — Kilpatrick Townsend & Stockton LLP

(57) ABSTRACT

The methods and systems of the present invention are useful in the diagnosis of inflammatory bowel disease (IBD) and in the prognosis of IBD progression and disease complications. With the present invention, it is possible to predict outcome of disease and patients who will have a particular risk of disease complications and/or progression to surgery.

11 Claims, 44 Drawing Sheets

(56) References Cited

FOREIGN PATENT DOCUMENTS

| | | | |
|---|---|---|---|
| WO | WO 2004/048600 A2 | 6/2004 |
| WO | WO 2004/095021 A1 | 11/2004 |
| WO | WO 2005/078452 A1 | 8/2005 |
| WO | WO 2006/063093 A2 | 6/2006 |
| WO | 2007/064964 A1 | 6/2007 |
| WO | 2008/022177 A2 | 2/2008 |
| WO | WO 2008/109782 A2 | 9/2008 |
| WO | WO 2008/141148 A2 | 11/2008 |
| WO | WO 2010/056682 A2 | 5/2010 |
| WO | 2010/120814 A1 | 10/2010 |
| WO | 2011/066458 A2 | 6/2011 |

OTHER PUBLICATIONS

Devlin et al: "NOD2 Variants and Antibody Response to Microbial Antigens in Crohn's Disease Patients and Their Unaffected Relatives" Gastroenterology, Elsevier, Philadelphia, PA LNKD-DOI:10. 1053/J.GASTRO.2006.11.013, vol. 132, No. 2, Feb. 19, 2007 (Feb. 19, 2007), pp. 576-586.

Dubinsky, M., "Clinical utility of serodiagnostic testing in suspect pediatric inflammatory bowel disease," The American Journal of Gastroenterology, 2001, 96(3):758-765.

Dubinsky Marla C et al: "Serum immune responses predict rapid disease progression among children with Crohn's disease: immune responses predict disease progression." The American Journal of Gastroenterology Feb. 2006, vol. 101, No. 2, Feb. 2006 (Feb. 2006), pp. 360-367.

Fleshner, P. et al., "High level perinuclear antineutrophil cytoplasmic antibody (pANCA) in ulcerative colitis patients before colectomy predicts the development of chronic pouchitis after ileal pouch-anal anastomosis," Gut, 2001, 49(5):671-677.

Landers C J et al: "Selected Loss of Tolerance Evidenced by Crohn's Disease-Associated Immune Responses to Auto and Microbial Antigens" Gastroenterology, Elsevier, Philadelphia, PA, vol. 123, Jan. 1, 2002 (Jan. 1, 2002), pp. 689-699.

Mow et al: "Association of antibody responses to microbial antigens and complications of small bowel Crohn's disease" Gastroenterology, Elsevier, Philadelphia, PA LNKD-DOI:10.1053/J.GASTRO. 2003.11.015, vol. 126, No. 2, Feb. 1, 2004 (Feb. 1, 2004), pp. 414-424.

Nakamura, R. et al., "Advances in clinical laboratory tests for inflammatory bowel disease," Clinica Chimica Acta, 2003, 335:9-20.

Papadakis Konstantinos A et al: "Anti-flagellin (CBir1) phenotypic and genetic Crohn's disease associations" Inflammatory Bowel Diseases, Willams and Wilkins, Hagerstown, MD, US LNKD-DOI:10.1002/IBD.20106, vol. 13, No. 5, May 1, 2007 (May 1, 2007), pp. 524-530.

Reumaux, D., "Serological markers in inflammatory bowel disease," Best Practice and Research Clinical Gastroenterology, 2003, 17(1):19-35.

Ruemele, F. et al., "Diagnostic accuracy of serological assays in pediatric inflammatory bowel disease," Gastroenterology, 1998, 115(4):822-829.

Targan, S., "The utility of ANCA and ASCA in Inflammatory bowel disease," Inflamm. Bowel Dis., 1999, 5(1):61-3.

Targan, S. et al., "Antibodies to CBir1 flagellin define a unique response that is associated independently with complicated Crohn's disease," Gastroenterology, 2005, 128:2020-2028.

Vasiliauskas, E. et al., "Marker antibody expression stratifies Crohn's disease into immunologically homogenous subgroups with distinct clinical characteristics Vasiliauskas," Gut, 2000, 47(4):487-496.

Vernier, G. et al., "Relevance of serologic studies in inflammatory bowel disease," Current Gastroenterology Reports, 2004, 6(6): 482-487.

Western Regional Pediatric IBD Research Alliance Pediatric IBD et al: "Increased Immune Reactivity Predicts Aggressive Complicating Crohn's Disease in Children" Clinical Gastroenterology and Hepatology, American Gastroenterological Association, US LNKD-DOI:10.1016/J.CGH.2008.04.032, vol. 6, No. 10, Oct. 1, 2008 (Oct. 1, 2008), pp. 1105-1111.

Zhao, H. et al. "Entity identification for heterogeneous database integration—a multiple classifier system approach and empirical evaluation," Information Systems, 2005, 30(2):119-132.

Abreu MT et al. Mutations in NOD2 are associated with fibrostenosing disease in patients with Crohn's disease. *Gastroenterology*. 2002;123:679-688.

Annese V. et al. Variants of CARD15 are associated with an aggressive clinical course of Crohn's disease—an IG-IBD study. *Am J Gastroenterol*. 2005;100:84-92.

Baert F. et al. Medical therapy for Crohn's disease: top-down or step-up? *Dig Dis*. 2007;25:260-266.

Baert F. et al. Mucosal healing predicts sustained clinical remission in patients with early-stage Crohn's Disease. *Gastroenterology*. 2010;138:463-468.

Cosnes J. et al. Impact of the increasing use of immunosuppressants in Crohn's disease on the need for intestinal surgery. *Gut*. 2005;54:237-241.

Cruyssen BV et al. CARD15 polymorphisms are associated with anti-*Saccharomyces cerevisiae* antibodies in caucasian Crohn's disease patients. *Clin Exp Immunol*. 2005;140:354-359.

Dalwadi H. et al. The Crohn's disease-associated bacterial protein I2 is a novel enteric t cell superantigen. *Immunity*. 2001;15:149-158.

Desir B. et al. Utility of serum antibodies in determining clinical course in pediatric Crohn's Disease. *Clin Gastroenterol and Hepatol*. 2004;2:139-146.

D'Haens G. et al. Early combined immunosuppression or conventional management in patients with newly diagnosed Crohn's disease: an open randomised trial. *Lancet*. 2008;371:660-667.

Faubion WA et al. The natural history of corticosteroid therapy for inflammatory bowel disease: a population-based study. *Gastroenterology*. 2001;121:255-260.

Ferrante M. et al. Predictors of early response to infliximab in patients with ulcerative colitis. *Inflamm Bowel Dis*. 2007;13:123-128.

Hanauer SB. Positioning biologic agents in the treatment of Crohn's disease. *Inflamm Bowel Dis*. 2009;15:1570-1582.

Lichtenstein GR. Emerging prognostic markers to determine Crohn's disease natural history and improve management strategies: a review of recent literature. *Gastroenterol & Hepatol*. 2010;6:99-107.

Loftus EV et al. The epidemiology and natural history of Crohn's disease in population-based patient cohorts from North America: a systematic review. *Aliment Pharmacol Ther*. 2002;16:51-60.

Louis E. et al. Behaviour of Crohn's disease according to the Vienna classification: changing pattern over the course of the disease. *Gut*. 2001;49:777-782.

Munkholm P. et al. Frequency of glucocorticoid resistance and dependency in Crohn's disease. *Gut*. 1994;35:360-362.

Rieder F. et al. Serum anti-glycan antibodies predict complicated Crohn's disease behavior: A cohort study. *Inflamm Bowel Dis*. 2009.

Sendid B. et al. Specific antibody response to oligomannosidic epitopes in Crohn's disease. *Clin Diagn Lab Immunol*. 1996;3:219-226.

Sutton CL et al. Identification of a novel bacterial sequence associated with Crohn's disease. *Gastroenterology*. 2000;119:23-31.

Voices of Progress Annual Report 2008 [CCFA web site]. Aug. 31, 2008. Available at: http://www.ccfa.org/images/ar09/fullannualrep09.pdf.

Wei B. et al. Pseudomonas fluorescens encodes the Crohn's disease-associated I2 sequence and T-cell superantigen. *Infect Immun*. 2002;70:6567-6575.

Bousvaros, A et al., "Elevated serum vascular endothelial growth factor in children and young adult with Crohn's Disease," Dig. Dis. Sci., 1999, 44:424-430.

Gasche, C. et al., "A simple classification of Crohn's Disease: Report of the working party for the World Congresses of Gastroenterology," Inflammatory Bowel Diseases, 2000, 6(1):8-15.

(56) References Cited

OTHER PUBLICATIONS

Henriksen, M etal., "C-reactive protein: a predictive factor of inflammation in inflammatory bowel disease. Results from a prospective population-based study," Gut, 2008, 57:1518-1523.
Jones, SC et al., "Adhesion molecules in inflammatory bowel disease," Gut, 1995, 36:724-730.
Khor, B et al., "Genetics and pathogenesis of inflammatory bowel disease," Nature, 2011, 474:307-317.
Lees, CW et al., "Genetics of inflammatory bowel disease: implications for disease pathogenesis and natural history," Expert Rev. Gastroenterol. Hepatol., 2009, 3:513-534.
Restriction Requirement mailed on Jun. 22, 2010 for U.S. Appl. No. 11/841,699; Filing Date: Aug. 20, 2007; 6 pages.
Schoepfer et al., "Phenotypic associations of Crohn's Disease with antibodies to flagellins A4-Fla2 and Fla-X, ASCA, p-ANCA, PAB, and NOD2 mutations in a Swiss cohort," Inflamm. Bowel Dis., 2009, 15:1358-1367.
Chen, C. et al., "Identification of novel serological biomarkers for inflammatory bowel disease using *Escherichia coli* proteome chip," Mol. Cell. Proteomics, 8(8):1765-76, 2009.

* cited by examiner

| | Inflammatory | Fibrostenosis | Fistulizing Internal preforating |
|---|---|---|---|
| ANCA(E) | 4 | 2 | 4 |
| ASCAA | 3 | 4 | 4 |
| ASCAG | 3 | 4 | 2 |
| OmpC | 2 | 3 | 3 |
| CBir1 | 3 | 2 | 3 |
| I2 | 1 | 2 | 1 |
| CRP | 0 | 1 | 1 |
| SAA | 1 | 2 | 1 |

| Surgery | pANCA |
|---|---|
| 1 | 1 |

| None | | Moderate | | Highest |
|---|---|---|---|---|
| 0 | 1 | 2 | 3 | 4 |

Concentration or titer

*FIG. 4*

| | Inflammatory | Fibrostenosis | Fistulizing Internal preforating |
|---|---|---|---|
| ANCA(E) | 4 | 2 | 4 |
| ASCAA | 1 | 4 | 4 |
| ASCAG | 3 | 4 | 3 |
| OmpC | 2 | 3 | 3 |
| CBir1 | 3 | 2 | 3 |
| I2 | 1 | 2 | 1 |
| CRP | 0 | 1 | 1 |
| SAA | 1 | 2 | 1 |

| Surgery | pANCA |
|---|---|
| 0 | 1 |

| None | | Moderate | | Highest |
|---|---|---|---|---|
| 0 | 1 | 2 | 3 | 4 |

Concentration or titer

*FIG. 5*

| | Inflammatory | Fibrostenosis | Fistulizing Internal preforating | Additional characteristic | Additional characteristic |
|---|---|---|---|---|---|
| ANCA(E) | 4 | 2 | 4 | | |
| ASCAA | 1 | 4 | 4 | | |
| ASCAG | 3 | 4 | 3 | | |
| OmpC | 2 | 3 | 3 | | |
| CBir1 | 3 | 2 | 3 | | |
| I2 | 1 | 2 | 1 | | |
| CRP | 0 | 1 | 1 | | |
| SAA | 1 | 2 | 1 | | |
| New Marker X | | | | | |
| New Marker Y | | | | | |

*FIG. 6*

Development of
Calibrators

Titer:
13486BL1, 63428
13486PB, 153
13485BL1, 34774
13485PB, 1833

Development of
Calibrators

Titer:
13488BL1, 43685
13488PB, 17
13487BL1, 71804
13487PB, 16

Key

| Lane | Lot |
|---|---|
| 1 | A |
| 2 | B |
| 3 | C |

*Note-70kDa band is due to dimer formation a b

ELISA Assays for Human IgA and IgG Antibodies Against I2

SEQUENCE LISTING

```
<160> NUMBER OF SEQ ID NOS: 42

<210> SEQ ID NO 1
<211> LENGTH: 212
<212> TYPE: PRT
<213> ORGANISM: Homo sapiens
<220> FEATURE:
<223> OTHER INFORMATION: human interleukin-6 (IL-6) precursor, hybridoma
      growth factor (HGF); interferon beta 2 (IFNB2),
      B-cell differentiation factor, B-cell stimulatory
      factor-2 (BSF2), CTL differentiation factor (CDF), HSF

<400> SEQUENCE: 1
```

```
Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 2
<211> LENGTH: 1201
<212> TYPE: DNA
<213> ORGANISM: Homo sapiens
<220> FEATURE:
<223> OTHER INFORMATION: human interleukin-6 (IL-6) precursor, hybridoma growth factor (HGF); interferon beta 2 (IFNB2), B-cell differentiation factor, B-cell stimulatory factor-2 (BSF2), CTL differentiation factor (CDF), HSF cDNA

<400> SEQUENCE: 2

```
aatattagag tctcaacccc caataaatat aggactggag atgtctgagg ctcattctgc     60

cctcgagccc accgggaacg aaagagaagc tctatctccc ctccaggagc ccagctatga    120

actccttctc cacaagcgcc ttcggtccag ttgccttctc cctggggctg ctcctggtgt    180

tgcctgctgc cttccctgcc ccagtacccc caggagaaga ttccaaagat gtagccgccc    240

cacacagaca gccactcacc tcttcagaac gaattgacaa acaaattcgg tacatcctcg    300

acggcatctc agccctgaga aaggagacat gtaacaagag taacatgtgt gaaagcagca    360

aagaggcact ggcagaaaac aacctgaacc ttccaaagat ggctgaaaaa gatggatgct    420

tccaatctgg attcaatgag gagacttgcc tggtgaaaat catcactggt cttttggagt    480

ttgaggtata cctagagtac ctccagaaca gatttgagag tagtgaggaa caagccagag    540

ctgtgcagat gagtacaaaa gtcctgatcc agttcctgca gaaaaaggca aagaatctag    600

atgcaataac cacccctgac ccaaccacaa atgccagcct gctgacgaag ctgcaggcac    660

agaaccagtg gctgcaggac atgacaactc atctcattct gcgcagcttt aaggagttcc    720
```

```
tgcagtccag cctgagggct cttcggcaaa tgtagcatgg gcacctcaga ttgttgttgt    780

taatgggcat tccttcttct ggtcagaaac ctgtccactg ggcacagaac ttatgttgtt    840

ctctatggag aactaaaagt atgagcgtta ggacactatt ttaattattt ttaatttatt    900

aatatttaaa tatgtgaagc tgagttaatt tatgtaagtc atatttatat ttttaagaag    960

taccacttga aacattttat gtattagttt tgaaataata atggaaagtg gctatgcagt   1020

ttgaatatcc tttgtttcag agccagatca tttcttggaa agtgtaggct tacctcaaat   1080

aaatggctaa cttatacata tttttaaaga aatatttata ttgtatttat ataatgtata   1140

aatggttttt ataccaataa atggcatttt aaaaaattca gcaaaaaaaa aaaaaaaaaa   1200

a                                                                   1201


<210> SEQ ID NO 3
<211> LENGTH: 269
<212> TYPE: PRT
<213> ORGANISM: Homo sapiens
<220> FEATURE:
<223> OTHER INFORMATION: human interleukin-1 beta (IL-1beta, IL1B)
      proprotein, preinterleukin 1 beta, catabolin,
      pro-interleukin-1-beta, IL1F2

<400> SEQUENCE: 3

Met Ala Glu Val Pro Glu Leu Ala Ser Glu Met Met Ala Tyr Tyr Ser
 1               5                  10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
```

260 265

<210> SEQ ID NO 4
<211> LENGTH: 1498
<212> TYPE: DNA
<213> ORGANISM: Homo sapiens
<220> FEATURE:
<223> OTHER INFORMATION: human interleukin-1 beta (IL-1beta, IL1B) proprotein, preinterleukin 1 beta, catabolin, pro-interleukin-1-beta, IL1F2 cDNA

<400> SEQUENCE: 4
accaaacctc ttcgaggcac aaggcacaac aggctgctct gggattctct tcagccaatc 60
ttcattgctc aagtgtctga agcagccatg gcagaagtac ctgagctcgc cagtgaaatg 120
atggcttatt acagtggcaa tgaggatgac ttgttctttg aagctgatgg ccctaaacag 180
atgaagtgct ccttccagga cctggacctc tgccctctgg atggcggcat ccagctacga 240
atctccgacc accactacag caagggcttc aggcaggccg cgtcagttgt tgtggccatg 300
gacaagctga ggaagatgct ggttccctgc ccacagacct tccaggagaa tgacctgagc 360
accttctttc ccttcatctt tgaagaagaa cctatcttct tcgacacatg ggataacgag 420
gcttatgtgc acgatgcacc tgtacgatca ctgaactgca cgctccggga ctcacagcaa 480
aaaagcttgg tgatgtctgg tccatatgaa ctgaaagctc tccacctcca gggacaggat 540
atggagcaac aagtggtgtt ctccatgtcc tttgtacaag gagaagaaag taatgacaaa 600
atacctgtgg ccttgggcct caaggaaaag aatctgtacc tgtcctgcgt gttgaaagat 660
gataagccca ctctacagct ggagagtgta gatcccaaaa attacccaaa gaagaagatg 720
gaaaagcgat ttgtcttcaa caagatagaa atcaataaca agctggaatt tgagtctgcc 780
cagttcccca actggtacat cagcacctct caagcagaaa acatgcccgt cttcctggga 840
gggaccaaag gcggccagga tataactgac ttcaccatgc aatttgtgtc ttcctaaaga 900
gagctgtacc cagagagtcc tgtgctgaat gtggactcaa tccctagggc tggcagaaag 960
ggaacagaaa ggtttttgag tacggctata gcctggactt tcctgttgtc tacaccaatg 1020
cccaactgcc tgccttaggg tagtgctaag aggatctcct gtccatcagc caggacagtc 1080
agctctctcc tttcagggcc aatccccagc ccttttgttg agccaggcct ctctcacctc 1140
tcctactcac ttaaagcccg cctgacagaa accacggcca catttggttc taagaaaccc 1200
tctgtcattc gctcccacat tctgatgagc aaccgcttcc ctatttattt atttatttgt 1260
ttgtttgttt tattcattgg tctaatttat tcaaaggggg caagaagtag cagtgtctgt 1320
aaaagagcct agtttttaat agctatggaa tcaattcaat ttggactggt gtgctctctt 1380
taaatcaagt cctttaatta agactgaaaa tatataagct cagattattt aaatgggaat 1440
atttataaat gagcaaatat catactgttc aatggttctg aaataaactt cactgaag 1498

<210> SEQ ID NO 5
<211> LENGTH: 249
<212> TYPE: PRT
<213> ORGANISM: Homo sapiens
<220> FEATURE:
<223> OTHER INFORMATION: human TNF-related WEAK inducer of apoptosis (TWEAK), tumor necrosis factor ligand superfamily member 12 (TNFSF12) precursor, APO3 ligand (APO3L), DR3 ligand, CD255, growth factor-inducible 14 (Fn14) ligand, MGC129581, MGC20669, UNQ181/PRO207

<400> SEQUENCE: 5

Met Ala Ala Arg Arg Ser Gln Arg Arg Arg Gly Arg Arg Gly Glu Pro

-continued

```
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245
```

```
<210> SEQ ID NO 6
<211> LENGTH: 1407
<212> TYPE: DNA
<213> ORGANISM: Homo sapiens
<220> FEATURE:
<223> OTHER INFORMATION: human TNF-related WEAK inducer of apoptosis
      (TWEAK), tumor necrosis factor ligand superfamily member 12
      (TNFSF12) precursor, APO3 ligand (APO3L), DR3 ligand, CD255,
      growth factor-inducible 14 (Fn14) ligand, MGC129581, MGC20669,
      UNQ181/PRO207 cDNA

<400> SEQUENCE: 6

ctctccccgg cccgatccgc ccgccggctc cccctccccc gatccctcgg gtcccgggat      60

ggggggggcgg tgaggcaggc acagcccccc gcccccatgg ccgcccgtcg gagccagagg     120

cggagggggc gccgggggga gccgggcacc gccctgctgg tcccgctcgc gctgggcctg     180

ggcctggcgc tggcctgcct cggcctcctg ctggccgtgg tcagtttggg gagccgggca     240

tcgctgtccg cccaggagcc tgcccaggag gagctggtgg cagaggagga ccaggacccg     300

tcggaactga atccccagac agaagaaagc caggatcctg cgcctttcct gaaccgacta     360

gttcggcctc gcagaagtgc acctaaaggc cggaaaacac gggctcgaag agcgatcgca     420

gcccattatg aagttcatcc acgacctgga caggacggag cgcaggcagg tgtggacggg     480

acagtgagtg gctgggagga agccagaatc aacagctcca gccctctgcg ctacaaccgc     540
```

-continued

```
cagatcgggg agtttatagt cacccgggct gggctctact acctgtactg tcaggtgcac     600

tttgatgagg ggaaggctgt ctacctgaag ctggacttgc tggtggatgg tgtgctggcc     660

ctgcgctgcc tggaggaatt ctcagccact gcggcgagtt ccctcgggcc ccagctccgc     720

ctctgccagg tgtctgggct gttggccctg cggccagggt cctccctgcg gatccgcacc     780

ctcccctggg cccatctcaa ggctgccccc ttcctcacct acttcggact cttccaggtt     840

cactgagggg ccctggtctc cccgcagtcg tcccaggctg ccggctcccc tcgacagctc     900

tctgggcacc cggtcccctc tgccccaccc tcagccgctc tttgctccag acctgcccct     960

ccctctagag gctgcctggg cctgttcacg tgttttccat cccacataaa tacagtattc    1020

ccactcttat cttacaactc ccccaccgcc cactctccac ctcactagct ccccaatccc    1080

tgaccctttg aggcccccag tgatctcgac tccccccctgg ccacagaccc ccagggcatt   1140

gtgttcactg tactctgtgg gcaaggatgg gtccagaaga ccccacttca ggcactaaga    1200

ggggctggac ctggcggcag gaagccaaag agactgggcc taggccagga gttcccaaat    1260

gtgaggggcg agaaacaaga caagctcctc ccttgagaat tccctgtgga tttttaaaac    1320

agatattatt tttattatta ttgtgacaaa atgttgataa atggatatta aatagaataa    1380

gtcataaaaa aaaaaaaaaa aaaaaaa                                        1407


<210> SEQ ID NO 7
<211> LENGTH: 1207
<212> TYPE: PRT
<213> ORGANISM: Homo sapiens
<220> FEATURE:
<223> OTHER INFORMATION: human pro-epidermal growth factor (EGF)
      isoform 1 preproprotein, beta-urogastrone (URG), HOMG4

<400> SEQUENCE: 7

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205
```

```
Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
    370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
            420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
    450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
            500                 505                 510

Met Val Tyr Ala Leu Asp His Asp Pro Val Glu Asn Lys Ile Tyr Phe
        515                 520                 525

Ala His Thr Ala Leu Lys Trp Ile Glu Arg Ala Asn Met Asp Gly Ser
    530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
        595                 600                 605

Ala Lys Arg Leu Phe Trp Thr Asp Thr Gly Ile Asn Pro Arg Ile Glu
    610                 615                 620
```

-continued

```
Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
            660                 665                 670

Gly Ser Lys Arg Arg Arg Leu Thr Gln Asn Asp Val Gly His Pro Phe
        675                 680                 685

Ala Val Ala Val Phe Glu Asp Tyr Val Trp Phe Ser Asp Trp Ala Met
    690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                725                 730                 735

Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
        755                 760                 765

Glu Gly Phe Met Lys Ala Ser Asp Gly Lys Thr Cys Leu Ala Leu Asp
    770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
        835                 840                 845

Glu Gly Glu Asp Ala Thr Cys Gln Cys Leu Lys Gly Phe Ala Gly Asp
    850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ile Asp Glu Cys Gln Leu Gly Glu His Ser Cys Gly Glu Asn Ala Ser
        915                 920                 925

Cys Thr Asn Thr Glu Gly Gly Tyr Thr Cys Met Cys Ala Gly Arg Leu
    930                 935                 940

Ser Glu Pro Gly Leu Ile Cys Pro Asp Ser Thr Pro Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg His
    1010                1015                1020

Ala Gly His Gly Gln Gln Gln Lys Val Ile Val Val Ala Val Cys Val
1025                1030                1035                1040

Val Val Leu Val Met Leu Leu Leu Leu Ser Leu Trp Gly Ala His Tyr
```

-continued

```
                1045                1050                1055

Tyr Arg Thr Gln Lys Leu Leu Ser Lys Asn Pro Lys Asn Pro Tyr Glu
            1060                1065                1070

Glu Ser Ser Arg Asp Val Arg Ser Arg Arg Pro Ala Asp Thr Glu Asp
        1075                1080                1085

Gly Met Ser Ser Cys Pro Gln Pro Trp Phe Val Val Ile Lys Glu His
    1090                1095                1100

Gln Asp Leu Lys Asn Gly Gly Gln Pro Val Ala Gly Glu Asp Gly Gln
1105                1110                1115                1120

Ala Ala Asp Gly Ser Met Gln Pro Thr Ser Trp Arg Gln Glu Pro Gln
                1125                1130                1135

Leu Cys Gly Met Gly Thr Glu Gln Gly Cys Trp Ile Pro Val Ser Ser
            1140                1145                1150

Asp Lys Gly Ser Cys Pro Gln Val Met Glu Arg Ser Phe His Met Pro
        1155                1160                1165

Ser Tyr Gly Thr Gln Thr Leu Glu Gly Gly Val Glu Lys Pro His Ser
    1170                1175                1180

Leu Leu Ser Ala Asn Pro Leu Trp Gln Gln Arg Ala Leu Asp Pro Pro
1185                1190                1195                1200

His Gln Met Glu Leu Thr Gln
                1205


<210> SEQ ID NO 8
<211> LENGTH: 4913
<212> TYPE: DNA
<213> ORGANISM: Homo sapiens
<220> FEATURE:
<223> OTHER INFORMATION: human pro-epidermal growth factor (EGF),
      transcript variant 1, preproprotein,
      beta-urogastrone (URG), HOMG4 cDNA

<400> SEQUENCE: 8

aaaaagagaa actgttggga gaggaatcgt atctccatat ttcttctttc agccccaatc     60

caagggttgt agctggaact ttccatcagt tcttcctttc tttttcctct ctaagccttt    120

gccttgctct gtcacagtga agtcagccag agcagggctg ttaaactctg tgaaatttgt    180

cataagggtg tcaggtattt cttactggct tccaaagaaa catagataaa gaaatctttc    240

ctgtggcttc ccttggcagg ctgcattcag aaggtctctc agttgaagaa agagcttgga    300

ggacaacagc acaacaggag agtaaaagat gccccagggc tgaggcctcc gctcaggcag    360

ccgcatctgg ggtcaatcat actcaccttg cccgggccat gctccagcaa aatcaagctg    420

ttttcttttg aaagttcaaa ctcatcaaga ttatgctgct cactcttatc attctgttgc    480

cagtagtttc aaaatttagt tttgttagtc tctcagcacc gcagcactgg agctgtcctg    540

aaggtactct cgcaggaaat gggaattcta cttgtgtggg tcctgcaccc ttcttaattt    600

tctcccatgg aaatagtatc tttaggattg acacagaagg aaccaattat gagcaattgg    660

tggtggatgc tggtgtctca gtgatcatgg attttcatta taatgagaaa agaatctatt    720

gggtggattt agaaagacaa cttttgcaaa gagtttttct gaatgggtca aggcaagaga    780

gagtatgtaa tatagagaaa aatgtttctg gaatggcaat aaattggata aatgaagaag    840

ttatttggtc aaatcaacag gaaggaatca ttacagtaac agatatgaaa ggaaataatt    900

cccacattct tttaagtgct ttaaaatatc ctgcaaatgt agcagttgat ccagtagaaa    960

ggtttatatt ttggtcttca gaggtggctg gaagccttta tagagcagat ctcgatggtg   1020

tgggagtgaa ggctctgttg gagacatcag agaaaataac agctgtgtca ttggatgtgc   1080
```

-continued

```
ttgataagcg gctgttttgg attcagtaca acagagaagg aagcaattct cttatttgct   1140
cctgtgatta tgatggaggt tctgtccaca ttagtaaaca tccaacacag cataatttgt   1200
ttgcaatgtc ccttttttggt gaccgtatct tctattcaac atggaaaatg aagacaattt   1260
ggatagccaa caaacacact ggaaaggaca tggttagaat taacctccat tcatcatttg   1320
taccacttgg tgaactgaaa gtagtgcatc cacttgcaca acccaaggca gaagatgaca   1380
cttgggagcc tgagcagaaa ctttgcaaat tgaggaaagg aaactgcagc agcactgtgt   1440
gtgggcaaga cctccagtca cacttgtgca tgtgtgcaga gggatacgcc ctaagtcgag   1500
accggaagta ctgtgaagat gttaatgaat gtgctttttg gaatcatggc tgtactcttg   1560
ggtgtaaaaa cacccctgga tcctattact gcacgtgccc tgtaggattt gttctgcttc   1620
ctgatgggaa acgatgtcat caacttgttt cctgtccacg caatgtgtct gaatgcagcc   1680
atgactgtgt tctgacatca gaaggtccct tatgtttctg tcctgaaggc tcagtgcttg   1740
agagagatgg gaaaacatgt agcggttgtt cctcacccga taatggtgga tgtagccagc   1800
tctgcgttcc tcttagccca gtatcctggg aatgtgattg ctttcctggg tatgacctac   1860
aactggatga aaaaagctgt gcagcttcag gaccacaacc atttttgctg tttgccaatt   1920
ctcaagatat tcgacacatg cattttgatg gaacagacta tggaactctg ctcagccagc   1980
agatgggaat ggtttatgcc ctagatcatg accctgtgga aaataagata tactttgccc   2040
atacagccct gaagtggata gagagagcta atatggatgg ttcccagcga gaaaggctta   2100
ttgaggaagg agtagatgtg ccagaaggtc ttgctgtgga ctggattggc cgtagattct   2160
attggacaga cagagggaaa tctctgattg gaaggagtga tttaaatggg aaacgttcca   2220
aaataatcac taaggagaac atctctcaac cacgaggaat tgctgttcat ccaatggcca   2280
agagattatt ctggactgat acagggatta atccacgaat tgaaagttct tccctccaag   2340
gccttggccg tctggttata gccagctctg atctaatctg gcccagtgga ataacgattg   2400
acttcttaac tgacaagttg tactggtgcg atgccaagca gtctgtgatt gaaatggcca   2460
atctggatgg ttcaaaacgc cgaagactta cccagaatga tgtaggtcac ccatttgctg   2520
tagcagtgtt tgaggattat gtgtggttct cagattgggc tatgccatca gtaatgagag   2580
taaacaagag gactggcaaa gatagagtac gtctccaagg cagcatgctg aagccctcat   2640
cactggttgt ggttcatcca ttggcaaaac caggagcaga tccctgctta tatcaaaacg   2700
gaggctgtga acatatttgc aaaaagaggc ttggaactgc ttggtgttcg tgtcgtgaag   2760
gttttatgaa agcctcagat gggaaaacgt gtctggctct ggatggtcat cagctgttgg   2820
caggtggtga agttgatcta aagaaccaag taacaccatt ggacatcttg tccaagacta   2880
gagtgtcaga agataacatt acagaatctc aacacatgct agtggctgaa atcatggtgt   2940
cagatcaaga tgactgtgct cctgtgggat gcagcatgta tgctcggtgt atttcagagg   3000
gagaggatgc cacatgtcag tgtttgaaag gatttgctgg ggatggaaaa ctatgttctg   3060
atatagatga atgtgagatg ggtgtcccag tgtgcccccc tgcctcctcc aagtgcatca   3120
acaccgaagg tggttatgtc tgccggtgct cagaaggcta ccaaggagat gggattcact   3180
gtcttgatat tgatgagtgc caactggggg agcacagctg tggagagaat gccagctgca   3240
caaatacaga gggaggctat acctgcatgt gtgctggacg cctgtctgaa ccaggactga   3300
tttgccctga ctctactcca ccccctcacc tcagggaaga tgaccaccac tattccgtaa   3360
gaaatagtga ctctgaatgt cccctgtccc acgatgggta ctgcctccat gatggtgtgt   3420
```

-continued

```
gcatgtatat tgaagcattg gacaagtatg catgcaactg tgttgttggc tacatcgggg   3480

agcgatgtca gtaccgagac ctgaagtggt gggaactgcg ccacgctggc cacgggcagc   3540

agcagaaggt catcgtggtg gctgtctgcg tggtggtgct tgtcatgctg ctcctcctga   3600

gcctgtgggg ggcccactac tacaggactc agaagctgct atcgaaaaac ccaaagaatc   3660

cttatgagga gtcgagcaga gatgtgagga gtcgcaggcc tgctgacact gaggatggga   3720

tgtcctcttg ccctcaacct tggtttgtgg ttataaaaga acaccaagac ctcaagaatg   3780

ggggtcaacc agtggctggt gaggatggcc aggcagcaga tgggtcaatg caaccaactt   3840

catggaggca ggagccccag ttatgtggaa tgggcacaga gcaaggctgc tggattccag   3900

tatccagtga taagggctcc tgtccccagg taatggagcg aagctttcat atgccctcct   3960

atgggacaca gacccttgaa gggggtgtcg agaagcccca ttctctccta tcagctaacc   4020

cattatggca acaaagggcc ctggacccac cacaccaaat ggagctgact cagtgaaaac   4080

tggaattaaa aggaaagtca agaagaatga actatgtcga tgcacagtat cttttctttc   4140

aaaagtagag caaaactata ggttttggtt ccacaatctc tacgactaat cacctactca   4200

atgcctggag acagatacgt agttgtgctt ttgtttgctc ttttaagcag tctcactgca   4260

gtcttatttc caagtaagag tactgggaga atcactaggt aacttattag aaacccaaat   4320

tgggacaaca gtgctttgta aattgtgttg tcttcagcag tcaatacaaa tagatttttg   4380

tttttgttgt tcctgcagcc ccagaagaaa ttaggggtta aagcagacag tcacactggt   4440

ttggtcagtt acaaagtaat ttctttgatc tggacagaac atttatatca gtttcatgaa   4500

atgattggaa tattacaata ccgttaagat acagtgtagg catttaactc ctcattggcg   4560

tggtccatgc tgatgatttt gcaaaatgag ttgtgatgaa tcaatgaaaa atgtaattta   4620

gaaactgatt tcttcagaat tagatggctt attttttaaa atatttgaat gaaaacattt   4680

tatttttaaa atattacaca ggaggcttcg gagtttctta gtcattactg tccttttccc   4740

ctacagaatt ttccctcttg gtgtgattgc acagaatttg tatgtatttt cagttacaag   4800

attgtaagta aattgcctga tttgttttca ttatagacaa cgatgaattt cttctaatta   4860

tttaaataaa atcaccaaaa acataaaaaa aaaaaaaaaa aaaaaaaaaa aaa          4913
```

<210> SEQ ID NO 9
<211> LENGTH: 224
<212> TYPE: PRT
<213> ORGANISM: Homo sapiens
<220> FEATURE:
<223> OTHER INFORMATION: human C-reactive protein (CRP), pentraxin-related, precursor, pentraxin 1 (PTX1), MGC149895, MGC88244

<400> SEQUENCE: 9

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95
```

-continued

```
Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220


<210> SEQ ID NO 10
<211> LENGTH: 2024
<212> TYPE: DNA
<213> ORGANISM: Homo sapiens
<220> FEATURE:
<223> OTHER INFORMATION: human C-reactive protein (CRP),
      pentraxin-related, precursor, pentraxin 1 (PTX1), MGC149895,
      MGC88244 cDNA

<400> SEQUENCE: 10

aaggcaagag atctaggact tctagcccct gaactttcag ccgaatacat cttttccaaa     60

ggagtgaatt caggcccttg tatcactggc agcaggacgt gaccatggag aagctgttgt    120

gtttcttggt cttgaccagc ctctctcatg cttttggcca gacagacatg tcgaggaagg    180

cttttgtgtt tcccaaagag tcggatactt cctatgtatc cctcaaagca ccgttaacga    240

agcctctcaa agccttcact gtgtgcctcc acttctacac ggaactgtcc tcgacccgtg    300

ggtacagtat tttctcgtat gccaccaaga gacaagacaa tgagattctc atattttggt    360

ctaaggatat aggatacagt tttacagtgg gtgggtctga aatattattc gaggttcctg    420

aagtcacagt agctccagta cacatttgta caagctggga gtccgcctca gggatcgtgg    480

agttctgggt agatgggaag cccagggtga ggaagagtct gaagaaggga tacactgtgg    540

gggcagaagc aagcatcatc ttggggcagg agcaggattc cttcggtggg aactttgaag    600

gaagccagtc cctggtggga gacattggaa atgtgaacat gtgggacttt gtgctgtcac    660

cagatgagat taacaccatc tatcttggcg ggcccttcag tcctaatgtc ctgaactggc    720

gggcactgaa gtatgaagtg caaggcgaag tgttcaccaa accccagctg tggccctgag    780

gcccagctgt gggtcctgaa ggtacctccc ggttttttac accgcatggg ccccacgtct    840

ctgtctctgg tacctcccgc tttttacac tgcatggttc ccacgtctct gtctctgggc    900

ctttgttccc ctatatgcat tgcaggcctg ctccaccctc ctcagcgcct gagaatggag    960

gtaaagtgtc tggtctggga gctcgttaac tatgctggga aacggtccaa aagaatcaga   1020

atttgaggtg ttttgttttc atttttattt caagttggac agatcttgga gataatttct   1080

tacctcacat agatgagaaa actaacaccc agaaaggaga aatgatgtta taaaaaactc   1140

ataaggcaag agctgagaag gaagcgctga tcttctattt aattccccac ccatgacccc   1200

cagaaagcag gagggcattg cccacattca cagggctctt cagtctcaga atcaggacac   1260
```

-continued

```
tggccaggtg tctggtttgg gtccagagtg ctcatcatca tgtcatagaa ctgctgggcc   1320

caggtctcct gaaatgggaa gcccagcaat accacgcagt ccctccactt tctcaaagca   1380

cactggaaag gccattagaa ttgccccagc agagcagatc tgcttttttt ccagagcaaa   1440

atgaagcact aggtataaat atgttgttac tgccaagaac ttaaatgact ggtttttgtt   1500

tgcttgcagt gctttcttaa ttttatggct cttctgggaa actcctcccc ttttccacac   1560

gaaccttgtg gggctgtgaa ttctttcttc atccccgcat tcccaatata cccaggccac   1620

aagagtggac gtgaaccaca gggtgtcctg tcagaggagc ccatctccca tctccccagc   1680

tccctatctg gaggatagtt ggatagttac gtgttcctag caggaccaac tacagtcttc   1740

ccaaggattg agttatggac tttgggagtg agacatcttc ttgctgctgg atttccaagc   1800

tgagaggacg tgaacctggg accaccagta gccatcttgt ttgccacatg gagagagact   1860

gtgaggacag aagccaaact ggaagtggag gagccaaggg attgacaaac aacagagcct   1920

tgaccacgtg gagtctctga atcagccttg tctggaacca gatctacacc tggactgccc   1980

aggtctataa gccaataaag cccctgttta cttgaaaaaa aaaa                    2024
```

```
<210> SEQ ID NO 11
<211> LENGTH: 122
<212> TYPE: PRT
<213> ORGANISM: Homo sapiens
<220> FEATURE:
<223> OTHER INFORMATION: human serum amyloid A1 protein (SAA, SAA1,
      SAA2) preproprotein, tumor protein p53 inducible protein
      4 (TP53I4), PIG4, MGC111216

<400> SEQUENCE: 11

Met Lys Leu Leu Thr Gly Leu Val Phe Cys Ser Leu Val Leu Gly Val
 1               5                  10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120


<210> SEQ ID NO 12
<211> LENGTH: 716
<212> TYPE: DNA
<213> ORGANISM: Homo sapiens
<220> FEATURE:
<223> OTHER INFORMATION: human serum amyloid A1 protein (SAA, SAA1,
      SAA2), transcript variant 1, preproprotein, tumor protein
      p53 inducible protein 4 (TP53I4), PIG4, MGC111216 cDNA

<400> SEQUENCE: 12

aggctcagta taaatagcag ccaccgctcc ctggcaggca gggacccgca gctcagctac     60

agcacagatc aggtgaggag cacaccaagg agtgattttt aaaacttact ctgttttctc    120

tttcccaaca agattatcat ttcctttaaa aaaaatagtt atcctggggc atacagccat    180
```

accattctga aggtgtctta tctcctctga tctagagagc accatgaagc ttctcacggg 240
cctggttttc tgctccttgg tcctgggtgt cagcagccga agcttctttt cgttccttgg 300
cgaggctttt gatggggctc gggacatgtg gagagcctac tctgacatga gagaagccaa 360
ttacatcggc tcagacaaat acttccatgc tcgggggaac tatgatgctg ccaaaagggg 420
acctgggggt gcctgggctg cagaagtgat cagcgatgcc agagagaata tccagagatt 480
ctttggccat ggtgcggagg actcgctggc tgatcaggct gccaatgaat ggggcaggag 540
tggcaaagac cccaatcact tccgacctgc tggcctgcct gagaaatact gagcttcctc 600
ttcactctgc tctcaggaga tctggctgtg aggccctcag ggcagggata caaagcgggg 660
agagggtaca caatgggtat ctaataaata cttaagaggt ggaatttgtg gaaact 716

<210> SEQ ID NO 13
<211> LENGTH: 68
<212> TYPE: PRT
<213> ORGANISM: Homo sapiens
<220> FEATURE:
<223> OTHER INFORMATION: human beta-defensin 1 (DEFB-1, BD1, BD-1, DEFB101, HBD1) preproprotein, MGC51822

<400> SEQUENCE: 13

Met Arg Thr Ser Tyr Leu Leu Leu Phe Thr Leu Cys Leu Leu Leu Ser
1 5 10 15

Glu Met Ala Ser Gly Gly Asn Phe Leu Thr Gly Leu Gly His Arg Ser
20 25 30

Asp His Tyr Asn Cys Val Ser Ser Gly Gly Gln Cys Leu Tyr Ser Ala
35 40 45

Cys Pro Ile Phe Thr Lys Ile Gln Gly Thr Cys Tyr Arg Gly Lys Ala
50 55 60

Lys Cys Cys Lys
65

<210> SEQ ID NO 14
<211> LENGTH: 484
<212> TYPE: DNA
<213> ORGANISM: Homo sapiens
<220> FEATURE:
<223> OTHER INFORMATION: human beta-defensin 1 (DEFB-1, BD1, BD-1, DEFB101, HBD1) preproprotein, MGC51822 cDNA

<400> SEQUENCE: 14
tcccttcagt tccgtcgacg aggttgtgca atccaccagt cttataaata cagtgacgct 60
ccagcctctg gaagcctctg tcagctcagc ctccaaagga gccagcgtct ccccagttcc 120
tgaaatcctg ggtgttgcct gccagtcgcc atgagaactt cctaccttct gctgtttact 180
ctctgcttac ttttgtctga gatggcctca ggtggtaact ttctcacagg ccttggccac 240
agatctgatc attacaattg cgtcagcagt ggagggcaat gtctctattc tgcctgcccg 300
atctttacca aaattcaagg cacctgttac agagggaagg ccaagtgctg caagtgagct 360
gggagtgacc agaagaaatg acgcagaagt gaaatgaact ttttataagc attcttttaa 420
taaaggaaaa ttgcttttga agtatacctc ctttgggcca aaaaaaaaaa aaaaaaaaaa 480
aaaa 484

<210> SEQ ID NO 15
<211> LENGTH: 64
<212> TYPE: PRT
<213> ORGANISM: Homo sapiens
<220> FEATURE:
<223> OTHER INFORMATION: human beta-defensin 2 (DEFB2, DEFB-2, DEFB102, BD-2, HBD-2) precursor, skin-antimicrobial peptide 1 (SAP1), defensin, beta 4 (DEFB4, DEFB4A)

<400> SEQUENCE: 15

```
Met Arg Val Leu Tyr Leu Leu Phe Ser Phe Leu Phe Ile Phe Leu Met
 1              5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 16
<211> LENGTH: 336
<212> TYPE: DNA
<213> ORGANISM: Homo sapiens
<220> FEATURE:
<223> OTHER INFORMATION: human beta-defensin 2 (DEFB2, DEFB-2, DEFB102, BD-2, HBD-2) precursor, skin-antimicrobial peptide 1 (SAP1), defensin, beta 4 (DEFB4, DEFB4A) cDNA

<400> SEQUENCE: 16

```
agactcagct cctggtgaag ctcccagcca tcagccatga gggtcttgta tctcctcttc      60

tcgttcctct tcatattcct gatgcctctt ccaggtgttt ttggtggtat aggcgatcct     120

gttacctgcc ttaagagtgg agccatatgt catccagtct tttgccctag aaggtataaa     180

caaattggca cctgtggtct ccctggaaca aaatgctgca aaaagccatg aggaggccaa     240

gaagctgctg tggctgatgc ggattcagaa agggctccct catcagagac gtgcgacatg     300

taaaccaaat taaactatgg tgtccaaaga tacgca                               336
```

<210> SEQ ID NO 17
<211> LENGTH: 882
<212> TYPE: PRT
<213> ORGANISM: Homo sapiens
<220> FEATURE:
<223> OTHER INFORMATION: human E-cadherin (CDHE, ECAD) preproprotein, cadherin-1 (CDH1), calcium-dependent adhesion protein, epithelial, CAM 120/80, cell-CAM 120/80, epithelial cadherin, uvomorulin (UVO), Arc-1, CD324, LCAM

<400> SEQUENCE: 17

```
Met Gly Pro Trp Ser Arg Ser Leu Ser Ala Leu Leu Leu Leu Leu Gln
 1              5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125
```

```
Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540
```

```
Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Gly Glu Glu Asp Gln Asp Phe Asp
        755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
    850                 855                 860

Trp Gly Asn Arg Phe Lys Lys Leu Ala Asp Met Tyr Gly Gly Gly Glu
865                 870                 875                 880

Asp Asp


<210> SEQ ID NO 18
<211> LENGTH: 4815
<212> TYPE: DNA
<213> ORGANISM: Homo sapiens
<220> FEATURE:
<223> OTHER INFORMATION: human E-cadherin (CDHE, ECAD) preproprotein,
      cadherin-1 (CDH1), calcium-dependent adhesion protein,
      epithelial, CAM 120/80, cell-CAM 120/80, epithelial cadherin,
      uvomorulin (UVO), Arc-1, CD324, LCAM cDNA

<400> SEQUENCE: 18

agtggcgtcg gaactgcaaa gcacctgtga gcttgcggaa gtcagttcag actccagccc     60
```

```
gctccagccc ggcccgaccc gaccgcaccc ggcgcctgcc ctcgctcggc gtccccggcc    120
agccatgggc ccttggagcc gcagcctctc ggcgctgctg ctgctgctgc aggtctcctc    180
ttggctctgc caggagccgg agccctgcca ccctggcttt gacgccgaga gctacacgtt    240
cacggtgccc cggcgccacc tggagagagg ccgcgtcctg ggcagagtga attttgaaga    300
ttgcaccggt cgacaaagga cagcctattt ttccctcgac acccgattca aagtgggcac    360
agatggtgtg attacagtca aaaggcctct acggtttcat aacccacaga tccatttctt    420
ggtctacgcc tgggactcca cctacagaaa gttttccacc aaagtcacgc tgaatacagt    480
ggggcaccac caccgccccc cgccccatca ggcctccgtt tctggaatcc aagcagaatt    540
gctcacattt cccaactcct ctcctggcct cagaagacag aagagagact gggttattcc    600
tcccatcagc tgcccagaaa atgaaaaagg cccatttcct aaaaacctgg ttcagatcaa    660
atccaacaaa gacaaagaag gcaaggtttt ctacagcatc actggccaag gagctgacac    720
accccctgtt ggtgtcttta ttattgaaag agaaacagga tggctgaagg tgacagagcc    780
tctggataga gaacgcattg ccacatacac tctcttctct cacgctgtgt catccaacgg    840
gaatgcagtt gaggatccaa tggagatttt gatcacggta accgatcaga atgacaacaa    900
gcccgaattc acccaggagg tctttaaggg gtctgtcatg gaaggtgctc ttccaggaac    960
ctctgtgatg gaggtcacag ccacagacgc ggacgatgat gtgaacacct acaatgccgc   1020
catcgcttac accatcctca gccaagatcc tgagctccct gacaaaaata tgttcaccat   1080
taacaggaac acaggagtca tcagtgtggt caccactggg ctggaccgag agagtttccc   1140
tacgtatacc ctggtggttc aagctgctga ccttcaaggt gaggggttaa gcacaacagc   1200
aacagctgtg atcacagtca ctgacaccaa cgataatcct ccgatcttca atcccaccac   1260
gtacaagggt caggtgcctg agaacgaggc taacgtcgta atcaccacac tgaaagtgac   1320
tgatgctgat gcccccaata ccccagcgtg ggaggctgta tacaccatat tgaatgatga   1380
tggtggacaa tttgtcgtca ccacaaatcc agtgaacaac gatggcattt tgaaaacagc   1440
aaagggcttg gattttgagg ccaagcagca gtacattcta cacgtagcag tgacgaatgt   1500
ggtacctttt gaggtctctc tcaccacctc cacagccacc gtcaccgtgg atgtgctgga   1560
tgtgaatgaa gcccccatct ttgtgcctcc tgaaaagaga gtggaagtgt ccgaggactt   1620
tggcgtgggc caggaaatca catcctacac tgcccaggag ccagacacat ttatggaaca   1680
gaaaataaca tatcggattt ggagagacac tgccaactgg ctggagatta atccggacac   1740
tggtgccatt tccactcggg ctgagctgga cagggaggat tttgagcacg tgaagaacag   1800
cacgtacaca gccctaatca tagctacaga caatggttct ccagttgcta ctggaacagg   1860
gacacttctg ctgatcctgt ctgatgtgaa tgacaacgcc cccataccag aacctcgaac   1920
tatattcttc tgtgagagga atccaaagcc tcaggtcata aacatcattg atgcagacct   1980
tcctcccaat acatctccct tcacagcaga actaacacac ggggcgagtg ccaactggac   2040
cattcagtac aacgacccaa cccaagaatc tatcattttg aagccaaaga tggccttaga   2100
ggtgggtgac tacaaaatca atctcaagct catggataac cagaataaag accaagtgac   2160
caccttagag gtcagcgtgt gtgactgtga aggggccgct ggcgtctgta ggaaggcaca   2220
gcctgtcgaa gcaggattgc aaattcctgc cattctgggg attcttggag gaattcttgc   2280
tttgctaatt ctgattctgc tgctcttgct gtttcttcgg aggagagcgg tggtcaaaga   2340
gcccttactg cccccagagg atgacacccg ggacaacgtt tattactatg atgaagaagg   2400
```

-continued

```
aggcggagaa gaggaccagg actttgactt gagccagctg cacaggggcc tggacgctcg   2460
gcctgaagtg actcgtaacg acgttgcacc aaccctcatg agtgtccccc ggtatcttcc   2520
ccgccctgcc aatcccgatg aaattggaaa ttttattgat gaaaatctga aagcggctga   2580
tactgacccc acagccccgc cttatgattc tctgctcgtg tttgactatg aaggaagcgg   2640
ttccgaagct gctagtctga gctccctgaa ctcctcagag tcagacaaag accaggacta   2700
tgactacttg aacgaatggg gcaatcgctt caagaagctg gctgacatgt acggaggcgg   2760
cgaggacgac taggggactc gagagaggcg ggccccagac ccatgtgctg ggaaatgcag   2820
aaatcacgtt gctggtggtt tttcagctcc cttcccttga gatgagtttc tggggaaaaa   2880
aaagagactg gttagtgatg cagttagtat agctttatac tctctccact ttatagctct   2940
aataagtttg tgttagaaaa gtttcgactt atttcttaaa gctttttttt ttttcccatc   3000
actctttaca tggtggtgat gtccaaaaga tacccaaatt ttaatattcc agaagaacaa   3060
ctttagcatc agaaggttca cccagcacct tgcagatttt cttaaggaat tttgtctcac   3120
ttttaaaaag aaggggagaa gtcagctact ctagttctgt tgttttgtgt atataatttt   3180
ttaaaaaaaa tttgtgtgct tctgctcatt actacactgg tgtgtccctc tgcctttttt   3240
ttttttttaa gacagggtct cattctatcg gccaggctgg agtgcagtgg tgcaatcaca   3300
gctcactgca gccttgtcct cccaggctca agctatcctt gcacctcagc ctcccaagta   3360
gctgggacca caggcatgca ccactacgca tgactaattt tttaaatatt tgagacgggg   3420
tctccctgtg ttacccaggc tggtctcaaa ctcctgggct caagtgatcc tcccatcttg   3480
gcctcccaga gtattgggat tacagacatg agccactgca cctgcccagc tccccaactc   3540
cctgccattt tttaagagac agtttcgctc catcgcccag gcctgggatg cagtgatgtg   3600
atcatagctc actgtaacct caaactctgg ggctcaagca gttctcccac cagcctcctt   3660
tttatttttt tgtacagatg gggtcttgct atgttgccca agctggtctt aaactcctgg   3720
cctcaagcaa tccttctgcc ttggcccccc aaagtgctgg gattgtgggc atgagctgct   3780
gtgcccagcc tccatgtttt aatatcaact ctcactcctg aattcagttg ctttgcccaa   3840
gataggagtt ctctgatgca gaaattattg ggctctttta gggtaagaag tttgtgtctt   3900
tgtctggcca catcttgact aggtattgtc tactctgaag acctttaatg gcttccctct   3960
ttcatctcct gagtatgtaa cttgcaatgg gcagctatcc agtgacttgt tctgagtaag   4020
tgtgttcatt aatgtttatt tagctctgaa gcaagagtga tatactccag gacttagaat   4080
agtgcctaaa gtgctgcagc caaagacaga gcggaactat gaaaagtggg cttggagatg   4140
gcaggagagc ttgtcattga gcctggcaat ttagcaaact gatgctgagg atgattgagg   4200
tgggtctacc tcatctctga aaattctgga aggaatggag gagtctcaac atgtgtttct   4260
gacacaagat ccgtggtttg tactcaaagc ccagaatccc caagtgcctg cttttgatga   4320
tgtctacaga aaatgctggc tgagctgaac acatttgccc aattccaggt gtgcacagaa   4380
aaccgagaat attcaaaatt ccaaattttt ttcttaggag caagaagaaa atgtggccct   4440
aaagggggtt agttgagggg tagggggtag tgaggatctt gatttggatc tctttttatt   4500
taaatgtgaa tttcaacttt tgacaatcaa agaaaagact tttgttgaaa tagctttact   4560
gtttctcaag tgttttggag aaaaaaatca accctgcaat cactttttgg aattgtcttg   4620
atttttcggc agttcaagct atatcgaata tagttctgtg tagagaatgt cactgtagtt   4680
ttgagtgtat acatgtgtgg gtgctgataa ttgtgtattt tctttggggg tggaaaagga   4740
aaacaattca agctgagaaa agtattctca aagatgcatt tttataaatt ttattaaaca   4800
```

attttgttaa accat 4815

<210> SEQ ID NO 19
<211> LENGTH: 3249
<212> TYPE: DNA
<213> ORGANISM: Homo sapiens
<220> FEATURE:
<223> OTHER INFORMATION: human intercellular adhesion molecule 1
(ICAM1), cell surface glycoprotein P3.58, human rhinovirus
receptor, major group rhinovirus receptor, BB2,
CD54 cDNA

<400> SEQUENCE: 19
caagcttagc ctggccggga aacgggaggc gtggaggccg ggagcagccc ccggggtcat 60
cgccctgcca ccgccgcccg attgctttag cttggaaatt ccggagctga agcggccagc 120
gagggaggat gaccctctcg gcccgggcac cctgtcagtc cggaaataac tgcagcattt 180
gttccggagg ggaaggcgcg aggtttccgg gaaagcagca ccgccccttg gcccccaggt 240
ggctagcgct ataaaggatc acgcgcccca gtcgacgctg agctcctctg ctactcagag 300
ttgcaacctc agcctcgcta tggctcccag cagcccccgg cccgcgctgc ccgcactcct 360
ggtcctgctc ggggctctgt tcccaggacc tggcaatgcc cagacatctg tgtccccctc 420
aaaagtcatc ctgccccggg gaggctccgt gctggtgaca tgcagcacct cctgtgacca 480
gcccaagttg ttgggcatag agaccccgtt gcctaaaaag gagttgctcc tgcctgggaa 540
caaccggaag gtgtatgaac tgagcaatgt gcaagaagat agccaaccaa tgtgctattc 600
aaactgccct gatgggcagt caacagctaa aaccttcctc accgtgtact ggactccaga 660
acgggtggaa ctggcacccc tcccctcttg gcagccagtg ggcaagaacc ttaccctacg 720
ctgccaggtg gagggtgggg caccccgggc caacctcacc gtggtgctgc tccgtgggga 780
gaaggagctg aaacgggagc cagctgtggg ggagcccgct gaggtcacga ccacggtgct 840
ggtgaggaga gatcaccatg gagccaattt ctcgtgccgc actgaactgg acctgcggcc 900
ccaagggctg gagctgtttg agaacacctc ggccccctac cagctccaga cctttgtcct 960
gccagcgact cccccacaac ttgtcagccc ccgggtccta gaggtggaca cgcaggggac 1020
cgtggtctgt tccctggacg ggctgttccc agtctcggag gcccaggtcc acctggcact 1080
gggggaccag aggttgaacc ccacagtcac ctatggcaac gactccttct cggccaaggc 1140
ctcagtcagt gtgaccgcag aggacgaggg cacccagcgg ctgacgtgtg cagtaatact 1200
ggggaaccag agccaggaga cactgcagac agtgaccatc tacagctttc cggcgcccaa 1260
cgtgattctg acgaagccag aggtctcaga agggaccgag gtgacagtga agtgtgaggc 1320
ccaccctaga gccaaggtga cgctgaatgg ggttccagcc cagccactgg gcccgagggc 1380
ccagctcctg ctgaaggcca ccccagagga caacgggcgc agcttctcct gctctgcaac 1440
cctggaggtg gccggccagc ttatacacaa gaaccagacc cgggagcttc gtgtcctgta 1500
tggcccccga ctggacgaga gggattgtcc gggaaactgg acgtggccag aaaattccca 1560
gcagactcca atgtgccagg cttgggggaa ccccattgcc gagctcaagt gtctaaagga 1620
tggcactttc ccactgccca tcggggaatc agtgactgtc actcgagatc ttgagggcac 1680
ctacctctgt cgggccagga gcactcaagg ggaggtcacc cgcaaggtga ccgtgaatgt 1740
gctctccccc cggtatgaga ttgtcatcat cactgtggta gcagccgcag tcataatggg 1800
cactgcaggc ctcagcacgt acctctataa ccgccagcgg aagatcaaga aatacagact 1860
acaacaggcc caaaaaggga cccccatgaa accgaacaca caagccacgc ctccctgaac 1920

```
ctatcccggg acagggcctc ttcctcggcc ttcccatatt ggtggcagtg gtgccacact   1980

gaacagagtg gaagacatat gccatgcagc tacacctacc ggccctggga cgccggagga   2040

cagggcattg tcctcagtca gatacaacag catttggggc catggtacct gcacacctaa   2100

aacactaggc cacgcatctg atctgtagtc acatgactaa gccaagagga aggagcaaga   2160

ctcaagacat gattgatgga tgttaaagtc tagcctgatg agaggggaag tggtggggga   2220

gacatagccc caccatgagg acatacaact gggaaatact gaaacttgct gcctattggg   2280

tatgctgagg ccccacagac ttacagaaga agtggccctc catagacatg tgtagcatca   2340

aaacacaaag gcccacactt cctgacggat gccagcttgg gcactgctgt ctactgaccc   2400

caacccttga tgatatgtat ttattcattt gttattttac cagctattta ttgagtgtct   2460

tttatgtagg ctaaatgaac ataggtctct ggcctcacgg agctcccagt cctaatcaca   2520

ttcaaggtca ccaggtacag ttgtacaggt tgtacactgc aggagagtgc ctggcaaaaa   2580

gatcaaatgg ggctgggact tctcattggc caacctgcct ttccccagaa ggagtgattt   2640

ttctatcggc acaaaagcac tatatggact ggtaatggtt acaggttcag agattaccca   2700

gtgaggcctt attcctccct tccccccaaa actgacacct ttgttagcca cctccccacc   2760

cacatacatt tctgccagtg ttcacaatga cactcagcgg tcatgtctgg acatgagtgc   2820

ccagggaata tgcccaagct atgccttgtc ctcttgtcct gtttgcattt cactgggagc   2880

ttgcactatg cagctccagt ttcctgcagt gatcagggtc ctgcaagcag tggggaaggg   2940

ggccaaggta ttggaggact ccctcccagc tttggaagcc tcatccgcgt gtgtgtgtgt   3000

gtgtatgtgt agacaagctc tcgctctgtc acccaggctg gagtgcagtg gtgcaatcat   3060

ggttcactgc agtcttgacc ttttgggctc aagtgatcct cccacctcag cctcctgagt   3120

agctgggacc ataggctcac aacaccacac ctggcaaatt tgattttttt tttttttcca   3180

gagacggggt ctcgcaacat tgcccagact tcctttgtgt tagttaataa agctttctca   3240

actgccaaa                                                           3249

<210> SEQ ID NO 20
<211> LENGTH: 532
<212> TYPE: PRT
<213> ORGANISM: Homo sapiens
<220> FEATURE:
<223> OTHER INFORMATION: human intercellular adhesion molecule 1 (ICAM1)
      precursor, cell surface glycoprotein P3.58, human
      rhinovirus receptor, major group rhinovirus
      receptor, BB2, CD54

<400> SEQUENCE: 20

Met Ala Pro Ser Ser Pro Arg Pro Ala Leu Pro Ala Leu Leu Val Leu
 1               5                  10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
```

-continued

```
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525
```

Ala Thr Pro Pro
530

<210> SEQ ID NO 21
<211> LENGTH: 3119
<212> TYPE: DNA
<213> ORGANISM: Homo sapiens
<220> FEATURE:
<223> OTHER INFORMATION: human vascular cell adhesion molecule 1
(VCAM1, V-CAM 1), transcript variant 1, INCAM-100, CD106,
DKFZp779G2333, MGC99561 cDNA

<400> SEQUENCE: 21
cgcggtatct gcatcgggcc tcactggctt caggagctga ataccctccc aggcacacac 60
aggtgggaca caaataaggg ttttggaacc actattttct catcacgaca gcaacttaaa 120
atgcctggga agatggtcgt gatccttgga gcctcaaata tactttggat aatgtttgca 180
gcttctcaag cttttaaaat cgagaccacc ccagaatcta gatatcttgc tcagattggt 240
gactccgtct cattgacttg cagcaccaca ggctgtgagt ccccattttt ctcttggaga 300
acccagatag atagtccact gaatgggaag gtgacgaatg aggggaccac atctacgctg 360
acaatgaatc ctgttagttt tgggaacgaa cactcttacc tgtgcacagc aacttgtgaa 420
tctaggaaat tggaaaaagg aatccaggtg gagatctact cttttcctaa ggatccagag 480
attcatttga gtggccctct ggaggctggg aagccgatca cagtcaagtg ttcagttgct 540
gatgtatacc catttgacag gctggagata gacttactga aaggagatca tctcatgaag 600
agtcaggaat ttctggagga tgcagacagg aagtccctgg aaaccaagag tttggaagta 660
acctttactc ctgtcattga ggatattgga aaagttcttg tttgccgagc taaattacac 720
attgatgaaa tggattctgt gcccacagta aggcaggctg taaaagaatt gcaagtctac 780
atatcaccca agaatacagt tatttctgtg aatccatcca caaagctgca agaaggtggc 840
tctgtgacca tgacctgttc cagcgagggt ctaccagctc cagagatttt ctggagtaag 900
aaattagata atgggaatct acagcacctt tctggaaatg caactctcac cttaattgct 960
atgaggatgg aagattctgg aatttatgtg tgtgaaggag ttaatttgat tgggaaaaac 1020
agaaaagagg tggaattaat tgttcaagag aaaccattta ctgttgagat ctcccctgga 1080
ccccggattg ctgctcagat tggagactca gtcatgttga catgtagtgt catgggctgt 1140
gaatccccat ctttctcctg gagaacccag atagacagcc ctctgagcgg gaaggtgagg 1200
agtgagggga ccaattccac gctgaccctg agccctgtga gttttgagaa cgaacactct 1260
tatctgtgca cagtgacttg tggacataag aaactggaaa agggaatcca ggtggagctc 1320
tactcattcc ctagagatcc agaaatcgag atgagtggtg gcctcgtgaa tgggagctct 1380
gtcactgtaa gctgcaaggt tcctagcgtg taccccttg accggctgga gattgaatta 1440
cttaaggggg agactattct ggagaatata gagtttttgg aggatacgga tatgaaatct 1500
ctagagaaca aaagtttgga aatgaccttc atccctacca ttgaagatac tggaaaagct 1560
cttgtttgtc aggctaagtt acatattgat gacatggaat tcgaacccaa acaaaggcag 1620
agtacgcaaa cactttatgt caatgttgcc cccagagata caaccgtctt ggtcagccct 1680
tcctccatcc tggaggaagg cagttctgtg aatatgacat gcttgagcca gggctttcct 1740
gctccgaaaa tcctgtggag caggcagctc cctaacgggg agctacagcc tctttctgag 1800
aatgcaactc tcaccttaat ttctacaaaa atggaagatt ctggggttta tttatgtgaa 1860
ggaattaacc aggctggaag aagcagaaag gaagtggaat taattatcca agttactcca 1920

```
aaagacataa aacttacagc ttttccttct gagagtgtca aagaaggaga cactgtcatc   1980

atctcttgta catgtggaaa tgttccagaa acatggataa tcctgaagaa aaaagcggag   2040

acaggagaca cagtactaaa atctatagat ggcgcctata ccatccgaaa ggcccagttg   2100

aaggatgcgg gagtatatga atgtgaatct aaaaacaaag ttggctcaca attaagaagt   2160

ttaacacttg atgttcaagg aagagaaaac aacaaagact atttttctcc tgagcttctc   2220

gtgctctatt ttgcatcctc cttaataata cctgccattg gaatgataat ttactttgca   2280

agaaaagcca acatgaaggg gtcatatagt cttgtagaag cacagaaatc aaaagtgtag   2340

ctaatgcttg atatgttcaa ctggagacac tatttatctg tgcaaatcct tgatactgct   2400

catcattcct tgagaaaaac aatgagctga gaggcagact tccctgaatg tattgaactt   2460

ggaaagaaat gcccatctat gtcccttgct gtgagcaaga agtcaaagta aaacttgctg   2520

cctgaagaac agtaactgcc atcaagatga gagaactgga ggagttcctt gatctgtata   2580

tacaataaca taatttgtac atatgtaaaa taaaattatg ccatagcaag attgcttaaa   2640

atagcaacac tctatattta gattgttaaa ataactagtg ttgcttggac tattataatt   2700

taatgcatgt taggaaaatt tcacattaat atttgctgac agctgacctt tgtcatcttt   2760

cttctatttt attccctttc acaaaatttt attcctatat agtttattga caataatttc   2820

aggttttgta aagatgccgg gttttatatt tttatagaca aataataagc aaagggagca   2880

ctgggttgac tttcaggtac taaatacctc aacctatggt ataatggttg actgggtttc   2940

tctgtatagt actggcatgg tacggagatg tttcacgaag tttgttcatc agactcctgt   3000

gcaactttcc caatgtggcc taaaaatgca acttcttttt atttcttttt gtaaatgttt   3060

aggttttttt gtatagtaaa gtgataattt ctggaattag aaaaaaaaaa aaaaaaaaa    3119
```

```
<210> SEQ ID NO 22
<211> LENGTH: 739
<212> TYPE: PRT
<213> ORGANISM: Homo sapiens
<220> FEATURE:
<223> OTHER INFORMATION: human vascular cell adhesion molecule 1 (VCAM1,
      V-CAM 1), isoform a, INCAM-100, CD106,
      DKFZp779G2333, MGC99561

<400> SEQUENCE: 22

Met Pro Gly Lys Met Val Val Ile Leu Gly Ala Ser Asn Ile Leu Trp
 1               5                  10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140
```

```
Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560
```

```
Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val


<210> SEQ ID NO 23
<211> LENGTH: 4485
<212> TYPE: DNA
<213> ORGANISM: Homo sapiens
<220> FEATURE:
<223> OTHER INFORMATION: human nucleotide-binding oligomerization domain
      containing 2 (NOD2, NOD2B), inflammatory bowel disease protein 1
      (IBD1), caspase recruitment domain-containing protein 15 (CARD15),
      NLR family, CARD domain containing 2 (NLRC2), ACUG, BLAU, CLR16.3,
      PSORAS1 cDNA

<400> SEQUENCE: 23

gtagacagat ccaggctcac cagtcctgtg ccactgggct tttggcgttc tgcacaaggc     60

ctacccgcag atgccatgcc tgctccccca gcctaatggg ctttgatggg ggaagagggt    120

ggttcagcct ctcacgatga ggaggaaaga gcaagtgtcc tcctcggaca ttctccgggt    180

tgtgaaatgt gctcgcagga ggcttttcag gcacagagga gccagctggt cgagctgctg    240

gtctcagggt ccctggaagg cttcgagagt gtcctggact ggctgctgtc ctgggaggtc    300

ctctcctggg aggactacga gggcttccac ctcctgggcc agcctctctc ccacttggcc    360

aggcgccttc tggacaccgt ctggaataag ggtacttggg cctgtcagaa gctcatcgcg    420

gctgcccaag aagcccaggc cgacagccag tcccccaagc tgcatggctg ctgggacccc    480

cactcgctcc acccagcccg agacctgcag agtcaccggc cagccattgt caggaggctc    540

cacagccatg tggagaacat gctggacctg gcatgggagc ggggtttcgt cagccagtat    600

gaatgtgatg aaatcaggtt gccgatcttc acaccgtccc agagggcaag aaggctgctt    660

gatcttgcca cggtgaaagc gaatggattg gctgccttcc ttctacaaca tgttcaggaa    720

ttaccagtcc cattggccct gcctttggaa gctgccacat gcaagaagta tatggccaag    780

ctgaggacca cggtgtctgc tcagtctcgc ttcctcagta cctatgatgg agcagagacg    840

ctctgcctgg aggacatata cacagagaat gtcctggagg tctgggcaga tgtgggcatg    900
```

-continued

```
gctggacccc cgcagaagag cccagccacc ctgggcctgg aggagctctt cagcacccct    960
ggccacctca atgacgatgc ggacactgtg ctggtggtgg gtgaggcggg cagtggcaag   1020
agcacgctcc tgcagcggct gcacttgctg tgggctgcag ggcaagactt ccaggaattt   1080
ctctttgtct tcccattcag ctgccggcag ctgcagtgca tggccaaacc actctctgtg   1140
cggactctac tctttgagca ctgctgttgg cctgatgttg gtcaagaaga catcttccag   1200
ttactccttg accaccctga ccgtgtcctg ttaacctttg atggctttga cgagttcaag   1260
ttcaggttca cggatcgtga acgccactgc tccccgaccg accccacctc tgtccagacc   1320
ctgctcttca accttctgca gggcaacctg ctgaagaatg cccgcaaggt ggtgaccagc   1380
cgtccggccg ctgtgtcggc gttcctcagg aagtacatcc gcaccgagtt caacctcaag   1440
ggcttctctg aacagggcat cgagctgtac ctgaggaagc gccatcatga gcccggggtg   1500
gcggaccgcc tcatccgcct gctccaagag acctcagccc tgcacggttt gtgccacctg   1560
cctgtcttct catggatggt gtccaaatgc caccaggaac tgttgctgca ggaggggggg   1620
tccccaaaga ccactacaga tatgtacctg ctgattctgc agcattttct gctgcatgcc   1680
acccccccag actcagcttc ccaaggtctg ggacccagtc ttcttcgggg ccgcctcccc   1740
accctcctgc acctgggcag actggctctg tggggcctgg gcatgtgctg ctacgtgttc   1800
tcagcccagc agctccaggc agcacaggtc agccctgatg acatttctct tggcttcctg   1860
gtgcgtgcca aaggtgtcgt gccagggagt acggcgcccc tggaattcct tcacatcact   1920
ttccagtgct tctttgccgc gttctacctg gcactcagtg ctgatgtgcc accagctttg   1980
ctcagacacc tcttcaattg tggcaggcca ggcaactcac caatggccag gctcctgccc   2040
acgatgtgca tccaggcctc ggagggaaag gacagcagcg tggcagcttt gctgcagaag   2100
gccgagccgc acaaccttca gatcacagca gccttcctgg cagggctgtt gtcccgggag   2160
cactggggcc tgctggctga gtgccagaca tctgagaagg ccctgctccg gcgccaggcc   2220
tgtgcccgct ggtgtctggc ccgcagcctc cgcaagcact tccactccat cccgccagct   2280
gcaccgggtg aggccaagag cgtgcatgcc atgcccgggt tcatctggct catccggagc   2340
ctgtacgaga tgcaggagga gcggctggct cggaaggctg cacgtggcct gaatgttggg   2400
cacctcaagt tgacattttg cagtgtgggc ccactgagt gtgctgccct ggcctttgtg    2460
ctgcagcacc tccggcggcc cgtggccctg cagctggact acaactctgt gggtgacatt   2520
ggcgtggagc agctgctgcc ttgccttggt gtctgcaagg ctctgtattt gcgcgataac   2580
aatatctcag accgaggcat ctgcaagctc attgaatgtg ctcttcactg cgagcaattg   2640
cagaagttag ctctattcaa caacaaattg actgacggct gtgcacactc catggctaag   2700
ctccttgcat gcaggcagaa cttcttggca ttgaggctgg ggaataacta catcactgcc   2760
gcgggagccc aagtgctggc cgagggggctc cgaggcaaca cctccttgca gttcctggga   2820
ttctggggca acagagtggg tgacgagggg gcccaggccc tggctgaagc cttgggtgat   2880
caccagagct tgaggtggct cagcctggtg gggaacaaca ttggcagtgt gggtgcccaa   2940
gccttggcac tgatgctggc aaagaacgtc atgctagaag aactctgcct ggaggagaac   3000
catctccagg atgaaggtgt atgttctctc gcagaaggac tgaagaaaaa ttcaagtttg   3060
aaaatcctga agttgtccaa taactgcatc acctacctag ggcagaagc cctcctgcag    3120
gcccttgaaa ggaatgacac catcctggaa gtctggctcc gagggaacac tttctctcta   3180
gaggaggttg acaagctcgg ctgcagggac accagactct tgctttgaag tctccgggag   3240
gatgttcgtc tcagtttgtt tgtgagcagg ctgtgagttt gggccccaga ggctgggtga   3300
```

```
catgtgttgg cagcctcttc aaaatgagcc ctgtcctgcc taaggctgaa cttgttttct   3360

gggaacacca taggtcacct ttattctggc agaggaggga gcatcagtgc cctccaggat   3420

agacttttcc caagcctact tttgccattg acttcttccc aagattcaat cccaggatgt   3480

acaaggacag cccctcctcc atagtatggg actggcctct gctgatcctc ccaggcttcc   3540

gtgtgggtca gtggggccca tggatgtgct tgttaactga gtgccttttg gtggagaggc   3600

ccggcctctc acaaaagacc ccttaccact gctctgatga agaggagtac acagaacaca   3660

taattcagga agcagctttc cccatgtctc gactcatcca tccaggccat tccccgtctc   3720

tggttcctcc cctcctcctg gactcctgca cacgctcctt cctctgaggc tgaaattcag   3780

aatattagtg acctcagctt tgatatttca cttacagcac ccccaaccct ggcacccagg   3840

gtgggaaggg ctacacctta gcctgccctc ctttccggtg tttaagacat ttttggaagg   3900

ggacacgtga cagccgtttg ttccccaaga cattctaggt ttgcaagaaa aatatgacca   3960

cactccagct gggatcacat gtggactttt atttccagtg aaatcagtta ctcttcagtt   4020

aagcctttgg aaacagctcg actttaaaaa gctccaaatg cagctttaaa aaattaatct   4080

gggccagaat ttcaaacggc ctcactaggc ttctggttga tgcctgtgaa ctgaactctg   4140

acaacagact tctgaaatag acccacaaga ggcagttcca tttcatttgt gccagaatgc   4200

tttaggatgt acagttatgg attgaaagtt tacaggaaaa aaaattaggc cgttccttca   4260

aagcaaatgt cttcctggat tattcaaaat gatgtatgtt gaagcctttg taaattgtca   4320

gatgctgtgc aaatgttatt attttaaaca ttatgatgtg tgaaaactgg ttaatattta   4380

taggtcactt tgttttactg tcttaagttt atactcttat agacaacatg gccgtgaact   4440

ttatgctgta aataatcaga ggggaataaa ctgttgagtc aaaac                    4485
```

```
<210> SEQ ID NO 24
<211> LENGTH: 1040
<212> TYPE: PRT
<213> ORGANISM: Homo sapiens
<220> FEATURE:
<223> OTHER INFORMATION: human nucleotide-binding oligomerization domain
      containing 2 (NOD2, NOD2B), inflammatory bowel disease protein 1
      (IBD1), caspase recruitment domain-containing protein 15 (CARD15),
      NLR family, CARD domain containing 2 (NLRC2), ACUG, BLAU, CLR16.3,
      PSORAS1

<400> SEQUENCE: 24

Met Gly Glu Glu Gly Gly Ser Ala Ser His Asp Glu Glu Glu Arg Ala
 1               5                  10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Ala Gln Glu Ala Gln Ala
            100                 105                 110

Asp Ser Gln Ser Pro Lys Leu His Gly Cys Trp Asp Pro His Ser Leu
        115                 120                 125
```

```
His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
        195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Pro Pro Gln Lys Ser
            260                 265                 270

Pro Ala Thr Leu Gly Leu Glu Glu Leu Phe Ser Thr Pro Gly His Leu
        275                 280                 285

Asn Asp Asp Ala Asp Thr Val Leu Val Val Gly Glu Ala Gly Ser Gly
    290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
        355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
        435                 440                 445

Glu Gln Gly Ile Glu Leu Tyr Leu Arg Lys Arg His His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
        515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
```

-continued

```
545                 550                 555                 560

Cys Cys Tyr Val Phe Ser Ala Gln Gln Leu Gln Ala Ala Gln Val Ser
                565                 570                 575

Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
        595                 600                 605

Phe Phe Ala Ala Phe Tyr Leu Ala Leu Ser Ala Asp Val Pro Pro Ala
    610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                645                 650                 655

Ser Ser Val Ala Ala Leu Leu Gln Lys Ala Glu Pro His Asn Leu Gln
            660                 665                 670

Ile Thr Ala Ala Phe Leu Ala Gly Leu Leu Ser Arg Glu His Trp Gly
        675                 680                 685

Leu Leu Ala Glu Cys Gln Thr Ser Glu Lys Ala Leu Leu Arg Arg Gln
    690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
                725                 730                 735

Pro Gly Phe Ile Trp Leu Ile Arg Ser Leu Tyr Glu Met Gln Glu Glu
            740                 745                 750

Arg Leu Ala Arg Lys Ala Ala Arg Gly Leu Asn Val Gly His Leu Lys
        755                 760                 765

Leu Thr Phe Cys Ser Val Gly Pro Thr Glu Cys Ala Ala Leu Ala Phe
    770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
            820                 825                 830

Cys Lys Leu Ile Glu Cys Ala Leu His Cys Glu Gln Leu Gln Lys Leu
        835                 840                 845

Ala Leu Phe Asn Asn Lys Leu Thr Asp Gly Cys Ala His Ser Met Ala
    850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
        915                 920                 925

Leu Arg Trp Leu Ser Leu Val Gly Asn Asn Ile Gly Ser Val Gly Ala
    930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975
```

```
Glu Gly Leu Lys Lys Asn Ser Ser Leu Lys Ile Leu Lys Leu Ser Asn
            980                 985                 990

Asn Cys Ile Thr Tyr Leu Gly Ala Glu Ala Leu Leu Gln Ala Leu Glu
        995                 1000                1005

Arg Asn Asp Thr Ile Leu Glu Val Trp Leu Arg Gly Asn Thr Phe Ser
    1010                1015                1020

Leu Glu Glu Val Asp Lys Leu Gly Cys Arg Asp Thr Arg Leu Leu Leu
1025                1030                1035                1040


<210> SEQ ID NO 25
<211> LENGTH: 17
<212> TYPE: DNA
<213> ORGANISM: Artificial Sequence
<220> FEATURE:
<223> OTHER INFORMATION: synthetic SNP 5 forward primer for NOD2
      genotyping Taqman MGB assay

<400> SEQUENCE: 25

ggtggctggg ctcttct                                                  17


<210> SEQ ID NO 26
<211> LENGTH: 24
<212> TYPE: DNA
<213> ORGANISM: Artificial Sequence
<220> FEATURE:
<223> OTHER INFORMATION: synthetic SNP 5 reverse primer for NOD2
      genotyping Taqman MGB assay

<400> SEQUENCE: 26

ctcgcttcct cagtacctat gatg                                          24


<210> SEQ ID NO 27
<211> LENGTH: 21
<212> TYPE: DNA
<213> ORGANISM: Artificial Sequence
<220> FEATURE:
<223> OTHER INFORMATION: synthetic SNP 8 forward primer for NOD2
      genotyping Taqman MGB assay

<400> SEQUENCE: 27

ctggctgagt gccagacatc t                                             21


<210> SEQ ID NO 28
<211> LENGTH: 17
<212> TYPE: DNA
<213> ORGANISM: Artificial Sequence
<220> FEATURE:
<223> OTHER INFORMATION: synthetic SNP 8 reverse primer for NOD2
      genotyping Taqman MGB assay

<400> SEQUENCE: 28

ggcgggatgg agtggaa                                                  17


<210> SEQ ID NO 29
<211> LENGTH: 21
<212> TYPE: DNA
<213> ORGANISM: Artificial Sequence
<220> FEATURE:
<223> OTHER INFORMATION: synthetic SNP 12 forward primer for NOD2
      genotyping Taqman MGB assay

<400> SEQUENCE: 29

ccacctcaag ctctggtgat c                                             21
```

<210> SEQ ID NO 30
<211> LENGTH: 23
<212> TYPE: DNA
<213> ORGANISM: Artificial Sequence
<220> FEATURE:
<223> OTHER INFORMATION: synthetic SNP 12 reverse primer for NOD2
genotyping Taqman MGB assay

<400> SEQUENCE: 30
gttgactctt ttggcctttt cag 23

<210> SEQ ID NO 31
<211> LENGTH: 23
<212> TYPE: DNA
<213> ORGANISM: Artificial Sequence
<220> FEATURE:
<223> OTHER INFORMATION: synthetic SNP 13 forward primer for NOD2
genotyping Taqman MGB assay

<400> SEQUENCE: 31
ccttaccaga cttccaggat ggt 23

<210> SEQ ID NO 32
<211> LENGTH: 25
<212> TYPE: DNA
<213> ORGANISM: Artificial Sequence
<220> FEATURE:
<223> OTHER INFORMATION: synthetic SNP 13 reverse primer for NOD2
genotyping Taqman MGB assay

<400> SEQUENCE: 32
tgtccaataa ctgcatcacg tacct 25

<210> SEQ ID NO 33
<211> LENGTH: 13
<212> TYPE: DNA
<213> ORGANISM: Artificial Sequence
<220> FEATURE:
<223> OTHER INFORMATION: synthetic SNP5 wild type allele ("1") Taqman
probe
<220> FEATURE:
<221> NAME/KEY: modified_base
<222> LOCATION: (1)...(1)
<223> OTHER INFORMATION: c modified by fluorescent reporter dye 6FAM
<220> FEATURE:
<221> NAME/KEY: modified_base
<222> LOCATION: (13)...(13)
<223> OTHER INFORMATION: c modified by minor groove binder and
non-fluorescent quencher dye (MGBNFQ)

<400> SEQUENCE: 33
catggctgga ccc 13

<210> SEQ ID NO 34
<211> LENGTH: 13
<212> TYPE: DNA
<213> ORGANISM: Artificial Sequence
<220> FEATURE:
<223> OTHER INFORMATION: synthetic SNP5 variant allele ("2") Taqman
probe
<220> FEATURE:
<221> NAME/KEY: modified_base
<222> LOCATION: (1)...(1)
<223> OTHER INFORMATION: c modified by fluorescent reporter dye TET
<220> FEATURE:
<221> NAME/KEY: modified_base
<222> LOCATION: (13)...(13)
<223> OTHER INFORMATION: c modified by minor groove binder and
non-fluorescent quencher dye (MGBNFQ)

<400> SEQUENCE: 34
catggctgga tcc 13

<210> SEQ ID NO 35
<211> LENGTH: 13
<212> TYPE: DNA
<213> ORGANISM: Artificial Sequence
<220> FEATURE:
<223> OTHER INFORMATION: synthetic SNP8 wild type allele ("1") Taqman probe
<220> FEATURE:
<221> NAME/KEY: modified_base
<222> LOCATION: (1)...(1)
<223> OTHER INFORMATION: t modified by fluorescent reporter dye 6FAM
<220> FEATURE:
<221> NAME/KEY: modified_base
<222> LOCATION: (13)...(13)
<223> OTHER INFORMATION: a modified by minor groove binder and non-fluorescent quencher dye (MGBNFQ)

<400> SEQUENCE: 35
tgctccggcg cca 13

<210> SEQ ID NO 36
<211> LENGTH: 14
<212> TYPE: DNA
<213> ORGANISM: Artificial Sequence
<220> FEATURE:
<223> OTHER INFORMATION: synthetic SNP8 variant allele ("2") Taqman probe
<220> FEATURE:
<221> NAME/KEY: modified_base
<222> LOCATION: (1)...(1)
<223> OTHER INFORMATION: c modified by fluorescent reporter dye TET
<220> FEATURE:
<221> NAME/KEY: modified_base
<222> LOCATION: (14)...(14)
<223> OTHER INFORMATION: a modified by minor groove binder and non-fluorescent quencher dye (MGBNFQ)

<400> SEQUENCE: 36
ctgctctggc gcca 14

<210> SEQ ID NO 37
<211> LENGTH: 16
<212> TYPE: DNA
<213> ORGANISM: Artificial Sequence
<220> FEATURE:
<223> OTHER INFORMATION: synthetic SNP12 wild type allele ("1") Taqman probe
<220> FEATURE:
<221> NAME/KEY: modified_base
<222> LOCATION: (1)...(1)
<223> OTHER INFORMATION: c modified by fluorescent reporter dye 6FAM
<220> FEATURE:
<221> NAME/KEY: modified_base
<222> LOCATION: (16)...(16)
<223> OTHER INFORMATION: a modified by minor groove binder and non-fluorescent quencher dye (MGBNFQ)

<400> SEQUENCE: 37
ctctgttgcc ccagaa 16

<210> SEQ ID NO 38
<211> LENGTH: 15
<212> TYPE: DNA
<213> ORGANISM: Artificial Sequence
<220> FEATURE:
<223> OTHER INFORMATION: synthetic SNP12 variant allele ("2") Taqman probe
<220> FEATURE:
<221> NAME/KEY: modified_base

```
<222> LOCATION: (1)...(1)
<223> OTHER INFORMATION: c modified by fluorescent reporter dye TET
<220> FEATURE:
<221> NAME/KEY: modified_base
<222> LOCATION: (15)...(15)
<223> OTHER INFORMATION: a modified by minor groove binder and
      non-fluorescent quencher dye (MGBNFQ)

<400> SEQUENCE: 38

ctctgttgcg ccaga                                                    15


<210> SEQ ID NO 39
<211> LENGTH: 15
<212> TYPE: DNA
<213> ORGANISM: Artificial Sequence
<220> FEATURE:
<223> OTHER INFORMATION: synthetic SNP13 wild type allele ("1") Taqman
      probe
<220> FEATURE:
<221> NAME/KEY: modified_base
<222> LOCATION: (1)...(1)
<223> OTHER INFORMATION: c modified by fluorescent reporter dye TET
<220> FEATURE:
<221> NAME/KEY: modified_base
<222> LOCATION: (15)...(15)
<223> OTHER INFORMATION: c modified by minor groove binder and
      non-fluorescent quencher dye (MGBNFQ)

<400> SEQUENCE: 39

ctttcaaggg cctgc                                                    15


<210> SEQ ID NO 40
<211> LENGTH: 15
<212> TYPE: DNA
<213> ORGANISM: Artificial Sequence
<220> FEATURE:
<223> OTHER INFORMATION: synthetic SNP13 variant allele ("2") Taqman
      probe
<220> FEATURE:
<221> NAME/KEY: modified_base
<222> LOCATION: (1)...(1)
<223> OTHER INFORMATION: c modified by fluorescent reporter dye 6FAM
<220> FEATURE:
<221> NAME/KEY: modified_base
<222> LOCATION: (15)...(15)
<223> OTHER INFORMATION: t modified by minor groove binder and
      non-fluorescent quencher dye (MGBNFQ)

<400> SEQUENCE: 40

cctttcaagg ggcct                                                    15


<210> SEQ ID NO 41
<211> LENGTH: 16
<212> TYPE: DNA
<213> ORGANISM: Artificial Sequence
<220> FEATURE:
<223> OTHER INFORMATION: synthetic JW1 wild type allele Taqman probe
<220> FEATURE:
<221> NAME/KEY: modified_base
<222> LOCATION: (1)...(1)
<223> OTHER INFORMATION: a modified by fluorescent reporter dye 6FAM
<220> FEATURE:
<221> NAME/KEY: modified_base
<222> LOCATION: (16)...(16)
<223> OTHER INFORMATION: t modified by minor groove binder and
      non-fluorescent quencher dye (MGBNFQ)

<400> SEQUENCE: 41

aagactcgag tgtcct                                                   16


<210> SEQ ID NO 42
```

-continued

```
<211> LENGTH: 16
<212> TYPE: DNA
<213> ORGANISM: Artificial Sequence
<220> FEATURE:
<223> OTHER INFORMATION: synthetic JW1 variant allele Taqman probe
<220> FEATURE:
<221> NAME/KEY: modified_base
<222> LOCATION: (1)...(1)
<223> OTHER INFORMATION: a modified by fluorescent reporter dye VIC
<220> FEATURE:
<221> NAME/KEY: modified_base
<222> LOCATION: (16)...(16)
<223> OTHER INFORMATION: c modified by minor groove binder and
      non-fluorescent quencher dye (MGBNFQ)

<400> SEQUENCE: 42

agactcaagt gtcctc                                                   16
```

METHOD FOR DETERMINING THE RISK OF CROHN'S DISEASE-RELATED COMPLICATIONS

CROSS-REFERENCE TO RELATED APPLICATIONS

This application is a continuation of PCT/US2010/030934, filed Apr. 13, 2010, which claims priority to U.S. Provisional Application No. 61/169,230, filed Apr. 14, 2009, U.S. Provisional Application No. 61/178,454, filed May 14, 2009, U.S. Provisional Application No. 61/220,453, filed Jun. 25, 2009, U.S. Provisional Application No. 61/255,066, filed Oct. 26, 2009, U.S. Provisional Application No. 61/262,903, filed Nov. 19, 2009, U.S. Provisional Application No. 61/265,324, filed Nov. 30, 2009, U.S. Provisional Application No. 61/265,723, filed Dec. 1, 2009, U.S. Provisional Application No. 61/286,356, filed Dec. 14, 2009, U.S. Provisional Application No. 61/300,787, filed Feb. 2, 2010, and U.S. Provisional Application No. 61/302,066, filed Feb. 5, 2010, all of which are hereby incorporated by reference in their entirety for all purposes.

BACKGROUND OF THE INVENTION

Inflammatory bowel disease (IBD), which occurs world-wide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases and how these diseases will progress. The cost of IBD and IBS is compounded by lost productivity, with people suffering from these disorders missing at least 8 more days of work annually than the national average.

Inflammatory bowel disease has many symptoms in common with irritable bowel syndrome, including abdominal pain, chronic diarrhea, weight loss, and cramping, making definitive diagnosis extremely difficult. Of the 5 million people suspected of suffering from IBD in the United States, only 1 million are diagnosed as having IBD. The difficulty in differentially diagnosing IBD and determining its outcome hampers early and effective treatment of these diseases. Thus, there is a need for rapid and sensitive testing methods for prognosticating the severity of IBD.

Although progress has been made in precisely diagnosing clinical subtypes of IBD, current methods for determining its prognosis are non-existent. Thus, there is a need for improved methods for prognosing an individual who has been diagnosed with IBD, the severity of the disease, and whether the individual will respond to therapy. Since 70% of CD patients will ultimately need a GI surgical operation, the ability to predict those patients who will need surgery in the future is important. The present invention satisfies these needs and provides related advantages as well.

BRIEF SUMMARY OF THE INVENTION

The present invention provides methods and systems to improve the diagnosis of inflammatory bowel disease (IBD) and to improve the prognosis of IBD progression and complications. With the present invention, it is possible to predict outcome of disease and patients who will have a particular risk of disease complications and/or progression to surgery.

In one aspect, the present invention provides a method for aiding in the prognosis of inflammatory bowel disease (IBD) in an individual diagnosed with IBD, the method comprising:

(a) analyzing a sample obtained from the individual to determine the presence, level or genotype of one or more markers in the sample to obtain a marker profile;

(b) applying a statistical analysis to the marker profile to obtain a prognostic profile for the individual; and (c) comparing the prognostic profile for the individual to a prognostic model to aid in the prognosis of IBD.

In particular embodiments, the methods utilize multiple serological, protein, and/or genetic markers to provide physicians with valuable prognostic insight.

In another aspect, the present invention provides a method for predicting the likelihood that an individual diagnosed with inflammatory bowel disease (IBD) will respond to an IBD therapeutic agent, the method comprising:

(a) analyzing a sample obtained from the individual to determine the presence, level or genotype of one or more markers in the sample to obtain a marker profile;

(b) applying a statistical analysis to the marker profile to obtain a therapeutic profile for the individual; and (c) comparing the therapeutic profile for the individual to a therapeutic model to aid in the prediction of the likelihood that an individual diagnosed with IBD will respond to an IBD therapeutic agent.

In particular embodiments, the methods utilize multiple serological, protein, and/or genetic markers to provide physicians with valuable therapeutic insight.

In a related aspect, the present invention provides a method for selecting a suitable drug for the treatment of inflammatory bowel disease (IBD) in an individual, the method comprising:

(a) analyzing a sample obtained from the individual to determine the presence, level or genotype of one or more markers in the sample to obtain a marker profile;

(b) applying a statistical analysis to the marker profile to obtain a therapeutic profile for the individual; and (c) comparing the therapeutic profile for the individual to a therapeutic model to aid in the selection of a suitable drug for the treatment of IBD.

In particular embodiments, the methods utilize multiple serological, protein, and/or genetic markers to provide physicians with valuable therapeutic insight.

In a further aspect, the present invention provides a method for predicting a probability of disease complications and/or surgery in an individual diagnosed with Crohn's disease (CD), the method comprising:

(a) analyzing a sample obtained from the individual to determine the level or genotype of one or more markers in the sample; and (b) comparing the level or genotype of each of the markers to a reference level or genotype to predict the probability of disease complications and/or surgery in an individual diagnosed with CD.

In a related aspect, the present invention provides a method for predicting a probability of disease complications and/or surgery in an individual diagnosed with Crohn's disease (CD), the method comprising:

(a) analyzing a sample obtained from the individual to determine the presence, level or genotype of one or more markers in the sample to obtain a marker profile;

(b) applying a statistical analysis to the marker profile to obtain a prognostic profile for the individual; and (c) comparing the prognostic profile for the individual to a prognostic model to predict the probability of disease complications and/or surgery in an individual diagnosed with CD.

In particular embodiments, the methods utilize multiple serological, protein, and/or genetic markers to provide physicians with valuable prognostic insight into an individual's risk of developing Crohn's disease complications and/or needing surgery.

In certain aspects, the methods described herein can predict the probability of response, serve as a guide for selecting an initial therapy, serve as a guide for selecting aggressive or non-aggressive treatment (e.g., at the start of therapy or anytime during a therapeutic regimen), and serve as a guide for changing disease behavior.

Advantageously, by using a prognostic profile composed of multiple markers (e.g., serological, protein, genetic, etc.) alone or in conjunction with statistical analysis, the assay methods and systems of the present invention provide prognostic value by identifying patients with a risk of complicated disease and/or surgery, as well as assisting in determining the rate of disease progression. In certain instances, the methods and systems described herein enable classification of disease severity along a continuum of IBD subgroups rather than merely as CD or UC. In other instances, the use of multiple markers (e.g., serological, protein, genetic, etc.) provide the ability to distinguish responders from non responders.

In another aspect, the present invention provides a method for aiding in the diagnosis of inflammatory bowel disease (IBD), the method comprising:

(a) analyzing a sample obtained from the individual to determine the level or genotype of one or more markers in the sample; and (b) comparing the level or genotype of each of the markers to a reference level or genotype to aid in the diagnosis of IBD.

In a related aspect, the present invention provides a method for aiding in the diagnosis of inflammatory bowel disease (IBD), the method comprising:

(a) analyzing a sample obtained from the individual to determine the presence, level or genotype of one or more markers in the sample to obtain a marker profile; and (b) applying a statistical analysis to the marker profile to aid in the diagnosis of IBD.

In certain embodiments, the methods further comprise comparing the results from the statistical analysis (i.e., diagnostic profile) to a reference (i.e., diagnostic model) to aid in the diagnosis of IBD. In particular embodiments, the methods utilize multiple serological, protein, and/or genetic markers to provide physicians with valuable diagnostic insight.

Other objects, features, and advantages of the present invention will be apparent to one of skill in the art from the following detailed description and figures.

BRIEF DESCRIPTION OF THE DRAWINGS

FIG. 4 illustrates an exemplary laboratory report using grey scaling or color for visualization and magnitude of disease behavior and/or prognosis.

FIG. 5 illustrates another exemplary laboratory report using grey scaling or color for visualization and magnitude of disease behavior and/or prognosis.

FIG. 6 illustrates an exemplary laboratory report having potential for adding disease characteristics as well as assay, genetic, and predictive outcome markers, which improves diagnostic and prognostic capabilities.

DETAILED DESCRIPTION OF THE INVENTION

I. Introduction

The present invention is based, in part, upon the surprising discovery that the accuracy of diagnosing or prognosing IBD or predicting response to an IBD therapeutic agent can be substantially improved by detecting the presence, level, or genotype of certain markers in a biological sample from an individual. As such, in one embodiment, the present invention provides diagnostic and prognostic platforms based on a serological and/or genetic panel of markers.

Figure 1:
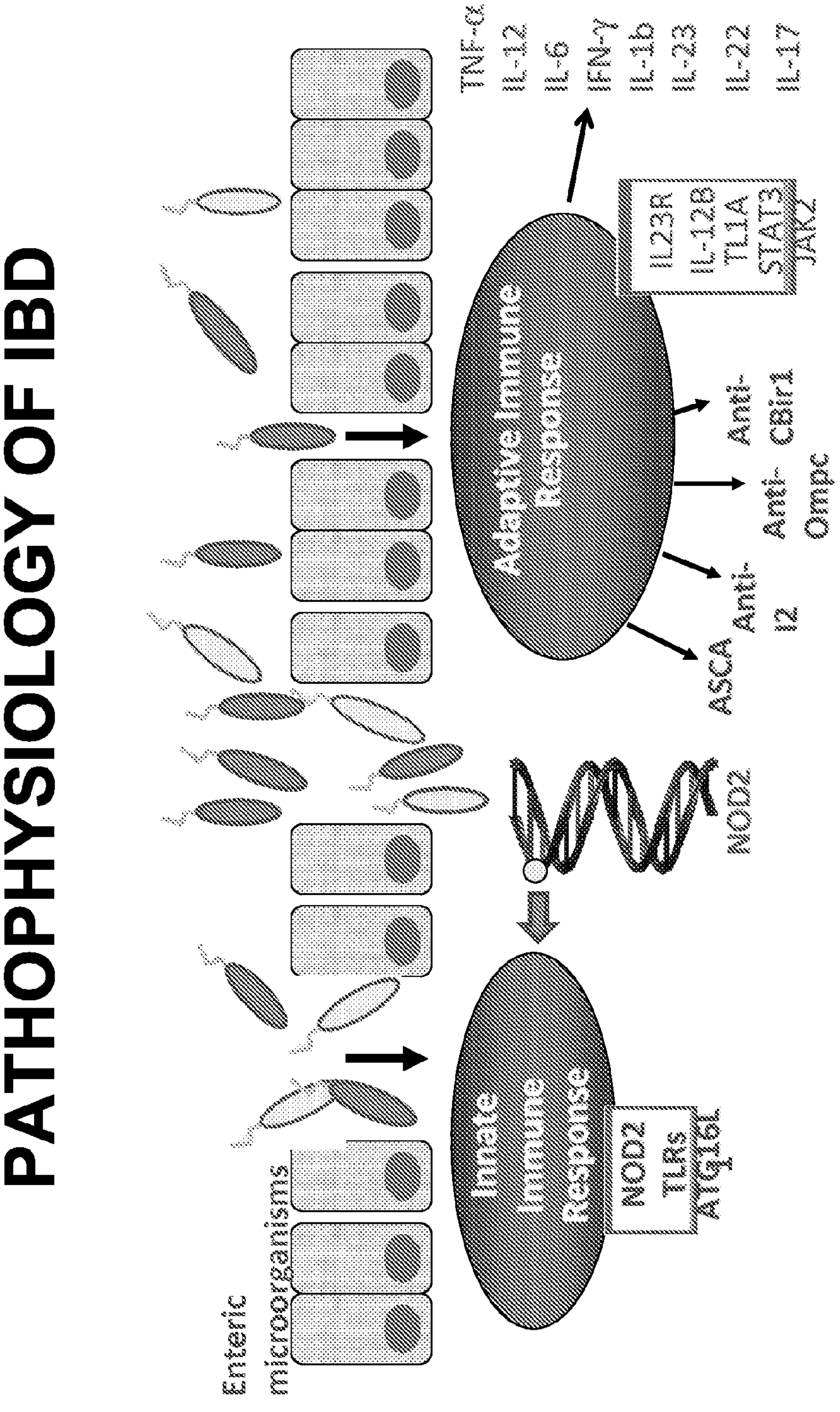
FIG. 1 illustrates a diagram of the pathophysiology of IBD.
Figure 2:
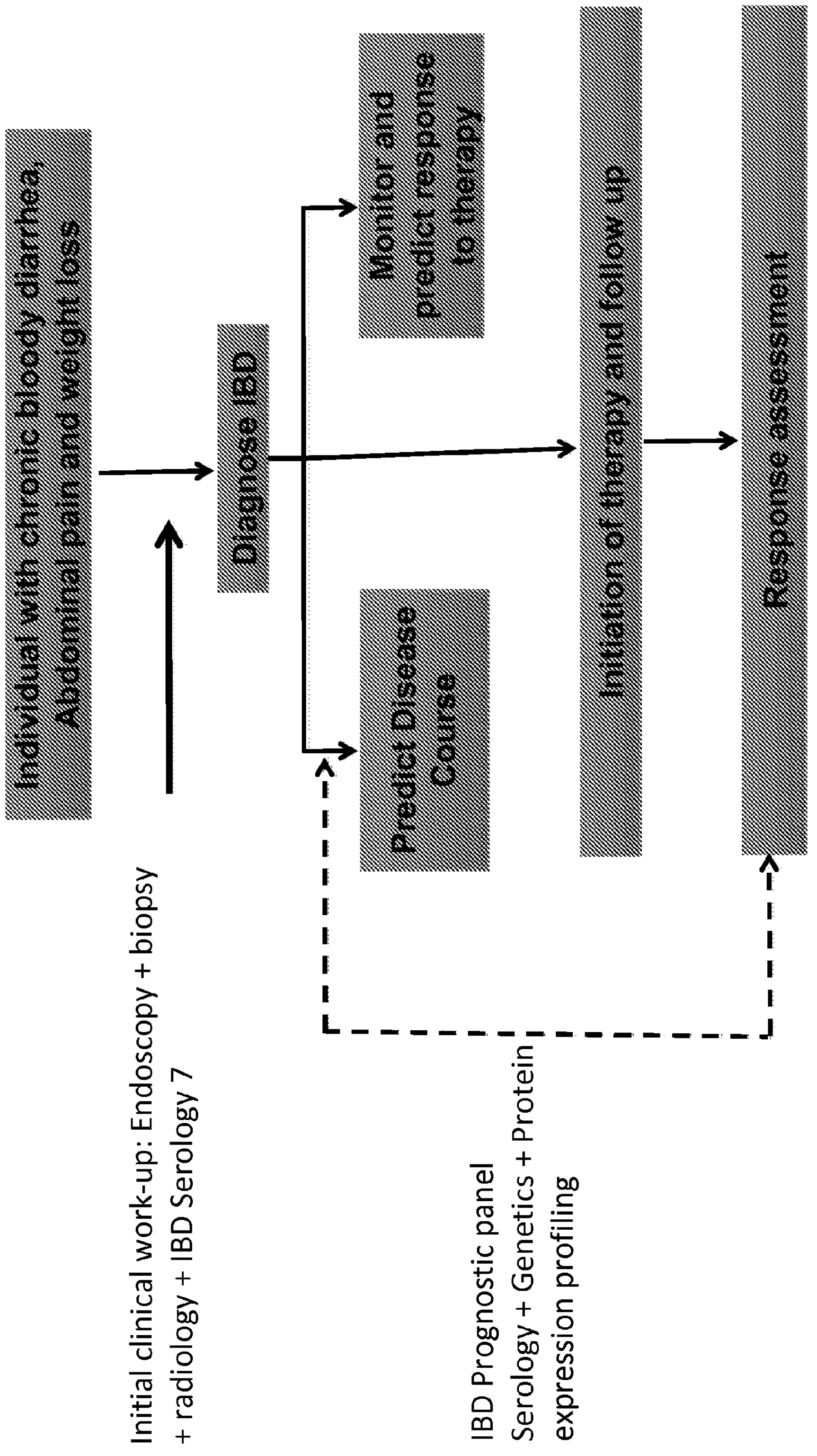
FIG. 2 illustrates an exemplary embodiment of an IBD decision tree of the present invention in which the IBD prognostic panel described herein is used (1) to predict disease course and (2) to monitor and predict response to therapy.

FIG. 1 is an illustration of the pathophysiology of IBD, which illustrates that in certain instances, a patient has a genetic predisposition, a mucosal immune system defect, a luminal inflammation (increased immune response to enteric microbial antigens), a barrier function which is compromised, or a combination thereof. FIG. 2 is an illustration of an IBD decision tree of the present invention.

The present invention provides methods and systems to improve the diagnosis and prognosis of UC and CD. In certain instances, the methods herein accurately predict "UC like CD," a disease which is known to be very difficult to diagnose and predict outcome. In one aspect, the methods described herein utilize multiple serological, protein, and/or genetic markers, alone or in combination with one or more algorithms or other types of statistical analysis, to provide physicians valuable diagnostic or prognostic insight. In some aspects, the methods and systems of the present invention provide an indication of a patient's projected response to biological therapy. In other aspects, the methods and systems of the present invention utilize multiple markers (e.g., serological, protein, and/or genetic) in conjunction with statistical analysis (e.g., quartile analysis) to provide prognostic value by identifying patients with complicated disease or a risk of developing disease complications (e.g., internal stricturing or internal penetrating disease) and/or a need for surgical intervention, while also assisting in assessing the rate of disease progression. In certain other instances, the methods enable classification of disease severity along a continuum of IBD subgroups rather than merely as CD or UC. Moreover, the methods guide therapeutic decisions of patients with advanced disease. In further aspects, the use of multiple markers (e.g., serological, protein, and/or genetic) provides the ability to distinguish responders from non-responders and guides initial therapeutic options (e.g., whether or not to prescribe aggressive treatment), with the potential to change disease behavior.

In certain instances, the methods and systems of the present invention comprise a step having a "transformation" or "machine" associated therewith. For example, an ELISA technique may be performed to measure the presence or concentration level of many of the markers described herein. An ELISA includes transformation of the marker, e.g., an auto-antibody, into a complex between the marker (e.g., auto-antibody) and a binding agent (e.g., antigen), which then can be measured with a labeled secondary antibody. In many instances, the label is an enzyme which transforms a substrate into a detectable product. The detectable product measurement can be performed using a plate reader such as a spectrophotometer. In other instances, genetic markers are determined using various amplification techniques such as PCR. Method steps including amplification such as PCR result in the transformation of single or double strands of nucleic acid into multiple strands for detection. The detection can include the use of a fluorophore, which is performed using a machine such as a fluoremeter.

II. Definitions

As used herein, the following terms have the meanings ascribed to them unless specified otherwise.

The term "classifying" includes "associating" or "categorizing" a sample or an individual with a disease state or prognosis. In certain instances, "classifying" is based on statistical evidence, empirical evidence, or both. In certain embodiments, the methods and systems of classifying use a so-called training set of samples from individuals with known disease states or prognoses. Once established, the training data set serves as a basis, model, or template against which the features of an unknown sample from an individual are compared, in order to classify the unknown disease state or provide a prognosis of the disease state in the individual. In some instances, "classifying" is akin to diagnosing the disease state and/or differentiating the disease state from another disease state. In other instances, "classifying" is akin to providing a prognosis of the disease state in an individual diagnosed with the disease state.

The term "inflammatory bowel disease" or "IBD" includes gastrointestinal disorders such as, e.g., Crohn's disease (CD), ulcerative colitis (UC), and indeterminate colitis (IC). Inflammatory bowel diseases (e.g., CD, UC, and IC) are distinguished from all other disorders, syndromes, and abnormalities of the gastroenterological tract, including irritable bowel syndrome (IBS). U.S. Patent Publication 20080131439, entitled "Methods of Diagnosing Inflammatory Bowel Disease" is incorporated herein by reference for all purposes.

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.,* 11:267-86 (1997)). One skilled in the art will appreciate that samples such as serum samples can be diluted prior to the analysis of marker levels.

The term "marker" includes any biochemical marker, serological marker, genetic marker, or other clinical or echographic characteristic that can be used in the diagnosis of IBD, in the prediction of the probable course and outcome of IBD, and/or in the prediction of the likelihood of recovery from the disease. Non-limiting examples of such markers include serological markers such as an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule; genetic markers such as NOD2/CARD15; and combinations thereof. In some embodiments, the markers are utilized in combination with a statistical analysis to provide a diagnosis or prognosis of IBD in an individual. In certain instances, the diagnosis can be IBD or a clinical subtype thereof such as Crohn's disease (CD), ulcerative colitis (UC), or indeterminate colitis (IC). In certain other instances, the prognosis can be the need for surgery (e.g., the likelihood or risk of needing small bowel surgery), development of a clinical subtype of CD or UC (e.g., the likelihood or risk of being susceptible to a particular clinical subtype CD or UC such as the stricturing, penetrating, or inflammatory CD subtype), development of one or more clinical factors (e.g., the likelihood or risk of being susceptible to a particular clinical factor), development of intestinal cancer (e.g., the likelihood or risk of being susceptible to intestinal cancer), or recovery from the disease (e.g., the likelihood of remission).

The term "marker profile" includes one, two, three, four, five, six, seven, eight, nine, ten, or more diagnostic and/or prognostic marker(s), wherein the markers can be a serological marker, a protein marker, a genetic marker, and the like. In some embodiments, the marker profile together with a statistical analysis can provide physicians and caregivers valuable diagnostic and prognostic insight. In other embodiments, the marker profile with optionally a statistical analysis provides a projected response to biological therapy. By using multiple markers (e.g., serological, protein, genetic, etc.) in conjunction with statistical analyses, the assays described herein provide diagnostic, prognostic and therapeutic value by identifying patients with IBD or a clinical subtype thereof, predicting risk of developing complicated disease, assisting in assessing the rate of disease progression (e.g., rate of progression to complicated disease or surgery), and assisting in the selection of therapy.

The term "prognostic profile" includes one, two, three, four, five, six, seven, eight, nine, ten, or more marker(s) of an individual, wherein the marker(s) can be a serological marker, a protein marker, a genetic marker, and the like. A statistical analysis transforms the marker profile into a prognostic profile. A preferred statistical analysis is a quartile score and the quartile score for each of the markers can be summed to generate a quartile sum score.

The term "prognostic model" includes serological models, genetic models, sero-genetic models, and a combination thereof. In a preferred aspect, a retrospective analysis is done on a cohort of known disease outcomes with known complications and surgical procedures performed. In one aspect, a regression analysis (e.g., logistic regression) can be performed on the presence or concentration level of one or more serological markers and/or the genotype of one or more genetic markers to develop a prognostic model. The model can be illustrated or depicted in, e.g., a look-up table, graph or other display. A prognostic profile of an individual can then be compared to a prognostic model and the prognosis determined (e.g., the risk or probability of developing a complication over time).

The term "therapeutic profile" includes one, two, three, four, five, six, seven, eight, nine, ten, or more marker(s) of an individual, wherein the marker(s) can be a serological marker, a protein marker, a genetic marker, and the like. A statistical analysis transforms the marker profile into a therapeutic profile. A preferred statistical analysis is a quartile score and the quartile score for each of the markers can be summed to generate a quartile sum score.

The term "therapeutic model" includes serological models, genetic models, sero-genetic models, and a combination thereof. In a preferred aspect, a retrospective analysis is done on a cohort of known therapeutic outcomes with known therapies being used, which include biologics, steroids, conventional drugs and surgical procedures performed. In one aspect, a regression analysis (e.g., logistic regression) can be performed on the presence or concentration level of one or more serological markers and/or the genotype of one or more genetic markers to develop a therapeutic model. The model can be illustrated or depicted in, e.g., a look-up table, graph or other display. A therapeutic profile of an individual can then be compared to a therapeutic model and the therapy determined (e.g., "step up" or "top down" strategies).

The term "efficacy profile" includes one, two, three, four, five, six, seven, eight, nine, ten, or more marker(s) of an individual, wherein the markers can be a serological marker, a protein marker, a genetic marker, and the like, and wherein each of the markers changes with therapeutic administration.

In certain instances, the marker profile is compared to the efficacy profile in order to assess therapeutic efficacy. In certain aspects, the efficacy profile is equivalent to the marker profile, but wherein the markers are measured later in time. In certain other aspects, the efficacy profile corresponds to a marker profile from IBD patients who responded to a particular therapeutic agent or drug. In these aspects, similarities or differences between the test marker profile and the reference efficacy profile indicate whether that particular drug is suitable or unsuitable for the treatment of IBD. In certain instances, a marker(s) is more indicative of efficacy than diagnosis or prognosis. As such, there may be a one-to-one correlation of diagnostic or prognostic markers in the marker profile compared to the markers in the efficacy profile, but it is not required.

The term "individual," "subject," or "patient" typically includes humans, but also includes other animals such as, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as an I2 protein can have one or more modifications such as amino acid additions, deletions, or substitutions relative to the amino acid sequence of the naturally-occurring I2 protein, provided that the modified polypeptide retains substantially at least one biological activity of I2 such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The term "clinical factor" includes a symptom in an individual that is associated with IBD. Examples of clinical factors include, without limitation, diarrhea, abdominal pain, cramping, fever, anemia, weight loss, anxiety, depression, and combinations thereof. In some embodiments, a diagnosis or prognosis of IBD is based upon a combination of analyzing a sample obtained from an individual to determine the presence, level, or genotype of one or more markers by applying one or more statistical analyses and determining whether the individual has one or more clinical factors.

In a preferred aspect, the methods of invention are used after an individual has been diagnosed with IBD. However, in other instances, the methods can be used to diagnose IBD or can be used as a "second opinion" if, for example, IBD is suspected or has been previously diagnosed using other methods. The term "diagnosing IBD" includes the use of the methods and systems described herein to determine the presence or absence of IBD in an individual. The term also includes assessing the level of disease activity in an individual. In some embodiments, a statistical analysis is used to diagnose a mild, moderate, severe, or fulminant form of IBD based upon the criteria developed by Truelove et al., *Br. Med. J.,* 12:1041-1048 (1955). In other embodiments, a statistical analysis is used to diagnose a mild to moderate, moderate to severe, or severe to fulminant form of IBD based upon the criteria developed by Hanauer et al., *Am. J. Gastroenterol.,* 92:559-566 (1997). One skilled in the art will know of other methods for evaluating the severity of IBD in an individual.

In certain instances, the methods of the invention are used in order to prognosticate the progression of IBD. The methods can be used to monitor the disease, both progression and regression. The term "monitoring the progression or regression of IBD" includes the use of the methods and marker profiles to determine the disease state (e.g., presence or severity of IBD) of an individual. In certain instances, the results of a statistical analysis are compared to those results obtained for the same individual at an earlier time. In some aspects, the methods, systems, and code of the present invention can also be used to predict the progression of IBD, e.g., by determining a likelihood for IBD to progress either rapidly or slowly in an individual based on the presence or level of at least one marker in a sample. In other aspects, the methods, systems, and code of the present invention can also be used to predict the regression of IBD, e.g., by determining a likelihood for IBD to regress either rapidly or slowly in an individual based on the presence or level of at least one marker in a sample.

The term "monitoring drug efficacy in an individual receiving a drug useful for treating IBD" includes the determination of a marker profile, alone or in combination with the application of a statistical analysis, to determine the disease state (e.g., presence or severity of IBD) of an individual after a therapeutic agent for treating IBD has been administered.

The term "optimizing therapy in an individual having IBD" includes the use of the methods of the present invention and a marker profile to determine the course of therapy for an individual before a therapeutic agent (e.g., IBD drug) has been administered or to adjust the course of therapy for an individual after a therapeutic agent has been administered in order to optimize the therapeutic efficacy of the therapeutic agent. In certain instances, the results of a statistical analysis are compared to those results obtained for the same individual at an earlier time during the course of therapy. As such, a comparison of the results provides an indication for the need to change the course of therapy or an indication for the need to increase or decrease the dose of the current course of therapy.

The term "course of therapy" includes any therapeutic approach taken to relieve or prevent one or more symptoms (i.e., clinical factors) associated with IBD. The term "course of therapy" encompasses administering any compound, drug, procedure, or regimen useful for improving the health of an individual with IBD and includes any of the therapeutic agents (e.g., IBD biologic agents and conventional drugs) described herein as well as surgery. One skilled in the art will appreciate that either the course of therapy or the dose of the current course of therapy can be changed, e.g., based upon the results obtained through applying an a statistical analysis in accordance with the present invention.

The term "therapeutically effective amount or dose" includes a dose of a drug (e.g., IBD biologic agent or conventional drug) that is capable of achieving a therapeutic effect in a subject in need thereof. For example, a therapeutically effective amount of a drug useful for treating IBD can be the amount that is capable of preventing or relieving one or more symptoms associated with IBD. The exact amount can be ascertainable by one skilled in the art using known techniques (see, e.g., Lieberman, *Pharmaceutical Dosage Forms* (vols. 1-3, 1992); Lloyd, *The Art, Science and*

*Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

The term "genotype" refers to the genetic composition of an organism, including, for example, whether a diploid organism is heterozygous or homozygous for one or more variant alleles of interest.

The term "polymorphism" refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (i.e., single nucleotide polymorphism or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The allele occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

The terms "miRNA," "microRNA" or "miR" are used interchangeably and include single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRs are partially complementary to one or more messenger RNA (mRNA) molecules, and their main function is to down-regulate gene expression. Embodiments described herein include both diagnostic and therapeutic applications.

In quartile analysis, there are three numbers (values) that divide a range of data into four equal parts. The first quartile (also called the 'lower quartile') is the number below which lies the 25 percent of the bottom data. The second quartile (the 'median') divides the range in the middle and has 50 percent of the data below it. The third quartile (also called the 'upper quartile') has 75 percent of the data below it and the top 25 percent of the data above it. As a non-limiting example, quartile analysis can be applied to the concentration level of a marker such as an antibody or other protein marker described herein, such that a marker level in the first quartile (<25%) is assigned a value of 1, a marker level in the second quartile (25-50%) is assigned a value of 2, a marker level in the third quartile (51%-<75%) is assigned a value of 3, and a marker level in the fourth quartile (75%-100%) is assigned a value of 4.

As used herein, "quartile sum score" or "QSS" includes the sum of quartile scores for all of the markers of interest. As a non-limiting example, a quartile sum score for a panel of 6 markers (e.g., serological, protein, and/or genetic) may range from 6-24, wherein each of the individual markers is assigned a quartile score of 1-4 based upon the presence or absence of the marker, the concentration level of the marker, or the genotype of the marker.

III. Description of the Embodiments

The present invention provides methods and systems to improve the diagnosis of inflammatory bowel disease (IBD) and to improve the prognosis of IBD progression and complications. By identifying patients with complicated disease and assisting in assessing the rate of disease progression, the methods and systems described herein provide invaluable information to assess the severity of the disease and treatment options. In certain instances, the methods and systems enable classification of disease severity along a continuum of IBD subgroups rather than merely as CD, UC or IC. In other aspects, the use of multiple markers (serological, protein, and/or genetic) provides the ability to distinguish responders from non-responders to certain therapies. In particular embodiments, applying a statistical analysis to a profile of serological, protein, and/or genetic markers improves the accuracy of predicting IBD progression and disease complications, and also enables the selection of appropriate treatment options, including therapy such as biological, conventional, surgery, or some combination thereof. Accordingly, with the present invention, it is possible to predict outcome of disease and patients who will have a particular risk of disease complications and/or progression to surgery.

In one aspect, the present invention provides a method for aiding in the prognosis of inflammatory bowel disease (IBD) in an individual diagnosed with IBD, the method comprising:

(a) analyzing a sample obtained from the individual to determine the presence, level or genotype of one or more markers selected from the group consisting of a serological marker, a genetic marker, and a combination thereof in the sample to obtain a marker profile;

(b) applying a statistical analysis to the marker profile to obtain a prognostic profile for the individual; and (c) comparing the prognostic profile for the individual to a prognostic model to aid in the prognosis of IBD.

In some embodiments, the serological marker is selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof. In another embodiment, the anti-*Saccharomyces cerevisiae* antibody comprises an anti-*Saccharomyces cerevisiae* immunoglobulin A (ASCA-IgA), anti-*Saccharomyces cerevisiae* immunoglobulin G (ASCA-IgG), or a combination thereof.

In yet another embodiment, the antimicrobial antibody comprises an anti-outer membrane protein C (anti-OmpC) antibody, an anti-I2 antibody, an anti-flagellin antibody, or a combination thereof. In certain instances, the anti-flagellin antibody comprises an anti-Cbir-1 flagellin antibody, an anti-flagellin X antibody, an anti-flagellin A antibody, an anti-flagellin B antibody, or a combination thereof. In a further embodiment, the acute phase protein is C-Reactive protein (CRP). In another embodiment, the apolipoprotein is serum amyloid A (SAA). In yet another embodiment, the defensin is β defensin (e.g., β defensin-1 (BD1) and/or β defensin-2 (BD2)). In still yet another embodiment, the growth factor is epidermal growth factor (EGF). In a further embodiment, the cytokine comprises TNF-related weak inducer of apoptosis (TWEAK), IL-1β, IL-6, or a combination thereof. In an additional embodiment, the cadherin is E-cadherin. In another embodiment, the cellular adhesion molecule comprises ICAM-1, VCAM-1, or a combination thereof.

In particular embodiments, the serological marker comprises or consists of ASCA-IgA, ASCA-IgG, anti-OmpC antibody, anti-CBir-1 antibody, anti-I2 antibody, pANCA (e.g., pANCA IFA and/or DNAse-sensitive pANCA IFA), or a combination thereof.

The presence or (concentration) level of the serological marker can be detected (e.g., determined, measured, analyzed, etc.) with a hybridization assay, amplification-based assay, immunoassay, immunohistochemical assay, or a combination thereof. Non-limiting examples of assays, techniques, and kits for detecting or determining the presence or level of one or more serological markers in a sample are described in Section VI below.

In other embodiments, the genetic marker is at least one of the genes set forth in Tables 1A-1E (e.g., Table 1A, 1B, 1C, 1D, and/or 1E). In particular embodiments, the genetic marker is NOD2. The genotype of the genetic marker can be detected (e.g., determined, analyzed, etc.) by genotyping an individual for the presence or absence of one or more variant alleles such as, for example, one or more single nucleotide polymorphisms (SNPs) in one or more genetic markers. In some embodiments, the SNP is at least one of the SNPs set forth in Tables 1B-1E (e.g., Table 1B, 1C, 1D, and/or 1E). Non-limiting examples of techniques for detecting or determining the genotype of one or more genetic markers in a sample are described in Section VII below. In certain embodiments, the genetic marker is NOD2 and the SNP is SNP8 (R702W), SNP12 (G908R), and/or SNP13 (1007fs). In certain instances, the presence or absence of one or more NOD2 SNPs is determined in combination with the presence or level of one or more serological markers, e.g., ASCA-IgA, ASCA-IgG, anti-OmpC antibody, anti-CBir-1 antibody, anti-I2 antibody, pANCA (e.g., pANCA IFA and/or DNAse-sensitive pANCA IFA), or a combination thereof.

In the methods of the present invention, the marker profile can be determined by detecting the presence, level, or genotype of at least two, three, four, five, six, seven, eight, nine, or ten markers. In particular embodiments, the sample is serum, plasma, whole blood, and/or stool. In other embodiments, the individual is diagnosed with Crohn's disease (CD), ulcerative colitis (UC), or indeterminate colitis (IC).

The statistical analysis applied to the marker profile can comprise any of a variety of statistical methods, models, and algorithms described in Section IX below. In particular embodiments, the statistical analysis is a quartile analysis. In some instances, the quartile analysis converts the presence, level or genotype of each marker into a quartile score. As a non-limiting example, the prognostic profile can correspond to a quartile sum score (QSS) for the individual that is obtained by summing the quartile score for each of the markers. In certain embodiments, the pANCA biomarker is a binary rather than a numerical variable since its value is either positive or negative. As described in Example 16 herein, a pANCA-positive status is associated with a lower rate and/or risk of complications (e.g., internal stricturing disease, internal penetrating disease, and/or surgery). In some instances, the quartile scoring for pANCA is inverted, such that a positive status is scored as "1" and a negative status is scored as "4".

In certain embodiments, the prognostic model is established using a retrospective cohort with known outcomes of a clinical subtype of IBD (e.g., CD, UC, or IC). In preferred embodiments, the prognostic model is selected from the group consisting of a serological model, a sero-genetic model, a genetic model, and a combination thereof. In one particular embodiment, the serological model is derived by applying logistic regression analysis to the presence or level of one or more serological markers determined in the retrospective cohort (see, e.g., Examples 16 and 17). In another particular embodiment, the sero-genetic model is derived by applying logistic regression analysis to the presence or level of one or more serological markers and the genotype of one or more genetic markers determined in the retrospective cohort (see, e.g., Examples 16 and 17). In other embodiments, the prognostic model is a standardized risk scale (see, e.g., Example 16). In one particular embodiment, the standardized risk scale converts a prognostic profile such as a quartile sum score (QSS) for the individual into a standardized scale number, which may correspond to the probability of a complication phenotype (e.g., internal stricturing disease, internal penetrating disease, need for small bowel surgery) by a specific year (e.g., Year 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc.) after diagnosis.

In some embodiments, the prognostic model comprises a display, print-out, and/or report such as a look-up table or graph. In particular embodiments, the look-up table or graph provides a cumulative probability of the individual developing or not developing a Crohn's disease (CD) complication over time. In certain other embodiments, the look-up table or graph provides a cumulative probability of the individual needing surgery or not needing surgery over time. The look-up table or graph can also provide a cumulative probability of the individual developing or not developing an ulcerative colitis (UC) complication over time.

In certain instances, the CD complication is selected from the group consisting of internal stricturing disease, internal penetrating disease, and a combination thereof. In certain other instances, the CD complication is selected from the group consisting of a fibrostenotic subtype of CD, CD characterized by small bowel disease, CD characterized by perianal fistulizing disease, CD characterized by internal perforating disease, CD characterized by the need for small bowel surgery, CD characterized by the presence of features of UC, CD characterized by the absence of features of UC, and a combination thereof. In yet other instances, the surgery is small bowel surgery. In further instances, the UC complication is selected from the group consisting of ulcerative proctitis, proctosigmoiditis, left-sided colitis, pancolitis, fulminant colitis, and a combination thereof.

In other embodiments, the prognostic profile is a quartile sum score (QSS) for the individual and the QSS is compared to a prognostic model (e.g., a serological model, a sero-genetic model, standardized risk scale, etc.). In certain instances, the prognostic model comprises the serological model depicted in FIG. 38*a*. In other instances, the prognostic model comprises the sero-genetic model depicted in FIG. 38*b*. In further instances, the prognostic model comprises the standardized risk scale shown in Table 53.

Figure 38:
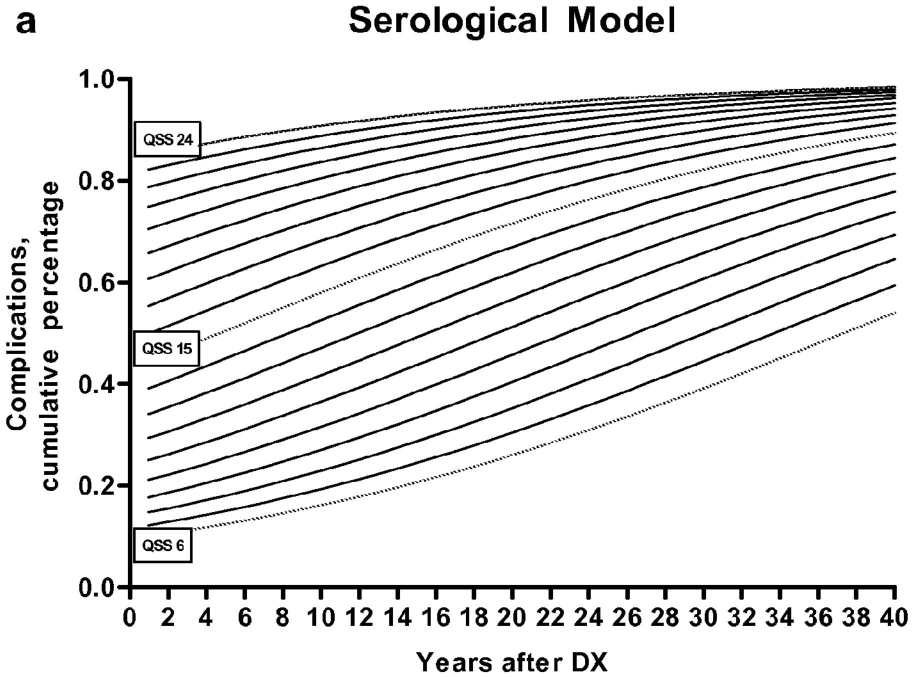
FIG. 38 illustrates predictions of the serological and sero-genetic logistic regression models. (A) The serological logistic regression model was constructed with QSS and duration of disease as predictors and complication status as the outcome. This model was used to predict probability of complication for a range of QSS (6-24) and durations (1-40). (B) The sero-genetic logistic regression model was constructed with QSS, duration of disease, and SNP13 mutation as predictors and complication status as the outcome. This model was used to predict probability of complication for a range of QSS (6-24) and durations (1-40), with SNP13 mutation present.
Figure 38:
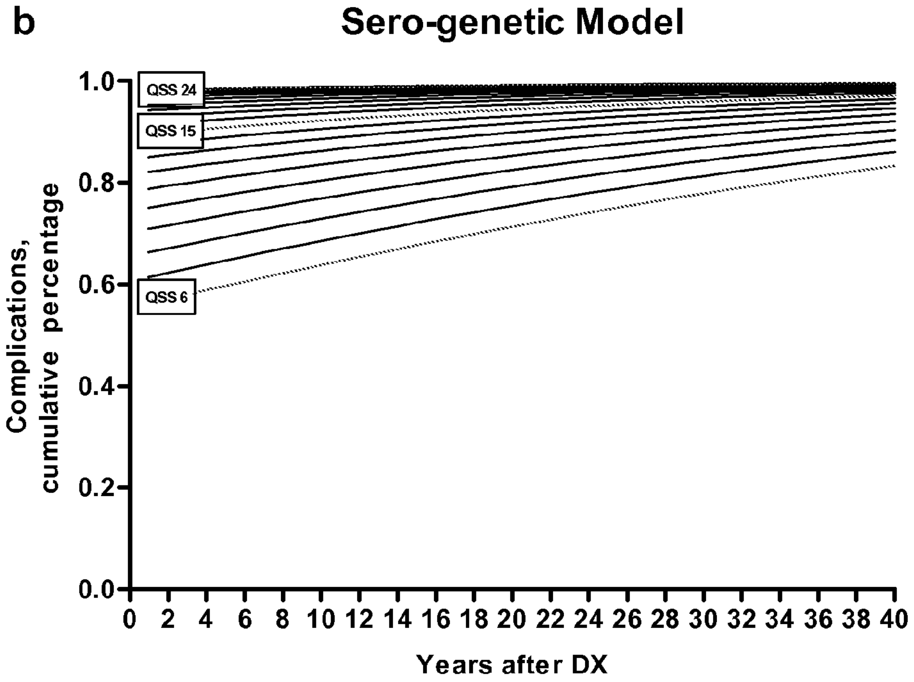

In particular embodiments, the methods described herein provide a prediction that CD complications and/or progression to surgery would occur at a rate of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) by a specific year (e.g., Year 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc.) after diagnosis based on an individual's prognostic profile, e.g., the individual's QSS, optionally in combination with the presence or absence of one or more variant alleles in one or more genetic markers, e.g., NOD2 (see, e.g., Examples 16-17, FIGS. 38*a*-38*b*, and Table 53).

In yet other embodiments, the methods of the present invention can further comprise recommending a course of therapy for the individual based upon the comparison between the prognostic profile and the prognostic model. In additional embodiments, the methods of the present invention can further comprise sending the results of the comparison to a clinician.

In another aspect, the present invention provides a method for predicting the likelihood that an individual diagnosed with inflammatory bowel disease (IBD) will respond to an IBD therapeutic agent, the method comprising:

(a) analyzing a sample obtained from the individual to determine the presence, level or genotype of one or more markers selected from the group consisting of a serological marker, a genetic marker, and a combination thereof in the sample to obtain a marker profile;

(b) applying a statistical analysis to the marker profile to obtain a therapeutic profile for the individual; and (c) comparing the therapeutic profile for the individual to a therapeutic model to aid in the prediction of the likelihood that an individual diagnosed with IBD will respond to an IBD therapeutic agent.

In a related aspect, the present invention provides a method for selecting a suitable drug for the treatment of inflammatory bowel disease (IBD) in an individual, the method comprising:

(a) analyzing a sample obtained from the individual to determine the presence, level or genotype of one or more markers in the sample to obtain a marker profile;

(b) applying a statistical analysis to the marker profile to obtain a therapeutic profile for the individual; and (c) comparing the therapeutic profile for the individual to a therapeutic model to aid in the selection of a suitable drug for the treatment of IBD.

The methods of the present invention find utility in predicting whether an individual will respond to a particular biologic agent and/or conventional drug including, but not limited to, anti-tumor necrosis factor (TNF) therapy (e.g., chimeric monoclonals (e.g., infliximab), humanized monoclonals (e.g., CDP571 and PEGylated CDP870), and human monoclonals (e.g., adalimumab)), p75 fusion proteins (e.g., etanercept), p55 soluble receptors (e.g., onercept), small molecules such as MAP kinase inhibitors, and a combination thereof. The methods of the present invention also find utility in selecting a suitable drug for the treatment of IBD such as a particular biologic agent and/or conventional drug described herein.

In some embodiments, the serological marker is selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof. In another embodiment, the anti-*Saccharomyces cerevisiae* antibody comprises an anti-*Saccharomyces cerevisiae* immunoglobulin A (ASCA-IgA), anti-*Saccharomyces cerevisiae* immunoglobulin G (ASCA-IgG), or a combination thereof.

In yet another embodiment, the antimicrobial antibody comprises an anti-outer membrane protein C (anti-OmpC) antibody, an anti-I2 antibody, an anti-flagellin antibody, or a combination thereof. In certain instances, the anti-flagellin antibody comprises an anti-Cbir-1 flagellin antibody, an anti-flagellin X antibody, an anti-flagellin A antibody, an anti-flagellin B antibody, or a combination thereof. In a further embodiment, the acute phase protein is C-Reactive protein (CRP). In another embodiment, the apolipoprotein is serum amyloid A (SAA). In yet another embodiment, the defensin is β defensin (e.g., β defensin-1 (BD1) and/or β defensin-2 (BD2)). In still yet another embodiment, the growth factor is epidermal growth factor (EGF). In a further embodiment, the cytokine comprises TNF-related weak inducer of apoptosis (TWEAK), IL-1β, IL-6, or a combination thereof. In an additional embodiment, the cadherin is E-cadherin. In another embodiment, the cellular adhesion molecule comprises ICAM-1, VCAM-1, or a combination thereof.

In particular embodiments, the serological marker comprises or consists of ASCA-IgA, ASCA-IgG, anti-OmpC antibody, anti-CBir-1 antibody, anti-I2 antibody, pANCA (e.g., pANCA IFA and/or DNAse-sensitive pANCA IFA), or a combination thereof.

The presence or (concentration) level of the serological marker can be detected (e.g., determined, measured, analyzed, etc.) with a hybridization assay, amplification-based assay, immunoassay, immunohistochemical assay, or a combination thereof. Non-limiting examples of assays, techniques, and kits for detecting or determining the presence or level of one or more serological markers in a sample are described in Section VI below.

In other embodiments, the genetic marker is at least one of the genes set forth in Tables 1A-1E (e.g., Table 1A, 1B, 1C, 1D, and/or 1E). In particular embodiments, the genetic marker is NOD2. The genotype of the genetic marker can be detected (e.g., determined, analyzed, etc.) by genotyping an individual for the presence or absence of one or more variant alleles such as, for example, one or more single nucleotide polymorphisms (SNPs) in one or more genetic markers. In some embodiments, the SNP is at least one of the SNPs set forth in Tables 1B-1E (e.g., Table 1B, 1C, 1D, and/or 1E). Non-limiting examples of techniques for detecting or determining the genotype of one or more genetic markers in a sample are described in Section VII below. In certain embodiments, the genetic marker is NOD2 and the SNP is SNP8 (R702W), SNP12 (G908R), and/or SNP13 (1007fs). In certain instances, the presence or absence of one or more NOD2 SNPs is determined in combination with the presence or level of one or more serological markers, e.g., ASCA-IgA, ASCA-IgG, anti-OmpC antibody, anti-CBir-1 antibody, anti-I2 antibody, pANCA (e.g., pANCA IFA and/or DNAse-sensitive pANCA IFA), or a combination thereof.

In the methods of the present invention, the marker profile can be determined by detecting the presence, level, or genotype of at least two, three, four, five, six, seven, eight, nine, or ten markers. In particular embodiments, the sample is serum, plasma, whole blood, and/or stool. In other embodiments, the individual is diagnosed with Crohn's disease (CD), ulcerative colitis (UC), or indeterminate colitis (IC).

The statistical analysis applied to the marker profile can comprise any of a variety of statistical methods, models, and algorithms described in Section IX below. In some instances, the statistical analysis predicts that the individual has a certain (e.g., high or low) likelihood of responding or not responding to the IBD therapeutic agent. In other instances, the statistical analysis predicts whether a certain drug (e.g., IBD therapeutic agent) is suitable for the treatment of IBD. In particular embodiments, the statistical analysis is a quartile analysis. In some instances, the quartile analysis converts the presence, level or genotype of each marker into a quartile score. As a non-limiting example, the therapeutic profile can correspond to a quartile sum score (QSS) for the individual that is obtained by summing the quartile score for each of the markers.

In certain embodiments, the therapeutic model is established using a retrospective cohort of known therapeutic outcomes with known therapies including biologics, steroids, conventional drugs, and/or surgical procedures. In particular embodiments, the therapeutic model is selected from the group consisting of a serological model, a sero-genetic model, a genetic model, and a combination thereof. In one particular embodiment, the therapeutic model is a serological model that is derived by applying logistic regression analysis to the presence or level of one or more serological markers determined in the retrospective cohort. In another particular embodiment, the therapeutic model is a sero-genetic model that is derived by applying logistic regression analysis to the presence or level of one or more serological markers and the genotype of one or more genetic markers determined in the retrospective cohort. In other embodiments, the therapeutic model is a standardized risk scale. In one particular embodiment, the standardized risk scale converts a therapeutic profile such as a quartile sum score (QSS) for the individual into a standardized scale number, which may correspond to the probability of response to an IBD therapeutic agent by a specific year (e.g., Year 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc.) after diagnosis.

In some embodiments, the therapeutic model comprises a display, print-out, and/or report such as a look-up table or graph. In particular embodiments, the look-up table or graph provides a cumulative probability of the individual responding or not responding to the IBD therapeutic agent over time.

In other embodiments, the therapeutic profile is a quartile sum score (QSS) for the individual and the QSS is compared to a therapeutic model (e.g., a serological model, a sero-genetic model, standardized risk scale, etc.).

In particular embodiments, the methods described herein provide a prediction that a response to an IBD therapeutic agent would occur at a rate of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) by a specific year (e.g., Year 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc.) after diagnosis based on an individual's therapeutic profile, such as, e.g., the individual's QSS, optionally in combination with the presence or absence of one or more variant alleles in one or more genetic markers, e.g., NOD2.

In yet other embodiments, the methods of the present invention can further comprise recommending a course of therapy for the individual based upon the comparison between the therapeutic profile and the therapeutic model. In additional embodiments, the methods of the present invention can further comprise sending the results of the comparison to a clinician.

In a further aspect, the present invention provides a method for predicting a probability of disease complications and/or surgery in an individual diagnosed with Crohn's disease (CD), the method comprising:

(a) analyzing a sample obtained from the individual to determine the level or genotype of one or more markers in the sample; and (b) comparing the level or genotype of each of the markers to a reference level or genotype to predict the probability of disease complications and/or surgery in an individual diagnosed with CD.

In some embodiments, the markers are selected from the serological and/or genetic markers described herein. As a non-limiting example, the serological marker can be selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof. In another embodiment, the anti-*Saccharomyces cerevisiae* antibody comprises an anti-*Saccharomyces cerevisiae* immunoglobulin A (ASCA-IgA), anti-*Saccharomyces cerevisiae* immunoglobulin G (ASCA-IgG), or a combination thereof.

In yet another embodiment, the antimicrobial antibody comprises an anti-outer membrane protein C (anti-OmpC) antibody, an anti-I2 antibody, an anti-flagellin antibody, or a combination thereof. In certain instances, the anti-flagellin antibody comprises an anti-Cbir-1 flagellin antibody, an anti-flagellin X antibody, an anti-flagellin A antibody, an anti-flagellin B antibody, or a combination thereof. In a further embodiment, the acute phase protein is C-Reactive protein (CRP). In another embodiment, the apolipoprotein is serum amyloid A (SAA). In yet another embodiment, the defensin is β defensin (e.g., β defensin-1 (BD1) and/or β defensin-2 (BD2)). In still yet another embodiment, the growth factor is epidermal growth factor (EGF). In a further embodiment, the cytokine comprises TNF-related weak inducer of apoptosis (TWEAK), IL-1β, IL-6, or a combination thereof. In an additional embodiment, the cadherin is E-cadherin. In another embodiment, the cellular adhesion molecule comprises ICAM-1, VCAM-1, or a combination thereof.

In particular embodiments, the markers comprise or consist of ASCA-IgG, ASCA-IgA, anti-OmpC antibody, anti-CBir-1 antibody, anti-I2 antibody, or a combination thereof.

In other embodiments, the genetic marker is at least one of the genes set forth in Tables 1A-1E (e.g., Table 1A, 1B, 1C, 1D, and/or 1E). In particular embodiments, the genetic marker is NOD2. The genotype of the genetic marker can be detected by genotyping an individual for the presence or absence of one or more variant alleles such as, for example, one or more SNPs in one or more genetic markers. In some embodiments, the SNP is at least one of the SNPs set forth in Tables 1B-1E (e.g., Table 1B, 1C, 1D, and/or 1E). In certain embodiments, the genetic marker is NOD2 and the SNP is SNP8 (R702W), SNP12 (G908R), and/or SNP13 (1007fs). In certain instances, the presence or absence of one or more NOD2 SNPs is determined in combination with the presence or level of one or more serological markers.

In the methods of the present invention, the presence, level, or genotype of at least two, three, four, five, six, seven, eight, nine, or ten markers can be determined. In particular embodiments, the sample is serum, plasma, whole blood, and/or stool.

In certain instances, the individual is predicted to have a higher probability of disease complications and/or surgery when the (concentration) level of at least one of the markers is higher than a reference (concentration) level. In certain other instances, the individual is predicted to have a higher probability of disease complications and/or surgery when the genotype of at least one of the markers is a variant allele of a reference genotype. Non-limiting examples of disease complications include internal stricturing disease and/or internal penetrating disease as well as any of the other CD complications described herein.

In certain embodiments, the reference (concentration) level corresponds to a (concentration) level of one of the markers in a sample from an individual not having CD (e.g., healthy individual, non-CD individual, non-IBD individual, UC individual, etc.). In certain other embodiments, the reference genotype corresponds to a wild-type genotype (e.g., non-variant allele or SNP) of one of the genetic markers.

In particular embodiments, the methods described herein provide a prediction that disease complications and/or surgery would occur at a rate of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) by a specific year (e.g., Year 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc.) after diagnosis based on an individual's marker levels and/or genotypes. In some instances, the individual is predicted to have about 40% to about 70% (e.g., about 40% to about 60%, about 50% to about 70%, etc.) probability of disease complications and/or surgery by about 10 years after being diagnosed with CD. In other instances, the individual is predicted to have about 70% to about 90% probability of disease complications and/or surgery by about 20 years after being diagnosed with CD. In further instances, the individual is predicted to have about 80% to about 100% probability of disease complications and/or surgery by about 30 years after being diagnosed with CD.

In other embodiments, the methods of the present invention can further comprise recommending a course of therapy for the individual based upon the comparison between the level or genotype of each of the markers and a reference level or genotype. In additional embodiments, the methods of the present invention can further comprise sending the results of the comparison to a clinician.

In a related aspect, the present invention provides a method for predicting a probability of disease complications and/or surgery in an individual diagnosed with Crohn's disease (CD), the method comprising:

(a) analyzing a sample obtained from the individual to determine the presence, level or genotype of one or more markers in the sample to obtain a marker profile;
(b) applying a statistical analysis to the marker profile to obtain a prognostic profile for the individual; and
(c) comparing the prognostic profile for the individual to a prognostic model to predict the probability of disease complications and/or surgery in an individual diagnosed with CD.

In some embodiments, the markers are selected from the serological and/or genetic markers described herein. As a non-limiting example, the serological marker can be selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof. In another embodiment, the anti-*Saccharomyces cerevisiae* antibody comprises an anti-*Saccharomyces cerevisiae* immunoglobulin A (ASCA-IgA), anti-*Saccharomyces cerevisiae* immunoglobulin G (ASCA-IgG), or a combination thereof.

In yet another embodiment, the antimicrobial antibody comprises an anti-outer membrane protein C (anti-OmpC) antibody, an anti-I2 antibody, an anti-flagellin antibody, or a combination thereof. In certain instances, the anti-flagellin antibody comprises an anti-Cbir-1 flagellin antibody, an anti-flagellin X antibody, an anti-flagellin A antibody, an anti-flagellin B antibody, or a combination thereof. In a further embodiment, the acute phase protein is C-Reactive protein (CRP). In another embodiment, the apolipoprotein is serum amyloid A (SAA). In yet another embodiment, the defensin is β defensin (e.g., β defensin-1 (BD1) and/or β defensin-2 (BD2)). In still yet another embodiment, the growth factor is epidermal growth factor (EGF). In a further embodiment, the cytokine comprises TNF-related weak inducer of apoptosis (TWEAK), IL-1β, IL-6, or a combination thereof. In an additional embodiment, the cadherin is E-cadherin. In another embodiment, the cellular adhesion molecule comprises ICAM-1, VCAM-1, or a combination thereof.

In particular embodiments, the markers comprise or consist of ASCA-IgG, ASCA-IgA, anti-OmpC antibody, anti-CBir-1 antibody, anti-I2 antibody, or a combination thereof.

In other embodiments, the genetic marker is at least one of the genes set forth in Tables 1A-1E (e.g., Table 1A, 1B, 1C, 1D, and/or 1E). In particular embodiments, the genetic marker is NOD2. The genotype of the genetic marker can be detected by genotyping an individual for the presence or absence of one or more variant alleles such as, for example, one or more SNPs in one or more genetic markers. In some embodiments, the SNP is at least one of the SNPs set forth in Tables 1B-1E (e.g., Table 1B, 1C, 1D, and/or 1E). In certain embodiments, the genetic marker is NOD2 and the SNP is SNP8 (R702W), SNP12 (G908R), and/or SNP13 (1007fs). In certain instances, the presence or absence of one or more NOD2 SNPs is determined in combination with the presence or level of one or more serological markers.

In the methods of the present invention, the presence, level, or genotype of at least two, three, four, five, six, seven, eight, nine, or ten markers can be determined. In particular embodiments, the sample is serum, plasma, whole blood, and/or stool.

The statistical analysis applied to the marker profile can comprise any of a variety of statistical methods, models, and algorithms described in Section IX below. In particular embodiments, the statistical analysis is a quartile analysis. In some instances, the quartile analysis converts the presence, level or genotype of each marker into a quartile score. As a non-limiting example, the prognostic profile can correspond to a quartile sum score (QSS) for the individual that is obtained by summing the quartile score for each of the markers.

In some embodiments, the prognostic model comprises a display, print-out, and/or report such as a look-up table or graph. In particular embodiments, the look-up table or graph provides a cumulative probability of the individual developing or not developing a Crohn's disease (CD) complication over time. In certain other embodiments, the look-up table or graph provides a cumulative probability of the individual needing surgery or not needing surgery over time. Non-limiting examples of disease complications include internal stricturing disease and/or internal penetrating disease as well as any of the other CD complications described herein.

In other embodiments, the prognostic profile is a quartile sum score (QSS) for the individual and the QSS is compared to a prognostic model (e.g., a serological model, a sero-genetic model, standardized risk scale, etc.). In certain embodiments, the individual is predicted to have a higher probability of disease complications and/or surgery when the QSS is greater than 5, 6, 7, 8, 9, 10, 11, 12, 13, 14, 15, 16, 17, 18, 19, 20, 21, 22, 23, 24, etc. (e.g., preferably greater than 10).

In particular embodiments, the methods described herein provide a prediction that disease complications and/or surgery would occur at a rate of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) by a specific year (e.g., Year 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc.) after diagnosis based on an individual's prognostic profile, such as, e.g., the individual's QSS, optionally in combination with the presence or absence of one or more variant alleles in one or more genetic markers, e.g., NOD2. In some instances, the individual is predicted to have about 40% to about 70% (e.g., about 40% to about 60%, about 50% to about 70%, etc.) probability of disease complications and/or surgery by about 10 years after being diagnosed with CD when the QSS is greater than 10. In other instances, the individual is predicted to have about 70% to about 90% probability of disease complications and/or surgery by about 20 years after being diagnosed with CD when the QSS is greater than 10. In further instances, the individual is predicted to have about 80% to about 100% probability of disease complications and/or surgery by about 30 years after being diagnosed with CD when the QSS is greater than 10.

In yet other embodiments, the methods of the present invention can further comprise recommending a course of therapy for the individual based upon the comparison between the prognostic profile and the prognostic model. In additional embodiments, the methods of the present invention can further comprise sending the results of the comparison to a clinician.

In another aspect, the present invention provides a method for aiding in the diagnosis of inflammatory bowel disease (IBD), the method comprising:

(a) analyzing a sample obtained from the individual to determine the level or genotype of one or more markers in the sample; and (b) comparing the level or genotype of each of the markers to a reference level or genotype to aid in the diagnosis of IBD.

In some embodiments, the markers are selected from the serological and/or genetic markers described herein. As a non-limiting example, the serological marker can be selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof. In another embodiment, the anti-*Saccharomyces cerevisiae* antibody comprises an anti-*Saccharomyces cerevisiae* immunoglobulin A (ASCA-IgA), anti-*Saccharomyces cerevisiae* immunoglobulin G (ASCA-IgG), or a combination thereof.

In yet another embodiment, the antimicrobial antibody comprises an anti-outer membrane protein C (anti-OmpC) antibody, an anti-I2 antibody, an anti-flagellin antibody, or a combination thereof. In certain instances, the anti-flagellin antibody comprises an anti-Cbir-1 flagellin antibody, an anti-flagellin X antibody, an anti-flagellin A antibody, an anti-flagellin B antibody, or a combination thereof. In a further embodiment, the acute phase protein is C-Reactive protein (CRP). In another embodiment, the apolipoprotein is serum amyloid A (SAA). In yet another embodiment, the defensin is β defensin (e.g., β defensin-1 (BD1) and/or β defensin-2 (BD2)). In still yet another embodiment, the growth factor is epidermal growth factor (EGF). In a further embodiment, the cytokine comprises TNF-related weak inducer of apoptosis (TWEAK), IL-1β, IL-6, or a combination thereof. In an additional embodiment, the cadherin is E-cadherin. In another embodiment, the cellular adhesion molecule comprises ICAM-1, VCAM-1, or a combination thereof.

In other embodiments, the genetic marker is at least one of the genes set forth in Tables 1A-1E (e.g., Table 1A, 1B, 1C, 1D, and/or 1E). In particular embodiments, the genetic marker is NOD2. The genotype of the genetic marker can be detected by genotyping an individual for the presence or absence of one or more variant alleles such as, for example, one or more SNPs in one or more genetic markers. In some embodiments, the SNP is at least one of the SNPs set forth in Tables 1B-1E (e.g., Table 1B, 1C, 1D, and/or 1E). In certain embodiments, the genetic marker is NOD2 and the SNP is SNP8 (R702W), SNP12 (G908R), and/or SNP13 (1007fs). In certain instances, the presence or absence of one or more NOD2 SNPs is determined in combination with the presence or level of one or more serological markers.

In the methods of the present invention, the presence, level, or genotype of at least two, three, four, five, six, seven, eight, nine, or ten markers can be determined. In particular embodiments, the sample is serum, plasma, whole blood, and/or stool.

In certain embodiments, the reference (concentration) level corresponds to a (concentration) level of one of the markers in a sample from an individual not having IBD (e.g., healthy individual, non-IBD individual, non-CD individual, non-UC individual, etc.). In certain other embodiments, the reference genotype corresponds to a wild-type genotype (e.g., non-variant allele or SNP) of one of the genetic markers.

In particular embodiments, the methods described herein provide a probability of IBD (or a clinical subtype thereof) of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) based on an individual's marker levels and/or genotypes.

In other embodiments, the methods of the present invention can further comprise recommending a course of therapy for the individual based upon the comparison between the level or genotype of each of the markers and a reference level or genotype. In additional embodiments, the methods of the present invention can further comprise sending the results of the comparison to a clinician.

In a related aspect, the present invention provides a method for aiding in the diagnosis of inflammatory bowel disease (IBD), the method comprising:

(a) analyzing a sample obtained from the individual to determine the presence, level or genotype of one or more markers in the sample to obtain a marker profile; and (b) applying a statistical analysis to the marker profile to aid in the diagnosis of IBD.

In some embodiments, the markers are selected from the serological and/or genetic markers described herein. As a non-limiting example, the serological marker can be selected from the group consisting of an anti-neutrophil antibody, an anti-*Saccharomyces cerevisiae* antibody, an antimicrobial antibody, an acute phase protein, an apolipoprotein, a defensin, a growth factor, a cytokine, a cadherin, a cellular adhesion molecule, and a combination thereof. In one embodiment, the anti-neutrophil antibody comprises an anti-neutrophil cytoplasmic antibody (ANCA) such as ANCA detected by an immunoassay (e.g., ELISA), a perinuclear anti-neutrophil cytoplasmic antibody (pANCA) such as pANCA detected by an immunohistochemical assay (e.g., IFA) or a DNAse-sensitive immunohistochemical assay, or a combination thereof. In another embodiment, the anti-*Saccharomyces cerevisiae* antibody comprises an anti-*Saccharomyces cerevisiae* immunoglobulin A (ASCA-IgA), anti-*Saccharomyces cerevisiae* immunoglobulin G (ASCA-IgG), or a combination thereof.

In yet another embodiment, the antimicrobial antibody comprises an anti-outer membrane protein C (anti-OmpC) antibody, an anti-I2 antibody, an anti-flagellin antibody, or a combination thereof. In certain instances, the anti-flagellin antibody comprises an anti-Cbir-1 flagellin antibody, an anti-flagellin X antibody, an anti-flagellin A antibody, an anti-flagellin B antibody, or a combination thereof. In a further embodiment, the acute phase protein is C-Reactive protein (CRP). In another embodiment, the apolipoprotein is serum amyloid A (SAA). In yet another embodiment, the defensin is β defensin (e.g., β defensin-1 (BD1) and/or β defensin-2 (BD2)). In still yet another embodiment, the growth factor is epidermal growth factor (EGF). In a further embodiment, the cytokine comprises TNF-related weak inducer of apoptosis (TWEAK), IL-1β, IL-6, or a combination thereof. In an additional embodiment, the cadherin is E-cadherin. In another embodiment, the cellular adhesion molecule comprises ICAM-1, VCAM-1, or a combination thereof.

In other embodiments, the genetic marker is at least one of the genes set forth in Tables 1A-1E (e.g., Table 1A, 1B, 1C, 1D, and/or 1E). In particular embodiments, the genetic marker is NOD2. The genotype of the genetic marker can be detected by genotyping an individual for the presence or absence of one or more variant alleles such as, for example, one or more SNPs in one or more genetic markers. In some embodiments, the SNP is at least one of the SNPs set forth in Tables 1B-1E (e.g., Table 1B, 1C, 1D, and/or 1E). In certain embodiments, the genetic marker is NOD2 and the SNP is SNP8 (R702W), SNP12 (G908R), and/or SNP13 (1007fs). In certain instances, the presence or absence of one or more NOD2 SNPs is determined in combination with the presence or level of one or more serological markers.

In the methods of the present invention, the presence, level, or genotype of at least two, three, four, five, six, seven, eight, nine, or ten markers can be determined. In particular embodiments, the sample is serum, plasma, whole blood, and/or stool.

The statistical analysis applied to the marker profile can comprise any of a variety of statistical methods, models, and algorithms described in Section IX below. In particular embodiments, the statistical analysis is a quartile analysis. In some instances, the quartile analysis converts the presence, level or genotype of each marker into a quartile score. As a non-limiting example, the diagnosis of IBD can be made based upon a quartile sum score (QSS) for the individual that is obtained by summing the quartile score for each of the markers. In other embodiments, the statistical analysis comprises one or more learning statistical classifier systems as described herein. In particular embodiments, the statistical analysis comprises a combination of at least two learning statistical classifier systems. A non-limiting example of such a combination includes a decision/classification tree (e.g., a classification and regression tree (C&RT), a random forest, etc.) and a neural network, e.g., applied in tandem. In certain instances, the methods comprise applying a first statistical analysis (e.g., a decision/classification tree) to the presence, level, or genotype determined for each of the markers to generate a prediction or probability value, and then applying a second statistical analysis (e.g., a neural network) to the prediction or probability value and the presence, level, or genotype determined for each of the markers to aid in the diagnosis of IBD (e.g., by classifying the sample as an IBD sample or non-IBD sample).

In certain embodiments, the methods further comprise comparing the results from the statistical analysis (i.e., diagnostic profile) to a reference (i.e., diagnostic model) to aid in the diagnosis of IBD. In some instances, the diagnostic model comprises a display, print-out, and/or report such as a look-up table or graph. In other instances, the diagnostic profile is a quartile sum score (QSS) for the individual and the QSS is compared to a diagnostic model. In some embodiments, the individual is predicted to have a higher probability of having IBD when the QSS is greater than 5, 6, 7, 8, 9, 10, 11, 12, 13, 14, 15, 16, 17, 18, 19, 20, 21, 22, 23, 24, etc.

In particular embodiments, the methods described herein provide a probability of IBD (or a clinical subtype thereof) of (at least) about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range therein) based on an individual's diagnostic profile, such as, e.g., the individual's QSS, optionally in combination with the presence or absence of one or more variant alleles in one or more genetic markers, e.g., NOD2.

In some embodiments, the methods of the present invention can further comprise recommending a course of therapy for the individual based upon the statistical analysis or comparison between the diagnostic profile and the diagnostic model. In other embodiments, the methods of the present invention can further comprise sending the results of the statistical analysis or comparison to a clinician.

IV. Clinical Subtypes of IBD

Inflammatory bowel disease (IBD) is a group of inflammatory conditions of the large intestine and small intestine. The main forms of IBD are Crohn's disease (CD) and ulcerative colitis (UC). Other less common forms of IBD include, e.g., indeterminate colitis (IC), collagenous colitis, lymphocytic colitis, ischemic colitis, diversion colitis, Behçet's syndrome, infective colitis, and the like. U.S. Patent Publication 20080131439, entitled "Methods of Diagnosing Inflammatory Bowel Disease" is incorporated herein by reference for all purposes.

A. Crohn's Disease

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

Crohn's disease may be categorized by the behavior of disease as it progresses. This was formalized in the Vienna classification of Crohn's disease. See, Gasche et al., *Inflamm. Bowel Dis.,* 6:8-15 (2000). There are three categories of disease presentation in Crohn's disease: (1) stricturing, (2) penetrating, and (3) inflammatory. Stricturing disease causes narrowing of the bowel which may lead to bowel obstruction or changes in the caliber of the feces. Penetrating disease creates abnormal passageways (fistulae) between the bowel and other structures such as the skin. Inflammatory disease (also known as non-stricturing, non-penetrating disease) causes inflammation without causing strictures or fistulae.

As such, Crohn's disease represents a number of heterogeneous disease subtypes that affect the gastrointestinal tract and may produce similar symptoms. As used herein in reference to CD, the term "clinical subtype" includes a classification of CD defined by a set of clinical criteria that distinguish one classification of CD from another. As non-limiting examples, subjects with CD can be classified as having stricturing (e.g., internal stricturing), penetrating (e.g., internal penetrating), or inflammatory disease as described herein, or these subjects can additionally or alternatively be classified as having fibrostenotic disease, small bowel disease, internal perforating disease, perianal fistulizing disease, UC-like disease, the need for small bowel surgery, the absence of features of UC, or combinations thereof.

In certain instances, subjects with CD can be classified as having complicated CD, which is a clinical subtype characterized by stricturing or penetrating phenotypes. In certain other instances, subjects with CD can be classified as having a form of CD characterized by one or more of the following complications: fibrostenosis, internal perforating disease, and the need for small bowel surgery. In further instances, subjects with CD can be classified as having an aggressive form of fibrostenotic disease requiring small bowel surgery. Criteria relating to these subtypes have been described, for example, in Gasche et al., *Inflamm. Bowel Dis.,* 6:8-15 (2000); Abreu et al., *Gastroenterology,* 123:679-688 (2002); Vasiliauskas et al., *Gut,* 47:487-496 (2000); Vasiliauskas et al., *Gastroenterology,* 110:1810-1819 (1996); and Greenstein et al., *Gut,* 29:588-592 (1988).

The "fibrostenotic subtype" of CD is a classification of CD characterized by one or more accepted characteristics of fibrostenosing disease. Such characteristics of fibrostenosing disease include, but are not limited to, documented persistent intestinal obstruction or an intestinal resection for an intestinal obstruction. The fibrostenotic subtype of CD can be accompanied by other symptoms such as perforations, abscesses, or fistulae, and can further be characterized by persistent symptoms of intestinal blockage such as nausea, vomiting, abdominal distention, and inability to eat solid food. Intestinal X-rays of patients with the fibrostenotic subtype of CD can show, for example, distention of the bowel before the point of blockage.

The requirement for small bowel surgery in a subject with the fibrostenotic subtype of CD can indicate a more aggressive form of this subtype. Additional subtypes of CD are also known in the art and can be identified using defined clinical criteria. For example, internal perforating disease is a clinical subtype of CD defined by current or previous evidence of entero-enteric or entero-vesicular fistulae, intra-abdominal abscesses, or small bowel perforation. Perianal perforating disease is a clinical subtype of CD defined by current or previous evidence of either perianal fistulae or abscesses or rectovaginal fistula. The UC-like clinical subtype of CD can be defined by current or previous evidence of left-sided colonic involvement, symptoms of bleeding or urgency, and crypt abscesses on colonic biopsies. Disease location can be classified based on one or more endoscopic, radiologic, or pathologic studies.

One skilled in the art understands that overlap can exist between clinical subtypes of CD and that a subject having CD can have more than one clinical subtype of CD. For example, a subject having CD can have the fibrostenotic subtype of CD and can also meet clinical criteria for a clinical subtype characterized by the need for small bowel surgery or the internal perforating disease subtype. Similarly, the markers described herein can be associated with more than one clinical subtype of CD.

B. Ulcerative Colitis

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra).

In certain instances, with respect to UC, the variability of symptoms reflect differences in the extent of disease (i.e., the amount of the colon and rectum that are inflamed) and the intensity of inflammation. Disease starts at the rectum and moves "up" the colon to involve more of the organ. UC can be categorized by the amount of colon involved. Typically, patients with inflammation confined to the rectum and a short segment of the colon adjacent to the rectum have milder symptoms and a better prognosis than patients with more widespread inflammation of the colon.

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

The different types of ulcerative colitis are classified according to the location and the extent of inflammation. As used herein in reference to UC, the term "clinical subtype" includes a classification of UC defined by a set of clinical criteria that distinguish one classification of UC from another. As non-limiting examples, subjects with UC can be classified as having ulcerative proctitis, proctosigmoiditis, left-sided colitis, pancolitis, fulminant colitis, and combinations thereof. Criteria relating to these subtypes have been described, for example, in Kornbluth et al., *Am. J. Gastroenterol.,* 99: 1371-85 (2004).

Ulcerative proctitis is a clinical subtype of UC defined by inflammation that is limited to the rectum. Proctosigmoiditis is a clinical subtype of UC which affects the rectum and the sigmoid colon. Left-sided colitis is a clinical subtype of UC which affects the entire left side of the colon, from the rectum to the place where the colon bends near the spleen and begins to run across the upper abdomen (the splenic flexure). Pancolitis is a clinical subtype of UC which affects the entire colon. Fulminant colitis is a rare, but severe form of pancolitis. Patients with fulminant colitis are extremely ill with dehydration, severe abdominal pain, protracted diarrhea with bleeding, and even shock.

In some embodiments, classification of the clinical subtype of UC is important in planning an effective course of treatment. While ulcerative proctitis, proctosigmoiditis, and left-sided colitis can be treated with local agents introduced through the anus, including steroid-based or other enemas and foams, pancolitis must be treated with oral medication so that active ingredients can reach all of the affected portions of the colon.

One skilled in the art understands that overlap can exist between clinical subtypes of UC and that a subject having UC can have more than one clinical subtype of UC. Similarly, the prognostic markers described herein can be associated with more than one clinical subtype of UC.

C. Indeterminate Colitis

Indeterminate colitis (IC) is a clinical subtype of IBD that includes both features of CD and UC. Such an overlap in the symptoms of both diseases can occur temporarily (e.g., in the early stages of the disease) or persistently (e.g., throughout the progression of the disease) in patients with IC. Clinically, IC is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with IC.

V. IBD Markers

A variety of IBD markers, including biochemical markers, serological markers, protein markers, genetic markers, and other clinical or echographic characteristics, are suitable for use in the methods of the present invention for diagnosing IBD, prognosing the future outcome of the disease, and predicting the response to therapy with therapeutic agents such as biologics. In certain aspects, the diagnostic and prognostic methods described herein utilize the application of an algorithm (e.g., statistical analysis) to the presence, concentration level, or genotype determined for one or more of the IBD markers to aid or assist in diagnosis of IBD or to provide a prognosis regarding the progression of the disease (e.g., the probability of developing complicated CD or requiring small bowel surgery at a future point in time).

Non-limiting examples of IBD markers include: (i) biochemical, serological, and protein markers such as, e.g., cytokines, growth factors, anti-neutrophil antibodies, anti-

*Saccharomyces cerevisiae* antibodies, antimicrobial antibodies, acute phase proteins, apolipoproteins, defensins, cadherins, cellular adhesion molecules, and combinations thereof; and (ii) genetic markers such as, e.g., any of the genes set forth in Tables 1A-1E (e.g., NOD2) and the miRNAs in Table 2.

A. Cytokines

The determination of the presence or level of at least one cytokine in a sample is particularly useful in the present invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, for example, in the regulation of body weight, hematopoiesis, angiogenesis, wound healing, insulin resistance, the immune response, and the inflammatory response.

In certain aspects, the presence or level of at least one cytokine including, but not limited to, TNF-α, TNF-related weak inducer of apoptosis (TWEAK), osteoprotegerin (OPG), IFN-α, IFN-β, IFN-γ, IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27 is determined in a sample. In certain other aspects, the presence or level of at least one chemokine such as, for example, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and $CX_3CL1$ is determined in a sample. In certain further aspects, the presence or level of at least one adipocytokine including, but not limited to, leptin, adiponectin, resistin, active or total plasminogen activator inhibitor-1 (PAI-1), visfatin, and retinol binding protein 4 (RBP4) is determined in a sample. Preferably, the presence or level of IL-6, IL-1β, and/or TWEAK is determined.

In certain instances, the presence or level of a particular cytokine is detected at the level of mRNA expression with an assay such as, for example, a hybridization assay or an amplification-based assay. In certain other instances, the presence or level of a particular cytokine is detected at the level of protein expression using, for example, an immunoassay (e.g., ELISA) or an immunohistochemical assay. Suitable ELISA kits for determining the presence or level of a cytokine such as IL-6, IL-1β, or TWEAK in a serum, plasma, saliva, or urine sample are available from, e.g., R&D Systems, Inc. (Minneapolis, Minn.), Neogen Corp. (Lexington, Ky.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.).

The human IL-6 polypeptide sequence is set forth in, e.g., Genbank Accession No. NP_000591 (SEQ ID NO:1). The human IL-6 mRNA (coding) sequence is set forth in, e.g., Genbank Accession No. NM_000600 (SEQ ID NO:2). One skilled in the art will appreciate that IL-6 is also known as interferon beta 2 (IFNB2), HGF, HSF, and BSF2.

The human IL-1β polypeptide sequence is set forth in, e.g., Genbank Accession No. NP_000567 (SEQ ID NO:3). The human IL-1β mRNA (coding) sequence is set forth in, e.g., Genbank Accession No. NM_000576 (SEQ ID NO:4). One skilled in the art will appreciate that IL-1β is also known as IL1F2 and IL-1beta.

The human TWEAK polypeptide sequence is set forth in, e.g., Genbank Accession Nos. NP_003800 (SEQ ID NO:5) and AAC51923. The human TWEAK mRNA (coding) sequence is set forth in, e.g., Genbank Accession Nos. NM_003809 (SEQ ID NO:6) and BC104420. One skilled in the art will appreciate that TWEAK is also known as tumor necrosis factor ligand superfamily member 12 (TNFSF12), APO3 ligand (APO3L), CD255, DR3 ligand, growth factor-inducible 14 (Fn14) ligand, and UNQ181/PRO207.

B. Growth Factors

The determination of the presence or level of one or more growth factors in a sample is also useful in the present invention. As used herein, the term "growth factor" includes any of a variety of peptides, polypeptides, or proteins that are capable of stimulating cellular proliferation and/or cellular differentiation.

In certain aspects, the presence or level of at least one growth factor including, but not limited to, epidermal growth factor (EGF), heparin-binding epidermal growth factor (HB-EGF), vascular endothelial growth factor (VEGF), pigment epithelium-derived factor (PEDF; also known as SERPINF1), amphiregulin (AREG; also known as schwannoma-derived growth factor (SDGF)), basic fibroblast growth factor (bFGF), hepatocyte growth factor (HGF), transforming growth factor-α (TGF-α), transforming growth factor-β (TGF-β), bone morphogenetic proteins (e.g., BMP1-BMP15), platelet-derived growth factor (PDGF), nerve growth factor (NGF), β-nerve growth factor (β-NGF), neurotrophic factors (e.g., brain-derived neurotrophic factor (BDNF), neurotrophin 3 (NT3), neurotrophin 4 (NT4), etc.), growth differentiation factor-9 (GDF-9), granulocyte-colony stimulating factor (G-CSF), granulocyte-macrophage colony stimulating factor (GM-CSF), myostatin (GDF-8), erythropoietin (EPO), and thrombopoietin (TPO) is determined in a sample. Preferably, the presence or level of EGF is determined.

In certain instances, the presence or level of a particular growth factor is detected at the level of mRNA expression with an assay such as, for example, a hybridization assay or an amplification-based assay. In certain other instances, the presence or level of a particular growth factor is detected at the level of protein expression using, for example, an immunoassay (e.g., ELISA) or an immunohistochemical assay. Suitable ELISA kits for determining the presence or level of a growth factor such as EGF in a serum, plasma, saliva, or urine sample are available from, e.g., Antigenix America Inc. (Huntington Station, N.Y.), Promega (Madison, Wis.), R&D Systems, Inc. (Minneapolis, Minn.), Invitrogen (Camarillo, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

The human epidermal growth factor (EGF) polypeptide sequence is set forth in, e.g., Genbank Accession No. NP_001954 (SEQ ID NO:7). The human EGF mRNA (coding) sequence is set forth in, e.g., Genbank Accession No. NM_001963 (SEQ ID NO:8). One skilled in the art will appreciate that EGF is also known as beta-urogastrone, URG, and HOMG4.

C. Anti-Neutrophil Antibodies

The determination of ANCA levels and/or the presence or absence of pANCA in a sample is also useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G.

ANCA levels in a sample from an individual can be determined, for example, using an immunoassay such as an enzyme-linked immunosorbent assay (ELISA) with alcohol-fixed neutrophils (see, e.g., Example 1). The presence or absence of a particular category of ANCA such as pANCA can be determined, for example, using an immunohistochemical assay such as an indirect fluorescent antibody (IFA) assay. In certain embodiments, the presence or absence of pANCA in a sample is determined using an immunofluorescence assay with DNase-treated, fixed neutrophils (see, e.g., Example 2). In addition to fixed neutrophils, antibodies directed against human antibodies can be used for detection. Antigens specific for ANCA are also suitable for determining ANCA levels, including, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, Bacteroides antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

D. Anti-*Saccharomyces cerevisiae* Antibodies

The determination of the presence or level of ASCA (e.g., ASCA-IgA, ASCA-IgG, ASCA-IgM, etc.) in a sample is also useful in the present invention. The term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA-IgG" includes antibodies of the immunoglobulin G isotype that react specifically with *S. cerevisiae*.

The determination of whether a sample is positive for ASCA-IgA or ASCA-IgG is made using an antibody specific for human antibody sequences or an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosachharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man β(1-2) D-Man β(1-2) D-Man β(1-2) D-Man-OR, D-Man α(1-2) D-Man α(1-2) D-Man α(1-2) D-Man-OR, and D-Man α(1-3) D-Man α(1-2) D-Man α(1-2) D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction technique known in the art, including, for example, by autoclaving, or can be obtained commercially (see, e.g., Lindberg et al., *Gut,* 33:909-913 (1992)). The acid-stable fraction of PPM is also useful in the statistical algorithms of the present invention (Sendid et al., *Clin. Diag. Lab. Immunol.,* 3:219-226 (1996)). An exemplary PPM that is useful in determining ASCA levels in a sample is derived from *S. uvarum* strain ATCC #38926. Example 3 describes the preparation of yeast cell well mannan and an analysis of ASCA levels in a sample using an ELISA assay.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.,* 11:438-446 (1992). One skilled in the art understands that the reactivity of such an oligomannoside antigen with ASCA can be optimized by varying the mannosyl chain length (Frosh et al., *Proc Natl. Acad. Sci. USA,* 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.,* 34:825-840 (1990); Poulain et al., *Eur. J. Clin. Microbiol.,* 23:46-52 (1993); Shibata et al., *Arch. Biochem. Biophys.,* 243:338-348 (1985); Trinel et al., *Infect. Immun.,* 60:3845-3851 (1992)); or the position of the linkage (Kikuchi et al., *Planta,* 190:525-535 (1993)).

Suitable oligomannosides for use in the methods of the present invention include, without limitation, an oligomannoside having the mannotetraose Man(1-3) Man(1-2) Man (1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

E. Anti-Microbial Antibodies

The determination of the presence or level of anti-OmpC antibody in a sample is also useful in the present invention. As used herein, the term "anti-outer membrane protein C antibody" or "anti-OmpC antibody" includes antibodies directed to a bacterial outer membrane porin as described in, e.g., U.S. Pat. No. 7,138,237 and PCT Patent Publication No. WO 01/89361. The term "outer membrane protein C" or "OmpC" refers to a bacterial porin that is immunoreactive with an anti-OmpC antibody.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display. Example 4 describes the preparation of OmpC protein and an analysis of anti-OmpC antibody levels in a sample using an ELISA assay.

The determination of the presence or level of anti-I2 antibody in a sample is also useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The microbial I2 protein is a polypeptide of 100 amino acids sharing some similarity weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display. Determination of anti-I2 antibody levels in a sample can be done by using an ELISA assay (see, e.g., Examples 5, 20, and 22) or a histological assay.

The determination of the presence or level of anti-flagellin antibody in a sample is also useful in the present invention. As used herein, the term "anti-flagellin antibody" includes antibodies directed to a protein component of bacterial flagella as described in, e.g., U.S. Pat. No. 7,361,733 and PCT Patent Publication No. WO 03/053220. The term "flagellin" refers to a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Butyrivibrio fibrisolvens*, and bacterium found in the cecum, by recombinant expression of a nucleic acid encoding a flagellin antigen, by synthetic means such as solution or solid phase peptide synthesis, or by using phage display. Determination of anti-flagellin (e.g., anti-Cbir-1) antibody levels in a sample can be done by using an ELISA assay or a histological assay.

F. Acute Phase Proteins

The determination of the presence or level of one or more acute-phase proteins in a sample is also useful in the present invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein, AGP), ceruloplasmin, haptoglobin, and combinations thereof. Non-limiting examples of negative acute-phase proteins include albumin, transferrin, transthyretin, transcortin, retinol-binding protein, and combinations thereof. Preferably, the presence or level of CRP and/or SAA is determined.

In certain instances, the presence or level of a particular acute-phase protein is detected at the level of mRNA expression with an assay such as, for example, a hybridization assay or an amplification-based assay. In certain other instances, the presence or level of a particular acute-phase protein is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410. Additional methods for determining CRP levels include, e.g., immunoturbidimetry assays, rapid immunodiffusion assays, and visual agglutination assays.

C-reactive protein (CRP) is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558 (SEQ ID NO:9). The human CRP mRNA (coding) sequence is set forth in, e.g., Genbank Accession No. NM_000567 (SEQ ID NO:10). One skilled in the art will appreciate that CRP is also known as PTX1, MGC88244, and MGC149895.

G. Apolipoproteins

The determination of the presence or level of one or more apolipoproteins in a sample is also useful in the present invention. Apolipoproteins are proteins that bind to fats (lipids). They form lipoproteins, which transport dietary fats through the bloodstream. Dietary fats are digested in the intestine and carried to the liver. Fats are also synthesized in the liver itself. Fats are stored in fat cells (adipocytes). Fats are metabolized as needed for energy in the skeletal muscle, heart, and other organs and are secreted in breast milk. Apolipoproteins also serve as enzyme co-factors, receptor ligands, and lipid transfer carriers that regulate the metabolism of lipoproteins and their uptake in tissues. Examples of apolipoproteins include, but are not limited to, ApoA (e.g., ApoA-I, ApoA-II, ApoA-IV, ApoA-V), ApoB (e.g., ApoB48, ApoB100), ApoC (e.g., ApoC-I, ApoC-II, ApoC-III, ApoC-IV), ApoD, ApoE, ApoH, serum amyloid A (SAA), and combinations thereof. Preferably, the presence or level of SAA is determined.

In certain instances, the presence or level of a particular apolipoprotein is detected at the level of mRNA expression with an assay such as, for example, a hybridization assay or an amplification-based assay. In certain other instances, the presence or level of a particular apolipoprotein is detected at the level of protein expression using, for example, an immunoassay (e.g., ELISA) or an immunohistochemical assay. Suitable ELISA kits for determining the presence or level of SAA in a sample such as serum, plasma, saliva, urine, or stool are available from, e.g., Antigenix America Inc. (Huntington Station, N.Y.), Abazyme (Needham, Mass.), USCN Life (Missouri City, Tex.), and/or U.S. Biological (Swampscott, Mass.).

Serum amyloid A (SAA) proteins are a family of apolipoproteins associated with high-density lipoprotein (HDL) in plasma. Different isoforms of SAA are expressed constitutively (constitutive SAAs) at different levels or in response to inflammatory stimuli (acute phase SAAs). These proteins are predominantly produced by the liver. The conservation of these proteins throughout invertebrates and vertebrates suggests SAAs play a highly essential role in all animals. Acute phase serum amyloid A proteins (A-SAAs) are secreted during the acute phase of inflammation. The human SAA polypeptide sequence is set forth in, e.g., Genbank Accession No. NP_000322 (SEQ ID NO:11). The human SAA mRNA (coding) sequence is set forth in, e.g., Genbank Accession No. NM_000331 (SEQ ID NO:12). One skilled in the art will appreciate that SAA is also known as PIG4, TP53I4, MGC111216, and SAA1.

H. Defensins

The determination of the presence or level of one or more defensins in a sample is also useful in the present invention. Defensins are small cysteine-rich cationic proteins found in both vertebrates and invertebrates. They are active against bacteria, fungi, and many enveloped and nonenveloped viruses. They typically consist of 18-45 amino acids, including 6 (in vertebrates) to 8 conserved cysteine residues. Cells of the immune system contain these peptides to assist in killing phagocytized bacteria, for example, in neutrophil granulocytes and almost all epithelial cells. Most defensins function by binding to microbial cell membranes, and once embedded, forming pore-like membrane defects that allow efflux of essential ions and nutrients. Non-limiting examples of defensins include α-defensins (e.g., DEFA1, DEFA1A3, DEFA3, DEFA4), β-defensins (e.g., β defensin-1 (DEFB1), β defensin-2 (DEFB2), DEFB103A/DEFB103B to DEFB107A/DEFB107B, DEFB110 to DEFB133), and combinations thereof. Preferably, the presence or level of DEFB1 and/or DEFB2 is determined.

In certain instances, the presence or level of a particular defensin is detected at the level of mRNA expression with an assay such as, for example, a hybridization assay or an amplification-based assay. In certain other instances, the presence or level of a particular defensin is detected at the level of protein expression using, for example, an immunoassay (e.g., ELISA) or an immunohistochemical assay. Suitable ELISA kits for determining the presence or level of DEFB1 and/or DEFB2 in a sample such as serum, plasma, saliva, urine, or stool are available from, e.g., Alpco Diagnostics (Salem, N.H.), Antigenix America Inc. (Huntington Station, N.Y.), PeproTech (Rocky Hill, N.J.), and/or Alpha Diagnostic Intl. Inc. (San Antonio, Tex.).

β-defensins are antimicrobial peptides implicated in the resistance of epithelial surfaces to microbial colonization. They are the most widely distributed of all defensins, being secreted by leukocytes and epithelial cells of many kinds. For example, they can be found on the tongue, skin, cornea, salivary glands, kidneys, esophagus, and respiratory tract. The human DEFB1 polypeptide sequence is set forth in, e.g., Genbank Accession No. NP_005209 (SEQ ID NO:13). The human DEFB1 mRNA (coding) sequence is set forth in, e.g., Genbank Accession No. NM_005218 (SEQ ID NO:14). One skilled in the art will appreciate that DEFB1 is also known as BD1, HBD1, DEFB-1, DEFB101, and MGC51822. The human DEFB2 polypeptide sequence is set forth in, e.g., Genbank Accession No. NP_004933 (SEQ ID NO:15). The human DEFB2 mRNA (coding) sequence is set forth in, e.g., Genbank Accession No. NM_004942 (SEQ ID NO:16). One skilled in the art will appreciate that DEFB2 is also known as SAP1, HBD-2, DEFB-2, DEFB102, and DEFB4.

I. Cadherins

The determination of the presence or level of one or more cadherins in a sample is also useful in the present invention. Cadherins are a class of type-1 transmembrane proteins which play important roles in cell adhesion, ensuring that cells within tissues are bound together. They are dependent on calcium ($Ca^{2+}$) ions to function. The cadherin superfamily includes cadherins, protocadherins, desmogleins, and desmocollins, and more. In structure, they share cadherin repeats, which are the extracellular $Ca^{2+}$-binding domains. Cadherins suitable for use in the present invention include, but are not limited to, CDH1—E-cadherin (epithelial), CDH2—N-cadherin (neural), CDH12—cadherin 12, type 2 (N-cadherin 2), CDH3—P-cadherin (placental), CDH4—R-cadherin (retinal), CDH5—VE-cadherin (vascular endothelial), CDH6—K-cadherin (kidney), CDH7—cadherin 7, type 2, CDH8—cadherin 8, type 2, CDH9—cadherin 9, type 2 (T1-cadherin), CDH10—cadherin 10, type 2 (T2-cadherin), CDH11—OB-cadherin (osteoblast), CDH13—T-cadherin—H-cadherin (heart), CDH15—M-cadherin (myotubule), CDH16—KSP-cadherin, CDH17—LI cadherin (liver-intestine), CDH18—cadherin 18, type 2, CDH19—cadherin 19, type 2, CDH20—cadherin 20, type 2, and CDH23—cadherin 23, (neurosensory epithelium). Preferably, the presence or level of E-cadherin is determined.

In certain instances, the presence or level of a particular cadherin is detected at the level of mRNA expression with an assay such as, for example, a hybridization assay or an amplification-based assay. In certain other instances, the presence or level of a particular cadherin is detected at the level of protein expression using, for example, an immunoassay (e.g., ELISA) or an immunohistochemical assay. Suitable ELISA kits for determining the presence or level of E-cadherin in a sample such as serum, plasma, saliva, urine, or stool are available from, e.g., R&D Systems, Inc. (Minneapolis, Minn.) and/or GenWay Biotech, Inc. (San Diego, Calif.).

E-cadherin is a classical cadherin from the cadherin superfamily. It is a calcium dependent cell-cell adhesion glycoprotein comprised of five extracellular cadherin repeats, a transmembrane region, and a highly conserved cytoplasmic tail. The ectodomain of E-cadherin mediates bacterial adhesion to mammalian cells and the cytoplasmic domain is required for internalization. The human E-cadherin polypeptide sequence is set forth in, e.g., Genbank Accession No. NP_004351 (SEQ ID NO:17). The human E-cadherin mRNA (coding) sequence is set forth in, e.g., Genbank Accession No. NM_004360 (SEQ ID NO:18). One skilled in the art will appreciate that E-cadherin is also known as UVO, CDHE, ECAD, LCAM, Arc-1, CD324, and CDH1.

J. Cellular Adhesion Molecules (IgSF CAMs)

The determination of the presence or level of one or more immunoglobulin superfamily cellular adhesion molecules in a sample is also useful in the present invention. As used herein, the term "immunoglobulin superfamily cellular adhesion molecule" (IgSF CAM) includes any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include Neural Cell Adhesion Molecules (NCAMs; e.g., NCAM-120, NCAM-125, NCAM-140, NCAM-145, NCAM-180, NCAM-185, etc.), Intercellular Adhesion Molecules (ICAMs, e.g., ICAM-1, ICAM-2, ICAM-3, ICAM-4, and ICAM-5), Vascular Cell Adhesion Molecule-1 (VCAM-1), Platelet-Endothelial Cell Adhesion Molecule-1 (PECAM-1), L1 Cell Adhesion Molecule (L1CAM), cell adhesion molecule with homology to L1CAM (close homolog of L1) (CHL1), sialic acid binding Ig-like lectins (SIGLECs; e.g., SIGLEC-1, SIGLEC-2, SIGLEC-3, SIGLEC-4, etc.), Nectins (e.g., Nectin-1, Nectin-2, Nectin-3, etc.), and Nectin-like molecules (e.g., Necl-1, Necl-2, Necl-3, Necl-4, and Necl-5). Preferably, the presence or level of ICAM-1 and/or VCAM-1 is determined.

1. Intercellular Adhesion Molecule-1 (ICAM-1)

ICAM-1 is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1 and VCAM-1. The increased expression of adhesion molecules recruit more lymphocytes to the infected tissue, resulting in tissue inflammation (see, Goke et al., *J., Gastroenterol.,* 32:480 (1997); and Rijcken et al., *Gut,* 51:529 (2002)). ICAM-1 is encoded by the intercellular adhesion molecule 1 gene (ICAM1; Entrez GeneID:3383; Genbank Accession No. NM_000201 (SEQ ID NO:19)) and is produced after processing of the intercellular adhesion molecule 1 precursor polypeptide (Genbank Accession No. NP_000192 (SEQ ID NO:20)).

2. Vascular Cell Adhesion Molecule-1 (VCAM-1)

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1; SEQ ID NO:21) or NM_080682 (variant 2)), and processing of the precursor polypeptide splice isoform (Genbank Accession No. NP_001069 (isoform a; SEQ ID NO:22) or NP 542413 (isoform b)).

In certain instances, the presence or level of an IgSF CAM is detected at the level of mRNA expression with an assay such as, for example, a hybridization assay or an amplification-based assay. In certain other instances, the presence or level of an IgSF CAM is detected at the level of protein expression using, for example, an immunoassay (e.g., ELISA) or an immunohistochemical assay. Suitable antibodies and/or ELISA kits for determining the presence or level of ICAM-1 and/or VCAM-1 in a sample such as a tissue sample, biopsy, serum, plasma, saliva, urine, or stool are available from, e.g., Invitrogen (Camarillo, Calif.), Santa Cruz Biotechnology, Inc. (Santa Cruz, Calif.), and/or Abcam Inc. (Cambridge, Mass.).

K. Genetic Markers

The determination of the presence or absence of allelic variants in one or more genetic markers in a sample is also useful in the present invention. Non-limiting examples of genetic markers include, but are not limited to, any of the genes set forth in Tables 1A-1E (e.g., a NOD2/CARD15 gene, an IL12/IL23 pathway gene, etc.). Preferably, the presence or absence of at least one single nucleotide polymorphism (SNP) in the NOD2/CARD15 gene and/or one or more genes in the IL12/IL23 pathway is determined. See, e.g., Barrett et al., *Nat. Genet.,* 40:955-62 (2008) and Wang et al., *Amer. J. Hum. Genet.,* 84:399-405 (2009).

Table 1A provides an exemplary list of IBD, UC, and CD genes wherein genotyping for the presence or absence of one or more allelic variants (e.g., SNPs) therein is useful in the diagnostic and prognostic methods of the present invention. Table 1B provides additional exemplary genetic markers and corresponding SNPs that can be genotyped in accordance with the IBD diagnostic and prognostic methods of the present invention. Tables 1C-1E provide additional exemplary IBD, UC, and CD genetic markers and corresponding SNPs that can be genotyped in accordance with the diagnostic and prognostic methods described herein.

TABLE 1A

IBD, CD & UC Genes

| IBD Genes (CD & UC) | Colonic IBD Genes | UC Genes | CD Genes |
|---|---|---|---|
| IL23R | HLA regions | ECM1 | NOD2 |
| IL12B/p40 | | IL10 | ATG16L1 |
| JAK2 | | IFNg | IRGM |
| STAT3 | | IL22 | NLRP3 |
| NKX2.3 | | IL26 | 5p13/PTGER4 |
| 3p21/MST1 | | OTUD3 | PTPN2 |
| CCNY | | PLA2G2E | TNFSF15 (TL1A) |
| IL18RAP | | ARPC2 | IBD5/5q31 |
| LYRM4 | | | ZNF365 |
| CDKAL4 | | | PTPN22 |
| TNFRSF6B | | | CCR6 |
| PSMG1 | | | LRRK2 |
| | | | ICOSLG |
| | | | ITLN1 |
| | | | ORMDL3 |

TABLE 1B

IBD, CD & UC Genes & SNPs

| Gene | SNP |
|---|---|
| NOD2/CARD15 | rs2066847 |
| IL23R | rs11465804 |
| ATG16L1 | rs3828309 |
| MST1 | rs3197999 |
| PTGER4 | rs4613763 |
| IRGM | rs11747270 |
| TNFSF15 | rs4263839 |
| ZNF365 | rs10995271 |
| NKX2-3 | rs11190140 |
| PTPN2 | rs2542151 |
| PTPN22 | rs2476601 |
| ITLN1 | rs2274910 |
| IL12B | rs10045431 |
| CDKAL1 | rs6908425 |
| CCR6 | rs2301436 |
| JAK2 | rs10758669 |
| C11orf30 | rs7927894 |
| LRRK2, MUC19 | rs11175593 |
| ORMDL3 | rs2872507 |
| STAT3 | rs744166 |
| ICOSLG | rs762421 |
| GCKR | rs780094 |
| BTNL2, SLC26A3, HLA-DRB1, HLA-DQA1 | rs3763313 |
| PUS10 | rs13003464 |
| CCL2, CCL7 | rs991804 |
| LYRM4 | rs12529198 |
| SLC22A23 | rs17309827 |
| IL18RAP | rs917997 |
| IL12RB2 | rs7546245 |
| IL12RB1 | rs374326 |
| CD3D | rs3212262 |
| CD3G | rs3212262 |
| CD247 | rs704853 |
| JUN | rs6661505 |
| CD3E | rs7937334 |
| IL18R1 | rs1035127 |
| CCR5 | |
| MAPK14 | rs2237093 |
| IL18 | rs11214108 |
| IFNG | rs10878698 |

TABLE 1B-continued

IBD, CD & UC Genes & SNPs

| Gene | SNP |
|---|---|
| MAP2K6 | rs2905443 |
| STAT4 | rs1584945 |
| IL12A | rs6800657 |
| TYK2 | rs12720356 |
| ETV5 | rs9867846 |
| MAPK8 | rs17697885 |

TABLE 1C

CD Genes & SNPs

| Gene | SNP |
|---|---|
| NOD2 (R702W) | rs2066844 |
| NOD2 (G908R) | rs2066845 |
| NOD2 (3020insC) | rs5743293 |
| ATG16L1 (T300A) | rs2241880 |
| ATG16L1 | rs3828309 |
| IRGM | rs13361189 |
| IRGM | rs4958847 |
| IRGM | rs1000113 |
| IRGM | rs11747270 |
| TL1A/TNFSF15 | rs6478109 |
| TL1A/TNFSF15 | rs6478108 |
| TL1A/TNFSF15 | rs4263839 |
| PTN22 | rs2476601 |
| CCR6 | rs1456893 |
| CCR6 | rs2301436 |
| 5p13/PTGER4 | rs1373692 |
| 5p13/PTGER4 | rs4495224 |
| 5p13/PTGER4 | rs7720838 |
| 5p13/PTGER4 | rs4613763 |
| ITLN1 | rs2274910 |
| ITLN1 | rs9286879 |
| ITLN1 | rs11584383 |
| IBD5/5q31 | rs2188962 |
| IBD5/5q31 | rs252057 |
| IBD5/5q31 | rs10067603 |
| GCKR | rs780094 |
| TNFRSF6B | rs1736135 |
| ZNF365 | rs224136 |
| ZNF365 | rs10995271 |
| C11orf30 | rs7927894 |
| LRRK2; MUC19 | rs1175593 |
| DLG5 | rs2165047 |
| IL-27 | rs8049439 |
| TLR2 | rs4696480 |
| TLR2 | rs3804099 |
| TLR2 | rs3804100 |
| TLR2 | rs5743704 |
| TLR2 | rs2405432 |
| TLR4 (D299G) | rs4986790 |
| TLR4 (T399I) | rs4986791 |
| TLR4 (S360N) | rs4987233 |
| TLR9 | rs187084 |
| TLR9 | rs352140 |
| NFC4 | rs4821544 |
| KIF21B | rs11584383 |
| IKZF1 | rs1456893 |
| C11orf30 | rs7927894 |
| CCL2, CCL7 | rs991804 |
| ICOSLG | rs762421 |
| TNFAIP3 | rs7753394 |
| FLJ45139 | rs2836754 |
| PTGER4 | rs4613763 |

TABLE 1D

| UC Genes & SNPs | |
|---|---|
| Gene | SNP |
| ECM1 | rs7511649 |
| ECM1 (T130M) | rs3737240 |
| ECM1 (G290S) | rs13294 |
| GLI1 (G933D) | rs2228224 |
| GLI1 (Q1100E) | rs2228226 |
| MDR1 (3435C > T) | rs1045642 |
| MDR1 (A893S/T) | rs2032582 |
| MAGI2 | rs6962966 |
| MAGI2 | rs2160322 |
| IL26 | rs12815372 |
| IFNG, IL26 | rs1558744 |
| IFNG, IL26 | rs971545 |
| IL26 | rs2870946 |
| ARPC2 | rs12612347 |
| IL10, IL19 | rs3024493 |
| IL10, IL19 | rs3024505 |
| IL23R | rs1004819 |
| IL23R | rs2201841 |
| IL23R | rs11209026 |
| IL23R | rs11465804 |
| IL23R | rs10889677 |
| BTLN2 | rs9268480 |
| HLA-DRB1 | rs660895 |
| MEP1 | rs6920863 |
| MEP1 | rs2274658 |
| MEP1 | rs4714952 |
| MEP1 | rs1059276 |
| PUS10 | rs13003464 |
| PUS10 | rs6706689 |
| RNF186 | rs3806308 |
| RNF186 | rs1317209 |
| RNF186 | rs6426833 |
| FCGR2A, C | rs10800309 |
| CEP72 | rs4957048 |
| DLD, LAMB1 | rs4598195 |
| CAPN10, KIF1A | rs4676410 |

TABLE 1E

| IBP Genes & SNPs | |
|---|---|
| Gene | SNP |
| IL23R (R381Q) | rs11209026 |
| IL23R | rs11805303 |
| IL23R | rs7517847 |
| IL12B/p40 | rs1368438 |
| IL12B/p40 | rs10045431 |
| IL12B/p40 | rs6556416 |
| IL12B/p40 | rs6887695 |
| IL12B/p40 | rs3212227 |
| STAT3 | rs744166 |
| JAK2 | rs10974914 |
| JAK2 | rs10758669 |
| NKX2-3 | rs6584283 |
| NKX2-3 | rs10883365 |
| NKX2-3 | rs11190140 |
| IL18RAP | rs917997 |
| LYRM4 | rs12529198 |
| CDKAL1 | rs6908425 |
| MAGI2 | rs2160322 |
| TNFRSF6B | rs2160322 |
| TNFRSF6B | rs2315008 |
| TNFRSF6B | rs4809330 |
| PSMG1 | rs2094871 |
| PSMG1 | rs2836878 |
| PTPN2 | rs2542151 |
| MST1/3p21 | rs9858542 |
| MST1/3p21 | rs3197999 |
| SLC22A23 | rs17309827 |
| MHC | rs660895 |
| XBP1 | rs35873774 |
| ICOSLG1 | rs762421 |

TABLE 1E-continued

| IBP Genes & SNPs | |
|---|---|
| Gene | SNP |
| BTLN2 | rs3763313 |
| BTLN2 | rs2395185 |
| BTLN2 | rs9268480 |
| ATG5 | rs7746082 |
| CUL2, CREM | rs17582416 |
| CARD9 | rs4077515 |
| ORMDL3 | rs2872507 |
| ORMDL3 | rs2305480 |

Additional SNPs useful in the present invention include, e.g., rs2188962, rs9286879, rs11584383, rs7746082, rs1456893, rs1551398, rs17582416, rs3764147, rs1736135, rs4807569, rs7758080, and rs8098673. See, e.g., Barrett et al., *Nat. Genet.,* 40:955-62 (2008).

1. NOD2/CARD15

The determination of the presence or absence of allelic variants such as SNPs in the NOD2/CARD15 gene is particularly useful in the present invention. As used herein, the term "NOD2/CARD15 variant" or "NOD2 variant" includes a nucleotide sequence of a NOD2 gene containing one or more changes as compared to the wild-type NOD2 gene or an amino acid sequence of a NOD2 polypeptide containing one or more changes as compared to the wild-type NOD2 polypeptide sequence. NOD2, also known as CARD15, has been localized to the IBD1 locus on chromosome 16 and identified by positional-cloning (Hugot et al., *Nature,* 411:599-603 (2001)) as well as a positional candidate gene strategy (Ogura et al., *Nature,* 411:603-606 (2001); Hampe et al., *Lancet,* 357:1925-1928 (2001)). The IBD1 locus has a high multipoint linkage score (MLS) for inflammatory bowel disease (MLS=5.7 at marker D16S411 in 16q12). See, e.g., Cho et al., *Inflamm. Bowel Dis.,* 3:186-190 (1997); Akolkar et al., *Am. J. Gastroenterol.,* 96:1127-1132 (2001); Ohmen et al., *Hum. Mol. Genet.,* 5:1679-1683 (1996); Parkes et al., *Lancet,* 348:1588 (1996); Cavanaugh et al., *Ann. Hum. Genet.,* 62:291-8 (1998); Brant et al., *Gastroenterology,* 115:1056-1061 (1998); Curran et al., *Gastroenterology,* 115:1066-1071 (1998); Hampe et al., *Am. J. Hum. Genet.,* 64:808-816 (1999); and Annese et al., *Eur. J. Hum. Genet.,* 7:567-573 (1999).

The mRNA (coding) and polypeptide sequences of human NOD2 are set forth in, e.g., Genbank Accession Nos. NM_022162 (SEQ ID NO:23) and NP_071445 (SEQ ID NO:24), respectively. In addition, the complete sequence of human chromosome 16 clone RP11-327F22, which includes NOD2, is set forth in, e.g., Genbank Accession No. AC007728. Furthermore, the sequence of NOD2 from other species can be found in the GenBank database.

The NOD2 protein contains amino-terminal caspase recruitment domains (CARDs), which can activate NF-kappa B (NF-kB), and several carboxy-terminal leucine-rich repeat domains (Ogura et al., *J. Biol. Chem.,* 276:4812-4818 (2001)). NOD2 has structural homology with the apoptosis regulator Apaf-1/CED-4 and a class of plant disease resistant gene products (Ogura et al., supra). Similar to plant disease resistant gene products, NOD2 has an amino-terminal effector domain, a nucleotide-binding domain and leucine rich repeats (LRRs). Wild-type NOD2 activates nuclear factor NF-kappa B, making it responsive to bacterial lipopolysaccharides (LPS; Ogura et al., supra; Inohara et al., *J. Biol. Chem.,* 276:2551-2554 (2001). NOD2 can function as an intercellular receptor for LPS, with the leucine rich repeats required for responsiveness.

Variations at three single nucleotide polymorphisms in the coding region of NOD2 have been previously described. These three SNPs, designated R702W ("SNP 8"), G908R ("SNP 12"), and 1007fs ("SNP 13"), are located in the carboxy-terminal region of the NOD2 gene (Hugot et al., supra). A further description of SNP 8, SNP 12, and SNP 13, as well as additional SNPs in the NOD2 gene suitable for use in the invention, can be found in, e.g., U.S. Pat. Nos. 6,835,815; 6,858,391; and 7,592,437; and U.S. Patent Publication Nos. 20030190639, 20050054021, and 20070072180.

In some embodiments, a NOD2 variant is located in a coding region of the NOD2 locus, for example, within a region encoding several leucine-rich repeats in the carboxy-terminal portion of the NOD2 polypeptide. Such NOD2 variants located in the leucine-rich repeat region of NOD2 include, without limitation, R702W ("SNP 8") and G908R ("SNP 12"). A NOD2 variant useful in the invention can also encode a NOD2 polypeptide with reduced ability to activate NF-kappa B as compared to NF-kappa B activation by a wild-type NOD2 polypeptide. As a non-limiting example, the NOD2 variant 1007fs ("SNP 13") results in a truncated NOD2 polypeptide which has reduced ability to induce NF-kappa B in response to LPS stimulation (Ogura et al., *Nature,* 411:603-606 (2001)).

A NOD2 variant useful in the invention can be, for example, R702W, G908R, or 1007fs. R702W, G908R, and 1007fs are located within the coding region of NOD2. In one embodiment, a method of the invention is practiced with the R702W NOD2 variant. As used herein, the term "R702W" includes a single nucleotide polymorphism within exon 4 of the NOD2 gene, which occurs within a triplet encoding amino acid 702 of the NOD2 protein. The wild-type NOD2 allele contains a cytosine (c) residue at position 138,991 of the AC007728 sequence, which occurs within a triplet encoding an arginine at amino acid 702. The R702W NOD2 variant contains a thymine (t) residue at position 138,991 of the AC007728 sequence, resulting in an arginine (R) to tryptophan (W) substitution at amino acid 702 of the NOD2 protein. Accordingly, this NOD2 variant is denoted "R702W" or "702W" and can also be denoted "R675W" based on the earlier numbering system of Hugot et al., supra. In addition, the R702W variant is also known as the "SNP 8" allele or a "2" allele at SNP 8. The NCBI SNP ID number for R702W or SNP 8 is rs2066844. As disclosed herein and described further below, the presence of the R702W NOD2 variant and other NOD2 variants can be conveniently detected, for example, by allelic discrimination assays or sequence analysis. Primers and probes specific for the R702W NOD2 variant can be found in Tables 3 and 4 in Example 6.

A method of the invention can also be practiced with the G908R NOD2 variant. As used herein, the term "G908R" includes a single nucleotide polymorphism within exon 8 of the NOD2 gene, which occurs within a triplet encoding amino acid 908 of the NOD2 protein. Amino acid 908 is located within the leucine rich repeat region of the NOD2 gene. The wild-type NOD2 allele contains a guanine (g) residue at position 128,377 of the AC007728 sequence, which occurs within a triplet encoding glycine at amino acid 908. The G908R NOD2 variant contains a cytosine (c) residue at position 128,377 of the AC007728 sequence, resulting in a glycine (G) to arginine (R) substitution at amino acid 908 of the NOD2 protein. Accordingly, this NOD2 variant is denoted "G908R" or "908R" and can also be denoted "G881R" based on the earlier numbering system of Hugot et al., supra. In addition, the G908R variant is also known as the "SNP 12" allele or a "2" allele at SNP 12. The NCBI SNP ID number for G908R SNP 12 is rs2066845. Primers and probes specific for the G908R NOD2 variant can be found in Tables 3 and 4 in Example 6.

A method of the invention can also be practiced with the 1007fs NOD2 variant. This variant is an insertion of a single nucleotide that results in a frame shift in the tenth leucine-rich repeat of the NOD2 protein and is followed by a premature stop codon. The resulting truncation of the NOD2 protein appears to prevent activation of NF-kappaB in response to bacterial lipopolysaccharides (Ogura et al., supra). As used herein, the term "1007fs" includes a single nucleotide polymorphism within exon 11 of the NOD2 gene, which occurs in a triplet encoding amino acid 1007 of the NOD2 protein. The 1007fs variant contains a cytosine which has been added at position 121,139 of the AC007728 sequence, resulting in a frame shift mutation at amino acid 1007. Accordingly, this NOD2 variant is denoted "1007fs" and can also be denoted "3020insC" or "980fs" based on the earlier numbering system of Hugot et al., supra. In addition, the 1007fs NOD2 variant is also known as the "SNP 13" allele or a "2" allele at SNP 13. The NCBI SNP ID number for 1007fs or SNP 13 is rs2066847. Primers and probes specific for the 1007fs NOD2 variant can be found in Tables 3 and 4 in Example 6.

One skilled in the art recognizes that a particular NOD2 variant allele or other polymorphic allele can be conveniently defined, for example, in comparison to a Centre d'Etude du Polymorphisme Humain (CEPH) reference individual such as the individual designated 1347-02 (Dib et al., *Nature,* 380:152-154 (1996)), using commercially available reference DNA obtained, for example, from PE Biosystems (Foster City, Calif.). In addition, specific information on SNPs can be obtained from the dbSNP of the National Center for Biotechnology Information (NCBI).

A NOD2 variant can also be located in a non-coding region of the NOD2 locus. Non-coding regions include, for example, intron sequences as well as 5' and 3' untranslated sequences. A non-limiting example of a NOD2 variant allele located in a non-coding region of the NOD2 gene is the JW1 variant, which is described in Sugimura et al., *Am. J. Hum. Genet.,* 72:509-518 (2003) and U.S. Patent Publication No. 20070072180. Examples of NOD2 variant alleles located in the 3' untranslated region of the NOD2 gene include, without limitation, the JW15 and JW16 variant alleles, which are described in U.S. Patent Publication No. 20070072180. Examples of NOD2 variant alleles located in the 5' untranslated region (e.g., promoter region) of the NOD2 gene include, without limitation, the JW17 and JW18 variant alleles, which are described in U.S. Patent Publication No. 20070072180.

As used herein, the term "JW1 variant allele" includes a genetic variation at nucleotide 158 of intervening sequence 8 (intron 8) of the NOD2 gene. In relation to the AC007728 sequence, the JW1 variant allele is located at position 128,143. The genetic variation at nucleotide 158 of intron 8 can be, but is not limited to, a single nucleotide substitution, multiple nucleotide substitutions, or a deletion or insertion of one or more nucleotides. The wild-type sequence of intron 8 has a cytosine at position 158. As non-limiting examples, a JW1 variant allele can have a cytosine (c) to adenine (a), cytosine (c) to guanine (g), or cytosine (c) to thymine (t) substitution at nucleotide 158 of intron 8. In one embodiment, the JW1 variant allele is a change from a cytosine (c) to a thymine (t) at nucleotide 158 of NOD2 intron 8.

The term "JW15 variant allele" includes a genetic variation in the 3' untranslated region of NOD2 at nucleotide position 118,790 of the AC007728 sequence. The genetic variation at nucleotide 118,790 can be, but is not limited to, a single nucleotide substitution, multiple nucleotide substitutions, or a deletion or insertion of one or more nucleotides. The wild-type sequence has an adenine (a) at position 118,790. As non-limiting examples, a JW15 variant allele can have an adenine (a) to cytosine (c), adenine (a) to guanine (g), or adenine (a) to thymine (t) substitution at nucleotide 118,790. In one embodiment, the JW15 variant allele is a change from an adenine (a) to a cytosine (c) at nucleotide 118,790.

As used herein, the term "JW16 variant allele" includes a genetic variation in the 3' untranslated region of NOD2 at nucleotide position 118,031 of the AC007728 sequence. The genetic variation at nucleotide 118,031 can be, but is not limited to, a single nucleotide substitution, multiple nucleotide substitutions, or a deletion or insertion of one or more nucleotides. The wild-type sequence has a guanine (g) at position 118,031. As non-limiting examples, a JW16 variant allele can have a guanine (g) to cytosine (c), guanine (g) to adenine (a), or guanine (g) to thymine (t) substitution at nucleotide 118,031. In one embodiment, the JW16 variant allele is a change from a guanine (g) to an adenine (a) at nucleotide 118,031.

The term "JW17 variant allele" includes a genetic variation in the 5' untranslated region of NOD2 at nucleotide position 154,688 of the AC007728 sequence. The genetic variation at nucleotide 154,688 can be, but is not limited to, a single nucleotide substitution, multiple nucleotide substitutions, or a deletion or insertion of one or more nucleotides. The wild-type sequence has a cytosine (c) at position 154,688. As non-limiting examples, a JW17 variant allele can have a cytosine (c) to guanine (g), cytosine (c) to adenine (a), or cytosine (c) to thymine (t) substitution at nucleotide 154,688. In one embodiment, the JW17 variant allele is a change from a cytosine (c) to a thymine (t) at nucleotide 154,688.

As used herein, the term "JW18 variant allele" includes a genetic variation in the 5' untranslated region of NOD2 at nucleotide position 154,471 of the AC007728 sequence. The genetic variation at nucleotide 154,471 can be, but is not limited to, a single nucleotide substitution, multiple nucleotide substitutions, or a deletion or insertion of one or more nucleotides. The wild-type sequence has a cytosine (c) at position 154,471. As non-limiting examples, a JW18 variant allele can have a cytosine (c) to guanine (g), cytosine (c) to adenine (a), or cytosine (c) to thymine (t) substitution at nucleotide 154,471. In one embodiment, the JW18 variant allele is a change from a cytosine (c) to a thymine (t) at nucleotide 154,471.

It is understood that the methods of the invention can be practiced with these or other NOD2 variant alleles located in a coding region or non-coding region (e.g., intron or promoter region) of the NOD2 locus. It is further understood that the methods of the invention can involve determining the presence of one, two, three, four, or more NOD2 variants, including, but not limited to, the SNP 8, SNP 12, and SNP 13 alleles, and other coding as well as non-coding region variants.

2. miRNAs

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA). Instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNAs is described, e.g., in Lagos-Quintana et al., *Science,* 294:853-858; Lau et al., *Science,* 294:858-862; and Lee et al., *Science,* 294:862-864.

Mammalian miRs are usually complementary to a site in the 3' UTR of the target mRNA sequence. The annealing of the miRNA to the target mRNA inhibits protein translation by blocking the protein translation machinery or facilitates the cleavage and degradation of the target mRNA through a process similar to RNA interference (RNAi). miRNAs may also target methylation of genomic sites which correspond to targeted mRNAs.

In some embodiments, the IBD prognostic marker of the invention comprises at least one miRNA sequence (e.g., pre-miRNA or mature miRNA). In preferred embodiments, the miRNA sequence targets the expression of any of the biochemical, serological, or genetic markers described herein, e.g., cytokines, growth factors, acute phase proteins, apolipoproteins, defensins, cadherins; or any of the genes set forth in Tables 1A-1E (e.g., NOD2). Generally, the presence or level of the miRNA sequence of interest is detected in an individual's sample and included in the prognostic marker profile to aid in the prognosis of IBD and the prediction of response to therapy. Exemplary miRNA sequences suitable for detection as diagnostic and/or prognostic markers in accordance with the invention are listed in Table 2.

TABLE 2

| Target Gene | Mature miRNA Names (Accession Nos.) |
| --- | --- |
| C-Reactive protein (CRP) | hsa-miR-142-5p (MIMAT0000433); hsa-miR-939 (MIMAT0004982); hsa-miR-323-5p (MIMAT0004696); hsa-miR-550* (MIMAT0003257); hsa-miR-920 (MIMAT0004970); hsa-miR-7 (MIMAT0000252); hsa-miR-424 (MIMAT0001341); hsa-miR-135a* (MIMAT0004595); hsa-miR-130b* (MIMAT0004680); hsa-miR-503 (MIMAT0002874); hsa-miR-16 (MIMAT0000069); hsa-miR-15b (MIMAT0000417); hsa-miR-20b* (MIMAT0004752); hsa-miR-30c-1* (MIMAT0004674); hsa-miR-578 (MIMAT0003243); hsa-miR-195 (MIMAT0000461); hsa-miR-141* (MIMAT0004598); hsa-miR-220c (MIMAT0004915); hsa-miR-362-5p (MIMAT0000705); hsa-miR-30c-2* (MIMAT0004550); hsa-miR-186 (MIMAT0000456); hsa-miR-497 (MIMAT0002820); hsa-miR-15a (MIMAT0000068); hsa-miR-873 (MIMAT0004953); hsa-miR-657 (MIMAT0003335); hsa-miR-10a (MIMAT0000253); hsa-miR-379* (MIMAT0004690); hsa-miR-371-5p (MIMAT0004687); hsa-miR-150 (MIMAT0000451); hsa-miR-890 (MIMAT0004912); hsa-miR-518f (MIMAT0002842); hsa-miR-624 (MIMAT0004807); hsa-miR-518a-3p (MIMAT0002863); hsa-miR-517* (MIMAT0002851); hsa-miR-943 (MIMAT0004986); hsa-miR-27a (MIMAT0000084); hsa-miR-27b (MIMAT0000419); hsa-miR-500 (MIMAT0004773); hsa-miR-30a* (MIMAT0000088); hsa-miR-30d* (MIMAT0004551); hsa-miR-411* (MIMAT0004813); hsa-miR-27b (MIMAT0000419); hsa-miR-518d-3p (MIMAT0002864); hsa-miR-518e (MIMAT0002861); hsa-miR-10b (MIMAT0000254); hsa-miR-551b (MIMAT0003233); hsa-miR-518c (MIMAT0002848); hsa-miR-934 (MIMAT0004977); hsa-miR-200c* |

TABLE 2-continued

| Target Gene | Mature miRNA Names (Accession Nos.) |
|---|---|
| | (MIMAT0004657); hsa-miR-542-5p (MIMAT0003340); hsa-miR-299-5p (MIMAT0002890); hsa-miR-299-3p (MIMAT0000687) |
| Serum amyloid A (SAA) | hsa-miR-339-5p (MIMAT0000764); hsa-miR-660 (MIMAT0003338); hsa-miR-18a* (MIMAT0002891); hsa-miR-125b (MIMAT0000423); hsa-miR-125a-5p (MIMAT0000443); hsa-miR-937 (MIMAT0004980); hsa-miR-874 (MIMAT0004911); hsa-miR-502-5p (MIMAT0002873); hsa-miR-526b (MIMAT0002835); hsa-miR-339-3p (MIMAT0004702); hsa-miR-643 (MIMAT0003313); hsa-miR-496 (MIMAT0002818) |
| β defensin-1 (DEFB1) | hsa-miR-186* (MIMAT0004612); hsa-miR-548d-5p (MIMAT0004812); hsa-miR-202 (MIMAT0002811); hsa-miR-548b-5p (MIMAT0004798); hsa-miR-198 (MIMAT0000228); hsa-miR-186 (MIMAT0000456); hsa-miR-335 (MIMAT0000765); hsa-miR-223* (MIMAT0004570); hsa-miR-196b (MIMAT0001080); hsa-miR-653 (MIMAT0003328); hsa-miR-668 (MIMAT0003881) |
| β defensin-2 (DEFB2) | hsa-miR-593 (MIMAT0004802); hsa-miR-299-5p (MIMAT0002890); hsa-miR-518c* (MIMAT0002847); hsa-miR-511 (MIMAT0002808); hsa-miR-646 (MIMAT0003316); hsa-miR-129-3p (MIMAT0004605); hsa-miR-767-5p (MIMAT0003882); hsa-miR-129* (MIMAT0004548); hsa-miR-588 (MIMAT0003255); hsa-miR-187 (MIMAT0000262) |
| Epidermal growth factor (EGF) | hsa-miR-625 (MIMAT0003294); hsa-miR-29a* (MIMAT0004503); hsa-miR-499-5p (MIMAT0002870); hsa-miR-335* (MIMAT0004703); hsa-miR-17* (MIMAT0000071); hsa-miR-199b-5p (MIMAT0000263); hsa-miR-7-2* (MIMAT0004554); hsa-miR-134 (MIMAT0000447); hsa-miR-890 (MIMAT0004912); hsa-miR-93* (MIMAT0004509); hsa-miR-7-1* (MIMAT0004553); hsa-miR-302b* (MIMAT0000714); hsa-miR-548c-3p (MIMAT0003285); hsa-miR-135b* (MIMAT0004698); hsa-miR-19b-2* (MIMAT0004492); hsa-miR-200a (MIMAT0000682); hsa-miR-26b (MIMAT0000083); hsa-miR-199a-5p (MIMAT0000231); hsa-miR-632 (MIMAT0003302); hsa-miR-644 (MIMAT0003314); hsa-miR-142-3p (MIMAT0000434); hsa-miR-518c (MIMAT0002848); hsa-miR-369-5p (MIMAT0001621) |
| TWEAK | hsa-miR-620 (MIMAT0003289); hsa-miR-939 (MIMAT0004982); hsa-miR-498 (MIMAT0002824); hsa-miR-452* (MIMAT0001636); hsa-miR-623 (MIMAT0003292); hsa-miR-21* (MIMAT0004494); hsa-miR-886-3p (MIMAT0004906); hsa-miR-423-5p (MIMAT0004748); hsa-miR-609 (MIMAT0003277); hsa-miR-27b* (MIMAT0004588); hsa-miR-222 (MIMAT0000279); hsa-miR-619 (MIMAT0003288); hsa-miR-585 (MIMAT0003250); hsa-miR-221 (MIMAT0000278); hsa-miR-654-3p (MIMAT0004814); hsa-miR-524-3p (MIMAT0002850); hsa-miR-199b-5p (MIMAT0000263); hsa-miR-566 (MIMAT0003230); hsa-miR-525-3p (MIMAT0002839); hsa-miR-598 (MIMAT0003266); hsa-miR-887 (MIMAT0004951); hsa-miR-551a (MIMAT0003214); hsa-miR-585 (MIMAT0003250) |
| IL-1β | hsa-miR-888 (MIMAT0004916); hsa-miR-616* (MIMAT0003284); hsa-miR-548d-3p (MIMAT0003323); hsa-miR-211 (MIMAT0000268); hsa-miR-587 (MIMAT0003253); hsa-miR-296-3p (MIMAT0004679); hsa-miR-548b-3p (MIMAT0003254); hsa-miR-595 (MIMAT0003263); hsa-miR-204 (MIMAT0000265); hsa-miR-578 (MIMAT0003243); hsa-miR-208 (MIMAT0000241); hsa-miR-208b (MIMAT0004960); hsa-miR-330-5p (MIMAT0004693); hsa-miR-26b* (MIMAT0004500); hsa-miR-495 (MIMAT0002817); hsa-miR-616 (MIMAT0004805); hsa-miR-590-5p (MIMAT0003258); hsa-miR-943 (MIMAT0004986); hsa-miR-135a* (MIMAT0004595); hsa-miR-361-5p (MIMAT0000703); hsa-miR-299-3p (MIMAT0000687); hsa-miR-603 (MIMAT0003271); hsa-miR-518e (MIMAT0002861); hsa-miR-556-3p (MIMAT0004793) |
| IL-6 | hsa-miR-548b-5p (MIMAT0004798); hsa-miR-335* (MIMAT0004703); hsa-miR-126* (MIMAT0000444); hsa-miR-376b (MIMAT0002172); hsa-miR-146a* (MIMAT0004608); hsa-miR-571 (MIMAT0003236); hsa-miR-153 (MIMAT0000439); hsa-miR-760 (MIMAT0004957); hsa-miR-106a* (MIMAT0004517); hsa-miR-371-5p (MIMAT0004687); hsa-miR-376a (MIMAT0000729); hsa-miR-144 (MIMAT0000436); hsa-miR-518c* (MIMAT0002847); hsa-miR-548d-5p (MIMAT0004812); hsa-miR-365 (MIMAT0000710); hsa-miR-548c-5p (MIMAT0004806); hsa-miR-587 (MIMAT0003253); hsa-miR-33a* (MIMAT0004506); hsa-miR-574-3p (MIMAT0003239); hsa-miR-568 (MIMAT0003232); hsa-let-7i (MIMAT0000415); hsa-miR-148b* (MIMAT0004699); hsa-miR-655 (MIMAT0003331); hsa-miR-548a-5p (MIMAT0004803); hsa-miR-148a* (MIMAT0004549); hsa-miR-613 (MIMAT0003281); hsa-miR-146b-3p (MIMAT0004766); hsa-miR-149 (MIMAT0000450); hsa-miR-217 (MIMAT0000274); hsa-miR-196b (MIMAT0001080); hsa-miR-22* (MIMAT0004495); hsa-miR-137 (MIMAT0000429); hsa-miR-498 (MIMAT0002824); hsa-let-7g (MIMAT0000414); hsa-miR-155 (MIMAT0000646); hsa-miR-383 (MIMAT0000738); hsa-miR-576-3p (MIMAT0004796); hsa-miR-183* (MIMAT0004560); hsa-miR-555 (MIMAT0003219); hsa-miR-589 (MIMAT0004799); hsa-miR-338-5p (MIMAT0004701); hsa-miR-522 (MIMAT0002868); hsa-miR-643 (MIMAT0003313); hsa-miR-369-3p (MIMAT0000721); hsa-miR-552 (MIMAT0003215); hsa-miR-499-5p (MIMAT0002870); hsa-miR-137 (MIMAT0000429); hsa-miR-338-5p (MIMAT0004701); hsa-miR-374b (MIMAT0004955); hsa-miR-376c (MIMAT0000720); hsa-miR-588 (MIMAT0003255); hsa-miR-212 (MIMAT0000269); hsa-miR-132 (MIMAT0000426) |
| E-cadherin | hsa-miR-143* (MIMAT0004599); hsa-miR-544 (MIMAT0003164); hsa-miR-920 (MIMAT0004970); hsa-miR-635 (MIMAT0003305); hsa-miR-340* (MIMAT0000750); hsa-miR-665 (MIMAT0004952); hsa-miR-217 (MIMAT0000274); hsa-miR-9* (MIMAT0000442); hsa-miR-612 (MIMAT0003280); hsa-miR-920 (MIMAT0004970); hsa-miR-382 (MIMAT0000737); hsa-miR-340 (MIMAT0004692); hsa-miR-34c-3p (MIMAT0004677); hsa-miR-1 (MIMAT0000416); hsa-miR-571 (MIMAT0003236); hsa-miR-499-3p (MIMAT0004772); hsa-miR-708* (MIMAT0004927); hsa-miR-220b (MIMAT0004908); hsa-miR-206 (MIMAT0000462); hsa-miR-92a (MIMAT0000092); hsa-miR-92b (MIMAT0003218); hsa-miR-217 (MIMAT0000274) |
| NOD2 | hsa-miR-671-5p (MIMAT0003880); hsa-miR-20a* (MIMAT0004493); hsa-miR-124 (MIMAT0000422); hsa-miR-122 (MIMAT0000421); hsa-miR-192 (MIMAT0000222); hsa-miR-215 (MIMAT0000272); hsa-miR-495 (MIMAT0002817); hsa-miR-342-5p (MIMAT0004694); hsa-miR-512-5p (MIMAT0002822); hsa-miR-453 (MIMAT0001630); hsa-miR-215 (MIMAT0000272); hsa-miR-192 (MIMAT0000222) |

The Accession Nos. for the mature miRNA sequences correspond to entries that can be found in the miRBase Sequence Database from the Sanger Institute. The miRBase Sequence Database is a searchable database of published miRNA sequences and annotation. The miRBase Sequence Database Accession Nos. are herein incorporated by reference in their entirety for all purposes.

In certain embodiments, the miR set forth in Table 2 is between about 17 to 25 nucleotides in length and comprises a sequence that is at least 90% identical to a miRNA set forth in the listed Accession No. for the mature miRNA sequence. In certain embodiments, a miRNA is 17, 18, 19, 20, 21, 22, 23, 24, or 25 nucleotides in length, or any range derivable therein. Moreover, in certain embodiments, a miR has a sequence that is or is at least 90, 91, 92, 93, 94, 95, 96, 97, 98, 99, 99.1, 99.2, 99.3, 99.4, 99.5, 99.6, 99.7, 99.8, 99.9 or 100% identical to the miRNA in Table 2.

In some therapeutic embodiments, the complement of the miR set forth in Table 2 is useful. This is known as a miRNA inhibitor. A miRNA inhibitor is between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miR inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA.

L. Other Diagnostic and Prognostic Markers

Additional diagnostic and/or prognostic markers suitable for use in the present invention include, but are not limited to, lactoferrin, anti-lactoferrin antibodies, elastase, calprotectin, hemoglobin, and combinations thereof.

The determination of the presence or level of lactoferrin in a sample is also useful in the present invention. In certain instances, the presence or level of lactoferrin is detected at the level of mRNA expression with an assay such as, for example, a hybridization assay or an amplification-based assay. In certain other instances, the presence or level of lactoferrin is detected at the level of protein expression using, for example, an immunoassay (e.g., ELISA) or an immunohistochemical assay. An ELISA kit available from Calbiochem (San Diego, Calif.) can be used to detect human lactoferrin in a plasma, urine, bronchoalveolar lavage, or cerebrospinal fluid sample. Similarly, an ELISA kit available from U.S. Biological (Swampscott, Mass.) can be used to determine the level of lactoferrin in a plasma sample. Likewise, ELISA kits available from TECHLAB, Inc. (Blacksburg, Va.) can be used to determine the level of lactoferrin in a stool sample. Additionally, U.S. Patent Publication No. 20040137536 describes an ELISA assay for determining the presence of elevated lactoferrin levels in a stool sample, and U.S. Patent Publication No. 20040033537 describes an ELISA assay for determining the concentration of endogenous lactoferrin in a stool, mucus, or bile sample. In some embodiments, then presence or level of anti-lactoferrin antibodies can be detected in a sample using, e.g., lactoferrin protein or a fragment thereof.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar colorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045, 5,081,040, and 5,310,684.

Calprotectin is a calcium and zinc-binding protein found in all cells, tissues, and fluids in the body. Calprotectin is a major protein in neutrophilic granulocytes and macrophages and accounts for as much as 60% of the total protein in the cytosolic fraction of these cells. It is therefore a surrogate marker of neutrophil turnover. Its concentration in stool correlates with the intensity of neutrophil infiltration of the intestinal mucosa and with the severity of inflammation. Calprotectin can be measured with an ELISA using small (50-100 mg) fecal samples (see, e.g., Johne et al., *Scand J Gastroenterol.,* 36:291-296 (2001)).

VI. Assays

Any of a variety of assays, techniques, and kits known in the art can be used to detect or determine the presence or level of one or more IBD markers in a sample to diagnose IBD, to classify the diagnosis of IBD (e.g., CD or UC), to classify the prognosis of IBD (e.g., the risk or likelihood of a more severe prognosis (e.g., the probability of developing disease complications and/or progression to surgery and/or susceptibility of developing a particular clinical subtype of CD or UC), or to predict the likelihood of response to therapy with one or more therapeutic agents (e.g., biologic therapy).

The present invention relies, in part, on determining the presence or level of at least one marker in a sample obtained from an individual. As used herein, the term "detecting the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "detecting the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for detecting the level of each marker of interest. One skilled in the art will appreciate that any assay useful for detecting the level of a marker is also useful for detecting the presence or absence of the marker.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or $F(ab')_2$ is included within the meaning of the term antibody.

Flow cytometry can be used to detect the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop and Davis, *J. Immunol. Methods,* 210:79-87 (1997); McHugh et al., *J. Immunol. Methods,* 116:213 (1989); Scillian et al., *Blood,* 73:2041 (1989)).

Phage display technology for expressing a recombinant antigen specific for a marker can also be used to detect the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.,* 267, San Diego: Academic Press, Inc. (1996)).

A variety of immunoassay techniques, including competitive and non-competitive immunoassays, can be used to detect the presence or level of one or more markers in a sample (see, e.g., Self and Cook, *Curr. Opin. Biotechnol.,* 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis,* 18:2184-2193 (1997); Bao, *J. Chromatogr. B. Biomed. Sci.,* 699:463-480 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.,* 27:261-276 (1989)).

Antigen capture ELISA can be useful for detecting the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}I$) labeled secondary antibody (Harlow and Lane, supra) is also suitable for detecting the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for detecting the presence or level of one or more markers in a sample. As a non-limiting example, a fixed neutrophil ELISA is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. An ELISA using I2 protein or a fragment thereof is useful for determining whether a sample is positive for anti-I2 antibodies, or for determining anti-I2 antibody levels in a sample. An ELISA using flagellin protein (e.g., Cbir-1 flagellin) or a fragment thereof is useful for determining whether a sample is positive for anti-flagellin antibodies, or for determining anti-flagellin antibody levels in a sample. In addition, the immunoassays described above are particularly useful for detecting the presence or level of other markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}I$) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat $F(ab')_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat $F(ab')_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays described herein can be automated or performed robotically, and the signal from multiple samples can be detected simultaneously.

Quantitative Western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.,* 28:669-675 (1998).

Alternatively, a variety of immunohistochemical assay techniques can be used to detect or determine the presence or level of one or more markers in a sample. The term "immunohistochemical assay" encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, SELDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.,* 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for detecting the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful prognostic and predictive information to facilitate in the treatment of IBD.

A panel for measuring one or more of the markers described above may be constructed to provide relevant information related to the approach of the invention for diagnosing IBD, for predicting the probable course and outcome of IBD, and for predicting the likelihood of response to IBD therapy. Such a panel may be constructed to detect or determine the presence or level of 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment, diagnosis, and prognosis in a timely fashion.

In view of the above, one skilled in the art realizes that the methods of the invention for providing diagnostic information regarding IBD or clinical subtypes thereof, for providing prognostic and predictive information regarding the outcome and course of progression of IBD, and for providing information regarding the selection of a suitable therapeutic regimen for the treatment of IBD (e.g., by determining the presence or concentration level of one or more IBD markers as described herein) can be practiced using one or any combination of the well-known assays described above or other assays known in the art.

VII. Methods of Genotyping

A variety of means can be used to genotype an individual at a polymorphic site in the NOD2 gene or any other genetic marker described herein to determine whether a sample (e.g., a nucleic acid sample) contains a specific variant allele or haplotype. For example, enzymatic amplification of nucleic acid from an individual can be conveniently used to obtain nucleic acid for subsequent analysis. The presence or absence of a specific variant allele or haplotype in one or more genetic markers of interest can also be determined directly from the individual's nucleic acid without enzymatic amplification. In certain preferred embodiments, an individual is genotyped at the NOD2 locus.

Genotyping of nucleic acid from an individual, whether amplified or not, can be performed using any of various techniques. Useful techniques include, without limitation, polymerase chain reaction (PCR) based analysis, sequence analysis, and electrophoretic analysis, which can be used alone or in combination. As used herein, the term "nucleic acid" means a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

Material containing nucleic acid is routinely obtained from individuals. Such material is any biological matter from which nucleic acid can be prepared. As non-limiting examples, material can be whole blood, serum, plasma, saliva, cheek swab, sputum, or other bodily fluid or tissue that contains nucleic acid. In one embodiment, a method of the present invention is practiced with whole blood, which can be obtained readily by non-invasive means and used to prepare genomic DNA. In another embodiment, genotyping involves amplification of an individual's nucleic acid using the polymerase chain reaction (PCR). Use of PCR for the amplification of nucleic acids is well known in the art (see, e.g., Mullis et al. (Eds.), *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor groove binder.

Any of a variety of different primers can be used to amplify an individual's nucleic acid by PCR in order to determine the presence or absence of a variant allele in the NOD2 gene or other genetic marker in a method of the invention. For example, the PCR primers listed in Table 3 (SEQ ID NOS:25-32) can be used to amplify specific regions of the NOD2 locus. As non-limiting examples, the region surrounding R702W ("SNP 8") can be amplified using SEQ ID NOS: 27 and 28, G908R ("SNP 12") can be amplified using SEQ ID NOS: 29 and 30, and the region surrounding 1007fs ("SNP 13") can be amplified using SEQ ID NOS: 31 and 32. As understood by one skilled in the art, additional primers for PCR analysis can be designed based on the sequence flanking the polymorphic site(s) of interest in the NOD2 gene or other genetic marker. As a non-limiting example, a sequence primer can contain from about 15 to about 30 nucleotides of a sequence upstream or downstream of the polymorphic site of interest in the NOD2 gene or other genetic marker. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a particular variant allele or haplotype in the NOD2 gene or other genetic marker described herein. In a Taqman® allelic discrimination assay, a specific fluorescent dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the individual. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor groove binder (MGB) group to a DNA probe as described, e.g., in Kutyavin et al., *Nuc. Acids Research* 28:655-661 (2000). Minor groove binders include, but are not limited to, compounds such as dihydrocyclopyrroloindole tripeptide (DPI3). Exemplary Taqman® probes suitable for detecting the SNP 8, SNP 12, and SNP 13 allelic variants in the NOD2 gene are set forth in Table 4 (SEQ ID NOS:33-42).

Sequence analysis can also be useful for genotyping an individual according to the methods described herein to determine the presence or absence of a particular variant allele or haplotype in the NOD2 gene or other genetic marker. As is known by those skilled in the art, a variant allele of interest can be detected by sequence analysis using the appropriate primers, which are designed based on the sequence flanking the polymorphic site of interest in the NOD2 gene or other genetic marker. For example, a NOD2 variant allele can be detected by sequence analysis using primers disclosed herein, e.g., the PCR primers set forth in Table 3 (SEQ ID NOS:25-32). Additional or alternative sequence primers can contain from about 15 to about 30 nucleotides of a sequence that corresponds to a sequence about 40 to about 400 base pairs upstream or downstream of the polymorphic site of interest in the NOD2 gene or other genetic marker. Such primers are generally designed to have sufficient guanine and cytosine content to attain a high melting temperature which allows for a stable annealing step in the sequencing reaction.

The term "sequence analysis" includes any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (see, Sears et al., *Biotechniques* 13:626-633 (1992)); solid-phase sequencing (see, Zimmerman et al., *Methods Mol. Cell Biol.* 3:39-42 (1992); and sequencing with mass spectrometry, such as matrix-assisted laser desorption/ionization time-of-flight mass spectrometry (see, MALDI-TOF MS; Fu et al., *Nature Biotech.* 16:381-384 (1998)). The term sequence analysis further includes, but is not limited to, sequencing by hybridization (SBH), which relies on an array of all possible short oligonucleotides to identify a segment of sequence (see, Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis also can be useful in genotyping an individual according to the methods of the present invention to determine the presence or absence of a particular variant allele or haplotype in the NOD2 gene or other genetic marker. "Electrophoretic analysis" as used herein in reference to one or more nucleic acids such as amplified fragments includes a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping an individual according to the methods of the present invention to determine the presence or absence of a particular variant allele or haplotype in the NOD2 gene or other genetic marker (see, Jarcho et al. in Dracopoli et al., *Current Protocols in Human Genetics* pages 2.7.1-2.7.5, John Wiley & Sons, New York; Innis et al., (Ed.), *PCR Protocols*, San Diego: Academic Press, Inc. (1990)). As used herein, "restriction fragment length polymorphism analysis" includes any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping an individual in the methods described herein to determine the presence or absence of a particular variant allele or haplotype in the NOD2 gene or other genetic marker. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping in the methods of the present invention to determine the presence or absence of a particular variant allele or haplotype in the NOD2 gene or other genetic marker. HMA is useful for detecting the presence of a variant allele since a DNA duplex carrying a mismatch has reduced mobility in a polyacrylamide gel compared to the mobility of a perfectly base-paired duplex (see, Delwart et al., *Science,* 262:1257-1261 (1993); White et al., *Genomics,* 12:301-306 (1992)).

The technique of single strand conformational polymorphism (SSCP) can also be useful for genotyping in the methods described herein to determine the presence or absence of a particular variant allele or haplotype in the NOD2 gene or other genetic marker (see, Hayashi, *Methods Applic.,* 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can also be useful in the methods of the invention to determine the presence or absence of a particular variant allele or haplotype in the NOD2 gene or other genetic marker. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (see, Sheffield et al., "Identifying DNA Polymorphisms by Denaturing Gradient Gel Electrophoresis" in Innis et al., supra, 1990).

In certain preferred embodiments, the presence or absence of one or more NOD2 variant alleles (e.g., SNP 8, SNP 12, and/or SNP 13) is determined using the NOD2/CARD15 assay available from Prometheus Laboratories Inc. (San Diego, Calif.; Cat. #6000).

Other molecular methods useful for genotyping an individual are known in the art and useful in the methods of the present invention. Such well-known genotyping approaches include, without limitation, automated sequencing and RNase mismatch techniques (see, Winter et al., *Proc. Natl. Acad. Sci.,* 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the present invention for prognosing the future outcome of IBD and for predicting the likelihood of response to IBD therapeutic agents such as biologics (e.g., by determining the presence or absence of one or more NOD2 variant alleles) can be practiced using one or any combination of the well-known genotyping assays described above or other assays known in the art.

VIII. miRNA Extraction, Purification, and Enrichment

For embodiments utilizing miRNA, cells are isolated and lysed to produce a cellular extract, small RNA species such as miRNAs may be extracted, purified, and/or enriched from the cellular extract by any technique known in the art.

In some instances, an alcohol solution may be added to, mixed with, or incubated with the lysate or cellular extract prior to extraction of miRNAs. The alcohol solution may comprise at least one alcohol and typically ranges from about 5% to about 100% in the concentration of alcohol. In specific embodiments, the amount of alcohol solution added to the lysate renders it with an alcohol concentration of about 35% to about 70%, or about 50% to about 60%. In other specific embodiments, the amount of alcohol solution added to the lysate gives it an alcohol concentration of about 55%. Suitable alcohols include, but are not limited to, ethanol, propanol, isopropanol, methanol, and mixtures thereof. It is further contemplated that an alcohol solution may be used in additional steps in methods for precipitating RNA.

In certain aspects, miRNAs may be extracted from the lysate or cellular extract with an extraction solution comprising a non-alcohol organic solvent prior to applying the lysate or cellular extract to a solid support. In specific embodiments, the extraction solution contains a non-alcohol organic solvent such as phenol and/or chloroform. The non-alcohol organic solvent solution is understood to contain at least one non-alcohol organic solvent, though it may also contain an alcohol. The concentrations described above with respect to alcohol solutions are applicable to concentrations of solutions having non-alcohol organic solvents. In certain instances, equal amounts of the lysate and phenol and/or chloroform are mixed. In specific embodiments, the alcohol solution is added to the lysate before extraction with a non-alcohol organic solvent.

In some embodiments, extraction of miRNAs from the lysate or cellular extract includes using a solid support, such as a mineral or polymer support. A "solid support" includes a physical structure containing a material which contacts the lysate and that does not irreversibly react to macromolecules in the lysate, particularly with small RNA molecules such as miRNAs. In particular embodiments, the solid support binds small RNA molecules; in additional cases, it binds small RNA molecules, but does not bind one or more other types of macromolecules in the sample. The material in the solid support may include a mineral or polymer, in which case the support is referred to as a "mineral or polymer support." Mineral or polymer supports include supports involving silica. In some embodiments, the silica is glass. Suitable supports include, but are not limited to, beads, columns, and filters. In further embodiments, the mineral or polymer support is a glass fiber filter (GFF) or column.

In certain other embodiments, the mineral or polymer support may include polymers or nonpolymers with electronegative groups. In some instances, the material comprises polyacrylate, polystyrene, latex, polyacrylonitrile, polyvinylchloride, methacrylate, and/or methyl methacrylate.

In further embodiments, a lysate that may or may not have been mixed with an alcohol or non-alcohol organic solvent solution is applied to a solid support and the RNA (containing miRNAs) is eluted from the support.

After a lysate is applied or mixed with a solid support, the material may be washed with a solution. In some embodiments, a mineral or polymer support is washed with a first wash solution after applying the lysate to the mineral or polymer support. In further embodiments, a wash solution comprises a chaotropic or reducing agent. The chaotropic agent is guanidinium in some wash solutions. A wash solution includes alcohol in some embodiments, and in some cases, it has both alcohol and guanidinium. It is further contemplated that the extraction step include 1, 2, 3, 4, 5, or more washes with a wash solution. The wash solution used when more than one washing is involved may be the same or different. In some embodiments, the wash solutions have the same components, but in different concentrations from each other. It is generally understood that molecules that come through the material in a wash cycle are discarded.

The desired RNA molecules are typically eluted from the solid support. In certain embodiments, small RNA molecules (e.g., miRNAs) are eluted from a solid support such as a mineral or polymer support at a temperature of about 60° C. to about 100° C. The temperature at which the RNA molecules are eluted may be about or at least about 5 to about 100° C. or more, or any range therein. The molecules may be eluted with any elution solution. In some embodiments, the elution solution is an ionic solution. In particular embodiments, the elution solution includes up to about 10 mM salt (e.g., about 0.1, 0.5, 1, 5, 10, or more mM salt). In certain embodiments, the salt consists of a combination of $Li^+$, $Na^+$, $K^+$, or $NH_4^+$ as the cation and $Cl^-$, $Br^-$, $I^-$, ethylenediaminetetraacetate, or citrate as the anion.

Additional steps include passing the small RNA molecules through a glass fiber filter (GFF) while binding only the larger RNAs. In some embodiments, the passed small RNA molecules are captured on a second GFF and then eluted. Material that is not captured on the second GFF filter may be discarded or not used.

In a specific embodiment, the extraction of miRNAs is performed as follows: adding an extraction solution to a cellular lysate containing miRNAs; adding an alcohol solution to the extracted sample; applying the sample to a mineral or polymer support; and eluting the RNA containing miRNAs from the mineral or polymer support with an ionic solution. In some embodiments, the eluted sample is enriched at least about 10-fold for miRNAs by mass.

As a non-limiting example, the extraction, purification, and enrichment of miRNAs may be performed according to the following protocol. 60 μl of 2M Na-acetate, pH 4.0, is added to a cellular lysate, followed immediately by 0.6 ml of acid phenol-chloroform. In certain instances, ethanol is added to the cellular lysate before phenol-chloroform extraction to provide a final concentration of about 55% ethanol. After 30 sec of vigorous agitation, the aqueous phase is separated by centrifugation at 16,000×G for 5 min. Four 100 μl aliquots of this aqueous phase are used in four separate separations. The four aliquots have 100 μl of 40%, 50%, 60%, and 70% ethanol added to each, then are passed through glass fiber filters as in the RNAqueous procedure (Ambion, Inc.; Austin, Tex.). The 20%, 25%, 30%, and 35% ethanol solutions that passed through these filters (the flow-through) are then adjusted to 55% ethanol final concentration by the addition of 156, 133, 111, and 88.9 μl of ethanol, respectively. All four samples are passed over separate glass fiber filter columns. The filters are then washed with 0.7 ml of 4M guanidinium isocyanate (GuSCN)/70% ethanol, followed by two washes with 0.5 ml 80% alcohol/0.1M NaCl/4.5 mM EDTA/10 mM TrisHCl, pH 7.5. After each wash is passed through the filter, the collection tube is emptied and replaced. Each wash is passed through the filter by centrifugation as per the RNAqueous protocol (Ambion, Inc.). The sample is then eluted off the filter with 100 μl of 0.1 mM EDTA, pH 8.0, which is applied directly to the filter at room temperature and centrifuged through into a fresh collection tube.

Additional methods for extracting, purifying, and enriching miRNAs are described in, e.g., U.S. Patent Publication No. 20050059024; and the mirVana™ miRNA Isolation Kit Protocol (Ambion, Inc.; Austin, Tex.), the disclosures of which are herein incorporated by reference in their entirety for all purposes.

IX. Statistical Analysis

In some aspects, the present invention provides methods, systems, and code for diagnosing IBD, for classifying the diagnosis of IBD (e.g., CD or UC), for classifying the prognosis of IBD (e.g., the risk or likelihood of a more severe prognosis (e.g., the probability of developing disease complications and/or progression to surgery and/or susceptibility of developing a particular clinical subtype of CD or UC)), or for predicting the likelihood of response to IBD therapy (e.g., biologic therapy). In particular embodiments, quantile analysis is applied to the presence, level, and/or genotype of one or more IBD markers determined by any of the assays described herein to diagnose IBD, prognose IBD, or predict response to IBD therapy. In other embodiments, one or more learning statistical classifier systems are applied to the presence, level, and/or genotype of one or more IBD markers determined by any of the assays described herein to diagnose IBD, prognose IBD, or predict response to IBD therapy. As described herein, the statistical analyses of the present invention advantageously provide improved sensitivity, specificity, negative predictive value, positive predictive value, and/or overall accuracy for diagnosing IBD, prognosing IBD, and predicting response to IBD therapy.

The term "statistical analysis" or "statistical algorithm" or "statistical process" includes any of a variety of statistical methods and models used to determine relationships between variables. In the present invention, the variables are the presence, level, or genotype of at least one marker of interest. Any number of markers can be analyzed using a statistical analysis described herein. For example, the presence or level of 1, 2, 3, 4, 5, 6, 7, 8, 9, 10, 11, 12, 13, 14, 15, 16, 17, 18, 19, 20, 25, 30, 35, 40, 45, 50, 55, 60, or more markers can be included in a statistical analysis. In one embodiment, logistic regression is used. In another embodiment, linear regression is used. In certain preferred embodiments, the statistical analyses of the present invention comprise a quantile measurement of one or more markers, e.g., within a given population, as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In preferred embodiments, the present invention involves detecting or determining the presence, level (e.g., magnitude), and/or genotype of one or more markers of interest using quartile analysis. In this type of statistical analysis, the level of a marker of interest is defined as being in the first quartile (<25%), second quartile (25-50%), third quartile (51%-<75%), or fourth quartile (75-100%) in relation to a reference database of samples. These quartiles may be assigned a quartile score of 1, 2, 3, and 4, respectively. In certain instances, a marker that is not detected in a sample is assigned a quartile score of 0 or 1, while a marker that is detected (e.g., present) in a sample (e.g., sample is positive for the marker) is assigned a quartile score of 4. In some embodiments, quartile 1 represents samples with the lowest marker levels, while quartile 4 represent samples with the highest marker levels. In other embodiments, quartile 1 represents samples with a particular marker genotype (e.g., wild-type allele), while quartile 4 represent samples with another particular marker genotype (e.g., allelic variant). The reference database of samples can include a large spectrum of IBD (e.g., CD and/or UC) patients. From such a database, quartile cut-offs can be established. A non-limiting example of quartile analysis suitable for use in the present invention is described in, e.g., Mow et al., *Gastroenterology,* 126:414-24 (2004).

In some embodiments, the statistical analyses of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem.

Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning,* 45:5-32 (2001); for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the $SVM^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological and/or genomic samples) from healthy individuals and IBD (e.g., CD and/or UC) patients. For example, samples from patients diagnosed by a physician, and preferably by a gastroenterologist, as having IBD or a clinical subtype thereof using a biopsy, colonoscopy, or an immunoassay as described in, e.g., U.S. Pat. No. 6,218,129, are suitable for use in training and testing the statistical methods and models of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the statistical methods and models of the present invention.

As used herein, the term "sensitivity" refers to the probability that a diagnostic, prognostic, or predictive method, system, or code of the present invention gives a positive result when the sample is positive, e.g., having the predicted diagnosis, prognostic outcome, or response to IBD therapy. Sensitivity is calculated as the number of true positive results divided by the sum of the true positives and false negatives. Sensitivity essentially is a measure of how well the present invention correctly identifies those who have the predicted diagnosis, prognostic outcome, or response to IBD therapy from those who do not have the predicted diagnosis, prognosis, or therapeutic response. The statistical methods and models can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" refers to the probability that a diagnostic, prognostic, or predictive method, system, or code of the present invention gives a negative result when the sample is not positive, e.g., not having the predicted diagnosis, prognostic outcome, or response to IBD therapy. Specificity is calculated as the number of true negative results divided by the sum of the true negatives and false positives. Specificity essentially is a measure of how well the present invention excludes those who do not have the predicted diagnosis, prognostic outcome, or response to IBD therapy from those who do have the predicted diagnosis, prognosis, or therapeutic response. The statistical methods and models can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

As used herein, the term "negative predictive value" or "NPV" refers to the probability that an individual identified as not having the predicted diagnosis, prognostic outcome, or response to IBD therapy actually does not have the predicted diagnosis, prognosis, or therapeutic response. Negative predictive value can be calculated as the number of true negatives divided by the sum of the true negatives and false negatives. Negative predictive value is determined by the characteristics of the diagnostic or prognostic method, system, or code as well as the prevalence of the disease in the population analyzed. The statistical methods and models can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" refers to the probability that an individual identified as having the predicted diagnosis, prognostic outcome, or response to IBD therapy actually has the predicted diagnosis, prognosis, or therapeutic response. Positive predictive value can be calculated as the number of true positives divided by the sum of the true positives and false positives. Positive predictive value is determined by the characteristics of the diagnostic or prognostic method, system, or code as well as the prevalence of the disease in the population analyzed. The statistical methods and models can be selected such that the positive predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the present invention, the statistical methods and models can be selected to produce a desired clinical parameter for a clinical population with a particular IBD prevalence. For example, statistical methods and models can be selected for an IBD prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a method, system, or code of the present invention diagnoses IBD, prognoses IBD, or predicts response to a particular IBD therapy. Overall accuracy is calculated as the sum of the true positives and true negatives divided by the total number of sample results and is affected by the prevalence of the disease in the population analyzed. For example, the statistical methods and models can be selected such that the overall accuracy in a patient population having a disease prevalence is at least about 40%, and can be, e.g., at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

X. Disease Classification System

Figure 3:
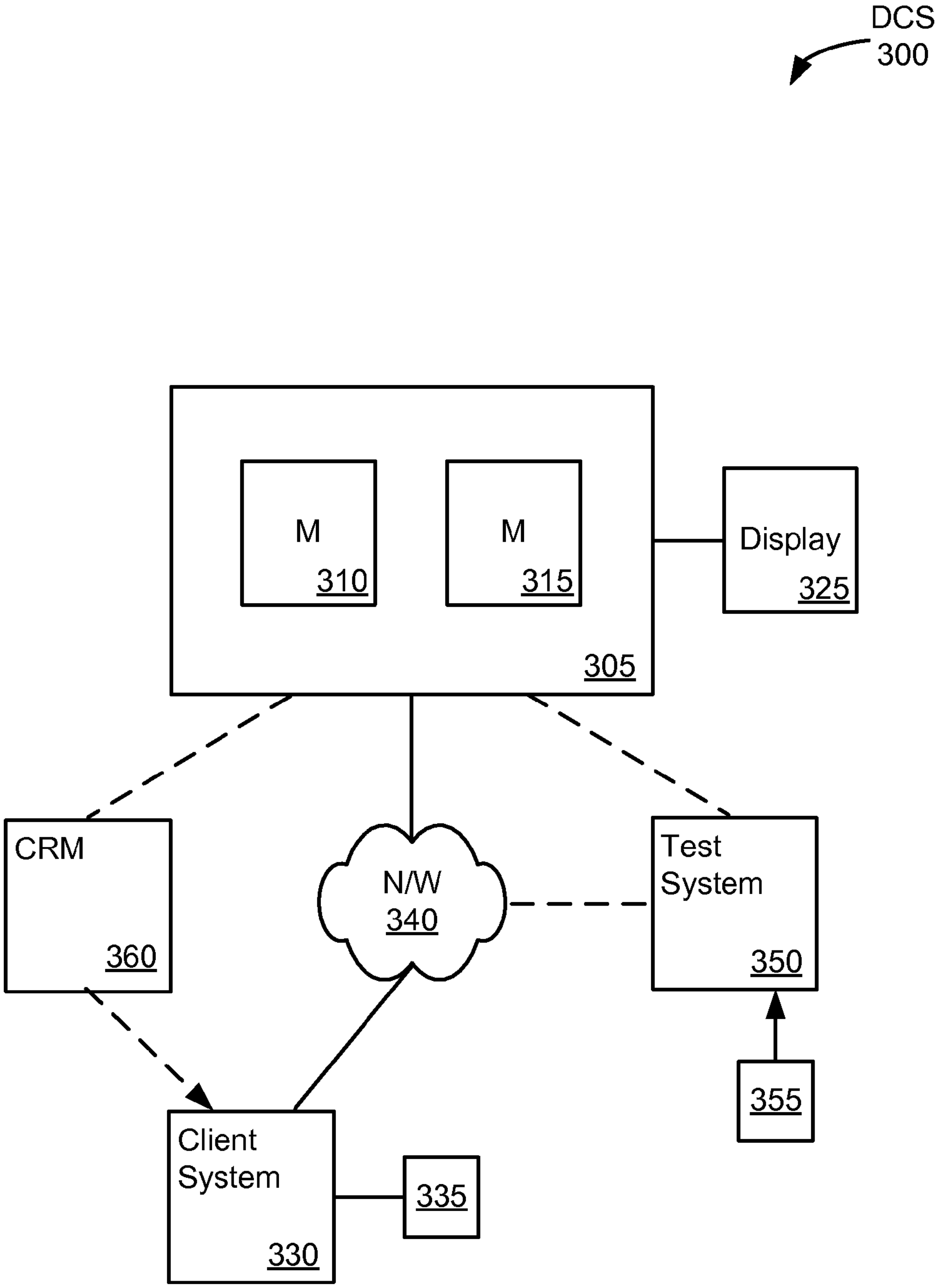
FIG. 3 illustrates a disease classification system (DCS) according to one embodiment of the present invention.

FIG. 3 illustrates a disease classification system (DCS) (300) according to one embodiment of the present invention. As shown therein, a DCS includes a DCS intelligence module (305), such as a computer, having a processor (315) and memory module (310). The intelligence module also includes communication modules (not shown) for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module (325), such as a monitor or printer. In one aspect, the intelligence module receives data such as patient test results from a data acquisition module such as a test system (350), either through a direct connection or over a network (340). For example, the test system may be configured to run multianalyte tests on one or more patient samples (355) and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems (330) over the network as is well known. For example, a requesting physician or healthcare provider may obtain and view a report from the intelligence module, which may be resident in a laboratory or hospital, using a client system (330).

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system shown in FIG. 3 may include conventional, well-known elements that need not be explained in detail here. For example, the intelligence module could be implemented as a desktop personal computer, workstation, mainframe, laptop, etc. Each client system could include a desktop personal computer, workstation, laptop, PDA, cell phone, or any WAP-enabled device or any other computing device capable of interfacing directly or indirectly to the Internet or other network connection. A client system typically runs an HTTP client, e.g., a browsing program, such as Microsoft's Internet Explorer™ browser, Netscape's Navigator™ browser, Opera's browser, or a WAP-enabled browser in the case of a cell phone, PDA or other wireless device, or the like, allowing a user of the client system to access, process, and view information and pages available to it from the intelligence module over the network. Each client system also typically includes one or more user interface devices, such as a keyboard, a mouse, touch screen, pen or the like, for interacting with a graphical user interface (GUI) provided by the browser on a display (e.g., monitor screen, LCD display, etc.) (335) in conjunction with pages, forms, and other information provided by the intelligence module. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel® Pentium® processor or the like. Similarly, the intelligence module and all of its components might be operator configurable using application(s) including computer code run using a central processing unit (315) such as an Intel Pentium processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium (160) capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in C, C++, C#, HTML, Java, JavaScript, or any other scripting language, such as VBScript. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/I P, HTTP, HTTPS, Ethernet, etc.) as are well known.

According to one embodiment, the intelligence module implements a disease classification process for analyzing patient test results to determine a diagnosis of IBD or the prognosis of IBD (e.g., the risk or likelihood of a more severe prognosis (e.g., the probability of developing disease complications and/or progression to surgery and/or susceptibility of developing a particular clinical subtype of CD or UC). According to another embodiment, the intelligence module implements a disease classification process for analyzing patient test results to predict the likelihood of response to IBD therapy with one or more therapeutic agents (e.g., biologic therapy). The data may be stored in one or more data tables or other logical data structures in memory (310) or in a separate storage or database system coupled with the intelligence module. One or more statistical analyses or processes are typically applied to a data set including test data for a particular patient. For example, the test data might include a diagnostic or prognostic marker profile, which comprises data indicating the presence, level, and/or genotype of at least one marker in a sample from the patient. In one embodiment, a statistical analysis such as a quantile (e.g., quartile) analysis is applied to test data for a particular patient, wherein the test data comprises the presence, level, and/or genotype of at least one marker determined in a sample from the patient. The statistically derived decision(s) may be displayed on a display device associated with or coupled to the intelligence module, or the decision(s) may be provided to and displayed at a separate system, e.g., a client system (330). In particular embodiments, the statistically derived decision(s) may be displayed in the form of a report or print-out, which can optionally include a look-up table, chart, graph, or model to enable a physician to compare and interpret the displayed results to make a reasoned IBD diagnosis, prognosis, or therapeutic response prediction.

XI. Therapy and Therapeutic Monitoring

Once the diagnosis or prognosis of IBD has been classified or the likelihood of response to an IBD therapeutic agent has been predicted in an individual diagnosed with IBD according to the methods described herein, the present invention may further comprise recommending a course of therapy based upon the classification or prediction. In certain instances, the present invention may further comprise administering to the individual a therapeutically effective amount of an IBD therapeutic agent useful for treating one or more symptoms associated with IBD, CD, UC, or clinical subtypes of CD or UC. For therapeutic applications, the IBD therapeutic agent can be administered alone or co-administered in combination with one or more additional IBD therapeutic agents and/or one or more drugs that reduce the side-effects associated with the IBD therapeutic agent. Examples of IBD therapeutic agents include, but are not limited to, biologic agents, conventional drugs, and combinations thereof. As such, the present invention advantageously enables a clinician to practice “personalized medicine” by guiding treatment decisions and informing therapy selection for IBD such that the right drug is given to the right patient at the right time.

IBD therapeutic agents can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By “co-administer” it is meant that an IBD therapeutic agent is administered at the same time, just prior to, or just after the administration of a second drug (e.g., another IBD therapeutic agent, a drug useful for reducing the side-effects of the IBD therapeutic agent, etc.).

A therapeutically effective amount of an IBD therapeutic agent may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term “unit dosage form” includes physically discrete units suitable as unitary dosages for human subjects and other mammals, each unit containing a predetermined quantity of an IBD therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the IBD therapeutic agent.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an IBD therapeutic agent, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An IBD therapeutic agent can also be formulated into a suppository disposed, for example, in a polyethylene glycol (PEG) carrier.

Liquid dosage forms can be prepared by dissolving or dispersing an IBD therapeutic agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBD therapeutic agent can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBD therapeutic agent can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of IBD or a clinical subtype thereof, an IBD therapeutic agent can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBD symptoms, and the IBD therapeutic agent being employed. For example, dosages can be empirically determined considering the type and severity of IBD symptoms in an individual classified as having a particular clinical subtype of CD or UC according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular IBD therapeutic agent in an individual. Determination of the proper dosage for a particular situation is within the skill of the practitioner. Generally, treatment is initiated with smaller dosages which are less than the optimum dose of the IBD therapeutic agent. Thereafter, the dosage is increased by small increments until the optimum effect under circumstances is reached. For convenience, the total daily dosage may be divided and administered in portions during the day, if desired.

As used herein, the term "IBD therapeutic agent" includes all pharmaceutically acceptable forms of a drug that is useful for treating one or more symptoms associated with IBD. For example, the IBD therapeutic agent can be in a racemic or isomeric mixture, a solid complex bound to an ion exchange resin, or the like. In addition, the IBD therapeutic agent can be in a solvated form. The term is also intended to include all pharmaceutically acceptable salts, derivatives, and analogs of the IBD therapeutic agent being described, as well as combinations thereof. For example, the pharmaceutically acceptable salts of an IBD therapeutic agent include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an IBD therapeutic agent is suitable for use in the methods of the present invention, e.g., a pharmaceutically acceptable salt of an IBD therapeutic agent, a free base of an IBD therapeutic agent, or a mixture thereof. Examples of suitable IBD therapeutic agents include, but are not limited to, biologic agents, conventional drugs, and combinations thereof.

Biologic agents include, e.g., anti-cytokine and chemokine antibodies such as anti-tumor necrosis factor alpha (TNFα) antibodies. Non-limiting examples of anti-TNFα antibodies include: chimeric monoclonal antibodies such as infliximab (Remicade®) (Centocor, Inc.; Horsham, Pa.), which is a chimeric IgG1 anti-TNFα monoclonal antibody; humanized monoclonal antibodies such as CDP571 and the PEGylated CDP870; fully human monoclonal antibodies such as adalimumab (Humira®) (Abbott Laboratories; Abbott Park, Ill.); p75 fusion proteins such as etanercept (Enbrel®) (Amgen; Thousand Oaks, Calif.; Wyeth Pharmaceuticals Inc.; Collegeville, Pa.), small molecules (e.g., MAP kinase inhibitors); and combinations thereof. See, Ghosh, *Novartis Found Symp.,* 263:193-205 (2004).

Other biologic agents include, e.g., anti-cell adhesion antibodies such as natalizumab (Tysabri®) (Elan Pharmaceuticals, Inc.; Dublin, Ireland; Biogen Idec; Cambridge, Mass.), which is a humanized monoclonal antibody against the cellular adhesion molecule α4-integrin, and MLN-02 (Millennium Pharmaceuticals; Cambridge, Mass.), which is a humanized IgG1 anti-α4β7-integrin monoclonal antibody; anti-T cell agents; anti-CD3 antibodies such as visilizumab (Nuvion®) (PDL BioPharma; Incline Village, Nev.), which is a humanized IgG2M3 anti-CD3 onoclonal antibody; anti-CD4 antibodies such as priliximab (cM-T412) (Centocor, Inc.; Horsham, Pa.), which is a chimeric anti-CD4 monoclonal antibody; anti-IL-2 receptor alpha (CD25) antibodies such as daclizumab Zenapax®) (PDL BioPharma; Incline Village, Nev.; Roche; Nutley, N.J.), which is a humanized IgG1 anti-CD25 monoclonal antibody, and basiliximab (Simulect®) (Novartis; Basel, Switzerland), which is a chimeric IgG1 anti-CD25 monoclonal antibody; and combinations thereof.

In addition to the foregoing biological agents, the miRs of Table 2, or an inhibitor of the miRs of Table 2 are useful in the present invention. As such, in certain embodiments, the present invention provides treatment or prevention of IBD by introducing into or providing to a patient with IBD an effective amount of i) an miRNA inhibitor molecule or ii) a miRNA molecule that corresponds to an miRNA sequence set forth in Table 2.

One useful formulation for the delivery of miRs are liposomes. Liposomes and emulsions are well-known examples of delivery vehicles that may be used to deliver nucleic acids of the invention. A nucleic acid of the invention can be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly (L-lysine).

Examples of conventional drugs include, without limitation, aminosalicylates (e.g., mesalazine, sulfasalazine, and the like), corticosteroids (e.g., prednisone), thiopurines (e.g., azathioprine, 6-mercaptopurine, and the like), methotrexate, free bases thereof, pharmaceutically acceptable salts thereof, derivatives thereof, analogs thereof, and combinations thereof.

One skilled in the art will know of additional IBD therapeutic agents suitable for use in the present invention (see, e.g., Sands, *Surg. Clin. North Am.,* 86:1045-1064 (2006); Danese et al., *Mini Rev. Med. Chem.,* 6:771-784 (2006); Domenech, *Digestion,* 73 (Suppl. 1):67-76 (2006); Nakamura et al., *World J. Gastroenterol.,* 12:4628-4635 (2006); and Gionchetti et al., *World J. Gastroenterol.,* 12:3306-3313 (2006)).

An individual can also be monitored at periodic time intervals to assess the efficacy of a certain therapeutic regimen once diagnostic, prognostic and/or predictive information has been obtained from the individual's sample. For example, the presence or level of certain markers may change based on the therapeutic effect of a treatment such as a drug. In certain embodiments, the patient can be monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

An individual can also be monitored at periodic time intervals to assess the concentrations or levels of various markers. The marker levels at various time points, as well as the rate of change of the marker levels over time is significant. In certain instances, the rate of increase of a marker(s) in an individual over a threshold amount indicates the individual has a significantly higher risk of developing complications or risk of undergoing surgery. Information obtained from serial testing in the form of a marker velocity (i.e., the change in marker level over a time period) is significantly associated with the severity of the disease, the risk of complications of disease, and the risk of undergoing surgical treatment.

In certain instances, the velocity of at least one marker, at least two markers, at least three markers, at least four markers, at least five markers, at least six markers, at least seven markers, etc., or the aggregate of marker velocity is calculated and an analysis is prepared to give a prognosis. In certain instances, the aggregate velocity of the markers is used to assess disease progression.

A quartile sum score (QSS) of markers (e.g., 6 markers) over time can be plotted. A quartile is any of the four categories that divide the data set into four equal parts, so that each part represents one fourth of the sampled population. For each marker, it is possible to have a value of 0-4 or 1-4 (e.g., zero or 1 if the marker is not present). For six markers, the quartile sum score can be 0-24 or 6-24. The quartile sum score over a number of years (e.g., 2-80) of the aggregate velocity of markers in a number of individuals with Crohn's disease can be analyzed. In other aspects, individual markers and their velocities are also significant.

In one instance, the velocity of certain markers as described herein are weighted in the aggregate of marker velocity. In other words, the velocity of certain markers is more significant in the analysis or the prognosis of certain complications. These significant markers are given more weight as their velocities are more significant in the aggregate velocity score.

In yet another aspect, once the individual is on a therapeutic regimen, the velocities and or levels of initial markers and/or the marker aggregate are monitored over time. As these velocities and/or levels decrease over time, information regarding the efficacy of the therapies is realized. Once prognostic and/or predictive information has been obtained from the individual's sample, the effect of the therapeutic regimen can be realized by monitoring the markers. For example, the presence or level and or velocity of certain marker(s) may change based on the therapeutic effect of a treatment such as a drug. In certain embodiments, the patient can be monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

The velocity of the markers can be further combined with other serological markers such as CRP, SAA (inflammatory markers) or with EGF, TGFalpha, Heregulin or other growth factors which are involved in mucosal repair. The combination of the markers together with statistical analysis such as an algorithm can further predict aggressiveness of disease. In certain instances, for example, the downward velocity of the markers can be further combined with CRP, SAA (inflammatory markers) or with EGF, TGFalpha, Heregulin or other growth factors (upward) which are involved in mucosal repair. A combined algorithm with a marker panel can predict or prognose mucosal healing or response to therapeutics.

XII. Examples

The following examples are offered to illustrate, but not to limit, the claimed invention.

Example 1. Determination of ANCA Levels

This example illustrates an analysis of ANCA levels in a sample using an ELISA assay.

A fixed neutrophil enzyme-linked immunosorbent assay (ELISA) may be used to detect ANCA as described in Saxon et al., *J. Allergy Clin. Immunol.,* 86:202-210 (1990). Briefly, microtiter plates are coated with $2.5\times10^5$ neutrophils per well from peripheral human blood purified by Ficoll-hypaque centrifugation and treated with 100% methanol for 10 minutes to fix the cells. Cells are incubated with 0.25% bovine serum albumin (BSA) in phosphate-buffered saline to block nonspecific antibody binding for 60 minutes at room temperature in a humidified chamber. Next, control and coded sera are added at a 1:100 dilution to the bovine serum/phosphate-buffered saline blocking buffer and incubated for 60 minutes at room temperature in a humidified chamber. Alkaline phosphatase-conjugated goat $F(ab')_2$ anti-human immunoglobulin G antibody (γ-chain specific; Jackson Immunoresearch Labs, Inc.; West Grove, Pa.) is added at a 1:1000 dilution to label neutrophil-bound antibody and incubated for 60 minutes at room temperature. A solution of p-nitrophenol phosphate substrate is added, and color development is allowed to proceed until absorbance at 405 nm in the positive control wells is 0.8-1.0 optical density units greater than the absorbance in blank wells.

ANCA levels may be determined relative to a standard consisting of pooled sera obtained from well-characterized pANCA-positive ulcerative colitis (UC) patients. Results are expressed as ELISA units. Sera with circulating ANCA levels exceeding the reference range value may also be termed ANCA positive, whereas numerical values that are below the reference range may also be termed ANCA negative.

Example 2. Determination of the Presence or Absence of pANCA

This example illustrates an analysis of the presence or absence of pANCA in a sample using an immunofluorescence assay as described, e.g., in U.S. Pat. Nos. 5,750,355 and 5,830,675. In particular, the presence of pANCA is detected by assaying for the loss of a positive value (e.g., loss of a detectable antibody marker and/or a specific cellular staining pattern as compared to a control) upon treatment of neutrophils with DNase.

Neutrophils isolated from a sample such as serum are immobilized on a glass side according to the following protocol:

1. Resuspend neutrophils in a sufficient volume of 1× Hanks' Balanced Salt Solution (HBSS) to achieve about $2.5\times10^6$ cells per ml.
2. Use a Cytospin3 centrifuge (Shandon, Inc.; Pittsburgh, Pa.) at 500 rpm for 5 minutes to apply 0.01 ml of the resuspended neutrophils to each slide.
3. Fix neutrophils to slide by incubating slides for 10 minutes in sufficient volume of 100% methanol to cover sample. Allow to air dry. The slides may be stored at −20° C.

The immobilized, fixed neutrophils are then treated with DNase as follows:

1. Prepare a DNase solution by combining 3 units of Promega RQ1™ DNase (Promega; Madison, Wis.) per ml buffer containing 40 mM of TRIS-HCl (pH 7.9), 10 mM of sodium chloride, 6 mM magnesium chloride, and 10 mM calcium chloride.
2. Rinse slides prepared using the above protocol with about 100 ml phosphate buffered saline (pH 7.0-7.4) for 5 minutes. Incubate immobilized neutrophils in 0.05 ml of DNase solution per slide for about 30 minutes at 37° C. Wash the slides three times with about 100-250 ml phosphate buffered saline at room temperature. The DNase reaction carried out as described herein causes substantially complete digestion of cellular DNA without significantly altering nuclear or cellular neutrophil morphology.

Next, an immunofluorescence assay is performed on the DNase-treated, fixed neutrophils according to the following protocol:

1. Add 0.05 ml of a 1:20 dilution of human sera in phosphate buffered saline to slides treated with DNase and to untreated slides. Add 0.05 ml phosphate buffered saline to clean slides as blanks Incubate for about 0.5 to 1.0 hour at room temperature in sufficient humidity to minimize volume loss.
2. Rinse off sera by dipping into a container having 100-250 ml phosphate buffered saline.
3. Soak slide in phosphate buffered saline for 5 minutes. Blot lightly.
4. Add 0.05 ml goat $F(ab')_2$ anti-human IgG(μ)-FITC (Tago Immunologicals; Burlingame, Calif.), at a 1:1000 antibody:phosphate buffered saline dilution, to each slide. Incubate for 30 minutes at room temperature in sufficient humidity to minimize volume loss.
5. Rinse off antibody with 100-250 ml phosphate buffered saline. Soak slides for 5 minutes in 100-250 ml phosphate buffered saline, then allow to air dry.

6. Read fluorescence pattern on fluorescence microscope at 40×.
7. If desired, any DNA can be stained with propidium iodide stain by rinsing slides well with phosphate buffered saline at room temperature and stain for 10 seconds at room temperature. Wash slide three times with 100-250 ml phosphate buffered saline at room temperature and mount cover slip.

The immunofluorescence assay described above can be used to determine the presence of pANCA in DNase-treated, fixed neutrophils, e.g., by the presence of a pANCA reaction in control neutrophils (i.e., fixed neutrophils that have not been DNase-treated) that is abolished upon DNase treatment or by the presence of a pANCA reaction in control neutrophils that becomes cytoplasmic upon DNase treatment.

Example 3. Determination of ASCA Levels

This example illustrates the preparation of yeast cell well mannan and an analysis of ASCA levels in a sample using an ELISA assay.

Yeast cell wall mannan may be prepared as described in Faille et al., *Eur. J. Clin. Microbiol. Infect. Dis.,* 11:438-446 (1992) and in Kocourek et al., *J. Bacteriol.,* 100:1175-1181 (1969). Briefly, a lyophilized pellet of yeast *Saccharomyces uvarum* is obtained from the American Type Culture Collection (#38926). Yeast are reconstituted in 10 ml 2×YT medium, prepared according to Sambrook et al., In "Molecular Cloning," Cold Spring Harbor Laboratory Press (1989). *S. uvarum* are grown for two to three days at 30° C. The terminal *S. uvarum* culture is inoculated on a 2×YT agar plate and subsequently grown for two to three days at 30° C. A single colony is used to inoculate 500 ml 2×YT media, and grown for two to three days at 30° C. Fermentation media (pH 4.5) is prepared by adding 20 g glucose, 2 g bacto-yeast extract, 0.25 g $MgSO_4$, and 2.0 ml 28% $H_3PO_4$ per liter of distilled water. The 500 ml culture is used to inoculate 50 liters of fermentation media, and the culture fermented for three to four days at 37° C.

*S. uvarum* mannan extract is prepared by adding 50 ml 0.02M citrate buffer (5.88 g/l sodium citrate; pH 7.0±0.1) to each 100 g of cell paste. The cell/citrate mixture is autoclaved at 125° C. for ninety minutes and allowed to cool. After centrifuging at 5000 rpm for 10 minutes, the supernatant is removed and retained. The cells are then washed with 75 ml 0.02M citrate buffer and the cell/citrate mixture again autoclaved at 125° C. for ninety minutes. The cell/citrate mixture is centrifuged at 5000 rpm for 10 minutes, and the supernatant is retained.

In order to precipitate copper/mannan complexes, an equal volume of Fehling's Solution is added to the combined supernatants while stirring. The complete Fehling's solution is prepared by mixing Fehling's Solution A with Fehling's Solution B in a 1:1 ratio just prior to use. The copper complexes are allowed to settle, and the liquid decanted gently from the precipitate. The copper/mannan precipitate complexes are then dissolved in 6-8 ml 3N HCl per 100 grams yeast paste.

The resulting solution is poured with vigorous stirring into 100 ml of 8:1 methanol:acetic acid, and the precipitate allowed to settle for several hours. The supernatant is decanted and discarded, then the wash procedure is repeated until the supernatant is colorless, approximately two to three times. The precipitate is collected on a scintered glass funnel, washed with methanol, and air dried overnight. On some occasions, the precipitate may be collected by centrifugation at 5000 rpm for 10 minutes before washing with methanol and air drying overnight. The dried mannan powder is dissolved in distilled water to a concentration of approximately 2 g/ml.

A *S. uvarum* mannan ELISA may be used to detect ASCA. *S. uvarum* mannan ELISA plates are saturated with antigen as follows. Purified *S. uvarum* mannan prepared as described above is diluted to a concentration of 100 μg/ml with phosphate buffered saline/0.2% sodium azide. Using a multi-channel pipettor, 100 μl of 100 μg/ml *S. uvarum* mannan is added per well of a Costar 96-well hi-binding plate (catalog no. 3590; Costar Corp., Cambridge, Mass.). The antigen is allowed to coat the plate at 4° C. for a minimum of 12 hours. Each lot of plates is compared to a previous lot before use. Plates are stored at 2-8° C. for up to one month.

Patient sera may be analyzed in duplicate for ASCA-IgA or ASCA-IgG reactivity. Microtiter plates saturated with antigen as described above are incubated with phosphate buffered saline/0.05% Tween-20 for 45 minutes at room temperature to inhibit nonspecific antibody binding. Patient sera are subsequently added at a dilution of 1:80 for analysis of ASCA-IgA and 1:800 for analysis of ASCA-IgG and incubated for 1 hour at room temperature. Wells are washed three times with PBS/0.05% Tween-20. Then, a 1:1000 dilution of alkaline phosphatase-conjugated goat anti-human IgA (Jackson Immunoresearch; West Grove, Pa.) or a 1:1000 dilution of alkaline phosphatase-conjugated goat anti-human IgG $F(ab')_2$ (Pierce; Rockford, Ill.) is added, and the microtiter plates are incubated for 1 hour at room temperature. A solution of p-nitrophenol phosphate in diethanolamine substrate buffer is added, and color development is allowed to proceed for 10 minutes. Absorbance at 405 nm is analyzed using an automated EMAX plate reader (Molecular Devices; Sunnyvale, Calif.).

ASCA levels (e.g., IgG, IgA, or both) may be determined relative to a standard consisting of pooled sera obtained from patients with an established diagnosis of Crohn's disease (CD). Results with test patient samples are expressed as ELISA units and may be expressed as a percentage of the standard binding of the reference CD sera. Sera with circulating ASCA levels exceeding the reference range value may also be termed ASCA positive, whereas numerical values that are below the reference range may also be termed ASCA negative.

Example 4. Determination of Anti-OmpC Antibody Levels

This example illustrates the preparation of OmpC protein and an analysis of anti-OmpC antibody levels in a sample using an ELISA assay.

The following protocol describes the purification of OmpC protein using spheroplast lysis. OmpF/OmpA-mutant *E. coli* are inoculated from a glycerol stock into 10-20 ml of Luria Bertani broth supplemented with 100 μg/ml streptomycin (LB-Strep; Teknova; Half Moon Bay, Calif.) and cultured vigorously at 37° C. for about 8 hours to log phase, followed by expansion to 1 liter in LB-Strep over 15 hours at 25° C. The cells are harvested by centrifugation. If necessary, cells are washed twice with 100 ml of ice cold 20 mM Tris-C1, pH 7.5. The cells are subsequently resuspended in ice cold spheroplast forming buffer (20 mM Tris-C1, pH 7.5; 20% sucrose; 0.1M EDTA, pH 8.0; 1 mg/ml lysozyme), after which the resuspended cells are incubated on ice for about 1 hour with occasional mixing by inversion. If required, the spheroplasts are centrifuged and resuspended in a smaller volume of spheroplast forming buffer (SFB). The spheroplast pellet is optionally frozen prior to resuspension in order to improve lysis efficiency. Hypotonic buffer is avoided in order to avoid bursting the spheroplasts and releasing chromosomal DNA, which significantly decreases the efficiency of lysis.

The spheroplast preparation is diluted 14-fold into ice cold 10 mM Tris-C1, pH 7.5 containing 1 mg/ml DNaseI and is vortexed vigorously. The preparation is sonicated on ice 4×30 seconds at 50% power at setting 4, with a pulse "On time" of 1 second, without foaming or overheating the sample. Cell debris is pelleted by centrifugation and the supernatant is removed and clarified by centrifugation a second time. The supernatant is removed without collecting any part of the pellet and placed into ultracentrifuge tubes. The tubes are filled to 1.5 mm from the top with 20 mM Tris-C1, pH 7.5. The membrane preparation is pelleted by ultracentrifugation at 100,000×g for 1 hr at 4° C. in a Beckman SW 60 swing bucket rotor. The pellet is resuspended by homogenizing into 20 mM Tris-C1, pH 7.5 using a 1 ml pipette tip and squirting the pellet closely before pipetting up and down for approximately 10 minutes per tube. The material is extracted for 1 hr in 20 mM Tris-C1, pH 7.5 containing 1% SDS, with rotation at 37° C. The preparation is transferred to ultracentrifugation tubes and the membrane is pelleted at 100,000×g. The pellet is resuspended by homogenizing into 20 mM Tris-C1, pH 7.5 as before. The membrane preparation is optionally left at 4° C. overnight.

OmpC is extracted for 1 hr with rotation at 37° C. in 20 mM Tris-C1, pH 7.5 containing 3% SDS and 0.5M NaCl. The material is transferred to ultracentrifugation tubes and the membrane is pelleted by centrifugation at 100,000×g. The supernatant containing extracted OmpC is then dialyzed against more than 10,000 volumes to eliminate high salt content. SDS is removed by detergent exchange against 0.2% Triton. Triton is removed by further dialysis against 50 mM Tris-Cl. Purified OmpC, which functions as a porin in its trimeric form, is analyzed by SDS-PAGE. Electrophoresis at room temperature results in a ladder of bands of about 100 kDa, 70 kDa, and 30 kDa. Heating for 10-15 minutes at 65-70° C. partially dissociates the complex and results in only dimers and monomers (i.e., bands of about 70 kDa and 30 kDa). Boiling for 5 minutes results in monomers of 38 kDa.

The OmpC direct ELISA assays may be performed essentially as follows. Plates (USA Scientific; Ocala, Fla.) are coated overnight at 4° C. with 100 μl/well OmpC at 0.25 μg/ml in borate buffered saline, pH 8.5. After three washes in 0.05% Tween 20 in phosphate buffered saline (PBS), the plates are blocked with 150 μl/well of 0.5% bovine serum albumin in PBS, pH 7.4 (BSA-PBS) for 30 minutes at room temperature. The blocking solution is then replaced with 100 μl/well of Crohn's disease or normal control serum, diluted 1:100. The plates are then incubated for 2 hours at room temperature and washed as before. Alkaline phosphatase-conjugated goat anti-human IgA (α-chain specific), or IgG (γ-chain specific) (Jackson ImmunoResearch; West Grove, Pa.) is added to the plates at a dilution of 1:1000 in BSA-PBS. The plates are incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01M Tris, pH 8.6) is added at 100 μl/well, and color is allowed to develop for one hour. The plates are then analyzed at 405 nm.

Anti-OmpC antibody levels may be determined relative to a standard consisting of pooled sera obtained from patients with an established diagnosis of Crohn's disease (CD). Sera with circulating anti-OmpC antibody levels exceeding the reference range value may also be termed anti-OmpC antibody positive, whereas numerical values that are below the reference range may also be termed anti-OmpC antibody negative. In certain instances, anti-OmpC antibody positive reactivity may be defined as reactivity greater than two standard deviations above the mean reactivity obtained with control (normal) sera analyzed at the same time as the test samples.

Example 5. Determination of Anti-I2 Antibody Levels

This example illustrates the preparation of recombinant I2 protein and an analysis of anti-I2 antibody levels in a sample using an ELISA assay or a histological assay.

The full-length I2-encoding nucleic acid sequence may be cloned into the GST expression vector pGEX. After expression in *E. coli*, the protein is purified on a GST column. The purified protein may be shown to be of the expected molecular weight by silver staining, and may be shown to have anti-GST reactivity upon Western blot analysis. The full-length I2-encoding nucleic acid sequence may also be cloned into a Hex-His6 expression vector, expressed in *E. coli*, and the resulting protein purified.

Human IgA and IgG antibodies that bind the GST-I2 fusion polypeptide may be detected by direct ELISA assays essentially as follows. Plates (Immulon 3; DYNEX Technologies; Chantilly, Va.) are coated overnight at 4° C. with 100 μl/well GST-I2 fusion polypeptide (5 μg/ml in borate buffered saline, pH 8.5). After three washes in 0.05% Tween 20 in phosphate buffered saline (PBS), the plates are blocked with 150 μl/well of 0.5% bovine serum albumin in PBS, pH 7.4 (BSA-PBS) for 30 minutes at room temperature. The blocking solution is then replaced with 100 μl/well of CD serum, ulcerative colitis (UC) serum, or normal control serum, diluted 1:100. The plates are then incubated for 2 hours at room temperature and washed as before. Alkaline phosphatase-conjugated secondary antibody (goat anti-human IgA (α-chain specific); Jackson ImmunoResearch; West Grove, Pa.) is added to the IgA plates at a dilution of 1:1000 in BSA-PBS. For IgG reactivity, alkaline phosphatase conjugated secondary antibody (goat anti-human IgG (γ-chain specific); Jackson ImmunoResearch) is added. The plates are incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01M Tris, pH 8.6, is added at 100 μl/well, and color allowed to develop for one hour. The plates are then analyzed at 405 nm. Nonspecific binding of sera to the control GST protein (typically <0.1) are subtracted from raw values of I2 binding to obtain I2-specific absorbances.

Anti-I2 antibody levels may be determined relative to a standard consisting of pooled sera obtained from patients with an established diagnosis of Crohn's disease (CD). Sera with circulating anti-I2 antibody levels exceeding the reference range value may also be termed anti-I2 antibody positive, whereas numerical values that are below the reference range may also be termed anti-I2 antibody negative. In certain instances, anti-I2 antibody positive reactivity may be defined as reactivity greater than two standard deviations above the mean reactivity obtained with control (normal) sera analyzed at the same time as the test samples.

For histological analysis, rabbit anti-I2 antibodies may be prepared using purified GST-I2 fusion protein as the immunogen. GST-binding antibodies are removed by adherence to GST bound to an agarose support (Pierce; Rockford, Ill.), and the rabbit sera validated for anti-I2 immunoreactivity by ELISA analysis. Slides are prepared from paraffin-embedded biopsy specimens from CD, UC, and normal controls. Hematoxylin and eosin staining are performed, followed by incubation with I2-specific antiserum. Binding of antibodies is detected with peroxidase-labeled anti-rabbit secondary antibodies (Pierce; Rockford, Ill.). The assay may be optimized to maximize the signal to background and the distinction between CD and control populations.

Example 6. Genotyping for Three Crohn's Disease Associated Variants of NOD2

This example shows a genotyping assay that can be used to detect the presence or absence of a NOD2 variant.

Genotyping may be performed using a genotyping assay employing 5'-exonuclease technology, the TaqMan MGB™ assay (PE Biosystems; Foster City, Calif.). Primers may be designed using the software PrimerExpress 1.5.™ (PE Biosystems) and sequence information may be found in dbSNP for NOD2 variants R702W ("SNP 8"), G908R ("SNP 12"), and 1007fs ("SNP 13"). The MGB™ design adds a "minor groove binder" to the 3' end of the TaqMan™ probes, thereby increasing the binding temperature of the probe and enabling the use of shorter probes than in conventional TaqMan™ assays (Kutyavin et al., *Nucleic Acids Res.*, 25:3718-3723 (1997)). This has the effect of increasing the discrimination between the alleles in the assay (Kutyavin et al., *Nucleic Acids Res.*, 28:655-661 (2000)). Assays may be performed following the manufacturer's recommendations (PE Biosystems bulletin 4317594) in an ABI 7900 instrument. Genotyping is typically performed blinded to clinical status of the subjects. Exemplary primers and probes suitable for use in the NOD2 genotyping assay are shown in Tables 3 and 4.

TABLE 4

TAQMAN PROBES

| Allele Detected | Probe Sequence | SED ID NO. |
|---|---|---|
| SNP5 wild type allele ("1") | 6FAM-CATGGCTGGACCC-MGBNFQ | 33 |
| SNP5 variant allele ("2") | TET-CATGGCTGGATCC-MGBNFQ | 34 |
| SNP8 wild type allele ("1") | 6FAM-TGCTCCGGCGCCA-MGBNFQ | 35 |
| SNP8 variant allele ("2") | TET-CTGCTCTGGCGCCA-MGBNFQ | 36 |
| SNP12 wild type allele ("1") | 6FAM-CTCTGTTGCCCCAGAA-MGBNFQ | 37 |
| SNP12 variant allele ("2") | TET-CTCTGTTGCGCCAGA-MGBNFQ | 38 |
| SNP13 wild type allele ("1") | TET-CTTTCAAGGGCCTGC-MGBNFQ | 39 |
| SNP13 variant allele ("2") | 6FAM-CCTTTCAAGGGGCCT-MGBNFQ | 40 |
| JW1 wild type allele | 6FAM-AAGACTCGAGTGTCCT-MGBNFQ | 41 |
| JW1 variant allele | VIC-AGACTCAAGTGTCCTC-MGBNFQ | 42 |

Example 7. Quartile-Based Matrix for Prognosing IBD

This example illustrates the use of a laboratory report of the present invention comprising a "heat map" corresponding to quartile scores for a panel of prognostic markers to aid in the prognosis of IBD.

In certain embodiments, the present invention provides a detailed display in easy to understand format. FIG. 4 is one embodiment of a laboratory report of the present invention. As can be seen therein, the use of grayscale or color for the

TABLE 3

Primers for use in the Taqman MGB™ assay for SNPs 5, 8, 12, and 13

| SNP | Forward Primer | Reverse Primer | SEQ ID NO. |
|---|---|---|---|
| SNP 5 | 5'GGTGGCTGGGCTCTTCT 3' | 5' CTCGCTTCCTCAGTACCTATGATG 3' | For: 25<br>Rev: 26 |
| SNP 8 | 5' CTGGCTGAGTGCCAGACATCT 3' | 5' GGCGGGATGGAGTGGAA 3' | For: 27<br>Rev: 28 |
| SNP 12 | 5' CCACCTCAAGCTCTGGTGATC 3' | 5' GTTGACTCTTTTGGCCTTTTCAG 3' | For: 29<br>Rev: 30 |
| SNP 13 | 5' CCTTACCAGACTTCCAGGATGGT 3' | 5' TGTCCAATAACTGCATCACGTACCT 3' | For: 31<br>Rev: 32 |

visualization and magnitude of IBD disease behavior/prognosis is displayed. In particular, a grayscale or color matrix of quartiles is used to "range and bin" individual prognostic markers. This "heat map" provides an almost instantaneous understanding of the level of each of the markers in the matrix and guides more accurate prognosis of the IBD disease state. The exemplary laboratory report advantageously provides a clearer prognosis because the panel of prognostic markers set forth in the "heat map" associates the quartile score assigned to each marker with a particular clinical subtype of CD such as, e.g., inflammatory, fibrostenosis, fistulizing, or internal perforating disease. The combination of quartile scores for the panel of prognostic markers may be used to visualize patterns, which provides a prognostic indication of IBD disease behavior. In some instances, the laboratory report provides more accurate predictions with increasing biomarker associations, and is indicative of the presence or absence of a given IBD disease state. In other instances, the laboratory report provides prognostic information regarding whether the individual has a high or low risk of needing surgery such as small bowel surgery. In the exemplary laboratory report shown in FIG. 4, the risk of surgery is assigned a quartile score of 1, which means a prognosis corresponding to a low risk of surgery. In addition to the prognostic markers shown in this exemplary laboratory report, other markers such as genetic markers (e.g., NOD2) may be included to assist in the prognosis of IBD.

FIG. 5 is another embodiment of a laboratory report of the present invention obtained from a pediatric patient. In this exemplary laboratory report, the risk of surgery is assigned a quartile score of 0, which means a prognosis corresponding to no risk of surgery (e.g., no need for small bowel surgery). However, depending on the quartile scores assigned to each of the prognostic markers in the panel, the patient may have a risk or susceptibility of developing a clinical subtype of CD such as inflammatory, fibrostenosis, fistulizing, or internal perforating disease. In addition to the prognostic markers shown in this exemplary laboratory report, other markers such as genetic markers (e.g., NOD2) may be included to assist in the prognosis of IBD in pediatric patients. As such, the quartile-based matrices or models described herein are also useful for providing prognostic information for pediatric patients diagnosed with IBD.

FIG. 6 is a further embodiment of a laboratory report of the present invention. As shown therein, the report can be expanded to add information regarding disease characteristics, assays, genetic information, and predictive markers which could improve diagnostic and predictive capabilities.

Figure 7:
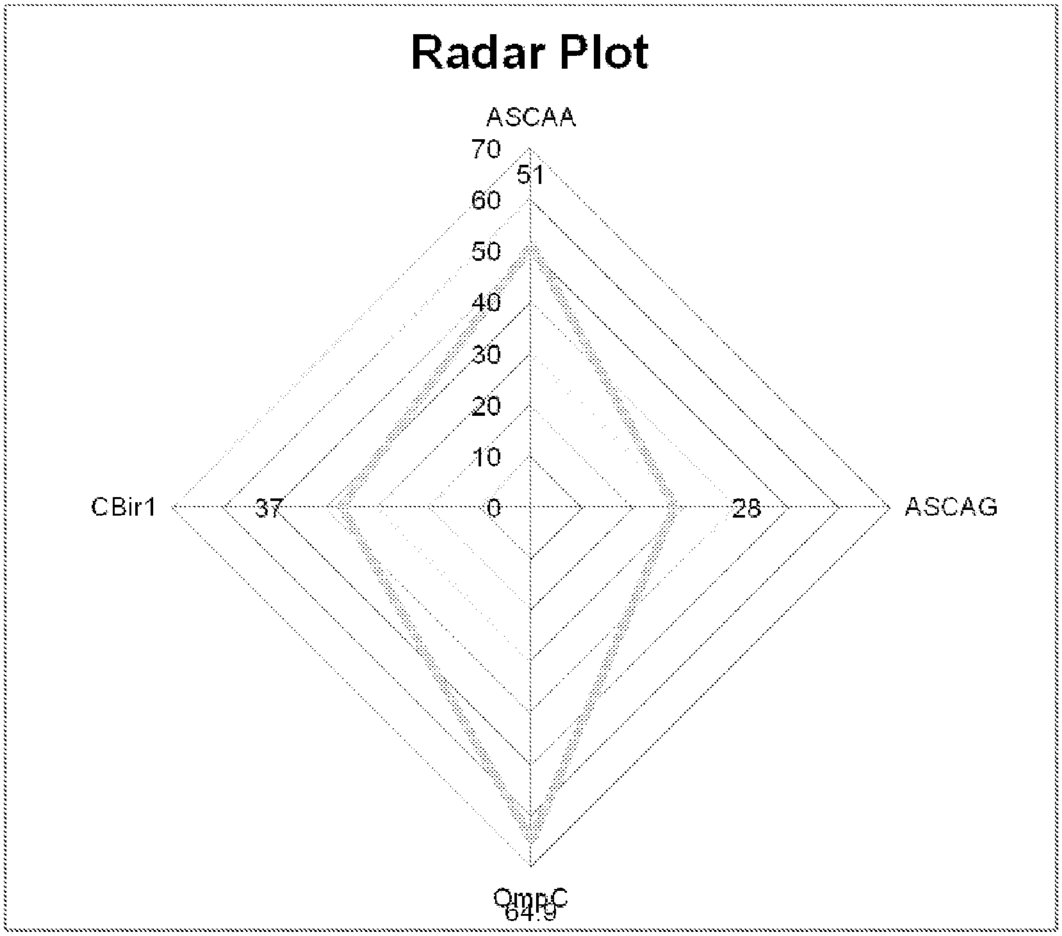
FIG. 7 illustrates a radar chart for visualization of magnitude as an indicator of disease behavior and/or prognosis.

In addition to "heat map" embodiments, FIG. 7 is one embodiment of a laboratory report of the present invention which is a radar plot. As shown therein, the radar plot or chart of the present invention can be used for visualization of the magnitude of markers as an indicator of IBD disease behavior and/or prognosis. For example, the radar plot uses the true concentration of marker levels or AUC data. In addition, the shape and size of the AUC can be used to provide prognosis and banding may be added to show range boundaries. Color or gray scaling can be added for visualization and immediate recognition of information.

Figure 8:
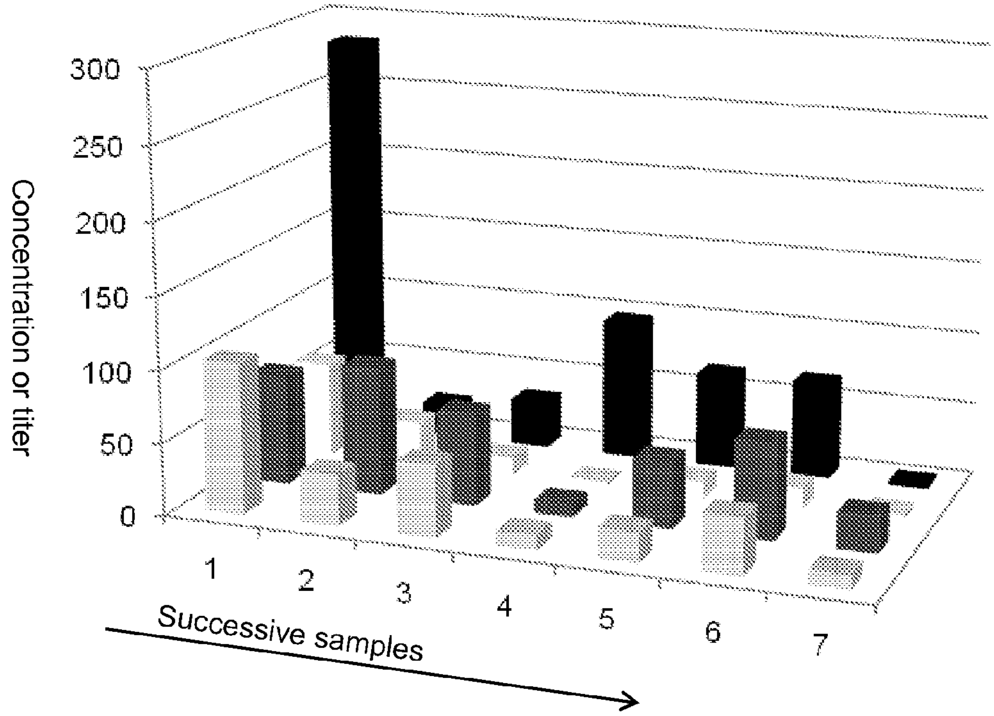
FIG. 8 illustrates serial quantitative biomarker measurements (SQBM) in combination with 'weighting" in determination of the course of disease in response to treatment.

Turning now to FIG. 8, this figure illustrates a bar graph displaying serial quantitative biomarker measurements (SQBM) in combination with 'weighting' in determination of the course of the disease in response to, for example, treatment. This figure shows a series of draws against a patient receiving treatment. The graph shows the patient's history as a function of time and provides longitudinal views of a patient's treatment effects, getting away from the single 'snapshot' of most current testing.

Example 8. EGF Contribution to an IBD Diagnostic Algorithm

In a cohort of 527 samples, the contributory effects of EGF concentration was evaluated in a smart algorithm. In this case, comparison Random Forest algorithms were built, which included or excluded (with and without) EGF concentration values. The other markers measured were ANCA, ASCA IgA, ASCA IgG, CBir-1, Omp C, and pANCA. See, U.S. patent application Ser. No. 11/565,544 (U.S. Patent Publication No. 2008/0131439), entitled "Methods of Diagnosing Inflammatory Bowel Disease," incorporated herein by reference.

Table 4 below shows that EGF increases UC sensitivity and UC specificity. In one aspect, EGF is useful in samples where ANCA cutoff is borderline (8-12 units). In these instances, by including EGF it is possible to increase IBD (e.g., UC) sensitivity and/or specificity. As such, these results indicate that EGF can increase IBD diagnostic prediction performance. In certain other instances, EGF is useful in determining the aggressiveness of IBD.

TABLE 5

|  | WITHOUT EGF | WITH EGF |
| --- | --- | --- |
| CD SEN | 70.89% | 73.42% |
| CD SPE | 86.38% | 85.49% |
| CD PPV | 47.86% | 47.15% |
| CD NPV | 94.39% | 94.80% |
| UC SEN | 67.63% | 71.94% |
| UC SPE | 86.08% | 87.63% |
| UC PPV | 63.51% | 67.57% |
| UC NPV | 88.13% | 89.71% |
| IBD SEN | 80.73% | 86.70% |
| IBD SPE | 71.20% | 73.46% |
| IBD PPV | 66.42% | 69.74% |
| IBD NPV | 83.97% | 88.67% |

Table 6 below illustrates in one embodiment, the magnitude of importance of EGF to a Random Forest algorithm (see, U.S. patent application Ser. No. 11/565,544 (U.S. Patent Publication No. 2008/0131439), entitled "Methods of Diagnosing Inflammatory Bowel Disease," incorporated herein by reference).

TABLE 6

| Variable | Score |  |
| --- | --- | --- |
| pANCA | 100 | ||||||||||||||||||||||||||||||||| |
| ASCA-IgA | 57.51 | ||||||||||||||||||| |
| OmpC | 49.88 | ||||||||||||||||| |
| EGF | 29.91 | |||||||||| |
| ASCA-IgC | 29.87 | |||||||||| |
| CBir-1 | 17.89 | |||||| |

Example 9. Defensin Contribution to an IBD Diagnostic Algorithm

In a cohort of 51 samples, the concentration of human defensin (HDβ1 and HDβ2) values were determined and its contributory effects evaluated in a diagnostic algorithm. In this instance, the cohort contained the following samples: UC=26; CD=18; and Healthy=7. In addition, 7 of the 18 CD samples were UC-like CD.

The assay included the following markers: ANCA >12; pANCA (DNase sensitive); and Defensin >Mean+2SD compared against healthy controls. The results indicate that a combination of HDβ1&2, ANCA, and pANCA DNase sensitivity increases UC diagnostic prediction performance. For example, in Tables 7A-B, Evaluation 1 shows that HDβ1&2, ANCA, and pANCA DNase sensitivity can be used to predict UC in 23/26 samples. In view of these results, it is evident that defensin is a good UC marker.

TABLE 7A

Evaluation 1,

| | Total | Prediction UC | Prediction Non-UC |
|---|---|---|---|
| UC | 26 | 23 | 3 |
| Non-UC | 25 | 14 | 11 |

TABLE 7B

Evaluation 2,

| | Total | Prediction UC | Prediction Non-UC |
|---|---|---|---|
| UC | 26 | 23 | 3 |
| UC-like CD? | 7 | 7 | 0 |
| Non-UC | 18 | 6 | 12 |

Example 10. E-Cadherin Contribution to an IBD Diagnostic Algorithm

In a cohort of 157 samples, E-cadherin concentration values were determined. Comparison Random Forest models were built including and excluding E-Cadherin (with or without E-Cadherin). See, U.S. patent application Ser. No. 11/565,544 (U.S. Patent Publication No. 2008/0131439), entitled "Methods of Diagnosing Inflammatory Bowel Disease," incorporated herein by reference. Other markers included: ANCA, ASCA IgA, ASCA IgG, CBir1, and OmpC. The results are shown in Tables 8A-B. The data indicates that E-Cadherin increases CD diagnostic prediction by about +6%.

TABLE 8A

I. Random Forest Model without E-Cadherin

| Actual Class | Total Cases | Percent Correct | 0 N = 54 | 1 N = 45 | 2 N = 58 |
|---|---|---|---|---|---|
| 0 | 64 | 64.063 | 41 | 10 | 13 |
| 1 | 48 | 47.917 | 6 | 23 | 19 |
| 2 | 45 | 57.778 | 7 | 12 | 26 |

TABLE 8B

II. Random Forest Model with E-Cadherin

| Actual Class | Total Cases | Percent Correct | 0 N = 56 | 1 N = 46 | 2 N = 55 |
|---|---|---|---|---|---|
| 0 | 64 | 64.063 | 41 | 9 | 14 |
| 1 | 48 | 54.167 | 7 | 26 | 15 |
| 2 | 45 | 57.778 | 8 | 11 | 26 |

Example 11. CRP and SAA Contributions to an IBD Diagnostic Algorithm

Figure 9:
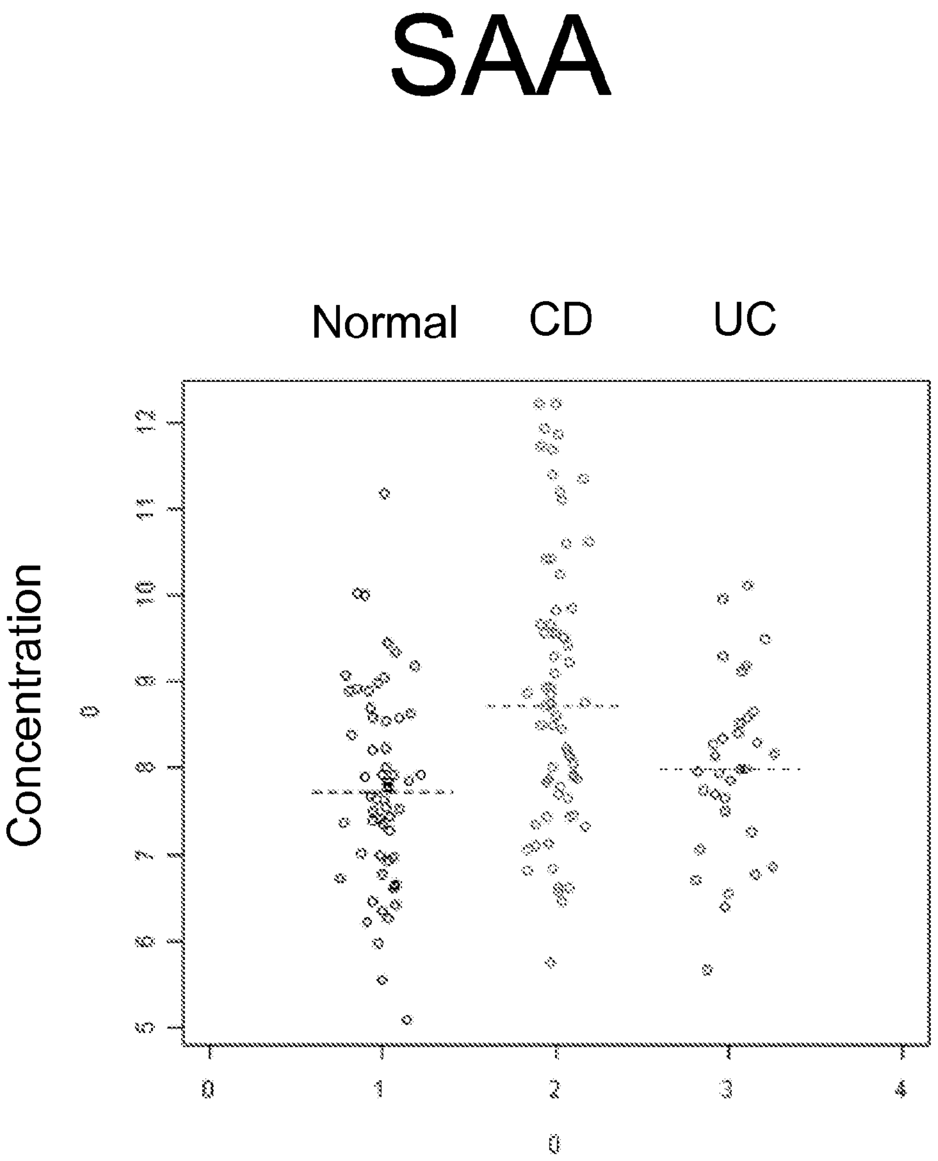
FIG. 9 illustrates separation of samples into normal, CD and UC based on concentration of SAA.
Figure 10:
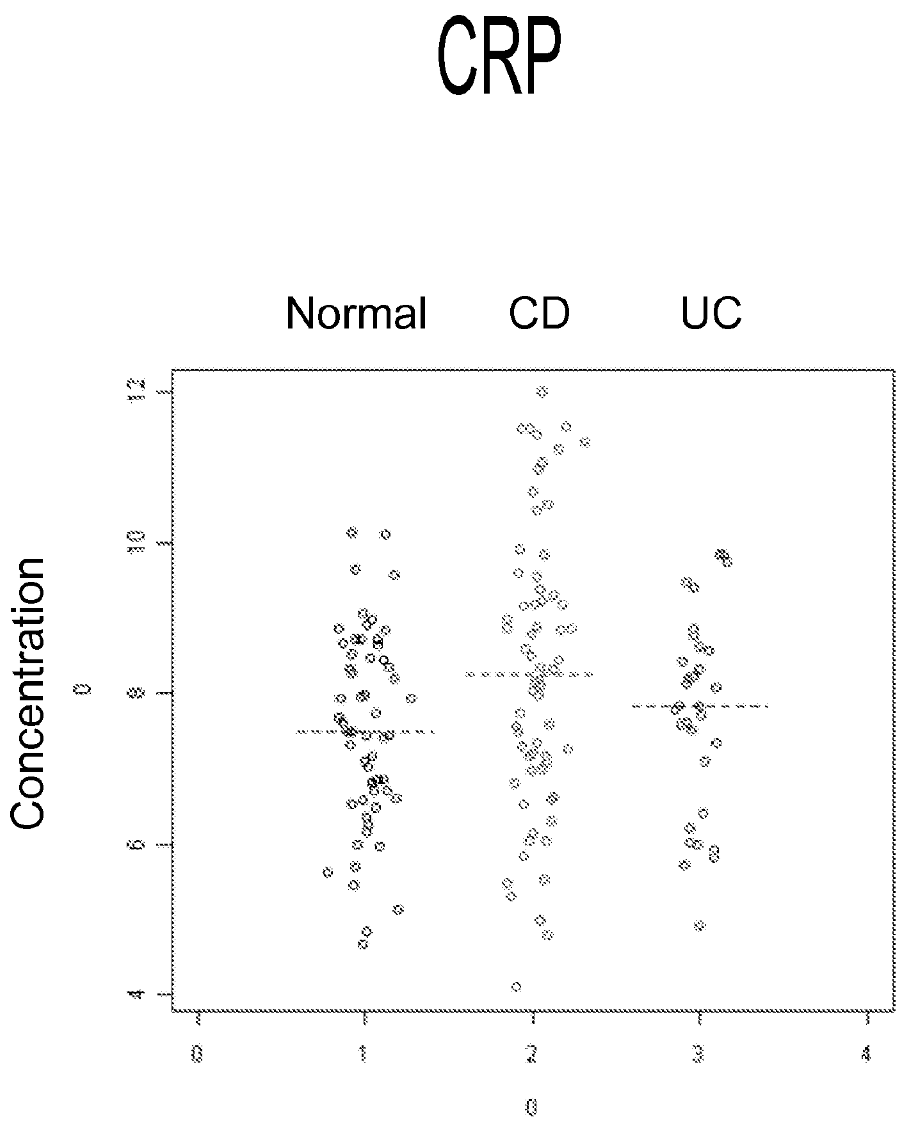
FIG. 10 illustrates separation of samples into normal, CD and UC based on concentration of CRP.

In a cohort of 768 samples, C-Reactive Protein (CRP) and Serum Amyloid A (SAA) concentration values were determined. Thereafter, CRP and SAA contributory effects were evaluated by comparing models built with or without CRP and SAA in a Random Forest algorithm. See, U.S. patent application Ser. No. 11/565,544 (U.S. Patent Publication No. 2008/0131439), entitled "Methods of Diagnosing Inflammatory Bowel Disease," incorporated herein by reference. Other markers included: ANCA, ASCA IgA, ASCA IgG, CBir1, and OmpC. The results are shown in Tables 9A-B. The data indicate that CRP and SAA increase IBD diagnostic prediction by about +5%. In addition, FIGS. 9 and 10 show that SAA and CRP are each independently elevated in CD and UC patient samples compared to normal control samples.

TABLE 9A

I. Random Forest Model without CRP/SAA

| Actual Class | Total Cases | Percent Correct | 0 N = 398 | 1 N = 185 | 2 N = 185 |
|---|---|---|---|---|---|
| 0 | 544 | 63.787 | 347 | 101 | 96 |
| 1 | 115 | 56.522 | 26 | 65 | 24 |
| 2 | 109 | 59.633 | 25 | 19 | 65 |

TABLE 9B

II. Random Forest Model with CRP/SAA

| Actual Class | Total Cases | Percent Correct | 0 N = 422 | 1 N = 171 | 2 N = 175 |
|---|---|---|---|---|---|
| 0 | 544 | 69.118 | 376 | 86 | 82 |
| 1 | 115 | 61.739 | 21 | 71 | 23 |
| 2 | 109 | 64.220 | 25 | 14 | 70 |

Example 12. Summary of Serological Marker Contribution to an IBD Diagnostic Algorithm Table 10 is a summary of the effects of the contribution of EGF, HDβ 1&2, E-Cadherin, CRP, and SAA to a Random Forest algorithm (see, U.S. patent application Ser. No. 11/565,544 (U.S. Patent Publication No. 2008/0131439), entitled "Methods of Diagnosing Inflammatory Bowel Disease," incorporated herein by reference).

TABLE 10

| Marker | Number | Evaluation Method | CD Prediction | UC Prediction | Non-IBD Prediction |
|---|---|---|---|---|---|
| EGF | 527 | RF | +2.5% | +4.3% | +2.3% |
| HDβ 1&2 | 51 | Cutoff (ANCA, DNase & HDB 1&2+) | — | 23/26 predict Correct | — |
| E-Cadherin | 157 | RF | +6.3% | — | — |
| CRP &SAA | 768 | RF | +5.2% | +4.6% | +5.4% |

Example 13. Elevated Serum Antibody Response to Microbial Components in Crohn's Disease Patients Predicts High Probability for Surgery Abstract Purpose:

Since 70% of Crohn's disease (CD) patients will ultimately require surgical intervention, the ability to predict which patients will progress to surgery would be extremely valuable. The purpose of this analysis was to derive a method that can be used to predict which CD patients are at risk for future gastrointestinal (GI) surgery.

Methods:

Blood samples and clinical data were collected previously from 200 adult CD patients whose disease was confirmed by biopsy. All patients had the diagnosis of CD made at least 1 year prior to the blood draw. Informed consent was obtained from all patients. In this retrospective analysis, levels of 4 serum IBD markers (ASCA-IgG, ASCA-IgA, anti-OmpC, and anti-CBir1) were measured. For each patient, each marker was scored into 1 of 4 quartiles (1-4), and the quartile scores for the 4 markers were summed (range: 4-16) to produce a quartile sum score (QSS). Patients were defined as high or low risk using 2 different metrics: by number of elevated markers (high risk: 1+ markers) or by quartile sum score (high risk: QSS 11+). For each of these metrics, Kaplan-Meier analysis was performed to compare the time-to-surgery for high- versus low-risk patients.

Results:

Those patients who had GI surgery were found to have statistically significantly higher levels of IBD markers compared with those patients who did not have GI surgery. Furthermore, 74% of the patients with high quartile sums (11-16) had at least 1 GI surgery compared with 28% of the patients with low quartile sums (4-10). Kaplan-Meier analysis also demonstrated that seropositive patients with at least 1 positive biomarker had a significantly higher rate of progression to surgery than those with no positive biomarkers (P=0.0014). Similar analyses comparing those with a QSS of 11-16 with those with a QSS of 4-10 showed that patients with higher QSS were also significantly more likely to have had surgery (P=0.0010). Ten years after diagnosis, 59% of the patients with high QSS have had surgery, compared with 24% of the patients with low QSS.

Conclusion:

This study demonstrates that increased immune reactivity toward microbial antigens was associated with increased risk of surgery in patients with CD. This study further suggests that serologic markers may have clinical utility in predicting disease progression and eventual need for surgery.

Introduction

Crohn's disease (CD) comprises a heterogenous group of diseases whose etiopathogenesis consists of immune reactivity to luminal bacteria in genetically susceptible individuals.[1] Antibody reactivity to antigens including anti-*Saccharomyces cerevisiae* (ASCA), bacterial sequence I2 (anti-I2), outer membrane porin C (OmpC),[2] and bacterial flagellin (CBir1) have been described in CD.[3] Immune reactivity to these antigens has been associated with various disease phenotypes in CD.[2,4-6] As 70% of CD patients will ultimately require surgical intervention, the ability to predict such disease progression would be extremely valuable.

Objective

This analysis was performed in an effort to derive a method to predict the future risk of surgery in CD patients.

Methods

Previously collected clinical data and blood samples from 200 biopsy-confirmed adult CD patients, diagnosed at least 1 year prior to blood sampling, were analyzed for 4 serum IBD biomarkers (ASCA-IgG, ASCA-IgA, anti-OmpC, and anti-CBir1) and compared in patients who had surgery versus those who did not.

Serum immune response for each biomarker was classified as "Positive" (higher than reference value) and "Negative" (lower than reference value).

For each patient, each marker was scored into 1 of 4 quartiles (1-4), and the quartile scores for the 4 markers were summed (range: 4-16) to produce a quartile sum score (QSS).

To quantify the antimicrobial antibody response in patients, the cohort was divided into 13 subgroups (4-16) based on their QSS:

QSS=4: All 4 biomarker values fall within the 25th percent quartile range.

QSS=16: All 4 biomarker values fall above the the 75th percent quartile range.

Whether seropositive patients had a greater risk of having surgery than seronegative patients was determined based on 2 analytical methods:

Analysis based on using IBD biomarker reference values:

Seropositive: 1 or more IBD biomarker values (ASCA-IgA, ASCA-IgG, anti-OmpC, and anti-CBir1) greater than the reference values.

Seronegative: All IBD marker values less than the reference value.

Analysis based on using the QSS:

Subgroups with QSS >10.

Subgroups with QSS ≤10.

For each of these metrics, Kaplan-Meier analysis was used to compare the time-to-surgery for those at high versus low risk.

Results

1. Clinical characteristics demonstrated different disease behavior between CD patients with and without surgery (Table 11).

TABLE 11

| Study Population Demographics | | |
|---|---|---|
| Clinical Characteristics | Surgery | No Surgery |
| Surgery, n (M/F) | 96 (48/48) | 104 (49/55) |
| Median age, yr (range) | 45 (21-80) | 39 (18-78) |
| Disease behavior, n (%) | | |
| Inflammatory | 44 (46%) | 87 (84%) |
| Fibrostenotic | 24 (25%) | 6 (6%) |
| Penetrating | 26 (29%) | 11 (10%) |

2. Those patients who had GI surgery were found to have statistically significantly higher serum antibody response to microbial components such as ASCA and CBir1 compared with those patients who did not have GI surgery (Table 12).

TABLE 12

Correlation of Immune Response to Microbial Antigens and an Autoantigen in CD Patients Who Had or Did Not Have GI Surgery

| | Positive | Negative | P Value |
|---|---|---|---|
| ANCA | | | |
| Had surgery | 26 | 70 | 0.0175 |
| Did not have surgery | 46 | 58 | |
| ASCA-IgA | | | |
| Had surgery | 62 | 34 | <0.001 |
| Did not have surgery | 21 | 83 | |
| ASCA-IgG | | | |
| Had surgery | 48 | 48 | <0.001 |
| Did not have surgery | 19 | 85 | |
| Anti-OmpC | | | |
| Had surgery | 42 | 54 | 0.05754 |
| Did not have surgery | 31 | 73 | |
| Anti-CBir1 | | | |
| Had surgery | 64 | 32 | 0.0121 |
| Did not have surgery | 50 | 54 | |

Serum antibodies against microbial antigens ASCA-IgG, ASCAIgA, OmpC, CBir1 and the autoantigen ANCA were determined in CD patients who had and did not have GI surgery. Serum immune response for each biomarker was classified as "Positive" (higher than reference value) and "Negative" (less than reference value). Chi-square analysis results suggest that ASCA-IgA, ASCA-IgG, anti-CBir1, and ANCA values are statistically different in CD cohorts who had versus did not have surgery.

Figure 11:
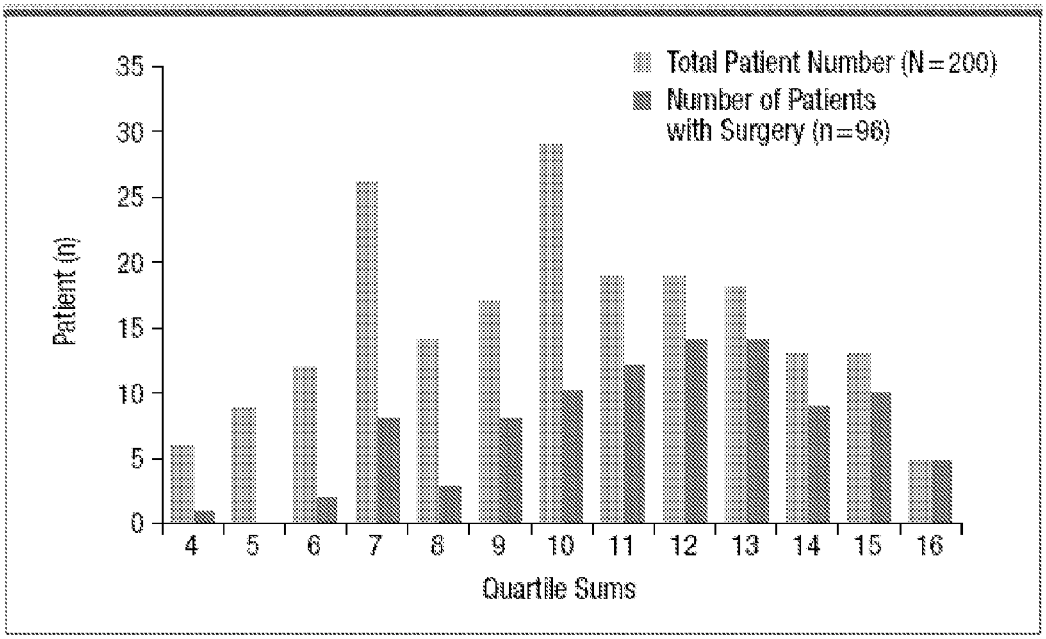
FIG. 11 illustrates CD patient distribution in the subgroups with QSS.

3. Seventy-four percent of the patients with high QSS (11-16) had at least 1 GI surgery compared with 28% of the patients with low QSS (4-10) [P<0.001] (FIG. 11).

TABLE 13

| Biomarker Quartiles | | | | |
|---|---|---|---|---|
| | ASCA-IgA EU/mL | ASCA-IgG EU/mL | Anti-OmpC EU/mL | Anti-CBir1 EU/mL |
| 25th percent quartile | 6.20 | 4.68 | 9.18 | 13.28 |
| 50th percent quartile | 11.20 | 15.35 | 21.05 | 22.95 |
| 75th percent quartile | 19.93 | 43.88 | 53.75 | 45.78 |

To quantify the antimicrobial antibody response in the patients, we divided the cohort into 13 subgroups (4-16) based on QSS. QSS=4 subgroup has all 4 biomarkers within the $1^{st}$ quartile range, and QSS=16 subgroup has all 4 biomarkers above the 75th percent quartile range:

- Results indicated that the percentage of patients who had GI surgery were among the subgroups with high QSS.
- Surgery probability in CD patients can be predicted by Kaplan-Meier analysis:
- Analysis based on using IBD biomarker reference values:
  - Seropositive: 1 of more IBD biomarker values (ASCA-IgA, ASCA-IgG, anti-OmpC, and anti-CBir1) greater than the reference values.
  - Seronegative: All IBD marker values less than the reference values.
- Patients who had surgery (N=56):
  - More than 1 positive marker response: n=52.
  - All-negative marker response: n=4.
  - Average time lapse between diagnosis and first GI surgery=9.0 yr.
  - Average serologic monitoring time after first GI surgery=12.2 yr.
- Patients who did not have surgery (control) based on the latest colonoscopy data available (N=53):
  - More than 1 positive marker response: n=31.
  - All-negative marker response: n=22.
  - Average time lapse between diagnosis and latest colonoscopy=7.0 yr.
  - Average serology monitoring time after latest colonoscopy=1.9 yr.

Figure 12:
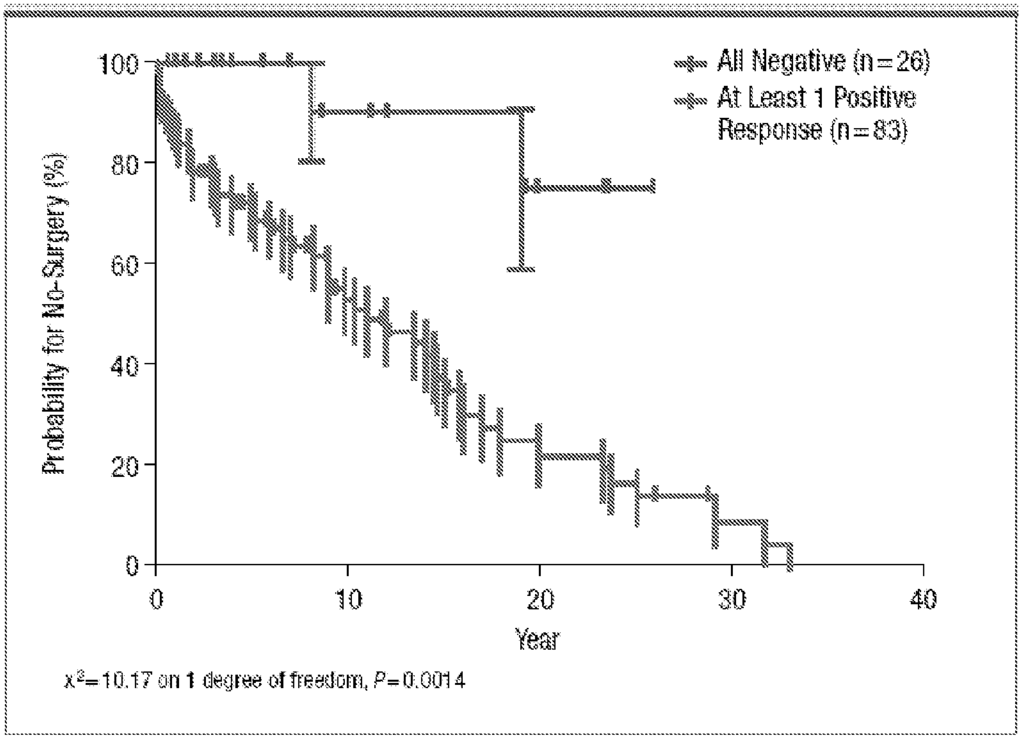
FIG. 12 illustrates Kaplan-Meier analysis based on serology biomarker levels.

Kaplan-Meier analysis demonstrated that seropositive patients with at least 1 positive biomarker had a significantly higher history of having surgery than those with no positive biomarkers (P=0.0014) (FIG. 12).

Figure 13:
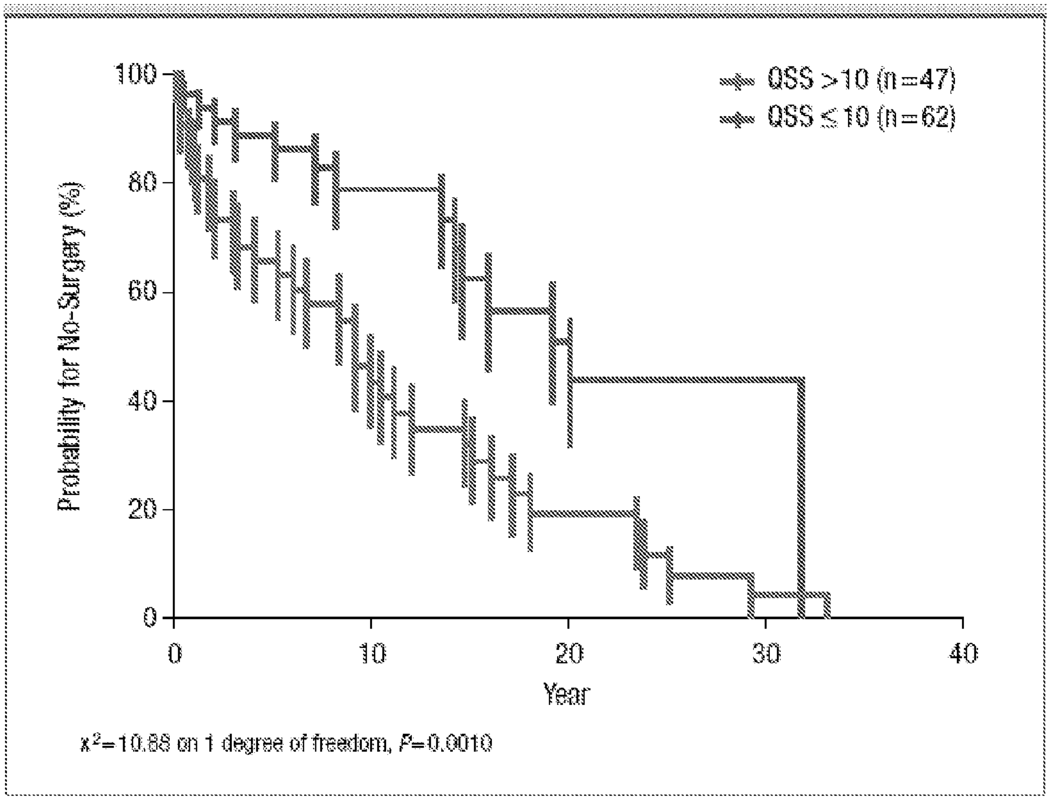
FIG. 13 illustrates Kaplan-Meier analysis based on serology activity QSS.

CD patients with all-negative IBD biomarker values had a lower risk for progressing to surgery in the future than those patients who had at least 1 IBD biomarker value higher than the reference value. FIG. 13 shows a Kaplan-Meier analysis comparing patients with QSS >10 (11-16) to those with QSS ≤10 (4-10).

The study showed that patients with higher QSS were also significantly more likely to have had surgery (P=0.0010). Ten years after diagnosis, 59% of the patients with higher QSS have had surgery, compared with 24% of the patients with low QSS. CD patients in the subgroups with QSS ≤10 have less risk for progressing to surgery than those patients in the subgroups with QSS greater than 10.

Conclusion

This study confirmed that elevated serologic markers have significant associations with surgery in CD patients. Additional prospective studies will further expand the clinical utility of serologic markers in predicting disease progression and severity in CD patients.

REFERENCES

1. Podolsky D K. *N Engl J Med.* 2002; 347:417-29.
2. Arnott I D R, et al. *Am J Gastroenterol.* 2004; 99:2376-84.
3. Targan S R, et al. *Gastroenterology.* 2005; 128:2020-8.
4. Mow W S, et al. *Gastroenterology.* 2004; 126:414-24.
5. Dubinsky M C, et al. *Am J Gastroenterol.* 2006; 101:360-7.
6. Dubinsky M C, et al. *Clin Gastroenterol Hepatol.* 2008; 6:1105-11.

Example 14. Selecting Patients for Top-Down Therapy: Prognosis Study Design

This example describes an IBD prognosis study design consisting of the following three studies (total N=1172):

1. N=200 from 25 secondary centers (see, Example 13).
2. N=451 additional samples from Institution A.
3. N=521 additional samples from Institution B.

This example illustrates a cross-sectional study where two prognostic outcomes were analyzed: (1) disease complications (stricturing/penetrating); and (2) need for surgery. The antigen preparation and characterization was robust with each test containing multipoint calibration curves and complete automation of all assay steps.

Figure 14:
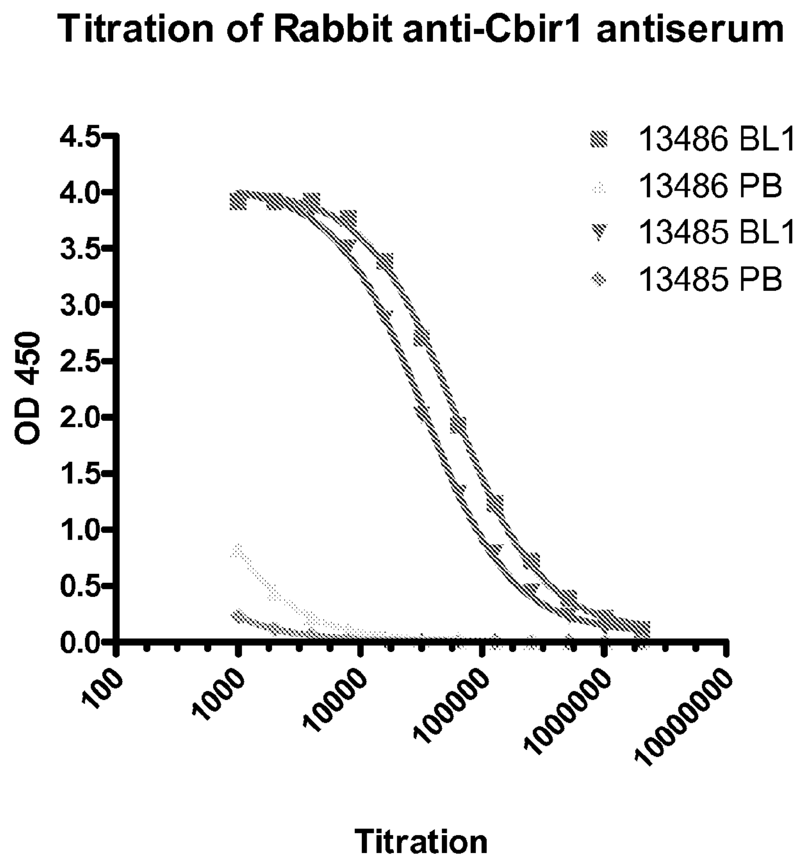
FIG. 14 illustrates an exemplary anti-CBir1 titration curve for one embodiment of the present invention.
Figure 15:
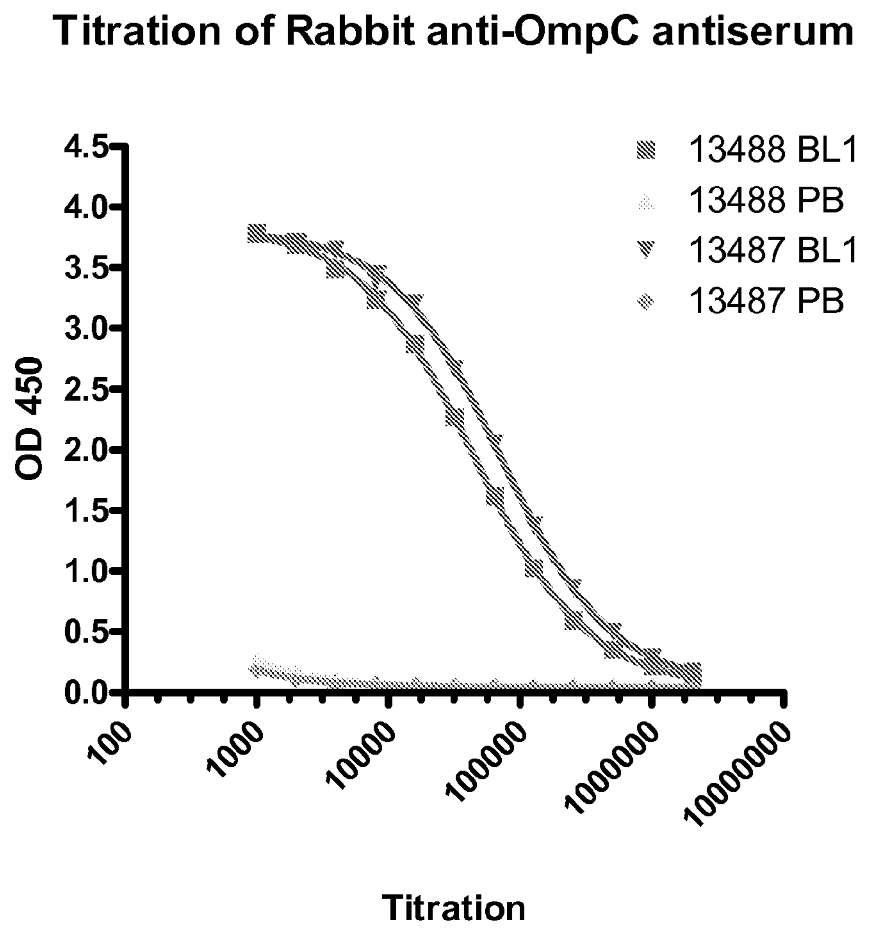
FIG. 15 illustrates an exemplary anti-OmpC titration curve for one embodiment of the present invention.

Rabbit antiserum was generated for CBir-1 (FIG. 14) and OmpC (FIG. 15) with very high titer. Panels were developed containing large numbers of patient sera with well-characterized disease and well-defined autoantibody profiles as well as normal sera that did not contain detectable autoantibodies. Table 14 provides a list of the serological and genetic markers analyzed in this prognostic study.

TABLE 14

| IBP Gen II markers | |
|---|---|
| ASCA-IgA | Anti-*Saccharomyces Cerevisae* IgA |
| ASCA-IgG | Anti-*Saccharomyces Cerevisae* IgG |
| Anti-OmpC | Outer Membrane Porin C from *E. Coli* |
| Anti-CBir1 | Bacterial Flagellin |
| pANCA | Perinuclear Anti-Neutrophilic Cytoplasmic Antibodies |
| Anti-I2 (re-folded) | Bacterial sequence I2 from *Pseudomonas Fluorescens* |
| CRP | C Reactive Protein |
| SAA | Serum Amyloid A |
| EGF | Epidermal Growth Factor |
| V-CAM1 | Vascular Cell Adhesion Molecule 1 |
| I-CAM1 | Intracellular Cell Adhesion Molecule 1 |

TABLE 14-continued

| IBP Gen II markers | |
|---|---|
| NOD2 | Nucleotide-Binding Oligomerization Domain 2 |
| | rs5743293 SNP13 - (3020insC) |
| | rs2066845 SNP12 - (G908R) |
| | rs2066844 SNP8 - (R702W) |

In this example, 1172 samples from multiple institutions were studied. Each plate had 5-6 calibrators/standards. The prognosis protocol comprised serological protein and genotyping analysis. All assays for anti-OmpC, anti-I2, ASCA IgG, ASCA IgA, CBir1, and ANCA were performed at two dilutions of serum (1:100 and 1:200). Antibody levels were determined and the results expressed as ELISA units (EU/mL), which are relative to a standard that is derived from a pool of patient sera with well-characterized disease.

The level for the analyte in the unknown samples was determined using the at least two closest standard. The CV for duplicates was set at 15%.

The genotyping analysis included three NOD2/CARD15 single nucleotide polymorphisms (SNPs): rs5743293 SNP13—(3020insC); rs2066845 SNP12—(G908R); and rs2066844 SNP8—(R702W).

Figure 16:
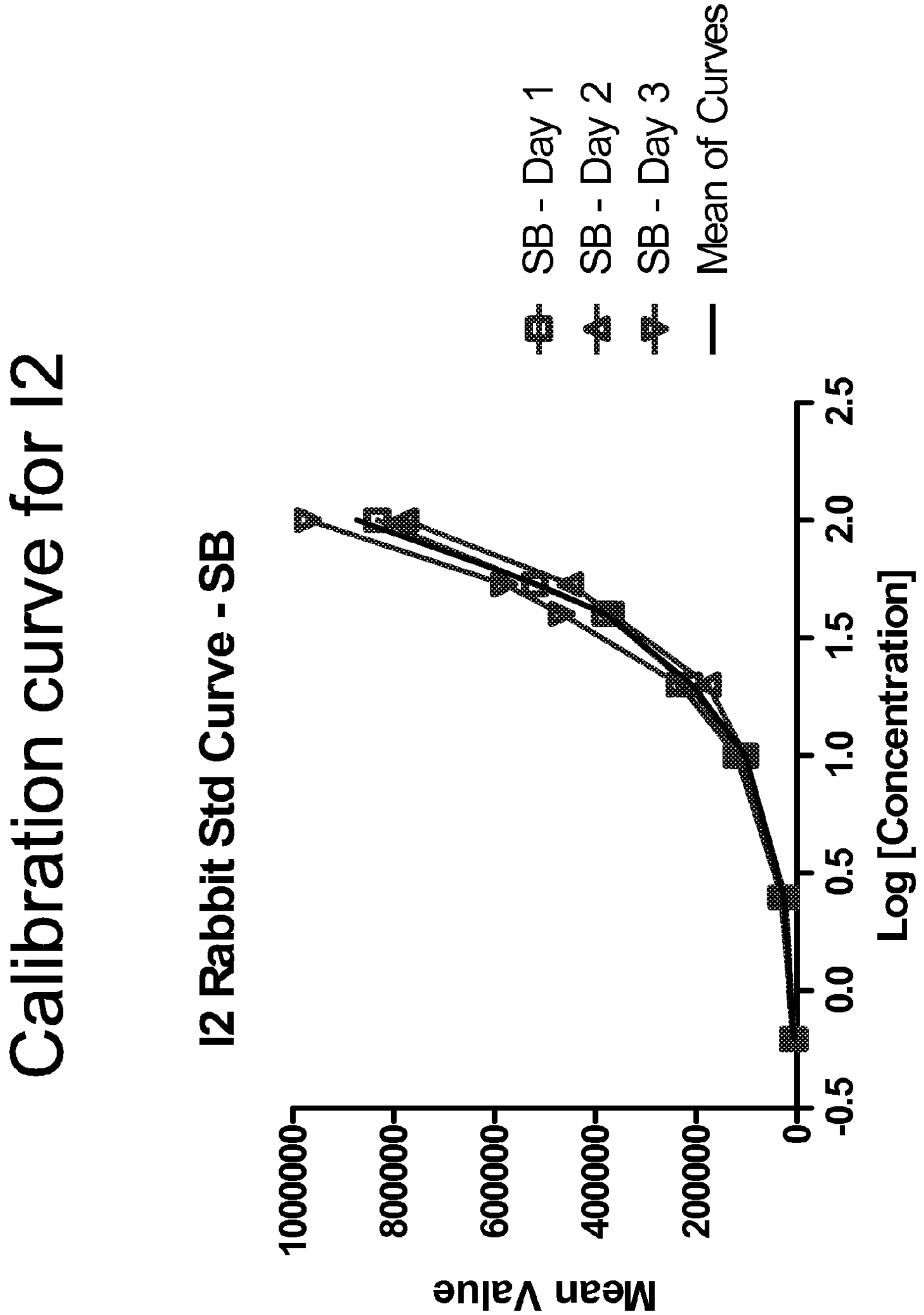
FIG. 16 illustrates an exemplary calibration curve for I2.
Figure 17:
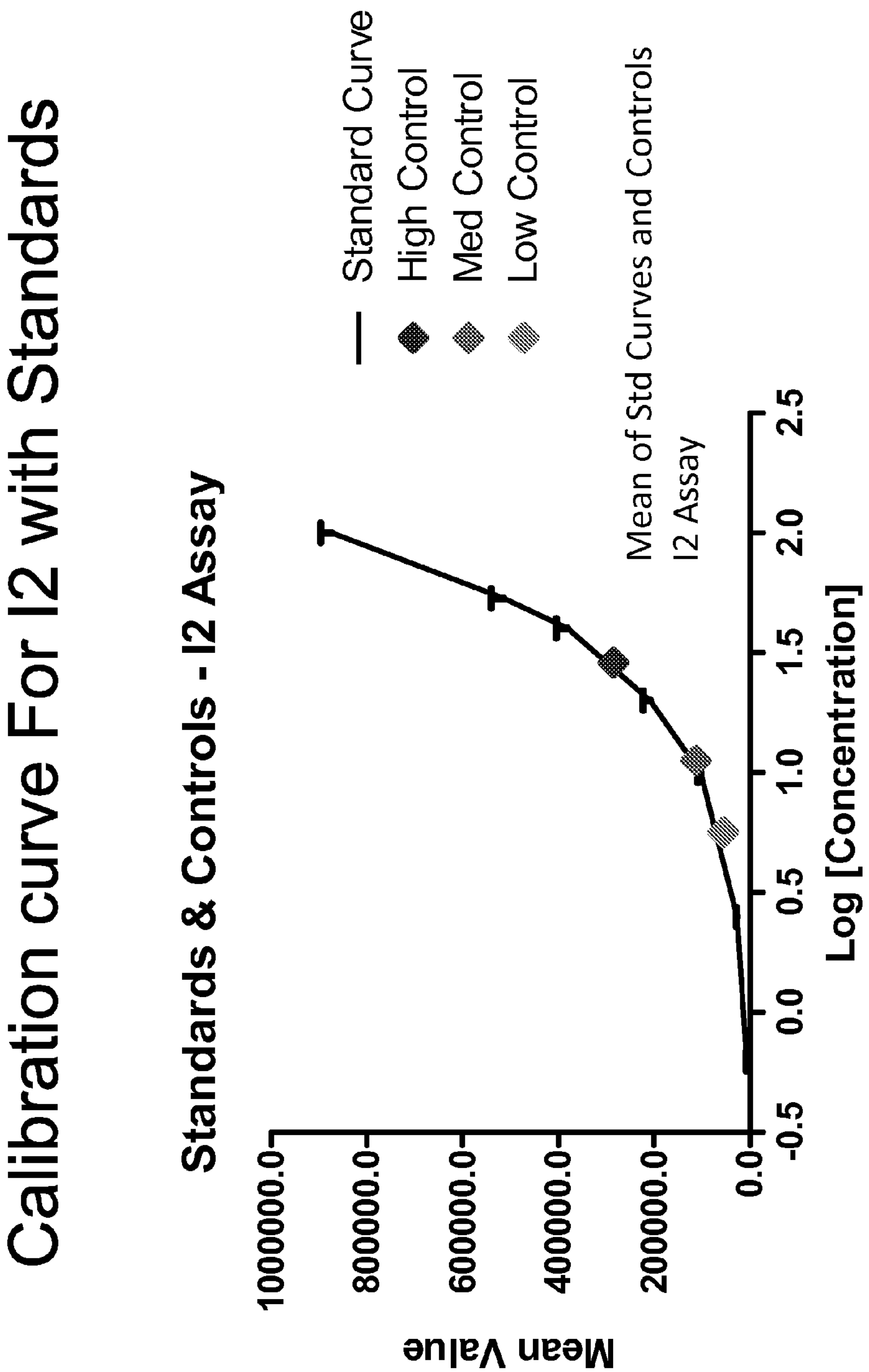
FIG. 17 illustrates an exemplary calibration curve for I2 with standards.
Figure 18:
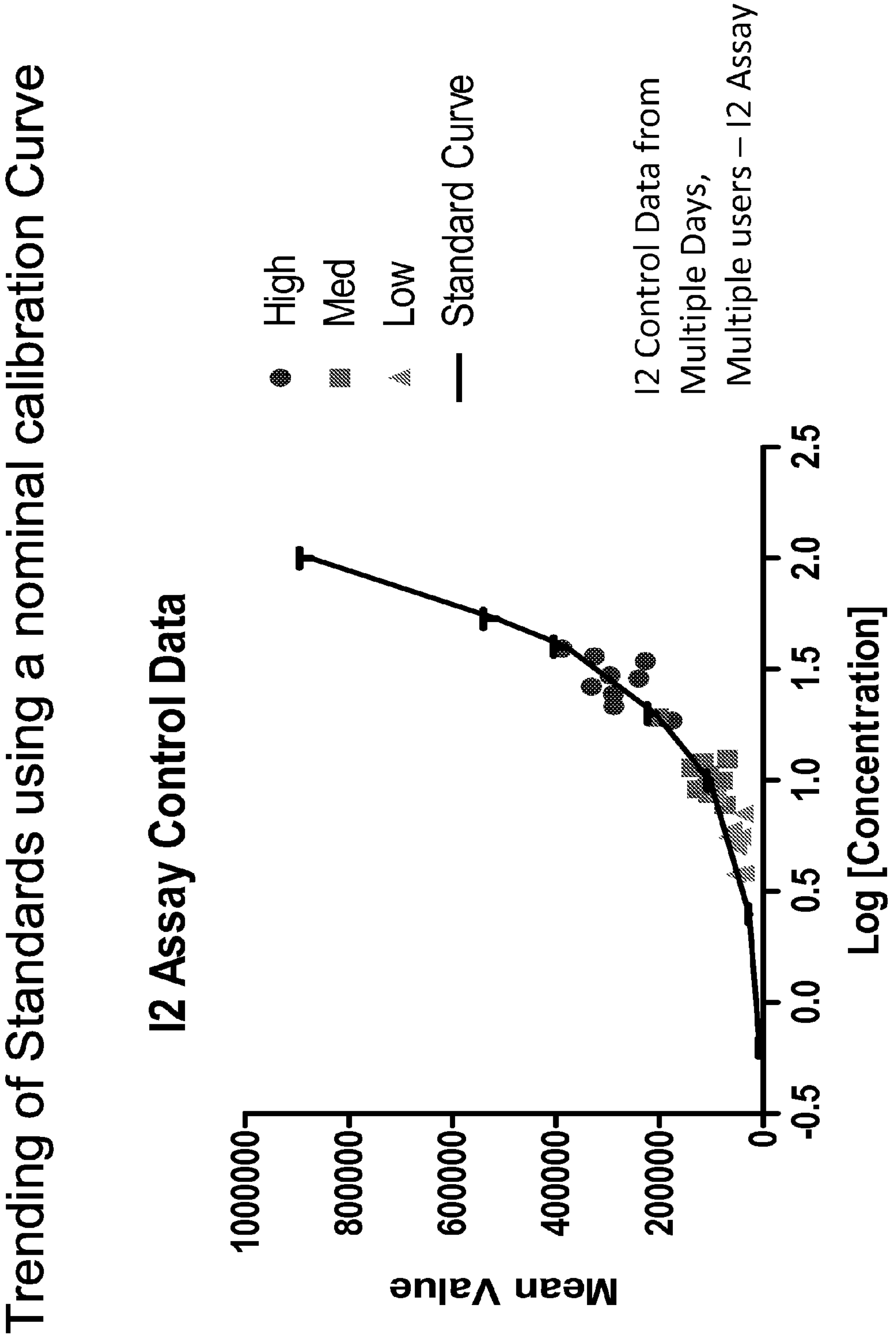
FIG. 18 illustrates an exemplary trending of standards using a nominal calibration curve.

FIG. 16 illustrates an exemplary calibration curve for I2. FIG. 17 illustrates an exemplary calibration curve for I2 with standards. FIG. 18 shows trending of standards using a nominal calibration curve.

In certain aspects, based on the number of elevated markers, each patient risk of complications and surgery is assessed. In certain aspects, a panel of biomarkers (serology, genetics and protein biomarkers) are measured and analyzed. In one embodiment, twelve biomarkers are used and at least one, at least two, at least three, at least four, at least five, at least six, at least seven, at least eight, at least nine, at least ten, at least eleven, or at least twelve markers are used. In one aspect, each biomarker is considered elevated if it is above median.

In some embodiments, the number of elevated markers is calculated and all markers contribute equally. In other embodiments, the markers may be a weighted average, or they may be a quartile analysis score (e.g., QSS), a percentile analysis, or in certain instances, interaction between certain markers (synergy) is weighted.

TABLE 15

Contingency Tables - Complications

| | | No Comp. | Comp. | No Comp. | Comp. | Fisher's exact test P value | | | No Comp. | Comp. | No Comp. | Comp. | Fisher's exact test P value |
|---|---|---|---|---|---|---|---|---|---|---|---|---|---|
| ASCA-IgA | Low | 295 | 251 | 54% | 46% | 0.0000 | SAA | Low | 260 | 302 | 46% | 54% | 0.0001 |
| | High | 156 | 390 | 29% | 71% | | | High | 196 | 366 | 35% | 65% | |
| ASCA-IgG | Low | 297 | 271 | 52% | 48% | 0.0000 | ICAM.1 | Low | 258 | 303 | 46% | 54% | 0.0004 |
| | High | 166 | 402 | 29% | 71% | | | High | 199 | 362 | 35% | 65% | |
| CBir1 | Low | 271 | 270 | 50% | 50% | 0.0000 | VCAM.1 | Low | 259 | 292 | 47% | 53% | 0.0000 |
| | High | 174 | 368 | 32% | 68% | | | High | 189 | 363 | 34% | 66% | |
| OmpC | Low | 251 | 253 | 50% | 50% | 0.0000 | EGF | Low | 251 | 309 | 45% | 55% | 0.0074 |
| | High | 154 | 351 | 30% | 70% | | | High | 206 | 354 | 37% | 63% | |
| I2 | Low | 219 | 268 | 45% | 55% | 0.0159 | CRP | Low | 256 | 311 | 45% | 55% | 0.0025 |
| | High | 181 | 306 | 37% | 63% | 0.0000 | SAA | High | 205 | 362 | 36% | 64% | |

In Table 15, ten markers are shown. For each marker, the samples were divided into above and below median ("Low" and "High"). Each sample was also classified as having complications (e.g., stricturing, penetrating disease phenotype/behavior) or no complications. For each marker, the counts of samples are shown in a 2×2 table (low vs high and complications vs not). For all ten markers, the population with "High" levels had a significantly higher percent of people with complications as compared to the population with "Low" levels of marker, as shown by the percents which can be read directly to the right of the counts for each marker. Statistical significance is shown; all values are <0.05.

TABLE 16

| Contingency Tables - Surgery | | | | | | | | | | | | | |
|---|---|---|---|---|---|---|---|---|---|---|---|---|---|
| | | No Surg | Surg | No Surg | Surg | Fisher's exact test P value | | | No Surg | Surg | No Surg | Surg | Fisher's exact test P value |
| ASCA-IgA | Low | 329 | 217 | 60% | 40% | 0.0000 | SAA | Low | 251 | 311 | 45% | 55% | 0.4021 |
| | High | 182 | 364 | 33% | 67% | | | High | 266 | 296 | 47% | 53% | |
| ASCA-IgG | Low | 337 | 231 | 59% | 41% | 0.0000 | ICAM.1 | Low | 255 | 306 | 45% | 55% | 0.7646 |
| | High | 188 | 380 | 33% | 67% | | | High | 261 | 300 | 47% | 53% | |
| CBir1 | Low | 277 | 264 | 51% | 49% | 0.0023 | VCAM.1 | Low | 271 | 280 | 49% | 51% | 0.0345 |
| | High | 227 | 315 | 42% | 58% | | | High | 236 | 316 | 43% | 57% | |
| OmpC | Low | 287 | 217 | 57% | 43% | 0.0000 | EGF | Low | 231 | 329 | 41% | 59% | 0.0012 |
| | High | 174 | 331 | 34% | 66% | | | High | 286 | 274 | 51% | 49% | |
| I2 | Low | 234 | 253 | 48% | 52% | 0.2746 | CRP | Low | 254 | 313 | 45% | 55% | 0.4386 |
| | High | 216 | 271 | 44% | 56% | | | High | 268 | 299 | 47% | 53% | |

In Table 16 above, ten markers are shown. For each marker, the samples were divided into above and below median ("Low" and "High"). Here, samples are classified as having surgery or no surgery, rather than complications or no complications (as in Table 15). Six of ten markers show significance, i.e., ASCA-IgA, ASCA-IgG, anti-CBir1, anti-OmpC, VCAM1, and EGF.

TABLE 17

| Low/High = below/above median for the CD population | | | |
|---|---|---|---|
| Number Elevated | Percent Complications | Count | Percent of Count |
| 0 | 6% | 16 | 2% |
| 1 | 38% | 37 | 5% |
| 2 | 39% | 88 | 12% |
| 3 | 33% | 92 | 12% |
| 4 | 62% | 132 | 18% |
| 5 | 66% | 138 | 19% |
| 6 | 73% | 106 | 14% |
| 7 | 78% | 81 | 11% |
| 8 | 80% | 45 | 6% |
| 9 | 90% | 10 | 1% |
| | Total: | 745 | |

Figure 19:
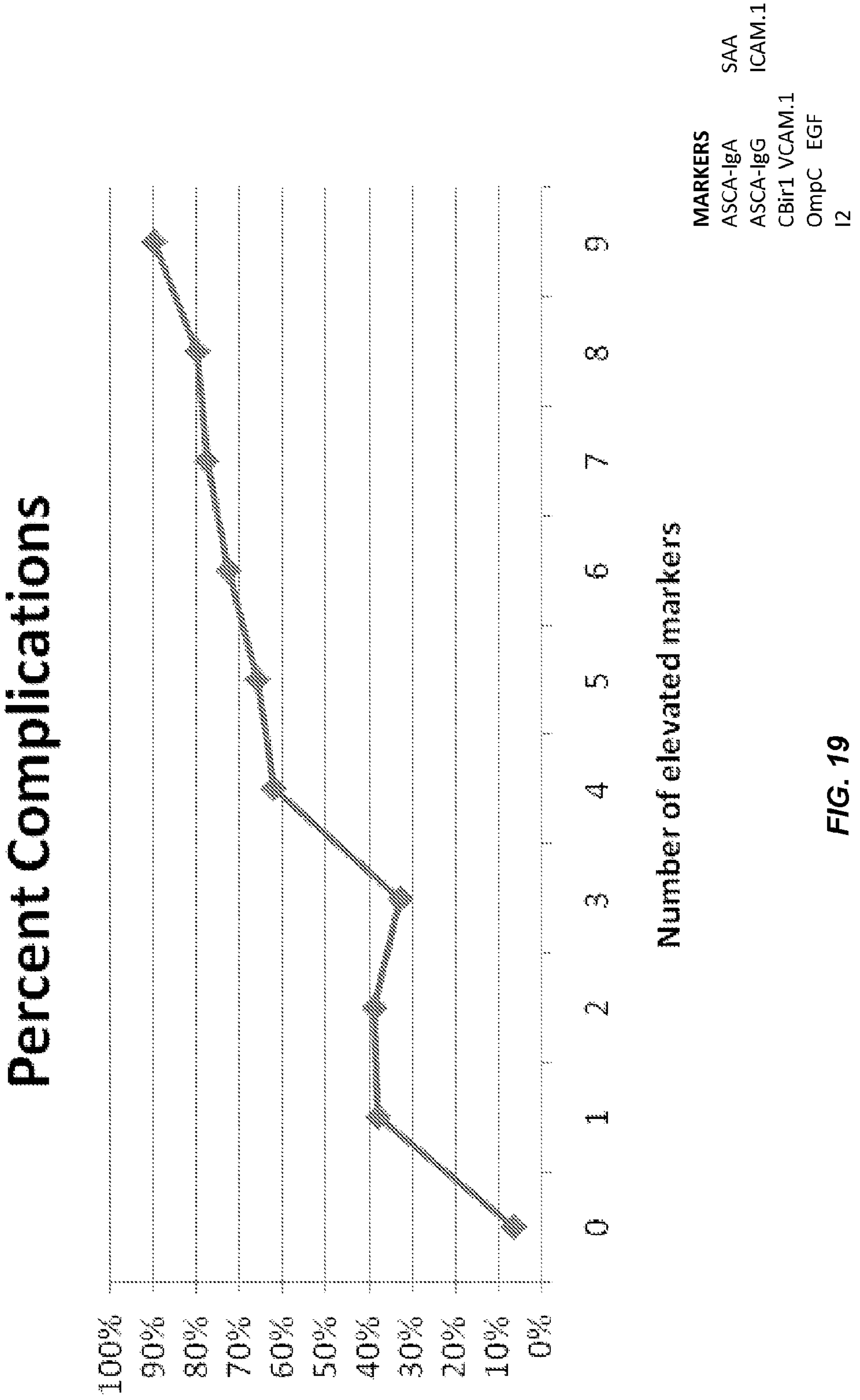
FIG. 19 illustrates a diagram of percent complications.

In Table 17, markers are considered "all at once" instead of individually. The markers included the following: ASCA-IgA, ASCA-IgG, anti-CBir1, anti-OmpC, anti-I2, VCAM1, ICAM, SAA, and EGF. Each of these nine markers were classified as "low" or "high" (vs the median) for each sample. In addition, the number of markers were summed that were "high" for each sample. That is, the number of elevated markers, which were 0-9 (since there were nine markers total in this example). Finally, for each subset of samples (samples with 0, 1, 2 . . . 9 elevated markers), the percent having complications is shown. FIG. 19 provides a graphic illustration of percent complications based on the number of elevated markers.

TABLE 18

| Surgery - # Markers Elevated (out of 9) | | | |
|---|---|---|---|
| Number Elevated | Percent Surgery | Count | Percent of Count |
| 0 | 44% | 16 | 2% |
| 1 | 32% | 37 | 5% |
| 2 | 40% | 88 | 12% |
| 3 | 41% | 92 | 12% |
| 4 | 57% | 132 | 18% |
| 5 | 51% | 138 | 19% |
| 6 | 64% | 106 | 14% |
| 7 | 62% | 81 | 11% |
| 8 | 67% | 45 | 6% |
| 9 | 70% | 10 | 1% |
| | Total: | 745 | |

Figure 20:
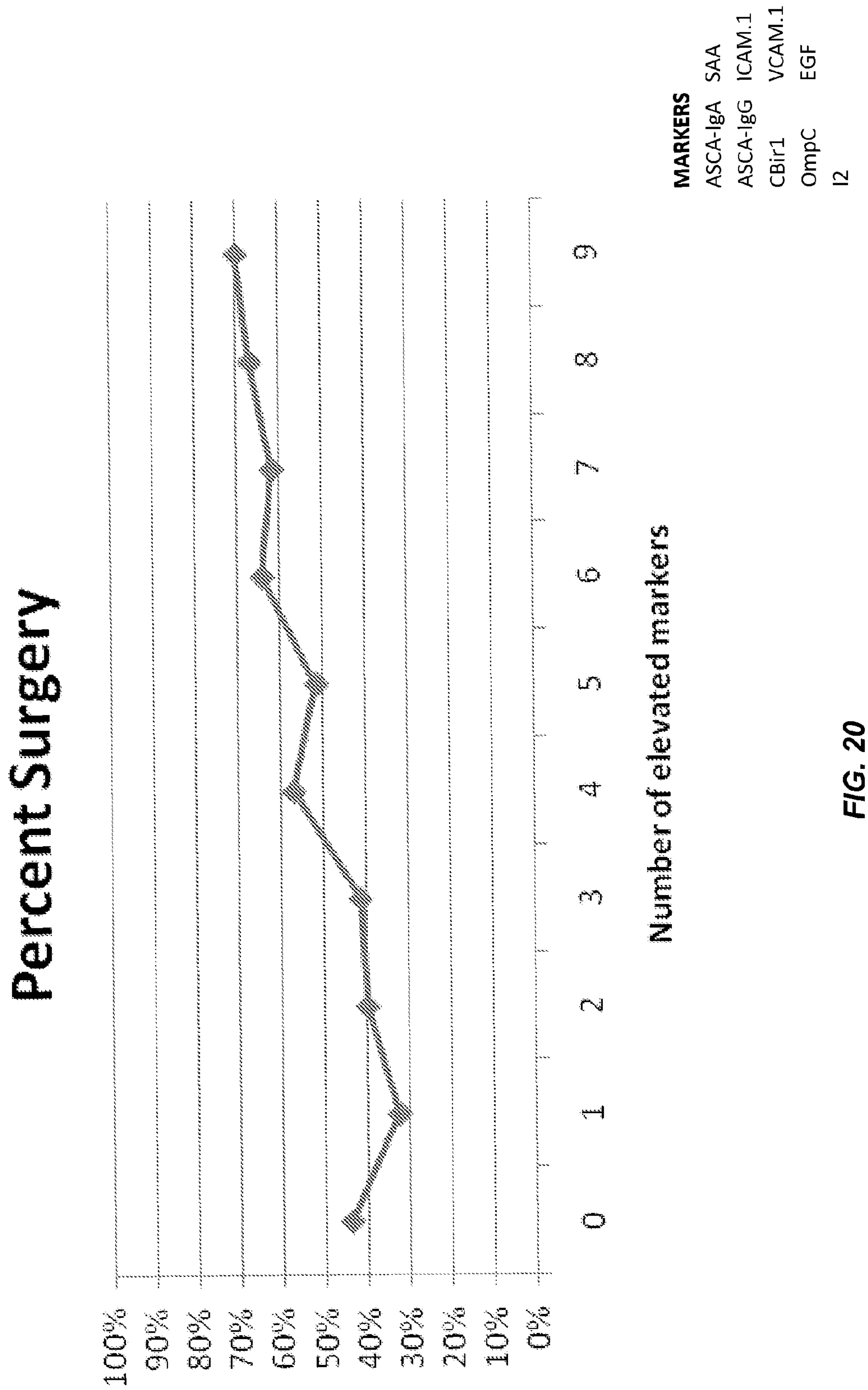
FIG. 20 illustrates a diagram of percent surgery.

In Table 18, markers are considered "all at once" instead of individually. The markers included the following: ASCA-IgA, ASCA-IgG, anti-CBir1, anti-OmpC, anti-I2, VCAM1, ICAM, SAA, and EGF. Each of these nine markers were classified as "low" or "high" (vs the median) for each sample. In addition, the number of markers were summed that were "high" for each sample. That is, the number of elevated markers, which were 0-9 (since there were nine markers total in this example). Finally, for each subset of samples (samples with 0, 1, 2 . . . 9 elevated markers), the percent having surgery is shown. FIG. 20 provides a graphic illustration of percent surgery based on the number of elevated markers.

TABLE 19A

| Complications - number of markers (% complications) | | | | | | | | | | |
|---|---|---|---|---|---|---|---|---|---|---|
| Number Elev. | ASCA-IgA | ASCA-IgG | CBir1 | OmpC | I2 | SAA | ICAM | VCAM | EGF | CRP |
| 0 | 46% | 43% | 34% | 28% | 24% | 22% | 18% | 14% | 6% | 8% |
| 1 | 71% | 62% | 55% | 47% | 44% | 33% | 31% | 35% | 38% | 34% |
| 2 | | 73% | 71% | 67% | 54% | 52% | 43% | 40% | 39% | 39% |
| 3 | | | 76% | 74% | 69% | 63% | 53% | 40% | 33% | 37% |
| 4 | | | | 78% | 72% | 70% | 72% | 70% | 62% | 53% |

TABLE 19A-continued

| Complications - number of markers (% complications) | | | | | | | | | | |
|---|---|---|---|---|---|---|---|---|---|---|
| Number Elev. | ASCA-IgA | ASCA-IgG | CBir1 | OmpC | I2 | SAA | ICAM | VCAM | EGF | CRP |
| 5 | | | | | 85% | 75% | 69% | 71% | 66% | 65% |
| 6 | | | | | | 90% | 82% | 70% | 73% | 64% |
| 7 | | | | | | | 87% | 81% | 78% | 73% |
| 8 | | | | | | | | 87% | 80% | 84% |
| 9 | | | | | | | | | 90% | 79% |
| 10 | | | | | | | | | | 88% |

TABLE 19B

| Counts | | | | | | | | | | |
|---|---|---|---|---|---|---|---|---|---|---|
| Number Elev. | ASCA-IgA | ASCA-IgG | CBir1 | OmpC | I2 | SAA | ICAM | VCAM | EGF | CRP |
| 0 | 546 | 435 | 255 | 151 | 71 | 45 | 34 | 28 | 16 | 12 |
| 1 | 546 | 226 | 277 | 206 | 153 | 106 | 67 | 51 | 37 | 35 |
| 2 | | 425 | 249 | 195 | 157 | 149 | 120 | 102 | 88 | 70 |
| 3 | | | 249 | 218 | 172 | 152 | 146 | 110 | 92 | 89 |
| 4 | | | | 143 | 148 | 168 | 163 | 151 | 132 | 97 |
| 5 | | | | | 78 | 103 | 127 | 121 | 138 | 124 |
| 6 | | | | | | 48 | 76 | 105 | 106 | 114 |
| 7 | | | | | | | 30 | 58 | 81 | 95 |
| 8 | | | | | | | | 23 | 45 | 68 |
| 9 | | | | | | | | | 10 | 33 |
| 10 | | | | | | | | | | 8 |
| Total: | 1092 | 1086 | 1030 | 913 | 779 | 771 | 763 | 749 | 745 | 745 |

In Tables 19A/B, reading from left to right, the first column shows what happens with exactly one marker—ASCA-IgA. Each sample can be "low" or "high" with respect to ASCA-IgA. Among the people that were "low" for ASCA-IgA, 46% had complications (as shown); among those that were "high", 71% had complications (as shown). In the next column, we consider a test with two markers: ASCA-IgA and ASCA-IgG. Now, each sample is classified as "low" or "high" for two markers, and each sample has a count of how many markers were elevated (which here can be 0 to 2). For those two markers, among the samples that had zero elevated, 43% had complications. Samples that had one elevated marker (out of two, could be either one) had complications 62% of the time. Samples that had both markers elevated had complications 73% of the time. The third column shows what happens with three markers (the third marker is CBir1, as shown in the first row). Each column (from left to right) adds an additional marker, segments the population by how many markers were elevated (in that subset), and shows, within each segment of the population, what percent had complications. Note that the order of markers (left to right, top row) is "hand-selected"—different orderings would have produced different charts (although the rightmost column would always be the same, since the rightmost column is "all the markers").

TABLE 20

| NOD2 | | | | | | | |
|---|---|---|---|---|---|---|---|
| MUTATION COUNTS | | | | | | | |
| Mutations | SNP 8 | SNP 12 | SNP 13 | Mutations | SNPs 12, 13 | Mutations | SNPs 8, 12, 13 |
| 0 | 249 | 270 | 268 | 0 | 244 | 0 | 193 |
| 1 | 33 | 27 | 26 | 1 | 38 | 1 | 67 |
| 2 | 3 | 4 | 7 | 2 | 17 | 2 | 22 |
| | | | | 3 | 1 | 3 | 1 |
| | | | | 4 | 0 | 4 | 0 |
| | | | | | | 5 | 0 |
| | | | | | | 6 | 0 |

| MUTATION PERCENTS | | | |
|---|---|---|---|
| | SNP 8 | SNP 12 | SNP 13 |
| Homologous Wild Type | 87.4% | 89.7% | 89.0% |
| Heterozygous Mutation | 11.6% | 9.0% | 8.6% |
| Homozygous Mutation | 1.1% | 1.3% | 2.3% |

TABLE 20-continued

NOD2

GROUPED COUNTS

| Mutations | SNP 8 | SNP 12 | SNP 13 | Mutations | SNPs 12, 13 | Mutations | SNPs 8, 12, 13 |
|---|---|---|---|---|---|---|---|
| 0 | 249 | 270 | 268 | 0 | 244 | 0 | 193 |
| 1+ | 36 | 31 | 33 | 1 | 38 | 1 | 67 |
| | | | | 2+ | 18 | 2+ | 23 |

Table 20 shows how many people had NOD2 mutations. For three locations within the NOD2 gene (SNP8, SNP12 and SNP13), this shows how many samples had zero, one or two mutations. The tables suggests that because there are so few people with 2 mutations, it is best to group people into "zero mutations" or "one or two" mutations.

TABLE 21

Complications - NOD2

| SNP 8 | No Comp. | Comp | No Comp | Comp | Fisher's Exact Test P Value | SNP 12, 13 | No Comp. | Comp | No Comp. | Comp | Fisher's Exact Test P Value |
|---|---|---|---|---|---|---|---|---|---|---|---|
| Wt | 100 | 149 | 40% | 60% | 0.858 | Wt | 106 | 138 | 43% | 57% | 0.070 |
| 1+ Mut | 15 | 21 | 42% | 58% | | 1 Mut | 11 | 27 | 29% | 71% | |
| | | | | | | 2+ Mut | 4 | 14 | 22% | 78% | |

| SNP 12 | No Comp | Comp | No Comp | Comp | Fisher's Exact Test P Value | SNP 8, 12, 13 | No Comp. | Comp | No Comp | Comp | Fisher's Exact Test P Value |
|---|---|---|---|---|---|---|---|---|---|---|---|
| Wt | 109 | 161 | 40% | 60% | 1 | Wt | 85 | 108 | 44% | 56% | 0.039 |
| 1+ Mut | 12 | 19 | 39% | 61% | | 1 Mut | 26 | 41 | 39% | 61% | |
| | | | | | | 2+ Mut | 4 | 19 | 17% | 83% | |

| SNP 13 | No Comp. | Comp | No Comp | Comp | Fisher's Exact Test P Value |
|---|---|---|---|---|---|
| Wt | 115 | 153 | 43% | 57% | 0.008 |
| 1+ Mut | 6 | 27 | 18% | 82% | |

Table 21 shows 2×2 tables, (on the left) dividing people into "zero mutations" and "one or two mutations". For each of those groups, people were divided into "Had complications" or "Did not have complications". Only SNP 13 was significant—for SNP 13, among the people with mutation at SNP13, a greater percent had complications (82%) compared to the population with no mutations at SNP13 (of those, only 57% had complications).

TABLE 22

Surgery - NOD2

| SNP 8 | No Surg. | Surgery | No Surg. | Surgery | Fisher's Exact Test P Value | SNP 12, 13 | No Surg. | Surgery | No Surg. | Surgery | Fisher's Exact Test P Value |
|---|---|---|---|---|---|---|---|---|---|---|---|
| Wt | 82 | 167 | 33% | 67% | 0.574 | Wt | 87 | 157 | 36% | 64% | 0.006 |
| 1+ Mut | 10 | 26 | 28% | 72% | | 1 Mut | 8 | 30 | 21% | 79% | |
| | | | | | | 2+ Mut | 1 | 17 | 6% | 94% | |

| SNP 12 | No Surg. | Surgery | No Surg. | Surgery | Fisher's Exact Test P Value | SNP 8, 12, 13 | No Surg. | Surgery | No Surg. | Surgery | Fisher's Exact Test P Value |
|---|---|---|---|---|---|---|---|---|---|---|---|
| Wt | 89 | 181 | 33% | 67% | 0.310 | Wt | 73 | 120 | 38% | 62% | 0.005 |
| 1+ Mut | 7 | 24 | 23% | 77% | | 1 Mut | 17 | 50 | 25% | 75% | |
| | | | | | | 2+ Mut | 2 | 21 | 9% | 91% | |

TABLE 22-continued

| Surgery - NOD2 | | | | | |
|---|---|---|---|---|---|
| SNP 13 | No Surg. | Surgery | No Surg. | Surgery | Fisher's Exact Test P Value |
| Wt | 93 | 175 | 35% | 65% | 0.002 |
| 1+ Mut | 3 | 30 | 9% | 91% | |

Table 22 shows 2×2 tables looking at "Surgery" vs "No Surgery", rather than "Complication" vs "No Complication". Again, only SNP13 had significance (considered individually).

The NOD2 gene encodes an intracellular pattern recognition receptor which is involved in innate immunity. Three specific mutations in this gene result in a loss of function and have been associated with approximately one third of Crohn's disease cases. In addition, these NOD2 variants may have prognostic value as they have been linked to ileal disease, the development of intestinal strictures, and early progression to surgery.

Three single nucleotide polymorphisms (SNP8/R702W, SNP12/G908R, and SNP13/3020insC) were genotyped in patients (N=301) with Crohn's disease. Contingency tables were constructed for mutations vs. complications (stricturing or penetrating behavior phenotype) and for mutations vs. need for surgery (gastrointestinal surgeries excluding perianal surgeries). The associations were assessed by Fisher's exact test. Due to the small number of samples with homozygous mutations, those with heterozygous or homozygous mutations were grouped into a single category and then compared with wild type genotypes. Contingency tables were constructed for both individual SNPs.

For SNP8, the genetic distribution was 87.4% wild type, 11.6% heterozygous mutant, and 1.1% homozygous mutant. For SNP12, the distribution was 89.7%, 9.0%, and 1.3%, respectively, and for SNP13, the distribution was 89%, 8.6% and 2.3%. For the combination of all three SNPs, the distribution was 81% wild type, 13% with one mutation, and 6% with two or more mutations.

For the combination of all three SNPs, the proportion with complications was 56%, 61%, and 83% for those with zero, one, or two or more mutations, respectively ($p<0.05$), and with respect to the proportion progressing to surgery, the rates were 62%, 75%, and 91%, respectively ($p<0.01$).

Mutations in NOD2/CARD15 are significantly associated with elevated rates of complicating disease behavior and progression to surgery for Crohn's disease patients, suggesting that genotyping of NOD2/CARD15 has prognostic value in the clinical management of Crohn's disease.

Example 15. Statistical Analysis of Markers and Crohn's Disease Progression

This example illustrates various statistical analyses of the marker data obtained from the cross-sectional study described in Example 14 to aid or assist in predicting the risk of disease complications (stricturing/penetrating) and/or need for surgery in Crohn's disease patients. In particular, this example demonstrates that patients with a higher number of markers and a higher level of markers have a higher probability of complicating disease behavior and/or progression to surgery.

In this study, a panel of biomarkers (serology, genetics, and/or protein biomarkers) was measured. Each biomarker score was converted to a percentile (0-100%). The average percentile was calculated. In one embodiment, all markers contribute equally. In another embodiment, a weighted average is used (e.g., to improve utility). Based on the average percentile, each patient was assigned to one of five risk categories: (1) very low; (2) low; (3) average; (4) high; or (5) very high. Tables 23-25 show the results for 773 (66%) of patients in the study.

TABLE 23

| Disease Complications (Stricturing/Penetrating) | | | |
|---|---|---|---|
| Category | Average Percentile | Count | Percent with Complications |
| Very low | 0%-20% | 53 | 17% |
| Low | 20%-40% | 218 | 42% |
| Average | 40%-60% | 303 | 60% |
| High | 60%-80% | 168 | 69% |
| Very High | 80%-100% | 31 | 87% |
| Total | | 773 | |

Based on an average of percentiles (eight markers)

Figure 21:
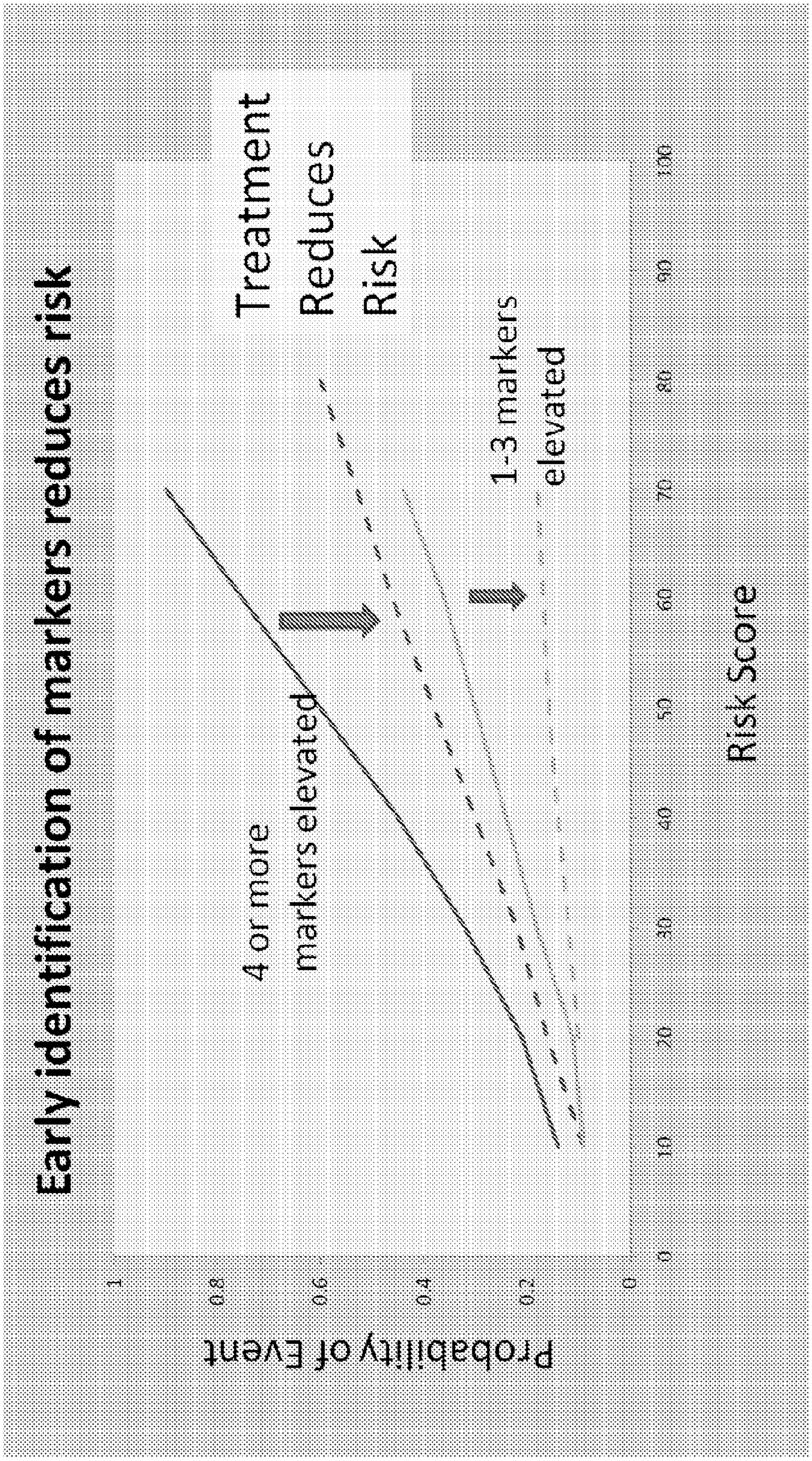
FIG. 21 illustrates that early identification of markers reduces risk.

Table 23 shows that patients with a higher number of elevated markers (and hence in a higher average percentile group and assigned to a higher risk category) have a higher risk of developing complications and thus have poor disease prognosis. FIG. 21 illustrates that early identification of markers in combination with appropriate treatment reduces risk, but also that a higher number of elevated markers is associated with a higher probability of an event such as complicating disease behavior.

TABLE 24A

| Disease Complications - Percentage Over Time | | | | | |
|---|---|---|---|---|---|
| Category | Average Percentile | Overall | 0-5 yrs | 0-10 yrs | 11+ years |
| Very low | 0%-20% | 0.19 | 0.06 | 0.11 | 0.24 |
| Low | 20%-40% | 0.43 | 0.34 | 0.40 | 0.45 |
| Average | 40%-60% | 0.60 | 0.53 | 0.56 | 0.62 |
| High | 60%-80% | 0.70 | 0.56 | 0.60 | 0.79 |
| Very high | 80%-100% | 0.88 | 0.67 | 0.86 | 0.89 |

TABLE 24B

| Disease Complications - Sample Counts | | | | | |
|---|---|---|---|---|---|
| Category | Average Percentile | years kno | 0-5 yrs | 0-10 yrs | 11+ years |
| Very low | 0%-20% | 48 | 16 | 19 | 23 |
| Low | 20%-40% | 188 | 59 | 93 | 95 |
| Average | 40%-60% | 257 | 73 | 110 | 147 |
| High | 60%-80% | 149 | 45 | 68 | 81 |
| Very high | 80%-100% | 26 | 3 | 7 | 19 |
| | Total | 668 | 196 | 297 | 371 |

Tables 24A/B show an unweighted average of percentiles from 8 biomarkers. In particular, Table 24A illustrates that patients with a higher number of elevated markers (and hence in a higher average percentile group and assigned to a higher risk category) have a higher risk of developing complications over time. As such, the methods described herein can identify such patients early in the course of their disease and allow physicians to consider more aggressive therapy.

TABLE 25A

Progression to Surgery - Percentage Over Time

| Category | Average Percentile | Overall | 0-5 yrs | 0-10 yrs | 11+ years |
|---|---|---|---|---|---|
| Very low | 0%-20% | 0.23 | 0.13 | 0.11 | 0.31 |
| Low | 20%-40% | 0.46 | 0.34 | 0.44 | 0.47 |
| Average | 40%-60% | 0.64 | 0.37 | 0.45 | 0.78 |
| High | 60%-80% | 0.68 | 0.44 | 0.53 | 0.81 |
| Very high | 80%-100% | 0.81 | 0.33 | 0.57 | 0.89 |

TABLE 25B

Progression to Surgery - Sample Counts

| Category | Average Percentile | Overall | 0-5 yrs | 0-10 yrs | 11+ years |
|---|---|---|---|---|---|
| Very low | 0%-20% | 48 | 16 | 19 | 29 |
| Low | 20%-40% | 188 | 59 | 93 | 95 |
| Average | 40%-60% | 257 | 73 | 110 | 147 |
| High | 60%-80% | 149 | 45 | 68 | 81 |
| Very high | 80%-100% | 26 | 3 | 7 | 19 |
| | Total | 668 | 196 | 297 | 371 |

Tables 25A/B show an unweighted average of percentiles from 8 biomarkers. In particular, Table 25A illustrates that patients with a higher number of elevated markers (and hence in a higher average percentile group and assigned to a higher risk category) have a higher probability of progression to surgery over time. As such, the methods described herein can identify such patients early in the course of their disease and allow physicians to consider more aggressive therapy.

TABLE 26

Complications - Quartile Analysis of Single Markers

| | Quartile 1 | Quartile 2 | Quartile 3 | Quartile 4 |
|---|---|---|---|---|
| ASCA-IgA | 38% | 54% | 68% | 74% |
| ASCA-IgG | 43% | 53% | 69% | 73% |
| CBir1 | 45% | 55% | 65% | 71% |
| OmpC | 43% | 57% | 65% | 74% |
| I2 | 50% | 60% | 65% | 60% |
| CRP | 53% | 56% | 60% | 68% |
| SAA | 46% | 61% | 63% | 67% |
| ICAM.1 | 51% | 57% | 65% | 63% |
| VCAM.1 | 53% | 53% | 64% | 67% |
| EGF | 51% | 59% | 61% | 65% |

Figure 22:
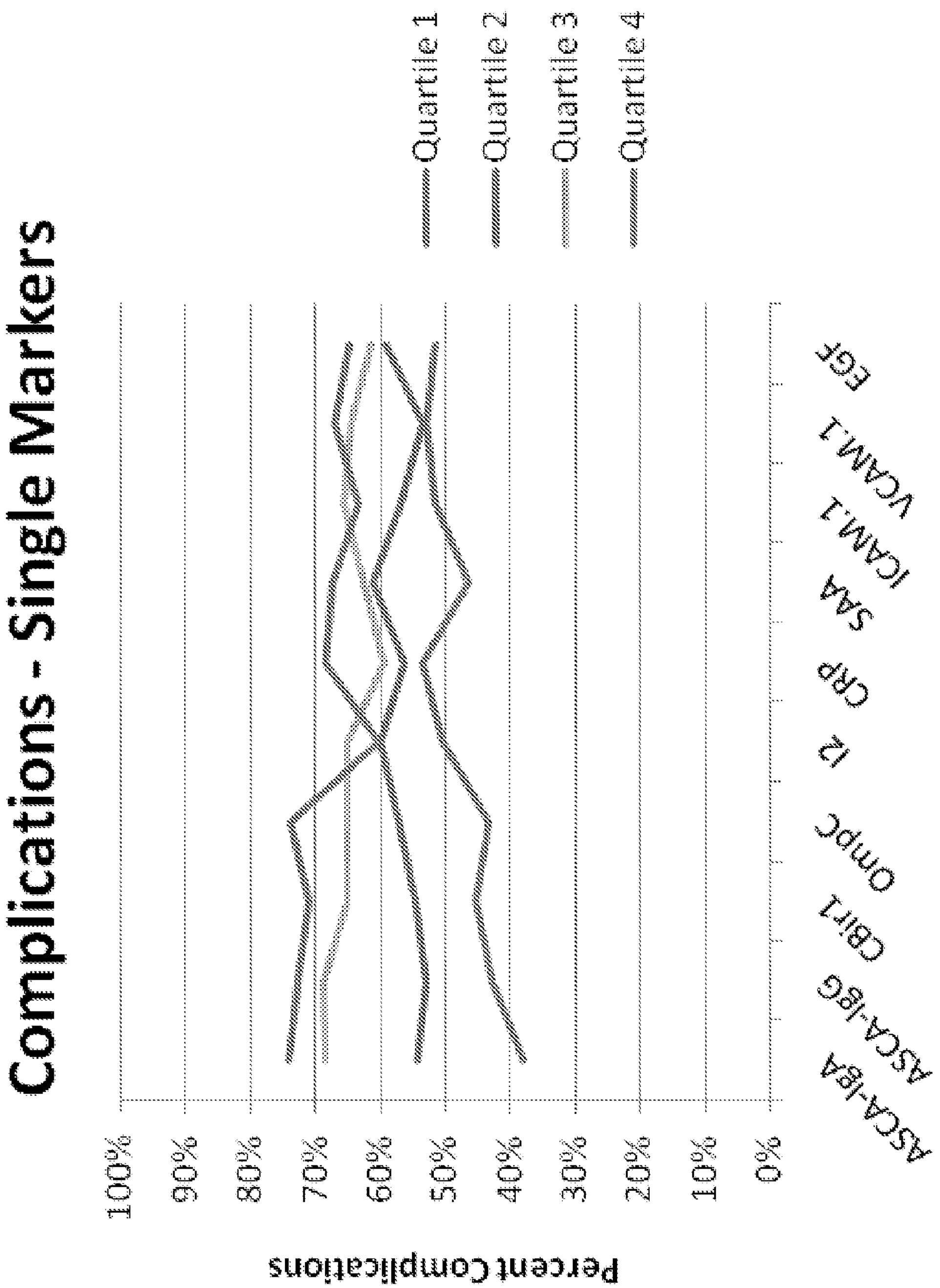
FIG. 22 illustrates a diagram which shows complications with a single marker.

Table 26 shows the association between quartile score and percent risk of disease complications for a single marker. Similarly, FIG. 22 provides a diagram which shows the association between quartile score and the percent risk of developing complicating disease behavior for a single marker. In particular, a higher quartile score for each individual marker was typically associated with a higher percent risk of disease complications such as internal stricturing and/or internal penetrating disease.

TABLE 27

Surgery - Quartile Analysis of Single Markers

| | Quartile 1 | Quartile 2 | Quartile 3 | Quartile 4 |
|---|---|---|---|---|
| ASCA-IgA | 32% | 48% | 64% | 69% |
| ASCA-IgG | 31% | 50% | 63% | 70% |
| CBir1 | 46% | 52% | 55% | 61% |
| OmpC | 40% | 46% | 62% | 69% |
| I2 | 47% | 57% | 60% | 52% |
| CRP | 54% | 56% | 54% | 52% |
| SAA | 53% | 58% | 49% | 56% |
| ICAM.1 | 51% | 58% | 57% | 50% |
| VCAM.1 | 51% | 51% | 62% | 52% |
| EGF | 58% | 60% | 48% | 50% |

Figure 23:
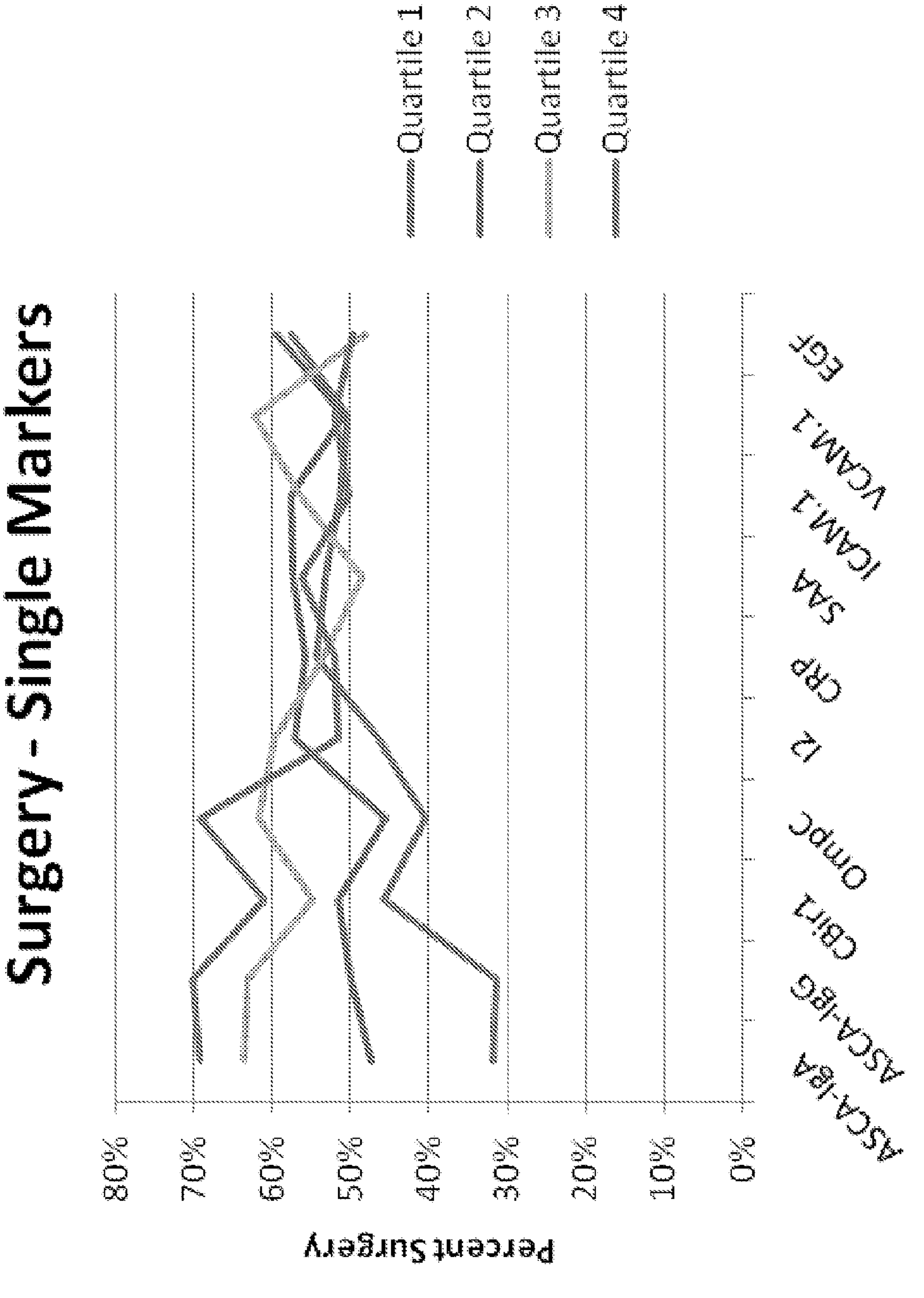
FIG. 23 illustrates a diagram which shows surgery with a single marker.

Table 27 shows the association between quartile score and percent risk of surgery for a single marker. Similarly, FIG. 23 provides a diagram which shows the association between quartile score and the percent risk of progression to surgery for a single marker. In particular, a higher quartile score for many of the individual markers was associated with a higher percent risk of the need for surgery.

TABLE 28

Surgery - # of Markers Elevated (out of 5)

| Number Elevated | Percent Surgery | Count | Percent of Count |
|---|---|---|---|
| 0 | 38% | 71 | 9% |
| 1 | 32% | 153 | 20% |
| 2 | 46% | 157 | 20% |
| 3 | 65% | 172 | 22% |
| 4 | 66% | 148 | 19% |
| 5 | 76% | 78 | 10% |
| | Total: | 779 | |

Figure 24:
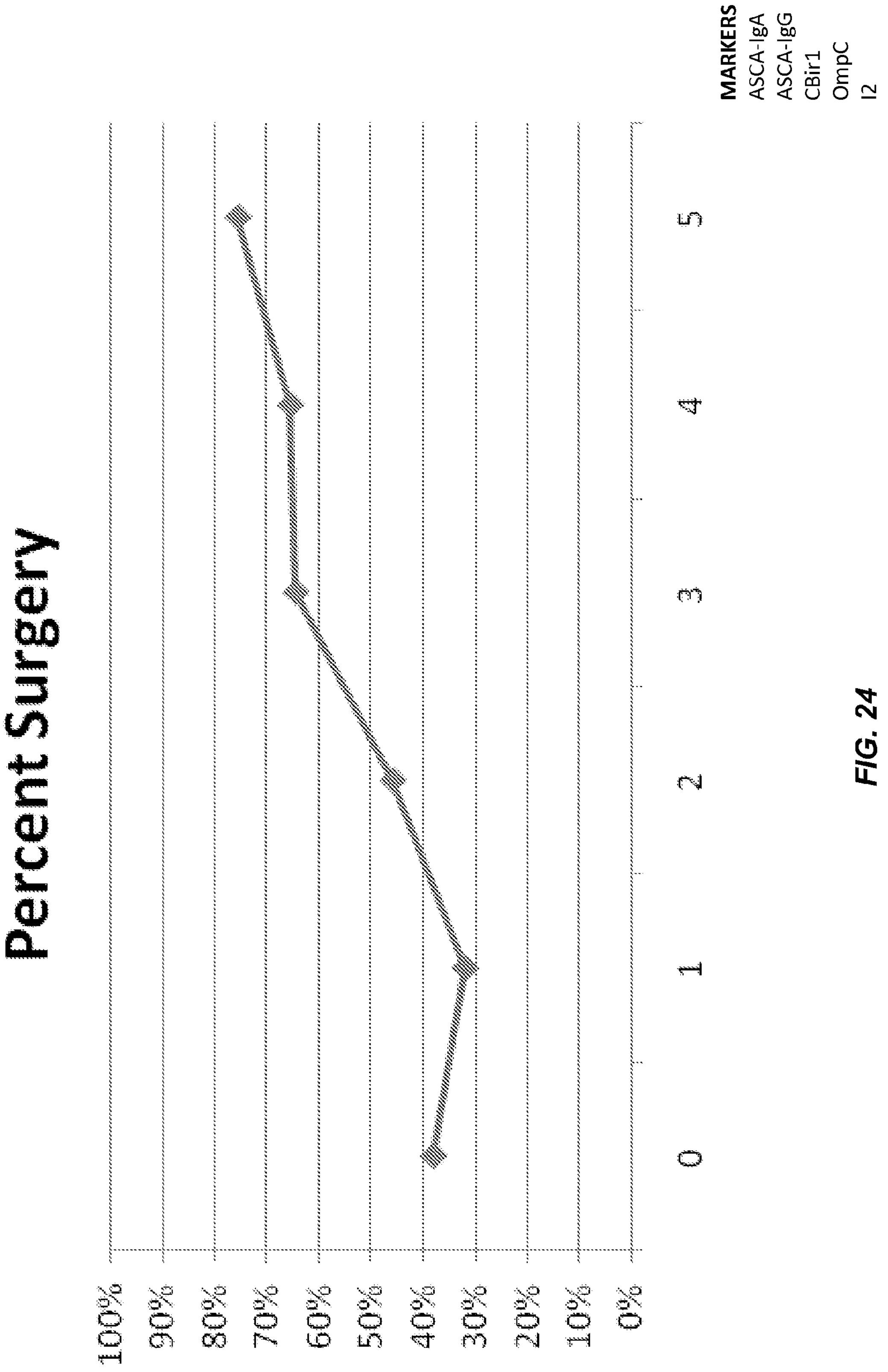
FIG. 24 illustrates a diagram which shows percent surgery.

Table 28 shows the association between the number of elevated markers and percent risk of surgery. The markers included the following: ASCA-IgA, ASCA-IgG, anti-CBir1, anti-OmpC, and anti-I2. FIG. 24 provides a diagram which shows the association between the number of elevated markers and the percent risk of progression to surgery. In particular, a higher number of elevated markers was associated with a higher percent risk of the need for surgery.

In conclusion, this example demonstrates the prognostic utility of the methods of the present invention to accurately predict the risk (e.g., probability, likelihood, etc.) of disease complications (e.g., internal stricturing and/or internal penetrating) and/or the progression to surgery in Crohn's disease patients.

Example 16. A Novel Prognostic Assay for Predicting the Clinical Course of Crohn's Disease I. Introduction 1. Overview Inflammatory bowel disease (IBD) is a chronic inflammatory disorder of the gastrointestinal tract. The precise cause of IBD is not well understood, but it is generally accepted that disease susceptibility involves genetic and environmental factors leading to dysregulation of the immune response (Strober et al., *J. Clin. Invest.*, 117:514-521 (2007)). IBD presents primarily as Crohn's disease (CD) or ulcerative colitis (UC). CD can be present in any portion of the gastrointestinal tract, although it is most frequently seen in the distal small bowel and proximal colon; and the inflammatory process extends transmurally.

In UC, the inflammation is confined to the colon and is limited to the mucosa. Approximately 1.4 million people in the U.S., this includes adults and children, have IBD, with about equal numbers having CD or UC (Loftus, *Gastroenterology,* 126:1504-1517 (2004)).

The course of IBD is not predictable. Some patients have only a few episodes of active disease in their lifetime with long lasting periods of remission in between; for others the active disease is persistent and even debilitating. Natural history studies in CD have shown that in many patients, there is a significant progression in disease behavior over time (Louis et al., *Gut,* 49:777-782 (2001)). In one study, this change was evident within one year, and by 10 years, 50% of patients progressed to a complicated disease phenotype marked by the presence of strictures and intestinal perforations. There is growing evidence that serologic biomarkers may provide clinical insight in predicting aggressive disease behavior, particularly in patients with CD. Clearly, the ability to stratify patients into low or high risk at diagnosis would assist the physicians in developing appropriate management plans. This is especially important given that recent data suggesting that the early use of biologic therapies such as infliximab can alter the natural history of the disease, decreasing hospitalizations and the incident of surgeries (Schnitzler et al., *Gut,* 58:492-500 (2009)). A key decision that physicians often face is how to determine, based on disease prognosis, which patients would benefit from an early and potentially chronic use of these aggressive, risky and more expensive therapies.

Currently, a limited number of clinical factors, including the age at diagnosis, presence of perianal disease and a need for steroids at first presentation, can be used to predict which CD patients will experience a difficult disease course (Beaugerie et al., *Gastroenterology,* 130:650-656 (2006)). Using serologic and genetic biomarkers, this example describes the development of a blood-based test that will assist physicians in predicting the clinical course of CD. This test was developed and validated using banked samples that had both a confirmed diagnosis of CD and extensive medical history describing the phenotype of the disease. The ability to be able to predict the likely course of CD using a simple blood-based test is beneficial to both physicians and patients because physicians will be better able to manage and treat patients, while patients will have more information with which to assess the risks and benefits of their therapeutic options.

2. Purpose and Description of the Assay 2.1 Prometheus Crohn's Prognosis Test

This example describes the development and validation of the Prometheus Crohn's Prognostic test, a blood test which can be used to assess the risk that CD may progress to a complicated disease type. Complicated CD is defined as having intestinal stricturing or internal penetrating disease, while "non-complicated" indicates non-stricturing, non-penetrating disease.

The Prometheus Crohn's Prognostic test contains a total of 9 markers including:

| Analyte | Assay format |
|---|---|
| ASCA-IgA | ELISA |
| ASCA-IgG | ELISA |
| Anti-OmpC | ELISA |
| Anti-CBir1 | ELISA |
| pANCA | Indirect Immunofluorescence |
| Anti-I2 | ELISA |

-continued

| Analyte | Assay format |
|---|---|
| NOD2 | Genotyping PCR to identify three NOD2 gene mutations: (1) R702 W; (2) G908R; (3) 3020InsC |

The anti-I2 assay utilizes a standard 96-well sandwich ELISA format plate. A refolded GST-tagged protein, consisting of a 100 amino acid I2 sequence, is captured on the plate using a monoclonal anti-GST antibody coated on the well surface. The patient serum samples are diluted 1:100 to bring the antibody concentration in the range of the standard curve. After incubation of the serum samples in the wells, detection of anti-I2 antibodies is accomplished using alkaline phosphatase enzyme conjugated anti-human IgA reagent. The reaction is revealed using cheminulescent substrate solution.

The analytical performance of the NOD2 genotyping PCR assay consists of testing three non-synonymous single nucleotide polymorphorisms (SNPs). SNP 8 is a 2104C-T in exon 4 resulting in a R702W substitution (rs2066845); SNP 12 is a 2722 G-C in exon 8 resulting in a G908R substitution (rs2066844); and SNP 13 is a C insertion in exon 11 (3020InsC) resulting in a frame shift (1007fs) (rs5743293). The allelic discrimination PCR method includes two specific oligonucleotide sequences with two different fluorescent dyes in the 5' of the sequence (i.e., fluorogenic probe with FAM dye or VIC dye), each of them having a non-fluorescent quencher in the 3' of the sequence linked with a minor groove binder (melting temperature enhancer). During the PCR amplification, each probe anneals specifically to its complementary sequence between a forward and reverse primer on the target DNA. Because the DNA polymerase has an intrinsic 5' nuclease activity, a selective cleavage of the probes that hybridized to the genomic sequence occurs. This results in an increased fluorescence due to the separation of the reporter dye from the quencher. Therefore, the selective increase of one dye versus another (FAM vs. VIC) indicates the alleles that are present in the genomic DNA under consideration. A sample genotype may be determined by examination of the relative fluorescent intensity of each probe's dye. Using ABI's SDS 7000 software, a graphic plot of the two dyes' intensities may be created.

The Prometheus Crohn's Prognostic test also includes a data analysis algorithm. The final test result is a probability score reflecting the predicted likelihood that the patient will progress to a complicated CD phenotype.

2.2 Advantages of the Prometheus Crohn's Prognosis Test

The Prometheus Crohn's Prognostic test advantageously provides both serologic and genetic data to help physicians stratify the risk probability of their Crohn's patients for developing disease complications over time. It is the first and only test on the market that utilizes serogenetics to assess probability of developing disease complications in Crohn's patients over time. It uses 6 serology biomarkers and 3 NOD2/CARD15 mutations to assess patient's risk profile. It provides comprehensive results that helps physicians, in combination with additional clinical findings, make the most informed decisions for management of their patients. It also provides a quick overview of the Crohn's patient serogenetic risk profile in a simple to read test report.

II. Methodology

1. Clinical Validity

For the Prometheus Crohn's Prognostic test described in this example, a subset of 619 samples from CD patients (51% female and 49% male) were used in the development and validation of the test. The patients were diagnosed with CD based on a combination of criteria which may include clinical symptoms, endoscopy, histopathology, video capsule, or radiographic studies. This cohort was used because there was extensive medical information available for these patients, including the date of diagnosis, number and type of CD related surgeries, disease location and disease phenotype. Patients were classified as non-penetrating/non-stricturing (non-complicated disease) or stricturing or penetrating (complicated disease) either (1) by medical personnel at the source based on the data in the medical record or (2) by Prometheus medical staff based on data on surgical procedures performed to address specific complications. Patients with perianal penetrating disease were classified as complicated; patients exclusively with uncomplicated perianal disease were not included in the cohort.

All of the serum samples were assayed by ELISA for anti-CBir1, anti-OmpC, anti-I2, ASCA IgA and ASCA IgG and by IFA for pANCA. DNA was isolated from 157 serum samples; these were genotyped for NOD2.

III. Validation Procedures

1. Anti-I2 Assay Purpose

The anti-I2 ELISA is used to determined the level of anti-I2 antibodies in the serum of patients. The anti-I2 assay along with the other makers is used for the prognosis of Crohn's disease.

2. Anti-I2 Assay Format

The anti-I2 assay utilizes a standard 96-well sandwich ELISA format plate. A refolded GST-tagged protein, consisting of 100 amino acids of I2 sequence is captured on the plate using a monoclonal anti-GST antibody coated on the well surface. Patient serum samples are diluted 1:100 and/or 1:200 to bring the antibody concentration in the range of the standard curve. After incubation of the serum samples in the wells, detection of anti-I2 antibodies is accomplished using alkaline phosphatase enzyme conjugated anti-human IgA reagent. The reaction is revealed using cheminulescent substrate solution.

Example 19 describes the purification of GST-I2 antigen. Example 20 describes the anti-I2 ELISA assay procedure.

3. Specimen Requirements

Patient's whole blood is drawn into Serum Separator Tubes (SST). The tubes are shipped within 7 days to Prometheus Laboratories, under room temperature conditions or using Cold pack. Prior to shipment, the tubes are stored under refrigerated conditions.

4. Validation Assay Performance

A series of anti-I2 ELISA assays were performed in accordance with the validation protocol described in Example 21. Performance of the assay was done by three analysts performing the assay on five different days (15 assays total). The validation was performed using three lots of antigen preparation. The study distinguished between operator and batch effects. Each of the three operators used a different lot at least one time during the five day validation.

The results of this study allow the assessment of the performance characteristics of anti-I2 ELISA for (i) the standard curve performance, (ii) Minimum Detectable Concentration (MDC), (iii) Reference Range, (iv) Precision/Accuracy, (v) Linearity of Dilution, (vi) Stability Studies, and (vii) Interference.

4.1 Standard Curves

The standard curve is derived from seven calibrators assigned as 100 ELISA Units (EU), 53.3 EU, 40 EU, 20 EU, 10 EU, 2.5 EU, 0.625 EU and a zero standard. The SoftMax software was used to fit a 4-parameter curve to the standards. Standard curves were run in duplicate on a series of 15 assays. Results are represented in Table 29:

TABLE 29

| Standard Curve | | | | | | | |
|---|---|---|---|---|---|---|---|
| Standard | 100 EU Std 7 | 53.3 EU Std 6 | 40 EU Std 5 | 20 EU Std 4 | 10 EU Std 3 | 2.5 EU Std 2 | 0.625 EU Std 1 |
| Mean % CV | 4.93% | 3.75% | 2.59% | 2.95% | 3.25% | 7.80% | 23.13% |
| SD | 0.04 | 0.02 | 0.02 | 0.03 | 0.03 | 0.09 | 0.28 |

The mean $R^2$ value for the 4-parameter curve fit (n=15) was 0.999. Based on the acceptance criteria of ≤10% CV, the reportable range will be fixed between standard 2 (2.5 EU) and standard 7 (100 EU) with a range of 2.59% CV to 7.8% CV. Standard 1 (0.625 EU) will not be used as a lower reportable value because of the 23.13% CV.

4.2 Detection and Quantification Limits

The Minimum Detectable Concentration (MDC) was determined using a total of 20 replicates of the zero standards (blank) in each of the 15 assays. The mean absorbance plus two standard deviations (+2SD) was calculated for each assay and converted to appropriate concentrations using the 4-parameter logistic curve equation generated for each assay.

TABLE 30

| Minimum Detection Limits | |
|---|---|
| | MDC n = 12* |
| mean | 0.57 EU |
| SD | 0.59 EU |
| min | 0.00 EU |
| max | 1.68 EU |
| mean + 2SD | 1.75 EU |

*Three assays were excluded from the MDC calculation.

Conclusion: The analytical sensitivity of the assay, defined as the MDC, is 1.75 EU.

4.3 Reference Range

The reference range was determined using 40 healthy controls. Samples were diluted 1/100 for the test. The results show the adjusted concentration. Ninety-five percent confidence intervals (mean+/−1.96 standard deviations) are defined as the normal range.

TABLE 31

| Reference Range | |
|---|---|
| | n = 40 |
| Mean conc. | 185.04 EU |
| SD | 93.25 EU |
| Mean + 1.96 × SD | 367.80 EU |
| Mean − 1.96 × SD | 2.27 EU |

Conclusion: Samples with values greater than 367.80 EU will be considered positive for anti-I2.

4.4 Precision/Accuracy

Intra-assay precision (precision within the assay) was determined using 16 replicates of three different controls (High, Medium and Low made from a pool of human sera) on a single plate run by three analysts in each of the assays. Samples were diluted 1/10 for the test. The results show the adjusted concentration. The mean concentration of the replicates, the Standard Deviation and % CV for each control are summarized in Table 32.

TABLE 32

| Intra-assay precision | | | | |
|---|---|---|---|---|
| | | Mean EU | SD | % CV |
| Analyst 1 | Low | 71.68 | 4.34 | 6.1% |
| | Medium | 155.02 | 12.18 | 7.9% |
| | High | 510.56 | 38.78 | 7.6% |
| Analyst 2 | Low | 62.71 | 4.95 | 7.9% |
| | Medium | 135.81 | 9.98 | 7.3% |
| | High | 471.59 | 37.44 | 7.9% |
| Analyst 3 | Low | 58.22 | 9.05 | 15.5% |
| | Medium | 107.56 | 9.03 | 8.4% |
| | High | 311.94 | 25.18 | 8.1% |

Inter-assay reproducibility (precision between assays) was determined by testing three different controls in fifteen different plates. The mean concentration of the replicates, the Standard Deviation and % CV for each control are summarized in Table 33.

TABLE 33

| Inter-assay reproducibility | | | |
|---|---|---|---|
| | Mean EU | SD | % CV |
| LOW | 77.50 | 7.95 | 9.85% |
| MED | 147.82 | 11.98 | 6.73% |
| HIGH | 500.12 | 49.81 | 9.18% |

Conclusion: The within-assay precision (intra-assay) ranged from 6.1% to 8.4% CV with the exception of Analyst 3 Low control sample with a % CV of 15.5%. Overall, the intra-assay precision was within acceptable limits. The precision between assays (inter-assay reproducibility) ranged from 6.73% to 9.85% CV and fell within acceptable limits as well.

4.5 Linearity of Dilution

For an assay to be quantitative, the samples must dilute linearly and in parallel with the standard curve. The linearity of dilution was evaluated using five serial two-fold dilutions of the High, Medium and Low controls (Neat), starting from ½. Samples were diluted 1/10 for the test. The results show the adjusted concentration. Percent of recovery was determined. Linear regression ($R^2$) was also calculated to confirm that the sample dilution correlates linearly with the calculated ELISA units. Linearity of dilution has been tested five times for each control and is represented below (Table 34).

TABLE 34

| Linearity of Dilution | | | |
|---|---|---|---|
| | Expected EU | Actual EU | % Recovery |
| High contol Intra-Assay mean (n = 5) | | | |
| 1;1 | 567.49 | | |
| 1;2 | 283.75 | 276.21 | 97% |
| 1;4 | 141.87 | 141.51 | 100% |
| 1;8 | 70.94 | 66.01 | 93% |
| 1;16 | 35.47 | 32.42 | 91% |
| 1;32 | 17.73 | 18.81 | 106% |
| $R^2$ = | 0.9994 | | |
| Medium contol Intra-Assay mean (n = 5) | | | |
| 1;1 | 158.47 | | |
| 1;2 | 79.23 | 74.86 | 94% |
| 1;4 | 39.62 | 37.69 | 95% |
| 1;8 | 19.81 | 18.79 | 95% |
| 1;16 | 9.90 | 11.39 | 115% |
| 1;32 | 4.95 | 6.50 | 131% |
| $R^2$ = | 0.9994 | | |
| Low control Intra-Assay mean (n = 5) | | | |
| 1;1 | 100.63 | | |
| 1;2 | 50.31 | 52.16 | 104% |
| 1;4 | 25.16 | 30.10 | 120% |
| 1;8 | 12.58 | 14.72 | 117% |
| 1;16 | 6.29 | 7.81 | 124% |
| 1;32 | 3.14 | 4.37 | 139% |
| $R^2$ = | 0.9946 | | |

Percent Recovery was acceptable. The actual EU values for the highest dilution of the medium control and the two highest dilutions of the low control are under the minimum detectable concentration of the assay and should not be considered. All of the Control samples had $R^2$ values between 0.993 and 0.999, and the linearity was considered acceptable.

4.6 Stability Studies

Stability assays were performed by 3 analysts on the same day (3 plates). Each sample assay was prepared and stored at −80° C. High, Medium, and Low controls were incubated at room temperature or at 2-8° C. for 1, 2, 4 or 7 days. The treated controls were assayed and compared to the non-treated controls (Table 35). The results are expressed as percent (%) recovery of the initial calculated concentration.

TABLE 35

| Room Temperature (RT) and 2-8° C. stability of anti-I2 Controls | | | |
|---|---|---|---|
| | % Recovery | | |
| | High | Medium | Low |
| RT day 1 | 93% | 86% | 94% |
| RT day 2 | 90% | 88% | 93% |
| RT day 4 | 92% | 86% | 87% |
| RT day 7 | 87% | 96% | 80% |
| 4° C. day 1 | 97% | 107% | 85% |
| 4° C. day 2 | 94% | 104% | 110% |

TABLE 35-continued

| Room Temperature (RT) and 2-8° C. stability of anti-I2 Controls | | | |
|---|---|---|---|
| | % Recovery | | |
| | High | Medium | Low |
| 4° C. day 4 | 101% | 97% | 113% |
| 4° C. day 7 | 103% | 93% | 88% |

Conclusion: Based on the % recovery value, anti-I2 antibodies in serum are stable up to 7 days at room temperature or 2-8° C.

High, Medium, and Low controls were subjected to five freeze and thaw cycles. The treated controls were assayed and compared to the non-treated controls (Table 36). The results are expressed in percent (%) recovery of the initial calculated concentration.

TABLE 36

| Freeze and Thaw (FT) stability of anti-I2 Controls | | | |
|---|---|---|---|
| | % Recovery | | |
| | High | Medium | Low |
| FT 1 | 106% | 88% | 81% |
| FT 2 | 94% | 95% | 102% |
| FT 3 | 94% | 90% | 124% |
| FT 4 | 96% | 91% | 93% |
| FT 5 | 108% | 106% | 110% |

Conclusion: Only one value falls outside a percent recovery range of 80 to 120%: the low control tested after three cycles of freeze thaw (124%). Subsequent testing of the low control after 4 and 5 cycles of freeze/thaw resulted in 93% and 110% recovery, respectively. Based on the % recovery values, serum samples containing anti-I2 antibodies are stable for 1-5 freeze/thaw cycles.

Aliquots of GST-I2 antigen were subjected to one, three, and five cycles of freeze-thaw and were assayed and compared with samples kept frozen. The plates with GST-I2 controls were assayed and compared to the treated GST-I2 (Table 37). The results are expressed in percent (%) recovery of High, Medium, and Low controls of the initial calculated concentration.

TABLE 37

| Freeze and Thaw (FT) stability of GST-I2 antigen | | | |
|---|---|---|---|
| | % recovery | | |
| | FT 1 | FT 3 | FT 5 |
| High | 89% | 105% | 101% |
| Medium | 107% | 110% | 116% |
| Low | 101% | 97% | 118% |

Conclusion: GST-I2 antigen is stable for up to 5 freeze/thaw cycles.

Standard stability was evaluated. Standard stock solution was divided into two aliquots and stored at 2-8° C. for 7 days and 14 days. The treated standards were assayed and compared to the non-treated standard (Table 38). The results are expressed as percent (%) recovery of the initial calculated concentration.

TABLE 38

| 2-8° C. Standard stability | | |
|---|---|---|
| | % recovery | |
| | Day 7 | Day 14 |
| Std 7 | 93% | 97% |
| Std 6 | 79% | 88% |
| Std 5 | 110% | 97% |
| Std 4 | 99% | 120% |
| Std 3 | 95% | 105% |
| Std 2 | 98% | 92% |
| Std 1 | 85% | 88% |

Conclusion: Standards can be stored at 4° C. for 14 days.

4.7 Interference

To determine if Rheumatoid Factor (RF) or hemolyzed serum interfere in the assay, High, Medium, and Low controls were tested in the presence of either RF positive serum (sample purchased from Aalto Scientific) or hemolyzed sample. First, baseline results of each of the components run alone as a 1/10 dilution into diluent are shown in Table 39. Hemolyzed blood alone anti-I2 result is above the low control value. RF positive serum alone shows a high positive signal. Second, the High, Medium, and Low controls were spiked with an equal volume of either hemolyzed serum or RF. Anti-I2 recoveries from the spiked controls were compared with the recoveries for each of the serum samples alone (Table 39). The results shown in Table 39 are expressed as percent (%) recovery of the initial calculated concentration.

$$\text{For example: } \% \text{ Recovery} = \frac{\text{High control with } RF}{\text{High control alone} + RF \text{ alone}} \times 100$$

TABLE 39

| Interference | | |
|---|---|---|
| | Mean EU | % Recovery |
| High | 233.28 | |
| Med | 115.62 | |
| Low | 76.21 | |
| Hemo | 91.38 | |
| RF | 572.39 | |
| High + Hemo | 229.38 | 71% |
| Med + Hemo | 145.06 | 70% |
| Low + hemo | 116.89 | 70% |
| High + RF | 726.35 | 90% |
| Med + RF | 619.55 | 90% |
| Low + RF | 582.77 | 90% |

When the High, Medium, and Low controls were tested in the presence of hemolyzed serum and RF positive serum, only hemolyzed serum showed a significant reduction in the % recovery.

Based on the results described here, both hemolyzed serum and RF positive serum interfere with accurate detection of anti-I2. To mitigate the effect of this interference on the test, samples with visible hemolyzed blood will be rejected. Mitigation of the interference with RF cannot be achieved by rejection of specific samples. However, medical literature suggests that there is no link between Crohn's disease and disease states in which RF is expressed in the serum (primarily rheumatoid arthritis). Rather, the frequency of rheumatoid arthritis in CD patients can be expected to be similar to what is seem in the general population; the prevalence of RA worldwide is estimated at 0.8% (Rindfleisch et al., *Am. Fam. Physician,* 72:1037-1047 (2005)). In addition, only about 80% of RA patients express RF. Thus, we estimate that only approximately 0.64% (0.008×0.8=0.0064) of the samples received will be impacted by RF interference.

The effects of various substances on the performance of the anti-I2 assay were determined. High, Medium and Low controls were spiked with bilirubin (400 μg/mL), cholesterol (5 mg/mL), heparin (80 U/mL), EDTA (1.8 mg/mL) or hemoglobin (5 mg/mL). Percent (%) anti-I2 recovered in the spiked control was calculated (Table 40). The results are expressed in percent (%) recovery of the initial calculated concentration.

TABLE 40

Interference of the anti-I2 assay with various substances

| | Mean EU | % Recovery |
|---|---|---|
| High | 386.11 | |
| Med | 135.78 | |
| Low | 67.05 | |
| High + Bil | 345.59 | 90% |
| Med + Bil | 127.38 | 94% |
| Low + Bil | 75.39 | 112% |
| High + Chol | 344.65 | 89% |
| Med + Chol | 121.51 | 89% |
| Low + Chol | 95.37 | 142% |
| High + Hep | 372.03 | 96% |
| Med + Hep | 142.19 | 105% |
| Low + Hep | 86.99 | 130% |
| High + EDTA | 469.69 | 122% |
| Med + EDTA | 171.01 | 126% |
| Low + EDTA | 75.44 | 113% |
| High + Hemog | 404.38 | 105% |
| Med + Hemog | 162.05 | 119% |
| Low + Hemog | 113.08 | 169% |

Conclusion: Anti-I2 detection is within an acceptable range with the exception of Low controls spiked with Cholesterol, Heparin and Hemoglobin. These three substances increase the % recovery (142%, 130%, and 169%, respectively) when the amount of anti-I2 in the serum is low.

IV. Reproducibility of GST-I2 Antigen Preparation

Figure 25:
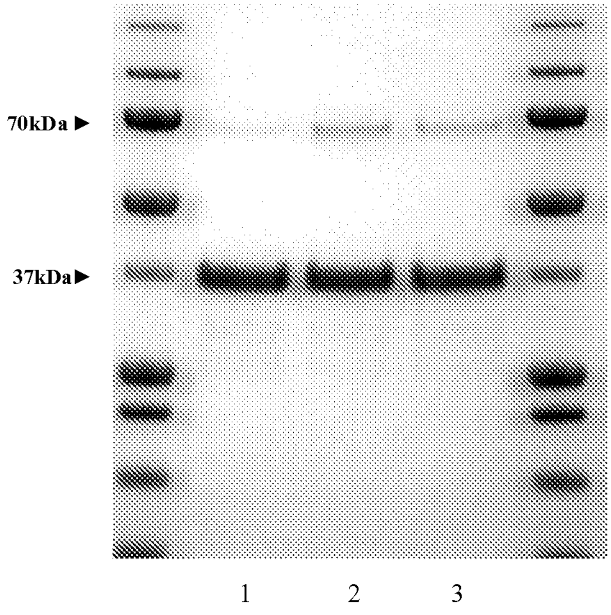
FIG. 25 illustrates a denaturing gel with three preparations of GST-I2 antigen.

Three antigen preparations were performed using the same protocol and 3 different batches of buffers. Two (2) μg of each purified antigen preparation were separated on a denaturing gel and stained with Coomasie Brilliant Blue as shown in FIG. 25. For each I2 antigen preparation, a consistent single band was detected at the predicted molecular weight (37 kDa). A higher 70 kDa band was also revealed, showing the presence of antigen dimer in the preparation.

Conclusion: The method for I2 antigen preparation is reproducible.

V. Statistical Analysis

The Prometheus Crohn's Prognostic test predicts the probability of developing a stricturing (fibrostenosing) or penetrating (fistulizing) disease phenotype, collectively referred to as a complication disease phenotype. In practice, the Prometheus Crohn's Prognostic test is a logistic regression model; the dependent variable is the desired probability of complication.

In the following sections, the biomarkers are first analyzed individually. Next, the compound score (QSS, or Quartile Sum Score) is described. The complete logistic regression model is then presented in detail. Finally, the performance of the logistic regression model is described in the next section, Algorithm Validation.

1. Individual Biomarkers

As described previously, there are nine biomarkers: five ELISAs, one indirect immunofluorescence, and three genotyping PCRs. For the ELISA and immunofluorescence biomarkers, 619 samples were assayed. For the genotyping biomarkers, a subset of 159 samples were assayed.

1.1 ELISA Markers

For each of the five ELISA biomarkers (ASCA-IgA, ASCA-IgG, anti-CBir1, anti-OmpC, and anti-I2), the numerical biomarker score (in standardized ELISA Units) is converted into a quartile score. Specifically, the bottom quarter of numerical scores are converted to a score of "1", the next 25% of scores are converted to a score of "2", the third quartile is converted to "3", and the top quartile is converted to "4". Table 41 shows the cutoffs for the quartiles for each of the five ELISA biomarkers:

TABLE 41

Quartile Cutoffs

| | Quartile 1 | Quartile 2 | Quartile 3 | Quartile 4 |
|---|---|---|---|---|
| ASCA-IgA | <6.2 | 6.2-18.0 | 18.1-50.9 | 60.0+ |
| ASCA-IgG | <11.7 | 11.7-29.3 | 29.4-71.9 | 72.0+ |
| Anti-CBir1 | <17.0 | 17.0-35.3 | 35.4-69.8 | 69.9+ |
| Anti-OmpC | <7.8 | 7.8-12.8 | 12.9-24.0 | 24.1+ |
| Anti-I2 | <206 | 206-330 | 331-488 | 489+ |

The following tables show the number of patients with and without disease complications for each biomarker, where the ELISA results were stratified by quartile.

TABLE 42

Stratification by Complication vs. Non-complication

| | Q1 | Q2 | Q3 | Q4 |
|---|---|---|---|---|
| ASCA-IgA | | | | |
| Non-compl. | 96 | 64 | 39 | 28 |
| Complication | 59 | 90 | 116 | 127 |
| ASCA-IgG | | | | |
| Non-compl. | 83 | 70 | 41 | 33 |
| Complication | 72 | 84 | 114 | 122 |
| Anti-CBir1 | | | | |
| Non-compl. | 79 | 62 | 46 | 40 |
| Complication | 76 | 92 | 109 | 115 |
| Anti-OmpC | | | | |
| Non-compl. | 87 | 64 | 48 | 28 |
| Complication | 68 | 90 | 107 | 127 |
| Anti-I2 | | | | |
| Non-compl. | 79 | 61 | 41 | 46 |
| Complication | 76 | 93 | 114 | 109 |

The following table summarizes the rates of complications for each biomarker, stratified by quartile.

TABLE 43

| Rates of Complications | | | | |
|---|---|---|---|---|
| % Compl. | Q1 | Q2 | Q3 | Q4 |
| ASCA-IgA | 38.1% | 58.4% | 74.8% | 81.9% |
| ASCA-IgG | 46.5% | 54.5% | 73.5% | 78.7% |
| Anti-CBir1 | 49.0% | 59.7% | 70.3% | 74.2% |
| Anti-OmpC | 43.9% | 58.4% | 69.0% | 81.9% |
| Anti-I2 | 49.0% | 60.4% | 73.5% | 70.3% |

The following table shows the p-values calculated by Pearson's Chi-square test of independence for each of the contingency (count) tables shown above, where the null hypothesis is that the occurrence of these outcomes is statistically independent. All values are highly significant, demonstrating an association between biomarker quadrant and complications. In other words, for all markers, those in higher quartiles have higher rates of complications. (The top two quartiles of anti-I2 are the only exception, but even they are roughly comparable.)

TABLE 44

| p-Values | |
|---|---|
| | p value |
| ASCA-IgA | <0.001 |
| ASCA-IgG | <0.001 |
| Anti-CBir1 | <0.001 |
| Anti-OmpC | <0.001 |
| Anti-I2 | <0.001 |

1.2 Indirect Immunofluorescence

The indirect immunofluorescence biomarker pANCA is a binary rather than a numerical variable—its value is either positive or negative. The following tables show the counts of complications (Table 45) and the rates of complications (Table 46), stratified by pANCA status.

TABLE 45

| Counts of Complications | | |
|---|---|---|
| pANCA | negative | positive |
| Non-compl. | 169 | 58 |
| Complication | 323 | 69 |

TABLE 46

| Rates of Complications | | |
|---|---|---|
| % Compl. | negative | positive |
| pANCA | 65.7% | 54.3% |

For the pANCA count (contingency) table shown above, the p-value calculated by Pearson's Chi-square test is 0.024 (statistically significant, $p<0.05$).

Because the data indicates that pANCA positive status is associated with a lower rate of complications, the scoring for pANCA is inverted, as described in the QSS section.

1.3 NOD2 Genotyping

The three genotyping biomarkers were all NOD2 single nucleotide polymorphisms: SNP8, SNP12, and SNP13. The following table shows the counts of patient genotypes:

TABLE 47

| Patient Genotypes | | | |
|---|---|---|---|
| | SNP8 | SNP12 | SNP13 |
| Homozygous Wild type | 141 | 146 | 138 |
| Heterozygous Mutant | 18 | 13 | 17 |
| Homozygous Mutant | 0 | 0 | 4 |

The following tables show the specific genotype counts stratified by complication status:

TABLE 48

| SNP 8 | | |
|---|---|---|
| | Non-compl. | Complications |
| Wild type | 44 | 97 |
| Mutant | 5 | 13 |

TABLE 49

| SNP 12 | | |
|---|---|---|
| | Non-compl. | Complications |
| Wild type | 44 | 102 |
| Mutant | 5 | 8 |

TABLE 50

| SNP 13 | | |
|---|---|---|
| | Non-compl. | Complications |
| Wild type | 48 | 90 |
| Mutant | 1 | 20 |

The following table shows the rates of complications stratified by genotype:

TABLE 51

| Rates of Complications by Genotype | | | |
|---|---|---|---|
| | SNP 8 | SNP 12 | SNP 13 |
| Wt | 68.8% | 69.9% | 65.2% |
| Mut | 72.2% | 61.5% | 95.2% |

The following table shows the p-values calculated by Fisher's Exact Test for each of the contingency (count) tables shown above, where the null hypothesis is that the occurrence of these outcomes is statistically independent.

TABLE 52

| p-Values | |
|---|---|
| | p value |
| SNP 8 | N.S. |
| SNP 12 | N.S. |
| SNP 13 | 0.0044 |

For single mutations, only SNP 13 was statistically significant at $p<0.05$. (Fisher's Exact test was used rather than Pearson's Chi-square test due to the presence of cells with counts <5; the p-values for the Chi-square tests were similar.)

The model also incorporates double mutations, which can be homozygous double mutations in a single SNP, or multiple heterozygous mutations across the three SNPS. There is extensive evidence (Lesage et al., *Am. J. Hum. Genet.,* 70:845-857 (2002); Abreu et al., *Gastroenterology,* 123:679-688 (2002); Annese et al., *Am. J. Gastroenterol.,* 100:84-92 (2005)) demonstrating that genotypes with multiple mutations have significantly elevated risk. The data presented herein consisted of 9 samples having two NOD2 mutations (four with double SNP13 mutations, five with two mutations among SNP8, SNP12, and SNP13). All nine samples (100%) had a complication phenotype. While this sample size is too small to prove statistical significance, it is consistent with the literature, which strongly indicates that genotypes with multiple mutations have significantly elevated risk.

2. Compound Scores: Quartile Sum Scores

The Quartile Sum Score (QSS) is a sum of six individual quartile scores. Since each individual quartile score can range from 1 to 4, the total can range from 6 to 24. The six biomarkers providing quartile scores are: ASCA-IgA, ASCA-IgG, anti-CBir1, anti-OmpC, anti-I2, and pANCA.

The pANCA biomarker can be positive or negative; since the positive status is protective, the quartile score for pANCA is a special case, in which a positive status is scored as "1" and a negative status is scored as "4". This scoring provides consistency with the other five markers, which also range from 1-4.

Figure 26:
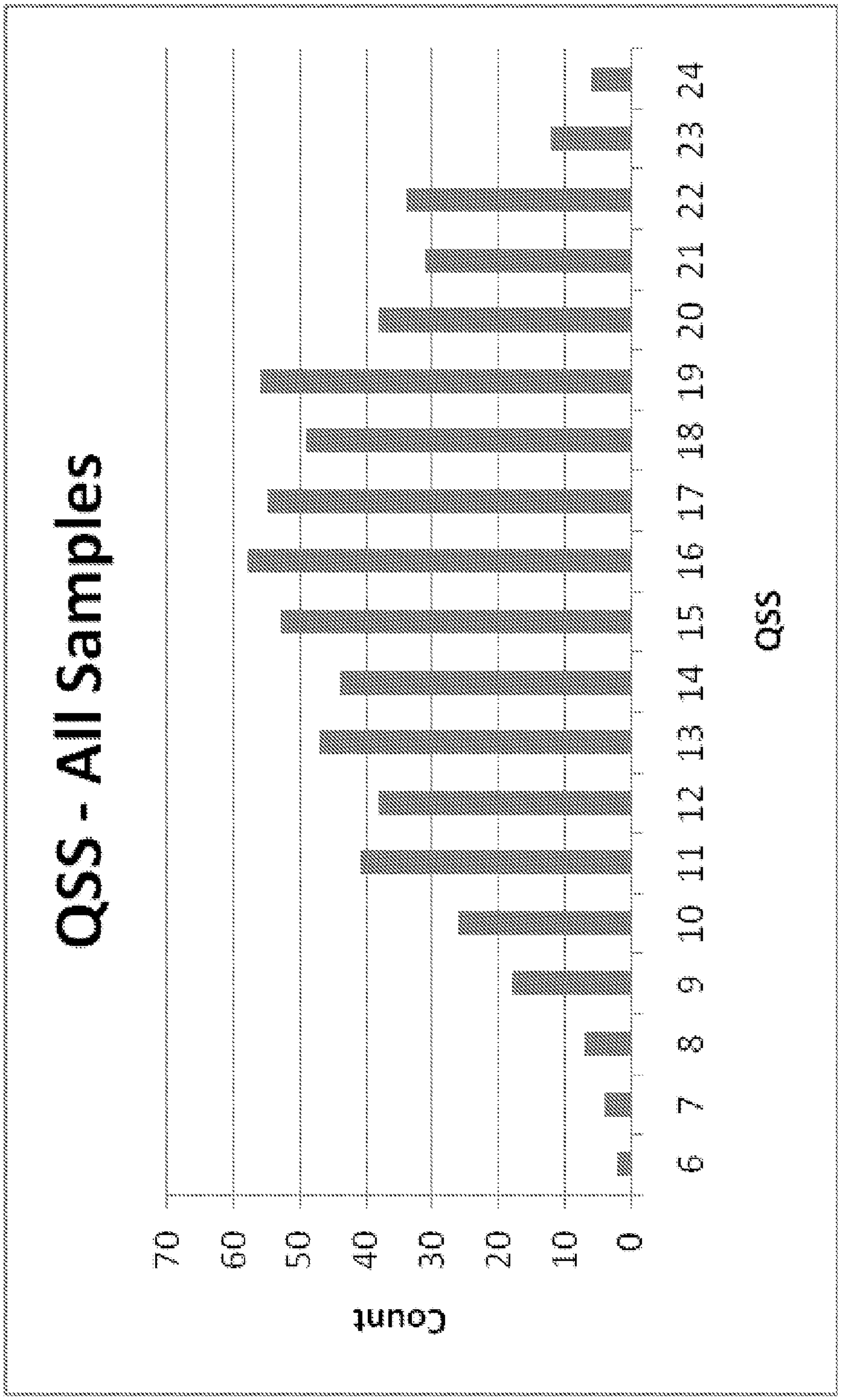
FIG. 26 illustrates a diagram which shows the distribution of QSS values for all samples evaluated in Example 16.
Figure 27:
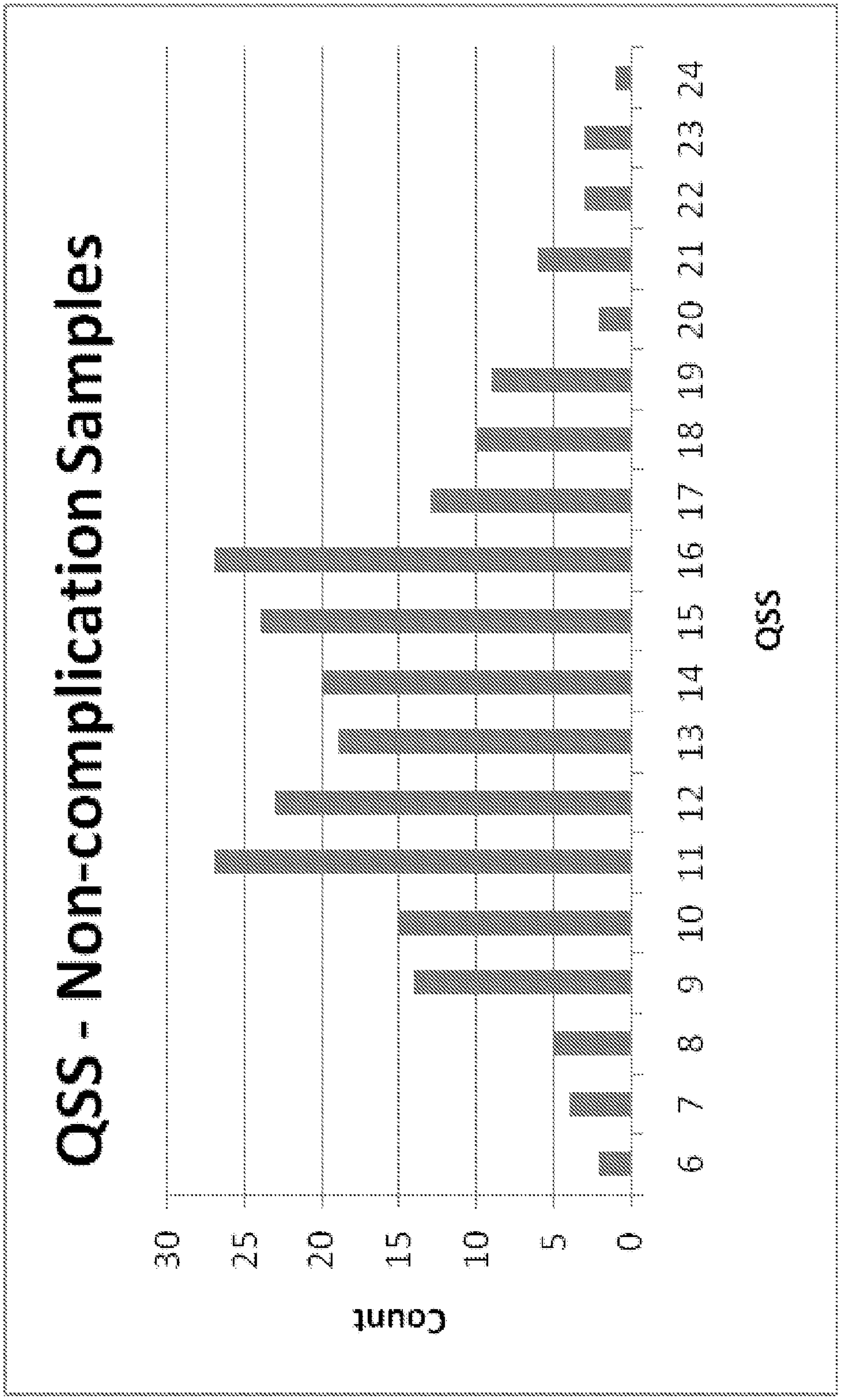
FIG. 27 illustrates a diagram which shows the distribution of QSS values for samples with non-complicated phenotypes as described in Example 16.
Figure 28:
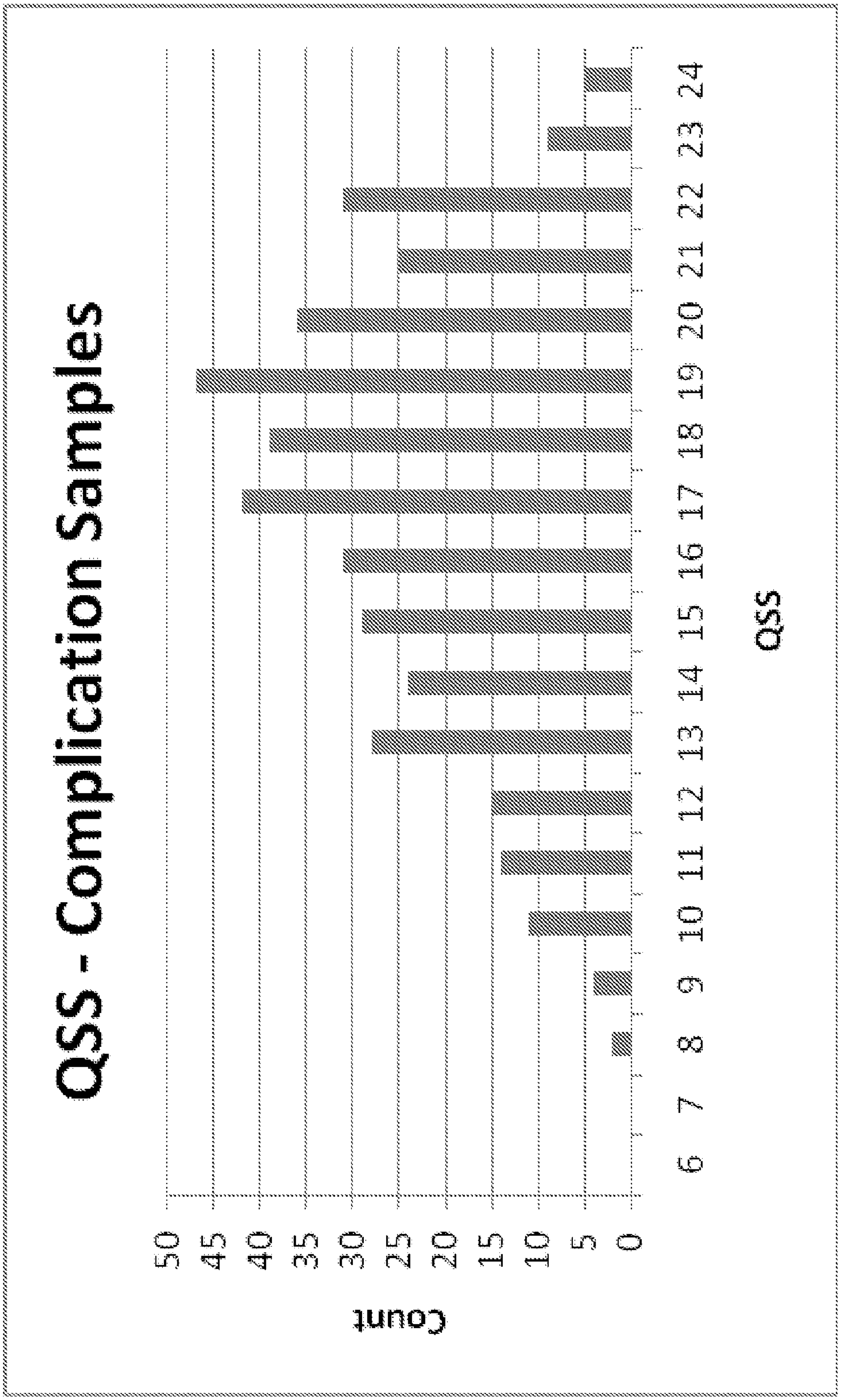
FIG. 28 illustrates a diagram which shows the distribution of QSS values for samples with complicated phenotypes as described in Example 16.

FIG. 26 shows the distribution of QSS values for the 619 samples. The QSS score is shown on the X axis and the number of patients is shown on the Y axis. FIG. 27 shows the distribution of QSS values for samples with non-complicated phenotypes. FIG. 28 shows the distribution of QSS values for samples with complicated phenotypes.

3. Complete Logistic Regression Model 3.1 Duration of Observation

Figure 29:
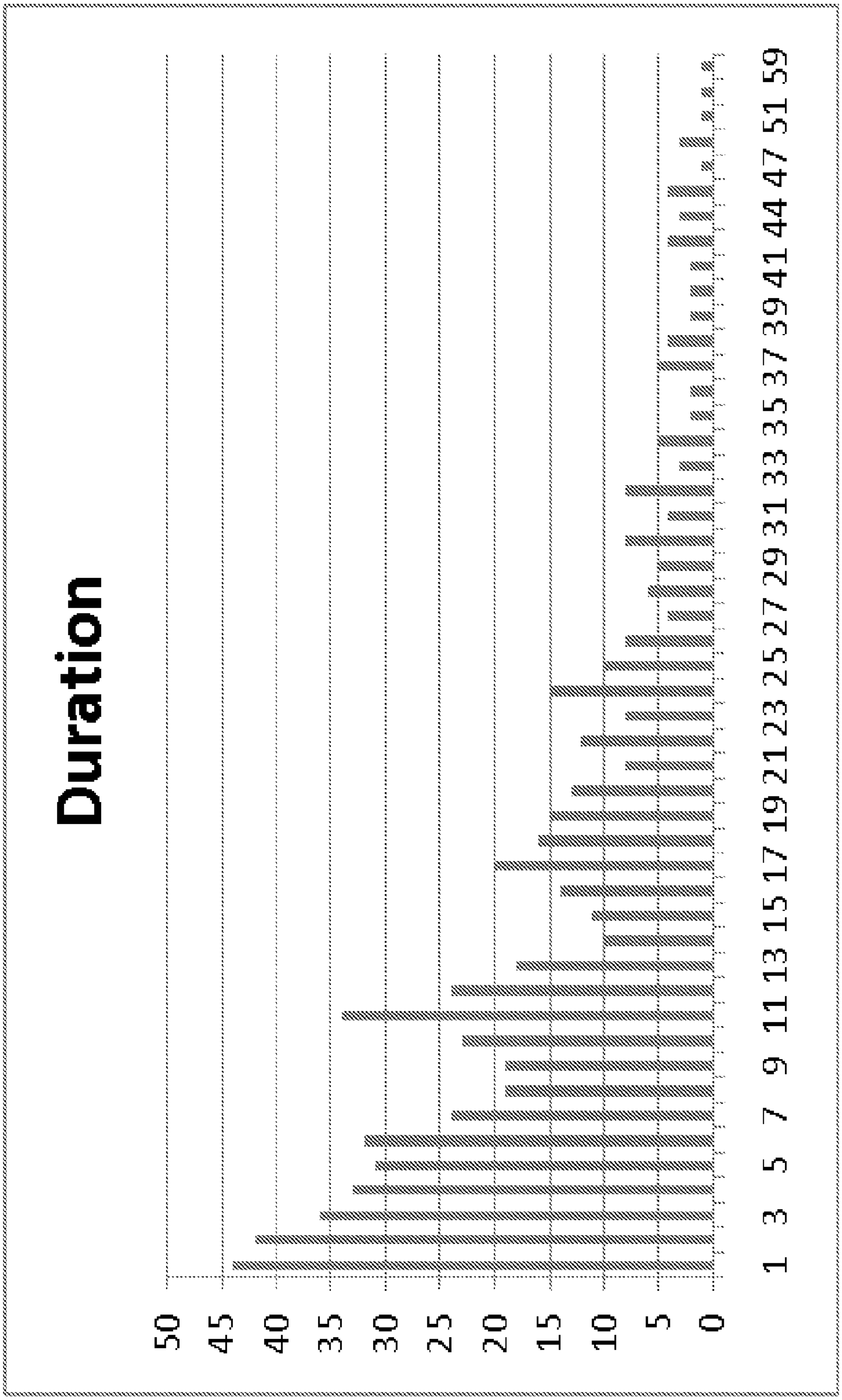
FIG. 29 illustrates a diagram which shows the distribution of durations for all samples evaluated in Example 16.
Figure 30:
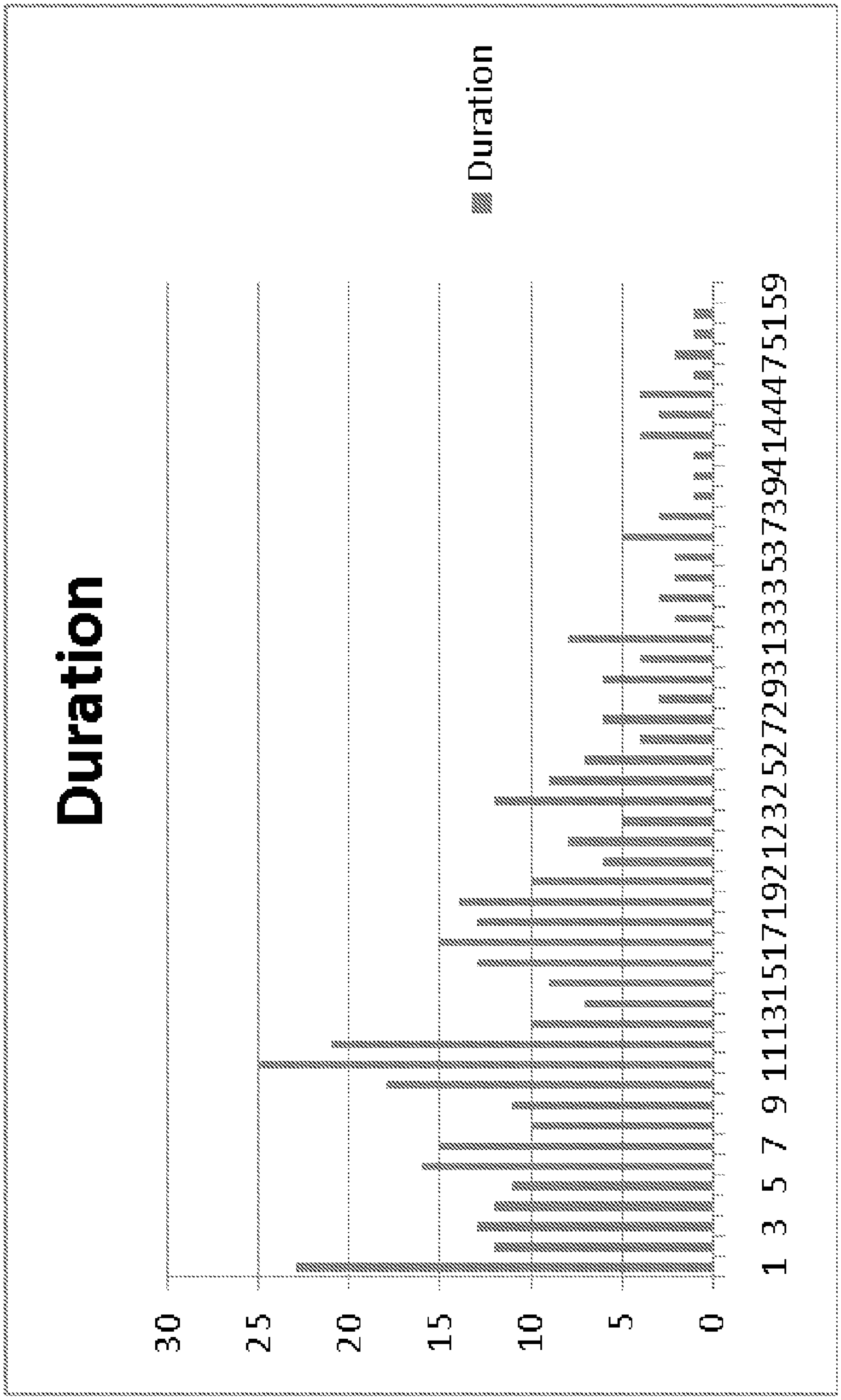
FIG. 30 illustrates a diagram which shows the durations for samples with a complication phenotype as described in Example 16.
Figure 31:
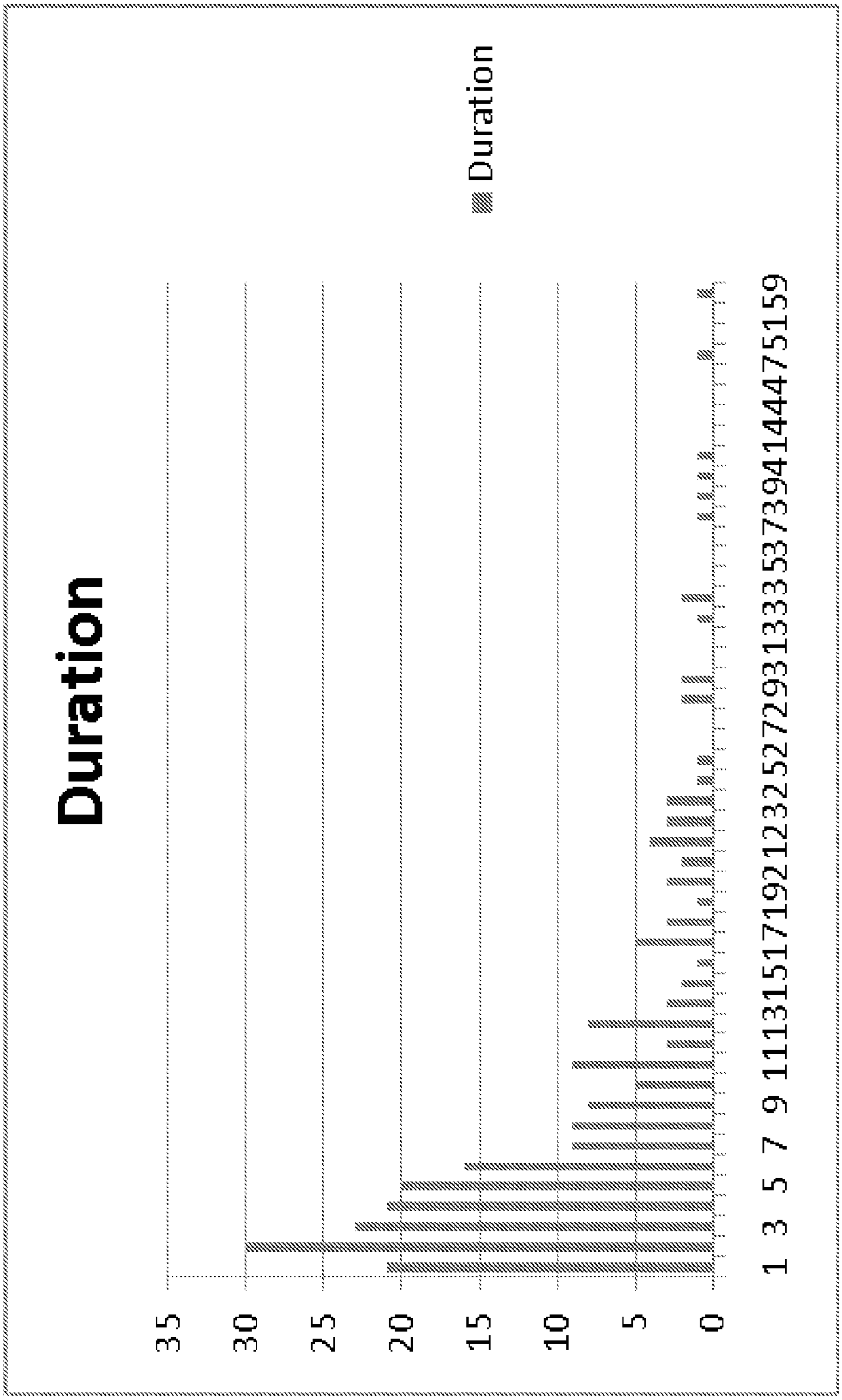
FIG. 31 illustrates a diagram which shows the durations for samples with a non-complication phenotype as described in Example 16.

Because this study utilizes a cross-sectional design, the 619 samples all have varying durations of disease, defined as the time interval from diagnosis to blood draw. FIG. 29 shows the distribution of durations in all samples. Time in years is shown on the X axis and the number of patients is shown on the Y axis. FIG. 30 shows the durations for samples with a complication phenotype. FIG. 31 shows the durations for samples with a non-complication phenotype.

Intuitively, a longer duration of observation implies a higher probability of observing a complication phenotype. In constructing a logistic regression model, it is clear that duration of observation must be incorporated as a covariate. The resulting model can then be used to make predictions across a range of durations, thus generating a set of probabilities over time.

3.2 Genotype Covariates—Serology and Sero-Genetic Models

Incorporating genotype information into the logistic regression model is complicated by the fact that SNP status is only available for 159 samples, rather than the full cohort of 619 samples. Two regression models were generated: a "serology only" model which is constructed with all 619 samples, but which does not incorporate genotype as a covariate, and a "sero-genetic" model which is constructed with a subset of 159 samples, and which does include genotypes as covariates. For samples without mutations; the "serology only" model's probability is reported, whereas for samples with mutations, the "sero-genetic" model's probability is reported.

3.3 Serology Logistic Regression

In the serological logistic regression model, the covariates are QSS and disease duration. The following figure shows the parameters, along with their standard errors and p values.

| Coefficients: | | | | | |
|---|---|---|---|---|---|
| | Estimate | Std. Error | z value | Pr(>\|z\|) | |
| (Intercept) | −3.56703 | 0.42806 | −8.333 | <2e−16 | *** |
| duration | 0.06038 | 0.01043 | 5.788 | 7.13e−09 | *** |
| QSS | 0.21898 | 0.02689 | 8.143 | 3.85e−16 | *** |

Signif. codes:
0 '*' 0.001 '' 0.01 '*' 0.05 '.' 0.1 ' ' 1

Both duration and QSS are highly significant ($p<0.001$).

Figure 32:
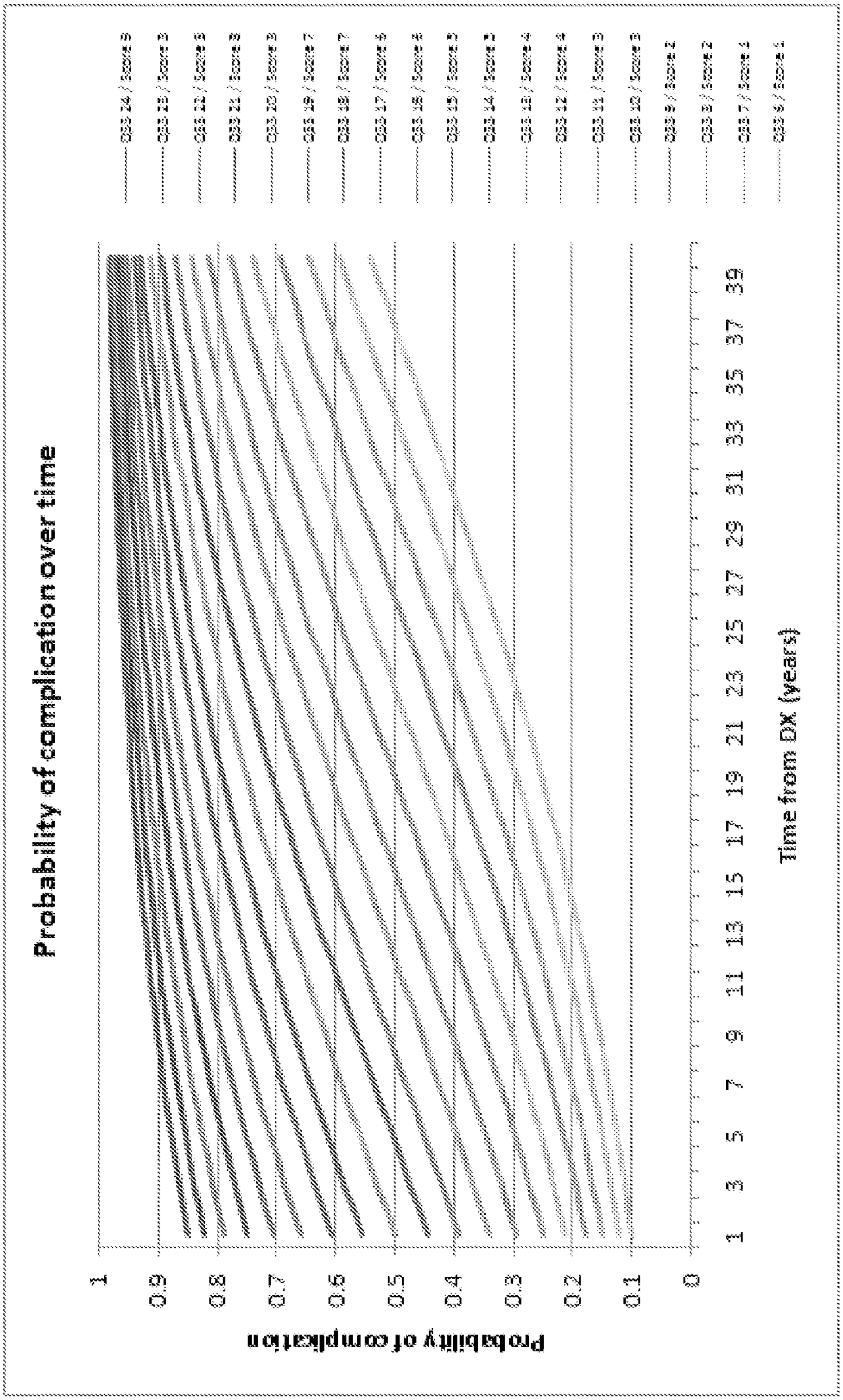
FIG. 32 illustrates a wild-type logistic regression model which shows the probabilities predicted by the model for a range of QSS and duration values as described in Example 16.

Using this model, FIG. 32 shows the probabilities (on the Y axis) predicted by the model for a range of QSS and duration values (on the X axis).

3.4 Sero-Genetic Logistic Regression

In the sero-genetic logistic regression model, the covariates are QSS, duration, and SNP 13 mutations. The covariate mut.13 is a categorical variable that is positive if a SNP 13 mutation is present. The following figure shows the parameters, along with their standard errors and p values.

| Coefficients: | | | | | |
|---|---|---|---|---|---|
| | Estimate | Std. Error | z value | Pr(>\|z\|) | |
| (Intercept) | −3.10037 | 0.89270 | −3.473 | 0.000515 | * * * |
| duration | 0.03465 | 0.02360 | 1.468 | 0.142101 | |
| QSS | 0.21200 | 0.05643 | 3.757 | 0.000172 | * * * |
| mut. 13 | 2.04744 | 1.06346 | 1.925 | 0.054196 | . |

Signif. codes:
0 '*' 0.001 '' 0.01 '*' 0.05 '.' 0.1 ' ' 1

In addition, the presence of two mutations (cross SNP 8, 12 and 13; including both heterozygous and homozygous) is treated as a special case with a fixed, highly elevated risk (99%).

Figure 33:
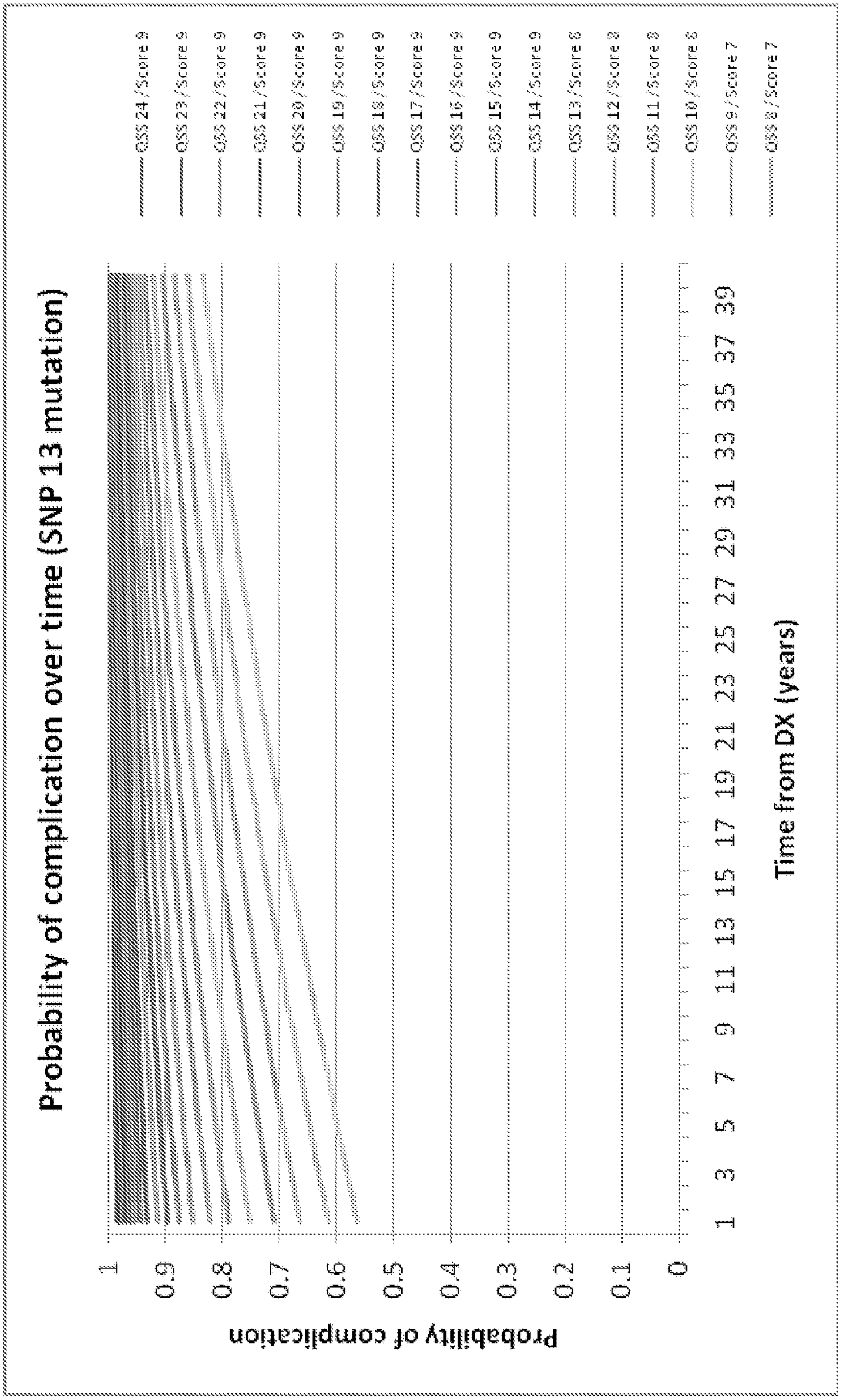
FIG. 33 illustrates a sero-genetic logistic regression model which shows the probabilities predicted by the model for a range of QSS and duration values as described in Example 16.

Using this mutation model (for samples with SNP 13 mutations), FIG. 33 shows the probabilities predicted by the model for a range of QSS and duration values.

3.5 Standardized Risk Scale

The QSS scale ranges from 6-24, rather than a more conventional 1-10. Furthermore, the interpretation of a given QSS score is different for patients with and without SNP13 mutations. A single common risk scale has been constructed which ranges from 1-10.

The following table shows how this is done. The probability of a complication phenotype within ten years of duration is taken as a benchmark. The standardized scale number is simply the first (leftmost) digit of the probability. The resulting scale has serology model values ranging from 1-9 and sero-genetic values ranging from 6-10. (The score of 10 is reserved for double mutations, not shown).

TABLE 53

| Standardized Risk Scale | | | | |
|---|---|---|---|---|
| Standardized Scale | Serological regression QSS | Yr 10 Prob. | Sero-genetics QSS | Mut Yr 10 Prob. |
| 1 | QSS 6 | 16% | | |
| 1 | QSS 7 | 19% | | |
| 2 | QSS 8 | 23% | | |
| 2 | QSS 9 | 27% | | |
| 3 | QSS 10 | 32% | | |
| 3 | QSS 11 | 36% | | |
| 4 | QSS 12 | 42% | | |
| 4 | QSS 13 | 47% | | |
| 5 | QSS 14 | 53% | | |
| 5 | QSS 15 | 58% | | |
| 6 | QSS 16 | 63% | QSS 6 | 64% |
| 6 | QSS 17 | 68% | QSS 7 | 69% |
| 7 | QSS 18 | 73% | QSS 8 | 73% |
| 7 | QSS 19 | 77% | QSS 9 | 77% |
| 8 | QSS 20 | 80% | QSS 10 | 80% |
| 8 | QSS 21 | 84% | QSS 11 | 84% |
| 8 | QSS 22 | 86% | QSS 12 | 86% |
| 8 | QSS 23 | 89% | QSS 13 | 89% |
| 9 | QSS 24 | 91% | QSS 14 | 91% |
| 9 | | | QSS 15 | 92% |
| 9 | | | QSS 16 | 94% |
| 9 | | | QSS 17 | 95% |
| 9 | | | QSS 18 | 96% |
| 9 | | | QSS 19 | 97% |
| 9 | | | QSS 20 | 97% |
| 9 | | | QSS 21 | 98% |
| 9 | | | QSS 22 | 98% |
| 9 | | | QSS 23 | 98% |
| 9 | | | QSS 24 | 99% |

VI. Algorithm Validation

1. Cross Validation Design

In order to validate the model, a leave-one-out cross validation procedure was used to generate unbiased performance estimates and avoid overfitting. In this well known validation design, the performance of the final logistic regression model is evaluated indirectly, by generating 619 submodels. For each of the 619 samples, a separate model is generated by taking the other 618 samples as the training set and then evaluating the "held out" sample on the generated submodel.

For each of the 619 submodels generated in this way, the exact same procedure is used to generate the model as is used to generate the final model. Thus, for each iteration, both the wild type and mutation models are generated, etc. This is computationally expensive but ensures that the sample being used to validate is never seen when training the models.

2. Evaluating Probabilities Vs Outcomes

The following table compares probabilities (predictions) to outcomes (actual rates of complication phenotypes).

TABLE 54

| Probabilities and Outcomes | | | | |
|---|---|---|---|---|
| Category (prediction) | Score | Count | Average Prediction | Rate of Complications |
| 10-20% | 1 | 13 | 16% | 31% |
| 20-30% | 2 | 49 | 25% | 16% |
| 30-40% | 3 | 54 | 35% | 39% |
| 40-50% | 4 | 64 | 45% | 44% |
| 50-60% | 5 | 74 | 55% | 45% |
| 60-70% | 6 | 83 | 65% | 67% |
| 70-80% | 7 | 85 | 76% | 84% |
| 80-90% | 8 | 112 | 85% | 85% |
| 90-99% | 9 | 76 | 95% | 88% |
| >99% | 10 | 9 | 99% | 100% |

The correlation between the average predictions and the observed rates of complications (the two right columns) is 0.964.

Note that the lowest point (10-20%) is based on significantly fewer samples (n=13), which may have led to a wider confidence interval for that outcome.

Figure 34:
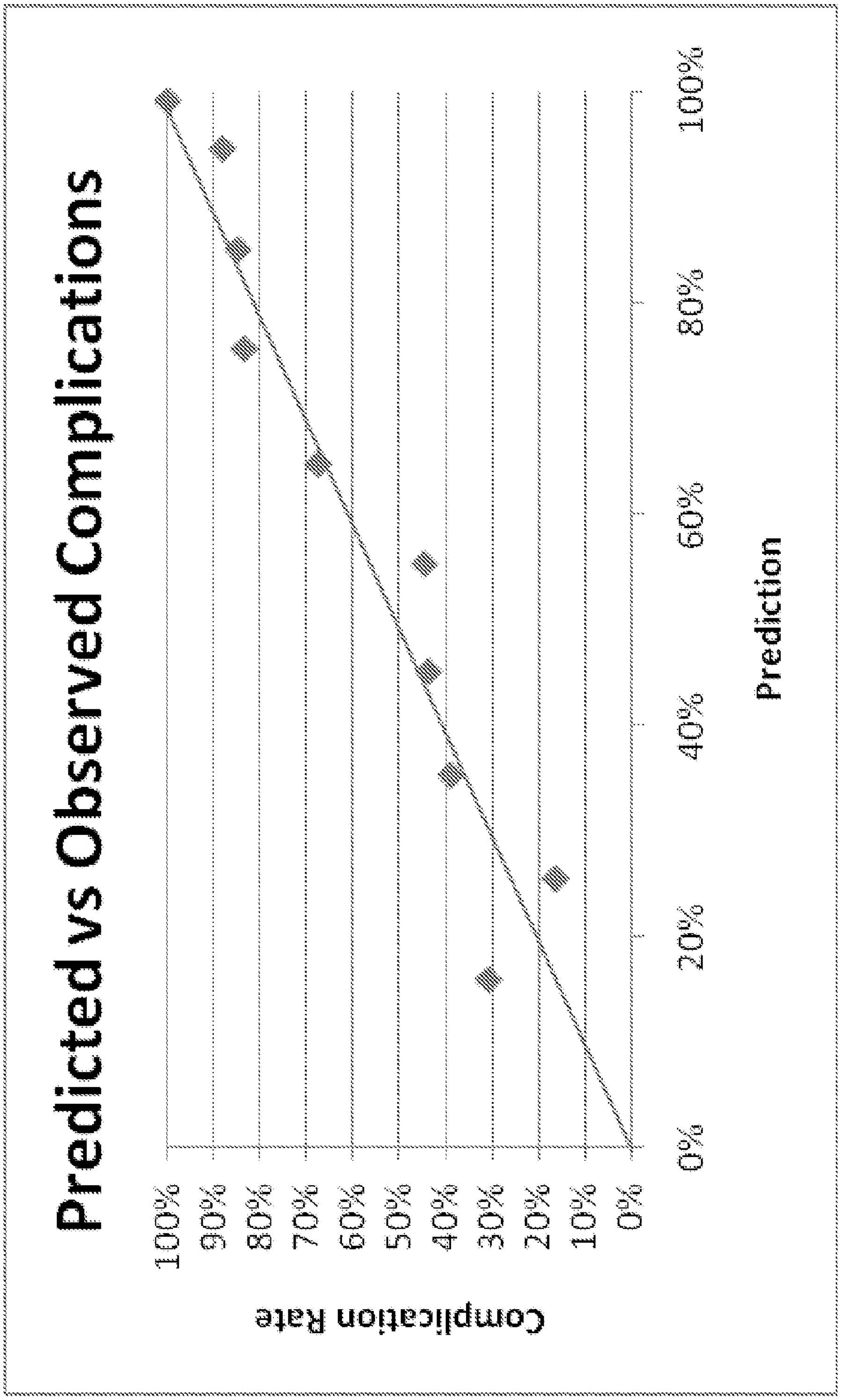
FIG. 34 illustrates the correspondence of predicted (on the Y axis) and actual complications (on the X axis) as described in Example 16.

FIG. 34 shows the correspondence of predicted (on the Y axis) and actual complications (on the X axis).

3. Evaluating Accuracy of Binary Predictions

Although this test provides a probability as an outcome, it is also possible to convert the probabilities into binary predictions (complication vs non-complication). This allows the performance of the test to be evaluated in terms more typically associated with diagnostic rather than prognostic tests, such as accuracy, receiver operator characteristic (ROC) curves, sensitivity, and specificity.

Figure 35:
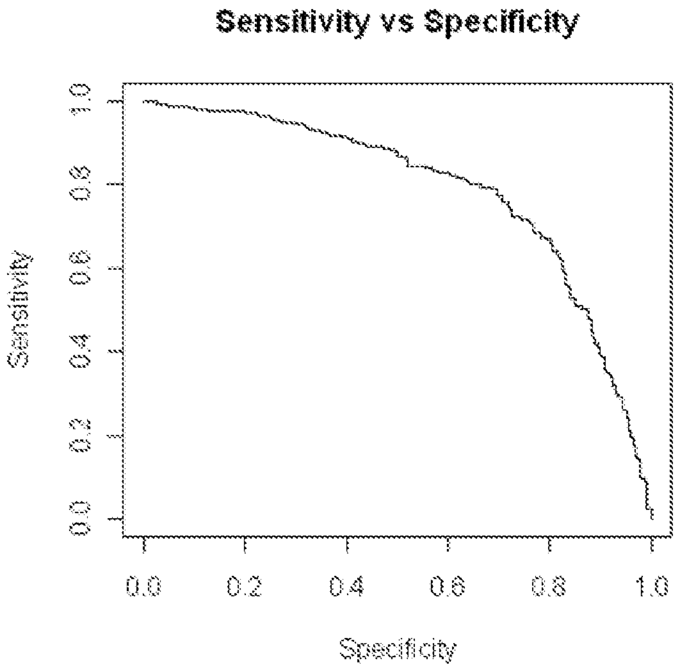
FIG. 35 illustrates an exemplary ROC curve generated using the probabilities reported by the cross-validation calculations described in Example 16.

The ROC curve shown in FIG. 35 was generated using the probabilities reported by the cross-validation calculations. It illustrates the combinations of sensitivity and specificity that are possible. The AUC (area under the curve) was 0.787, with 95% confidence interval of (0.749-0.824).

Figure 36:
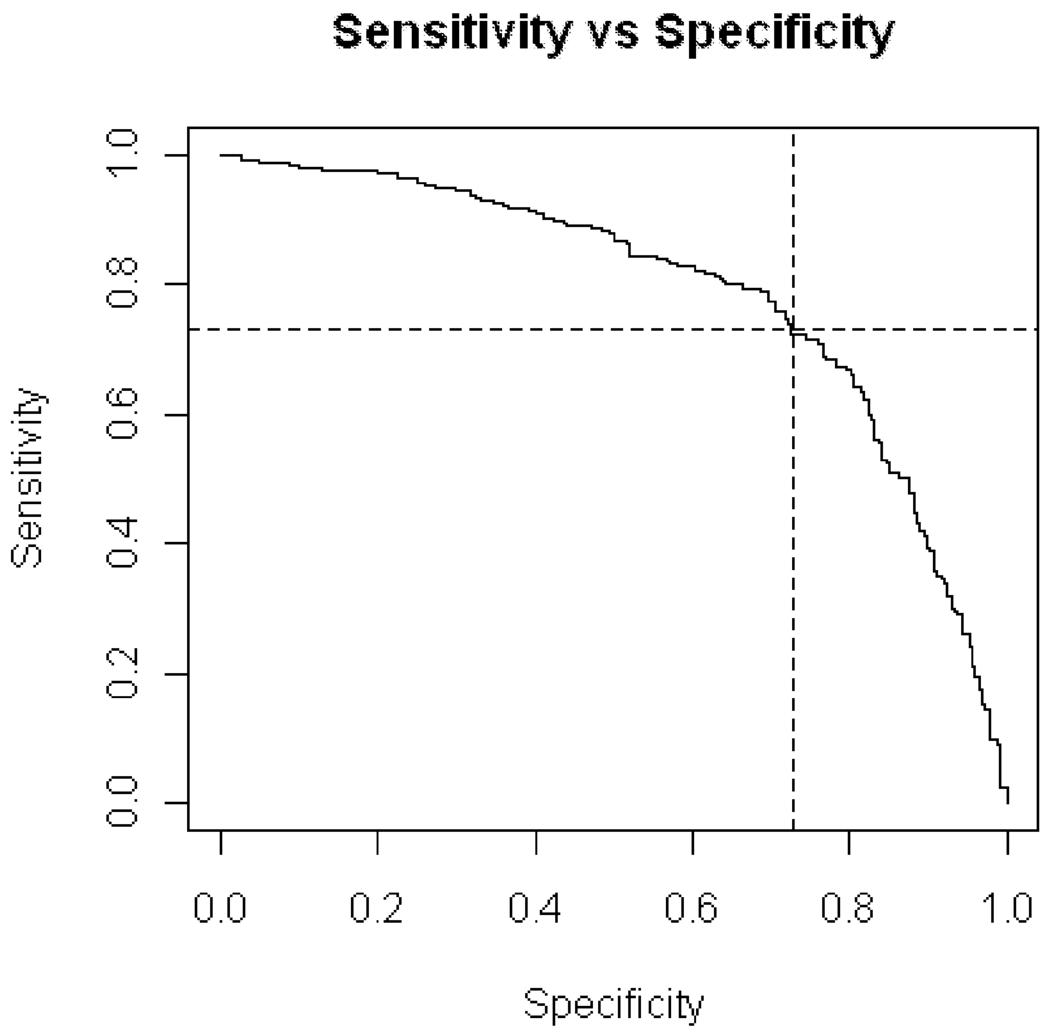
FIG. 36 illustrates an exemplary ROC curve with lines drawn at 73% sensitivity and specificity as described in Example 16.

The optimal operating point is a cutoff of 0.58; at this point, the accuracy is 75% (465/619), sensitivity is 79% (309/392), and specificity is 69% (156/227). If the objective is balanced sensitivity and specificity, rather than maximum accuracy, then an operating point of 0.615 may be selected, resulting in an accuracy of 73% (451/619), a sensitivity of 73% (286/392) and a specificity of 73% (165/227). Note that these cutpoints are selected in a non-blinded fashion, after the predictions have been made—this is the equivalent of picking a point on the ROC curve. FIG. 36 shows the ROC curve with lines drawn at 73% sensitivity and specificity.

VII. Conclusions

The Prometheus Crohn's Prognostic test has been designed to assist the physician in the clinical management of Crohn's disease by providing valuable prognostic information related to stricturing and penetrating disease phenotypes.

The test has been constructed and validated in a robust study incorporating 619 diverse CD patient samples. Furthermore, the test has been carefully designed, using a sound statistical approach based on logistic regression modeling, to maximize both the ease of interpretation and the potential clinical benefit to Crohn's Disease patients.

Example 17. A Novel Prognostic Tool Combining Genetic and Serological Markers to Predict Complicated Crohn's Disease Behavior This example illustrates additional embodiments related to the development and validation of the Crohn's disease prognostic test described in Example 16.

Abstract

Background:

There is evidence that early treatment with biologic therapy may alter the progression of disease and lead to fewer complications. However, these medications are expensive and are associated with medical risks. Thus, it is valuable to know which patients will progress to complicated disease and would benefit from this treatment. Previous studies suggest biomarkers can predict severity or aggressiveness of disease in patients with Crohn's disease (CD). This cross-sectional study aims to identify a set of biomarkers that forecast increased risk of a more aggressive disease course.

Methods:

Blood from 619 well-characterized patients with CD (mean follow up: 13 years) was analyzed for six serological biomarkers (ASCA-IgA, ASCA-IgG, anti-OmpC, anti-CBir1, anti-I2, pANCA). In a subset of patients (n=159), genetic analysis was carried out for three NOD2 variants (SNP8, SNP12, SNP13). Complications assessed were the presence of internal stricturing or internal penetrating disease. Biomarkers were assessed individually and collectively; the latter included quartile sum scores and multivariate logistic regression analysis. A logistic regression model with serological and sero-genetic sub-models was constructed and evaluated by cross-validation.

Results:

For each marker, complication rates were stratified by quartile. All markers had significant differences across quartiles (Fisher's exact test, $p \leq 0.003$). Patients with heterozygous NOD2-SNP13 mutations had increased complication rates ($p=0.004$). For the logistic regression prognostic model, average predictions grouped by categories correlated to observed complication rates ($R=0.964$). Receiver Operating Characteristic (ROC) curve analysis of predictions demonstrated clear diagnostic utility (AUC=0.787; 95% CI: 0.749-0.824).

Conclusions:

The combination of serological and genetic markers is associated with disease complications, providing physicians with a tool for optimizing treatment decisions.

Introduction

Inflammatory bowel disease (IBD) is a chronic inflammatory disorder of the digestive tract, consisting of ulcerative colitis (UC) and Crohn's Disease (CD), which together affect approximately 1.4 million patients in the United States.[1] There is currently no cure for CD, thus the main goal of treatment is to suppress the inflammatory response and achieve clinical and histological remission. Approximately 50% of patients with CD will experience a benign clinical course.[2] The remaining patients face a chronic, intermittent, and progressive disease course leading to the development of complications such as internal stricturing and internal penetrating disease, which are associated with significant morbidity and mortality.[3,4] It has been shown that the need for corticosteroids is a marker for progression of CD; once corticosteroids are used, most patients experience an acceleration of the disease course with approximately 35% of patients to having small bowel surgery within 1 year.[2] Moreover, 25-33% of patients with uncomplicated disease have been reported to transition to internal stricturing or internal penetrating disease after 5 years—suggesting that most patients will transition from uncomplicated to complicated disease if followed for sufficient time.[5]

A growing body of evidence suggests that with appropriate therapy, progression to disease complications can be minimized.[3] D'Haens and colleagues recently demonstrated that newly diagnosed patients treated early with an aggressive regiment of biologics and immunomodulators had significantly higher rates of remission compared to patients treated with a conventional management approach utilizing corticosteroids.[6] This treatment regimen utilized infliximab, an anti-tumor necrosis factor-α (TNFα) antibody, and azathioprine, an immunomodulating agent that functions partially by blockading DNA synthesis, and thus the proliferation of lymphocytes, and also by inducing apoptosis of mononuclear cells. Moreover, the same group demonstrated in a prospective clinical study in patients with early-stage CD, that combination treatment also resulted in mucosal healing.[7] Together these data provide evidence that early and aggressive therapy—the "top-down" approach—can benefit patients with CD. However, these medications are costly and are associated with rare but severe and sometimes fatal adverse events including risk of infections such as tuberculosis, and hepatosplenic T-cell lymphoma.[2] Therefore, in order to maximize the risk-benefit balance inherent in the use of this approach, it would be a great advantage to physicians to be able to identify, at diagnosis, those patients who are appropriate for early aggressive treatment.

There is strong evidence to suggest that the immune response to intestinal microorganism antigens is indicative of disease progression and the need for surgery.[8] The risk of developing complications in CD and/or the need for small intestinal surgery is associated with an autoimmune response to specific microbial antigens such as I2, OmpC, CBir1, and ASCA.[9-11] Many of these serological markers are already in use in clinical practice as a diagnostic tool to differentiate between CD and UC, but their value to predict disease severity has only become apparent in recent years.[4] Multiple studies have shown that both the presence and the level of individual markers and of marker combinations are correlated with specific phenotypes and with the presence of surgery.[8,9,11,12] In a recent prospective pediatric study, the magnitude of immune response against microbial antigens was shown to be strongly correlated with aggressive CD phenotypes and disease progression.[13] These observations suggest that responses to microbial antigens are closely associated to clinical disease characteristics and can be used to predict disease phenotypes and progression to complicated disease.

Genetics has also been demonstrated to play an important role in determining disease phenotype in CD. While a number of CD susceptibility loci have been identified to date, the innate immunity gene NOD2 (Nucleotide Oligomeric Domain 2) appears to have the greatest influence on disease phenotype.[4,14] NOD2 is a cytoplasmic protein that binds to muramyl dipeptide (MDP), a conserved component of peptidoglycan commonly found in Gram—and Gram+ bacteria. NOD2 is responsible for activation of various inflammatory pathways and is restrictively expressed in macrophages, dendritic cells and Paneth cells found in the crypt of small intestinal mucosa.[14] Although at least 27 NOD2 variants have been characterized, three major single nucleotide polymorphorisms (SNPs): SNP8, SNP12, and SNP13 are associated with the development of complicated disease.[14,15]

While serological markers and NOD2 variants have independently been shown to predict disease severity, previous studies have not determined if a combinatorial approach to the analysis of these markers will be able to predict the course of clinical disease. The purpose of this study is to integrate the key serological and genetic markers known to be associated with a complicated CD phenotype, and to develop an algorithm for clinical use to predict complicated disease behavior in patients with CD.

Materials and Methods

Study Population:

The initial cohort consisted of 770 samples. A set of 151 samples were excluded due to inadequate clinical documentation, resulting in a final cohort of 619 samples from CD patients (51% female and 49% male). The patient samples were obtained from (1) Cedars Sinai Medical Center, Los Angeles (n=298), (2) Mt. Sinai Hospital, Toronto, Canada (n=237), and (3) a multicenter Prometheus study (n=84). In addition, 159 DNA samples were collected from those patients in the Mt. Sinai Hospital population for NOD2 genotyping. Study protocols were approved for each site.

The patients were diagnosed with CD based on a combination of criteria that included clinical symptoms, endoscopy, histopathology, video capsule, and/or radiographic studies. This cohort was used because there was extensive medical information available for these patients, including the date of diagnosis, number and type of CD-related surgeries, disease location and disease phenotype. Patients were classified as non-penetrating/non-stricturing (uncomplicated disease) or internal stricturing or internal penetrating (complicated disease), either by medical personal at the source based on data in the medical record, or by Prometheus medical staff based on data from surgical procedures performed to address specific complications (Table 55). Patients with perianal penetrating disease were classified as complicated. Patients diagnosed exclusively with uncomplicated perianal disease were not included in the cohort.

TABLE 55

Clinical Characteristics of the Crohn's Disease Cohort.

| | n = 619 |
|---|---|
| Clinical Characteristics | |
| Sex | 51% female |
| Average age at diagnosis | 26 years (range 0-68) |
| Average age at blood draw | 38 years (range 10-91) |
| Average disease duration | 13 years (range 1-59) |
| Disease Behavior | |
| Complicated disease* | 390 (63%) |
| Stricturing | 180 (29%) |
| Penetrating | 210 (34%) |
| Uncomplicated disease (inflammatory) | 229 (37%) |
| Surgery | 223 (36%) |
| Disease Location | |
| Ileum | 149 (24%) |
| Colon | 118 (19%) |
| Ileum and colon | 285 (46%) |
| Upper gastrointestinal | 62 (10%) |

*Stricturing or penetrating phenotypes are defined as complicated Crohn's Disease.

NOD2 Genotyping:

NOD2 genotyping consisted of testing three SNPs; SNP8 is a 2104C-T in exon 4 resulting in a R702W substitution (rs2066844); SNP12 is a 2722G-C in exon 8 resulting in a G908R substitution (rs2066845); and SNP13 is a C insertion in exon 11 (3020InsC) resulting in a frame shift (1007fs) (rs5743293). Briefly, NOD2 genotyping consisted of an allelic discrimination polymerase chain reaction (PCR) method including two specific oligonucleotide sequences and two TaqMan probes for each assay (Applied Biosystems, Foster City, Calif.). The genotyping assays were performed on an ABI 7000 Real-Time PCR system (Applied Biosystems, Foster City, Calif.).

Detection of Anti-I2:

An anti-I2 enzyme-linked immunosorbent assay (ELISA) was originally developed by Sutton and colleagues, and was modified at Prometheus Laboratories to detect concentrations of anti-I2 in the blood.[16] Briefly, the anti-I2 assay utilized a standard 96-well sandwich ELISA format plate. A refolded GST-tagged protein, consisting of 100 amino acids from the I2 sequence was captured on the plate using a monoclonal anti-GST antibody coated on the well surface (Genscript, Piscataway, N.J.). Test human serum samples were diluted 1:100 in order ensure the antibody concentration was within the range of the standard curve. After incubation of the serum samples in the wells, anti-I2 antibodies were detected using an alkaline phosphatase enzyme conjugated to an anti-human IgA reagent (Jackson ImmunoResearch Laboratories, Inc., West Grove, Pa.). The reactions were revealed using a chemiluminescent substrate solution (Applied Biosystems, Foster City, Calif.) and expressed as ELISA units that were relative to standards prepared from a pool of reactive patient sera.

Other Serological Analyses:

Serum concentrations of anti-Cbir1, anti-OmpC, ASCA-IgA, and ASCA-IgG antibodies were measured by ELISA. Testing for pANCA (protoplasmic-staining antineutrophil cytoplasmic antibodies) was performed by immunofluorescence staining of neutrophils—with the aim of visualizing perinuclear localization and a disrupted staining pattern associated with deoxyribonuclease (DNase) treatment. All the assays were performed at Prometheus Laboratories using a commercial assay (IBD-57, Prometheus Laboratories, San Diego, Calif.). For the ELISA, measurements were expressed as ELISA units, relative to standards prepared from a pool of reactive patient sera. Anti-*Saccharomyces cerevisiae* antibodies (ASCA) ELISA was based on a method designed by Sendid and colleagues.[17] Two ASCA ELISAs—ASCA-A and ASCA-G—were used to measure IgA and IgG antibodies, respectively. An anti-CBir1 ELISA procedure was designed to measure IgG antibodies to a bacterial flagellin antigen, whereas the anti-OmpC ELISA procedure was designed to measure IgA antibodies to the outer membrane porin (OmpC) antigen, purified from the enteric bacteria, *Escherichia coli*. The test for pANCA was conducted using indirect immunofluorescence on polymorphonuclear leukocytes (PMNs), that were either untreated or digested with DNase. Treated and untreated PMNs were fixed to glass slides and diluted patient serum added. Following incubation and washing, a fluoresceinated goat anti-human IgG antibody was added to the slides. Epi-fluorescent microscopy was used to confirm characteristic perinuclear staining pattern on the untreated cells. If the perinuclear pattern presented, the reactivity on the DNase-digested cells was assessed.

Statistical Methods:

The assay results for the serological markers were converted into a categorical variable (quartile). The independence of the two categorical variables, quartile and complication status, was assessed using Pearson's Chi-Square test. However, since the pANCA and the genetic variable results were already binary, no transformation was necessary, and the Pearson's Chi-Square test was similarly applied.

In order to assess the response of the six combined serology markers, the quartile sum score (QSS) technique was applied. Thus, the minimum score of 6 represents a patient with every serological marker in the lowest quartile, and a maximum score of 24 represents every marker in the highest quartile. Because the pANCA results were dichotomous in nature and negatively correlated with disease complication, patients with positive pANCA were assigned a score of 1 and those with a negative score were assigned a score of 4.

Two logistic regression models were constructed, both with logit link functions. The serological model was derived using the serology data and incorporated QSS and duration of disease as predictors. Similarly, the sero-genetic model was derived using a subset of patients with both serology and NOD2-SNP13 data, along with QSS and duration of disease as predictors. The parameters of the multiple logistic regression models were assessed using a Wald test. The predictions of the logistic regression model were assessed using a leave-one-out cross validation, with two complementary statistical assessments. The output of the logistic regression model was transformed into a categorical variable, through a simple discretization, into 10 categories. Within each category, the true complication rate was computed and the agreement of predicted and observed complication rates was assessed via Pearson's correlation. In addition, the accuracy of the predictions was assessed using a Receiver Operating Characteristic (ROC) curve. Under this assessment, the performance of the test was reported via the AUC (Area Under the Curve) statistic with confidence intervals. All statistical results were computed using the R open source package, version 2.8.1 (R Development Core Team (2008). R: A language and environment for statistical computing. R Foundation for Statistical Computing, Vienna, Austria. ISBN 3-900051-07-0).

TABLE 56

Patients with Elevated Serological Markers

| Marker | Total Number of Patients with Elevated Serological Markers |
|---|---|
| ASCA-IgA | 291 (47%) |
| ASCA-IgG | 254 (41%) |
| OmpC | 235 (38%) |
| CBir1 | 415 (67%) |
| I2 | 260 (42%) |
| 0 marker | 66 (11%) |
| 1 markers | 137 (22%) |
| 2 markers | 132 (21%) |
| 3 markers | 137 (22%) |
| 4 markers | 86 (14%) |
| 5 markers | 61 (10%) |

Elevated serological markers were defined as being above healthy reference range concentrations.

TABLE 57A

Percentage of Complicated Disease Within Each Serologic Marker Quartile

| | | Q1 | | Q2 | | Q3 | | Q4 | |
|---|---|---|---|---|---|---|---|---|---|
| Serologic Marker | Disease Behavior | n | % comp. | n | % comp. | n | % comp. | n | % comp. |
| ASCA-IgA | Complicated | 59 | 38.1 | 90 | 58.4 | 116 | 74.8 | 127 | 81.9* |
| | Uncomplicated | 96 | | 64 | | 39 | | 28 | |
| ASCA-IgG | Complicated | 72 | 46.5 | 84 | 54.5 | 114 | 73.5 | 122 | 78.7* |
| | Uncomplicated | 83 | | 70 | | 41 | | 33 | |
| Anti-CBir1 | Complicated | 76 | 49.0 | 92 | 59.7 | 109 | 70.3 | 115 | 74.2* |
| | Uncomplicated | 79 | | 62 | | 46 | | 40 | |
| Anti-OmpC | Complicated | 68 | 43.9 | 90 | 58.4 | 107 | 69.0 | 127 | 81.9* |
| | Uncomplicated | 87 | | 64 | | 48 | | 28 | |
| Anti-I2 | Complicated | 76 | 49.0 | 93 | 60.4 | 114 | 73.5 | 109 | 70.3* |
| | Uncomplicated | 79 | | 61 | | 41 | | 46 | |

*p < 0.001 complicated vs. uncomplicated Crohn's disease.

Results

Fifty-one percent of the patients were female and the average age at the time of blood draw was 38 years. The average disease duration was 13 years and the range of follow-up was 1 to 59 years. Sixty-three percent of patients had complications at the time of the blood draw. Clinical characteristics of the patient cohort are shown in Table 55.

Correlation of Serological and Genetic Markers to Disease Behavior

A summary of the patients' serological marker status is shown in Table 56. Quartile scores were calculated from the study population of 619 CD patients, based upon reference ranges derived from healthy populations. The proportion of patients with disease complications significantly increased with each increasing quartile (Table 57A) (Fisher's exact test, p≤0.003). Interestingly, significant differences in complicated and uncomplicated disease were observed for each marker in the highest quartile (p<0.001). The pANCA result was unlike other serological markers in that the presence of pANCA was a negatively correlated with CD complications (Table 57B) (p=0.004).

TABLE 57B

Correlation of Negative pANCA Marker and Incidence of Complicated Disease.

| | Negative | | Positive | |
|---|---|---|---|---|
| pANCA | n | % comp. | n | % comp. |
| Complicated | 323 | 65.7* | 69 | 54.3 |
| Uncomplicated | 169 | | 58 | |

*p = 0.004 complicated vs. uncomplicated Crohn's disease.

Figure 37:
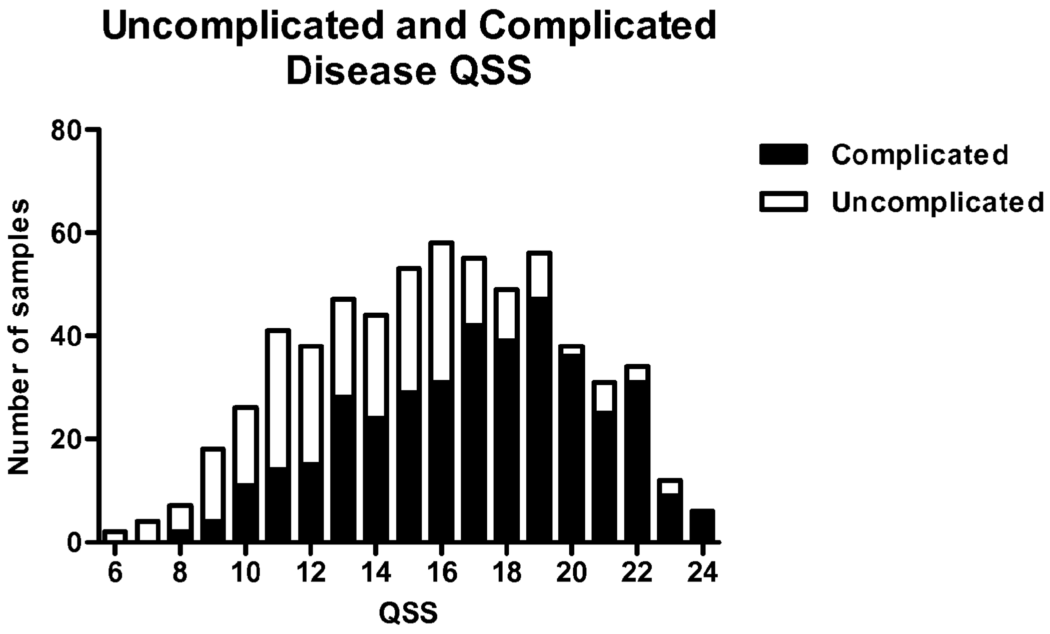
FIG. 37 illustrates quartile sum score (QSS) distributions by complication status—complicated and uncomplicated disease.

Since each individual serological marker was significant in predicting disease by differentiating disease complication based on quartile analysis, quartile sum scores (QSS) were used to assess the response of the six combined serology markers (range: 6-24) to complicated and uncomplicated disease. The most common QSS of 19 was scored by 46 patients with complicated disease, with most patients ranging from QSS 10 to 22 (FIG. 37). In comparison, the most common bimodal QSS of 11 and 16 was scored by 27 patients with uncomplicated disease (each), in a more even distribution where most patients ranged from QSS 9 to 17 (FIG. 37). The median QSS for patients with complicated disease was 17, compared to a QSS of 14 for patients with uncomplicated disease. The median follow-up time from diagnosis to blood draw for patients without complications was 5 years, compared to 13 years in patients with complications.

The relationship of NOD2 markers to complicated and uncomplicated disease. Three NOD2 variants were assessed for their relationship to the incidence of disease complications (Table 58). There were a total of 18 (heterozygous), 13 (heterozygous), and 21 (17 heterozygous, 4 homozygous) mutations respectively for the SNP8, SNP12, and SNP13 polymorphisms in these patients. Crohn's disease complications were strongly associated with patients with homozygous mutations or compound heterozygous mutations. Even though the number of patients with NOD2 mutations was small, there was a striking association between disease complications and the presence of a mutation for SNP13; 20/21 patients who were either heterozygous or homozygous had complicated disease (95%, p=0.004) (Table 58). Although significance was not demonstrated with heterozygous mutations in the cohort, they have been independently demonstrated to be significant in cases of homozygous mutations or compound heterozygous mutations across multiple NOD2 SNPs. In this cohort there were only nine samples in the sero-genetic model with double mutations among the three SNPs. All nine of these samples were observed to have complications. This sample size is too small to assess statistical significance, but significant prior research has demonstrated a strong association between multiple mutations and a complicated disease phenotype.[14, 15] Therefore, in this model, patients with multiple NOD2 SNP mutations are assigned a high (>99%) probability of complications. A significant association between a single heterozygous mutation for either SNP8 or SNP12 with complicated disease was not observed.

TABLE 58

Percentage of Complicated and Uncomplicated Disease by NOD2 SNP Status

| NOD2 SNP | Status | Uncomplicated n | Uncomplicated % | Complicated n | Complicated % |
|---|---|---|---|---|---|
| SNP8 | No mutation | 44 | 31 | 97 | 69 |
| | mutation | 5 | 27 | 13 | 72 |
| SNP12 | No mutation | 44 | 30 | 102 | 70 |
| | mutation | 5 | 38 | 8 | 62 |
| SNP13 | No mutation | 48 | 35 | 90 | 65 |
| | mutation | 1 | 5 | 20 | 95* |

*p = 0.004 complicated vs. uncomplicated Crohn's disease.

Logistic Regression Modeling

The parameters and predictions for the serological and sero-genetic models are shown in Table 59 and illustrated in FIGS. 38A and 38B, where the cumulative probability of complications over time are displayed for various QSS. In both models, the complication status was presented as the outcome variable. There is a wide spread in terms of early complications if serology is used alone (FIG. 38A), and the likelihood of complication increases more steeply over time in those with lower QSS. As an example, the lowest curve in FIG. 38A corresponds to QSS 6, which predicts that complications would occur at the rate of approximately 10% by Year 1, 16% by Year 10, and 26% by Year 20. In contrast, for a patient with a QSS 20, complications would occur at the rate of approximately 70% by Year 1, 80% by Year 10, and 88% by Year 20. When the NOD2 genetics are applied, there is a significant transformation to a higher probability of complication in all patients, even early in the disease course (FIG. 38B).

TABLE 59

Serological and Sero-genetic Regression Models - Predicting the Risk of Complicated Crohn's Disease

| | Estimate | St. error | z value | p value | Odds ratio |
|---|---|---|---|---|---|
| **Serological Regression Model (n = 619)** | | | | | |
| Intercept | −3.567 | 0.428 | −8.333 | <0.001 | — |
| Duration | 0.060 | 0.010 | 5.788 | <0.001 | 1.06 (1.04-1.08)/year |
| QSS | 0.219 | 0.027 | 8.143 | <0.001 | 1.24 (1.18-1.31)/point |
| SNP13 | — | — | — | — | — |
| **Sero-genetic Regression Model (n = 159)** | | | | | |
| Intercept | −3.100 | 0.893 | −3.473 | 0.001 | |
| Duration | 0.035 | 0.024 | 1.468 | 0.142 | 1.04 (0.99-1.09)/year |
| QSS | 0.212 | 0.056 | 3.757 | <0.001 | 1.24 (1.11-1.39)/point |
| SNP13 | 2.047 | 1.063 | 1.925 | 0.054 | 7.74 (1.43-144) if mutated |

Figure 39:
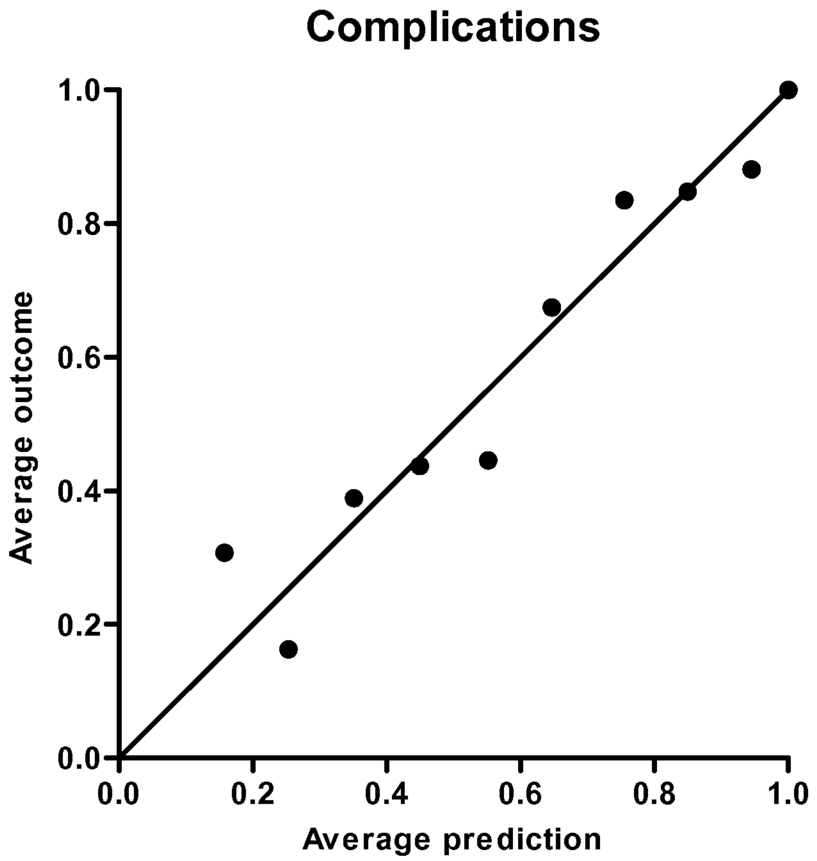
FIG. 39 illustrates a comparison of predicted and observed rates of complication by category (decile). Predictions were grouped into categories, and compared to observed rates of complications for each category. Number of patients in each category prediction group were: 0 in the 0-10% category; 13 in the >10-20% category; 49 in the >20-30% category; 54 in the >30-40% category; 64 in the >40-50% category; 74 in the >50-60% category; 83 in the >60-70% category; 85 in the >70-80% category; 112 in the >80-90% category; 76 in the >90-99% category; and 9 in the >99% category.
Figure 40:
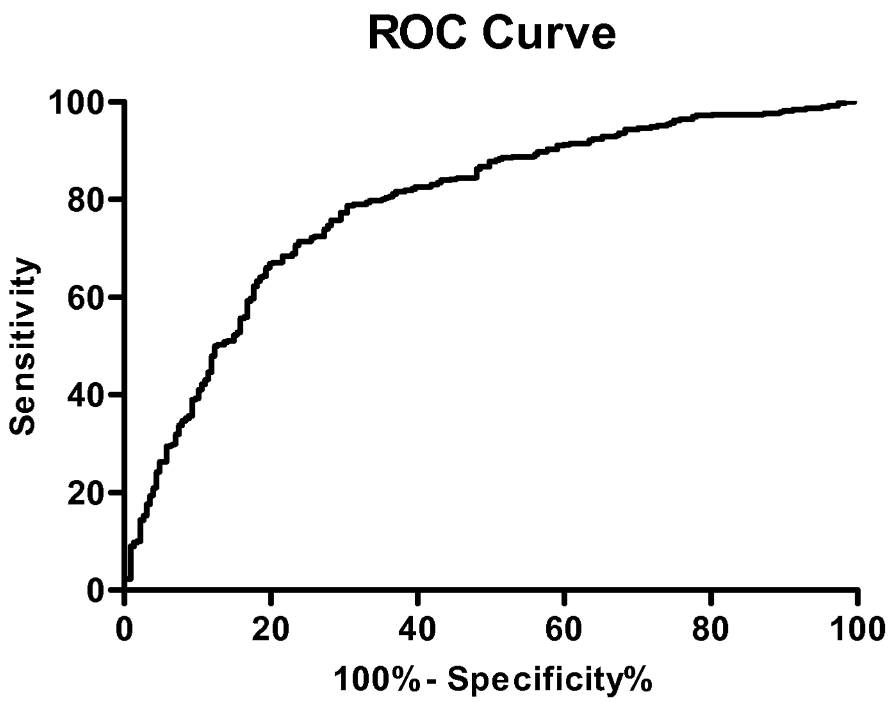
FIG. 40 illustrates a Receiver Operating Characteristic (ROC) curve for cross-validation predictions. Probabilities were generated using a leave-one-out cross validation to repeatedly generate a serological and sero-genetic logistic regression.

Use of Stratified Serological and Sero-Genetic Regression Models to Predict the Development of Complicated Crohn's Disease The accuracy of the overall test is demonstrated by the correlation for this comparison (R=0.964), indicating that the model accurately predicted the rate of disease complications in each category (FIG. 39). The cross-validation probabilities were also evaluated by ROC analysis. Here, the area under the ROC curve was 0.787 (95% CI: 0.749-824), thus confirming the accuracy of the model in discriminating complicated and uncomplicated CD (FIG. 40).

Discussion

This example presents data in support of a novel prognostic test, designed to assist the physician in the clinical management of Crohn's disease by integrating data from seven biomarkers, with the aim of predicting patient populations likely to suffer from complicated forms of CD such as internal stricturing and internal penetrating disease phenotypes.

The test has been designed using logistic regression modeling and validated in a study incorporating 619 diverse CD patient samples. It includes seven biomarkers, ASCA-IgA, ASCA-IgG, anti-OmpC, anti-CBir1, anti-I2, pANCA and mutations of the NOD2 gene. Several studies have established a relationship between NOD2 variants and seroreactivity to microorganism antigens. Over 27 mutations of NOD2 gene have been described, but CD susceptibility has been consistently attributed to three main mutations.[14] Specifically, these are two non-synonymous SNPs (in exon 4 resulting in the amino acid substitution R702W and in exon 8 resulting in the amino acid substitution G908R). The third mutation is a nucleotide insertion (3020InsC) in exon 11 resulting in a frame shift 1007fs. Patients carrying the frameshift substitution or two risk alleles either homozygote or compound heterozygote have an increased risk of developing CD.[18,19] Patients carrying NOD2 variants have an increased adaptive immune response, and several studies have demonstrated the association between NOD2 variants and serum concentration of ASCA.[14,15,18] I2 is a class of T-cell super antigen associated with CD, and reports have shown that I2, derived from the pfiT gene of *Pseudomonas fluorecens*, accounts for antigenic activity detected in CD.[20, 21] It has been reported that the sero-prevalence for anti-I2 is 50% in CD.[22] Interestingly, elevated serum level of anti-I2 has been associated with increased prevalence of stricturing disease and small bowel surgery.[9] Patients presenting high levels of serum reactivity toward ASCA, I2 and OmpC have significantly more complications such as stricturing and penetrating disease, with a greater likelihood of small bowel surgery.[9,10]

An aspect of a cross-sectional study that could be of concern is the stability of the serological response in CD. If the marker pattern changes dramatically over the course of the disease, then samples taken later in the disease state may not be representative of samples taken at diagnosis. Although there does appear to be an association between marker presence and response level with disease duration,[8] several studies suggest that there is a basic stability in marker status despite changes in disease activity,[22] or during the disease course.[23,24] In this study, the serum samples were taken after diagnosis and in some cases after the complications had occurred. This is similar to other cross-sectional studies that have shown a correlation with serology markers and disease phenotype.[9,11,12] It is especially important to note that data from recent prospective studies has shown that the serology markers assessed at or near diagnosis are able to identify patients who are more likely to have complications, thus supporting the conclusions based on cross-sectional data.[13,23]

Crohn's disease management is clinically driven and the course of the disease is hardly predictable. Some patients have only a few episodes of active disease in their lifetime with long periods of remission; for others the active disease is persistent. For many CD patients, there is a significant progression in disease behavior over time. The change is often evident within a year, and at 10 years, over 50% of patients progressed to a complicated disease phenotype.[4,25]

The management of CD is generating intense clinical debate, as two main therapeutic approaches are available—the "step-up" and "top-down" strategies. The "step-up" strategy is the classical therapeutic approach consisting of increasing the treatment intensity as the disease progresses. Frequently, the patient will start treatment with corticosteroids—a down side of this strategy is that long lasting corticosteroid exposure can generate dependence and other severe complications.[26,27] The "top-down" treatment refers to a more aggressive therapeutic approach, where intensive therapy such as biological and immunosuppressant agents are introduced earlier during the disease course. It has been recently demonstrated that an early combination of infliximab and immunosuppressant was more beneficial for the patient than the classical treatment supporting corticosteroid as first-line therapy.[6] However, epidemiological studies suggest that 50% of CD patients will not develop severe disease,[28] and consequently will not require aggressive therapy. In addition, there is concern about the long-term safety and cost of biological agents as first line treatments. In light of these observations, there is a clear clinical need for prognostic tools that can help predict CD behavior, and therefore help to classify patients presenting high and low risk of developing complicated disease. Patient adherence to treatment medication is generally poor. Therefore, by identifying the patients with a bad prognosis early, another potential clinical utility of the prognostic test described herein is to improve patient adherence by emphasizing the benefits of optimal therapy to prevent disease progression.

The model used in this study demonstrates increased rates of complications when stratified by quartiles. Quartile analysis involved the classification of marker levels into individual quartile scores, which were then combined into a quartile sum score (QSS). In particular, predicting with the aggregate QSS score substantially outperformed equivalent models with individual markers (comparing AUC for ROC curves), reflecting the superiority of an aggregate score. Finally, QSS are by themselves informative, but when used as a predictor in a logistic regression model, it is possible to more specifically quantify, in probabilistic terms, the expected risk of complications for a range of observation times. The fitted model incorporated duration of disease as an explicit predictor.

This example demonstrates that the present cross-sectional data is a valid model to predict CD progression. Over time, clinical covariates such as disease location, smoking, biomarker stability over time, relative biomarker abundance at diagnosis, as well as other additional sero-genetic markers, may be added to further refine the model.

This example also demonstrates that combinatorial use of serological and genetic markers provides a powerful prognostic test to predict the clinical course of Crohn's disease. This concept generates a new prognosis platform to aid in early identification of patients at risk of complicated disease phenotypes, providing the physician and patient with the option of commencing early, aggressive therapy.

Example 18. Quartile Sum Score Analysis of Crohn's Disease Markers Over Time

Figure 41:
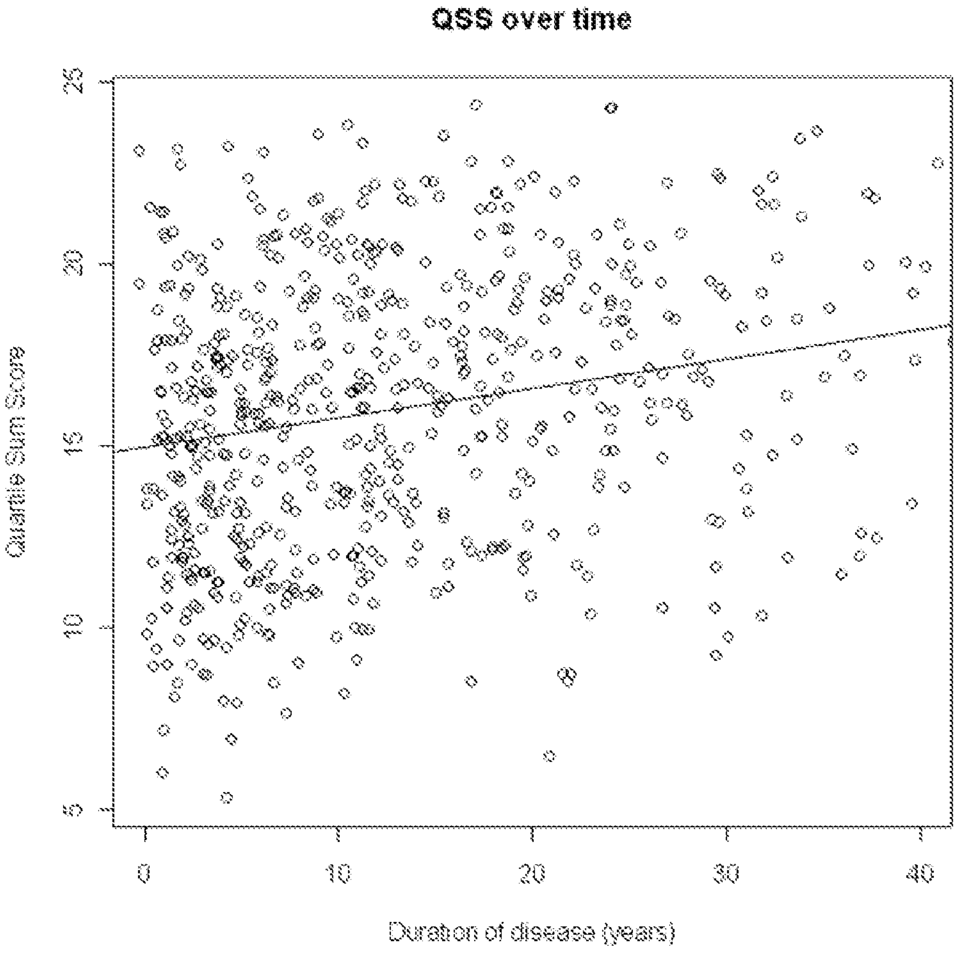
FIG. 41 illustrates a diagram showing the velocity of quartile sum score over time.

This example shows a quartile sum score (QSS) analysis of 6 markers over time. A quartile is any of the four categories that divide the data set into four equal parts, so that each part represents one fourth of the sampled population. For each marker, it is possible to have a value of 0-4 (i.e., zero if the marker is not present). For six markers, the quartile sum score can be 0-24. FIG. 41 shows the quartile sum score over 40 years of the aggregate velocity of 6 markers in 619 individuals with Crohn's disease.

Example 19. Protocol for the Purification and Refolding of GST-I2

Purpose

This example describes a procedure for the purification and refolding of the GST-I2 antigen from frozen bacterial glycerol stock. This process will take eight days to complete.

Scope

The rGST-I2 Antigen Prep is the antigen used to capture antibodies to *Psuedomonas fluorescens*-related peptide in the serum of patients with Crohn's Disease (CD) as described in Example 20.

Principle

The purpose of the rGST-I2 Antigen Prep procedure is to purify and refold the GST-I2 so it can be further purified from bacterial contaminants. The refolding process allows the antigen to be purified and allows it to properly interact with anti-GST antibodies in the I2 ELISA.

Definitions

GST-I2: Glutathione S-transferase fused to *Pseudomonas fluorescens*-related peptide.

Procedure

1. Day 1
   - 1.1 Prepare the overnight culture. Start with 60 mls of LB media that has been autoclave sterilized in a 250 ml Erlenmeyer flask. Label this flask with "I2 Antigen overnight culture" and today's date.
   - 1.2 Pre-warm this media in the incubator shaker that has been set at 37° C. Warm the media for 30 minutes.

1.3 While the media is incubating pull one aliquot of Ampicillin (50 mg/ml) out of the −70° C. freezer and thaw it out at room temperature.
1.4 Add 60 μl of 50 mg/ml Ampicillin to the pre-warmed media. Let the media mix in the incubator for 5 minutes at 200 rpm.
1.5 Remove the GST-I2 Glycerol Stock from the −70° C. freezer and place it directly in a bucket of dry ice. Do not allow the glycerol stock to thaw.
1.6 Inoculate the LB/Ampicillin media with the frozen GST-I2 glycerol stock. Turn the incubator/shaker off. While still keeping the glycerol stock on dry ice, open the cap of the glycerol stock tube. Using an inoculation loop scrape the surface of the frozen GST-I2 glycerol stock. Slightly remove the aluminum foil from the top of the 250 ml flask that contains the LB/Ampicillin media. Just open the foil top enough to the point where you can fit an inoculation loop inside. Place the inoculation loop (with glycerol scrapings) in the flask and slowly move it around for a few seconds. Remove the inoculation loop and secure the foil on the flask.
1.7 Turn the shaker on and let the culture incubate over night at 200 rpm and 37° C.
1.8 Take this time to set up the LB media that will be used the following day. Take two 500 ml volumes of LB media that has been autoclaved sterilized in 2 L Erlenmeyer flasks and place them in a 37° C. incubator overnight with no shaking. Be sure to place them in an incubator that is not being used for the overnight culturing of the glycerol stock. This is being done to ensure that pre-warmed media will be ready for use the next day.

2. Day 2
2.1 Check the two 500 ml volumes of LB media that have been warming overnight. They should still be clear with no visible growth.
2.2 Next, check the OD 600 of the overnight culture using the Nanospec spectrophotometer. Use 1 ml of LB media as your blank. Use 1 ml of overnight culture to check the OD 600. The OD 600 of the overnight culture should be around 1.9-2.3. If it is not in this range discard the culture and start again.
2.3 Place the two 500 ml volumes of pre-warmed LB media in the same incubator shaker that contains the overnight culture. Next, pull out two aliquots of Ampicillin (50 mg/ml) from the −70° C. freezer and thaw them out to room temperature.
2.4 Add 500 μl of Ampicillin to each of the 500 ml volumes of LB Media. Let these flasks shake in the incubator for 5 mins at 37° C. and 200 rpm.
2.5 Next, perform a 1:20 dilution of the overnight culture into both of the 500 ml volumes of LB/Amp media. This is done by adding 25 ml of the overnight culture to 500 ml of the LB/Amp media. At this point each 500 ml culture will be designated as either culture A or B. Label both cultures with today's date. In addition, label each culture as either "GST-I2 culture A" or "GST-I2 culture B".
2.6 Incubate these cultures for 1 hr at 37° C. and 200 rpm.
2.7 After 1 hour of incubating, check the OD 600 of both of the cultures. The OD 600 of the cultures needs to reach 0.6-0.9 before protein expression can be induced with isopropyl β-D-1-thiogalactopyranoside (IPTG). If your initial 1 hour OD 600 reading is under 0.6, continue to check the OD 600 of the culture every 15 mins until the OD 600 reaches the range of 0.6-0.9. Record the OD 600 of each culture at this point.
2.8 Once the OD 600 of the cultures have reached the accepted range for IPTG induction a 1 ml aliquot of each culture is taken and placed into a 1.5 ml micro centrifuge tube. Each tube is labeled with today's date, "GST-I2 culture A/B", and T=0. Place these two T=0 aliquots on ice. It is important to take these aliquots before IPTG induction because they will be used for later gel analysis.
2.9 Induce expression of the GST-I2 antigen using 1 mM IPTG. Add 500 μl of 1M IPTG solution to each 500 ml culture. Note the time that the cultures were induced.
2.10 Incubate these cultures for 4 hours at 37° C. and 200 rpm. The following procedures .2.11.-2.14. should be performed during this incubation process.
2.11 Take the 1 ml T=0 culture aliquots that have been sitting on ice and place them into a centrifuge (Eppendorf 5402 centrifuge). Spin the aliquots at 5,000×g for 10 mins at 4° C. Remove the supernatant carefully without disturbing the bacterial pellet. Store the pellets at −70° C.
2.12 Label two 500 ml centrifuge bottles with today's date and "GST-I2 Bacterial Pellet A/B". Weigh each bottle and record their mass in grams.
2.13 Place the weighed bottles on ice right before the 4 hour incubation period is over.
2.14 Label two micro centrifuge tubes with today's date, "GST-I2 culture A/B", and T=4 hr. Place these two T=4 hr tubes on ice.
2.15 When the 4 hour time point is reached, turn off the incubator. Record the OD 600 of each culture.
2.16 Take a 1 ml aliquot of each culture and place it into the appropriately labeled micro centrifuge tube. Place the aliquots on ice.
2.17 Pour the remaining volume of each culture into the appropriately labeled 500 ml centrifuge bottle. Place these bottles into the Sorvall RC-3B centrifuge with H-6000 rotor.
2.18 Centrifuge the cultures for 10 minutes at 5,000×g and 4° C.
2.19 Remove the bottles from the centrifuge and place them on ice. Empty the supernatant into the 2 L Erlenmeyer flasks that were used for culturing. These will be used as waste containers. Remove all the supernatant while keeping the bacterial pellet intact at the bottom of the bottle. Place the bottles back on ice.
2.20 Weigh the bottles to determine the mass of the bottles plus the bacterial pellets. Use a kim wipe to wipe off the excess moisture from the outer surface of the bottles. This will allow for a more accurate mass determination.
2.21 Determine the weight of the bacterial pellet by subtracting the values determined in step 2.12. from the values in step 2.20.
2.22 Write the weight of the pellet on each of the bottles and store them at −70° C.
2.23 Take the 1 ml aliquots from step 5.2.16. and place them into a centrifuge (Eppendorf 5402 centrifuge). Spin the aliquots at 5,000×g for 10 mins at 4° C. Remove the supernatant carefully without disturbing the bacterial pellet. Store the pellets at −70° C.

3. Day 3
3.1 Steps 3.9. through 3.51. will require the making of fresh reagents and take approximately 6 hours to complete.
3.2 An SDS-PAGE protein gel must be run to confirm that the protein expression of the GST-I2 antigen was induced. This must be done before any further steps can be carried out.

3.2.1 Remove the 1 ml bacterial pellet time points (T=0.4 hr) from the −70° C. freezer and place them on ice.

3.2.2 Suspend the pellets in Nanopure distilled $H_20$, as follows: The amount of $H_20$ that will be used for suspension is based on the OD 600 of each time point.

3.2.3 To determine the amount of $H_20$ to add to the pellet of each time point, plug the OD 600 of each time point into the following equation.

Water to add to pellet=((OD600)/0.418)*192)/2

Record the volume of $H_20$ added to suspend each bacterial pellet time point.

3.3 Label 4 new 1.5 ml micro centrifuge tubes with the time points shown above in 3.2.3. These new tubes will be used to prepare the samples for gel analysis.

3.4 Into each new micro centrifuge tube load 29 µl of its respective bacterial pellet suspension. Next, load 10 ul of 4× sample buffer into each micro centrifuge tube. Then, load 1 µl of 2.5% beta-mercaptoethanol. Mix each tube and then incubate them in a heat block at 90° C. for 5 minutes.

3.5 Prepare the 4-12% Bis-Tris gel. Refer to the instructions of the XCell SureLock™ Mini Cell (Invitrogen—Part number EI0001) for setting up the gel.

3.5.1 Manual Pgs 9-13, 17. The running buffer that is used in this process is MES SDS Running Buffer.

3.6 Load 30 µl of each sample into separate wells. Load 10 µl of the Protein Ladder in a separate well. Run the gel for 35 minutes at 200 volts.

3.7 Remove the gel from its casing and place it in a flat bottom container. Empty pipette tip box lids work well. Briefly wash the gel for 15 seconds with 50 mls of Nanopure distilled $H_20$. Then add 100 mls of Simply Blue Safe Stain and incubate the gel on a rocker for 50 mins.

Figure 42:
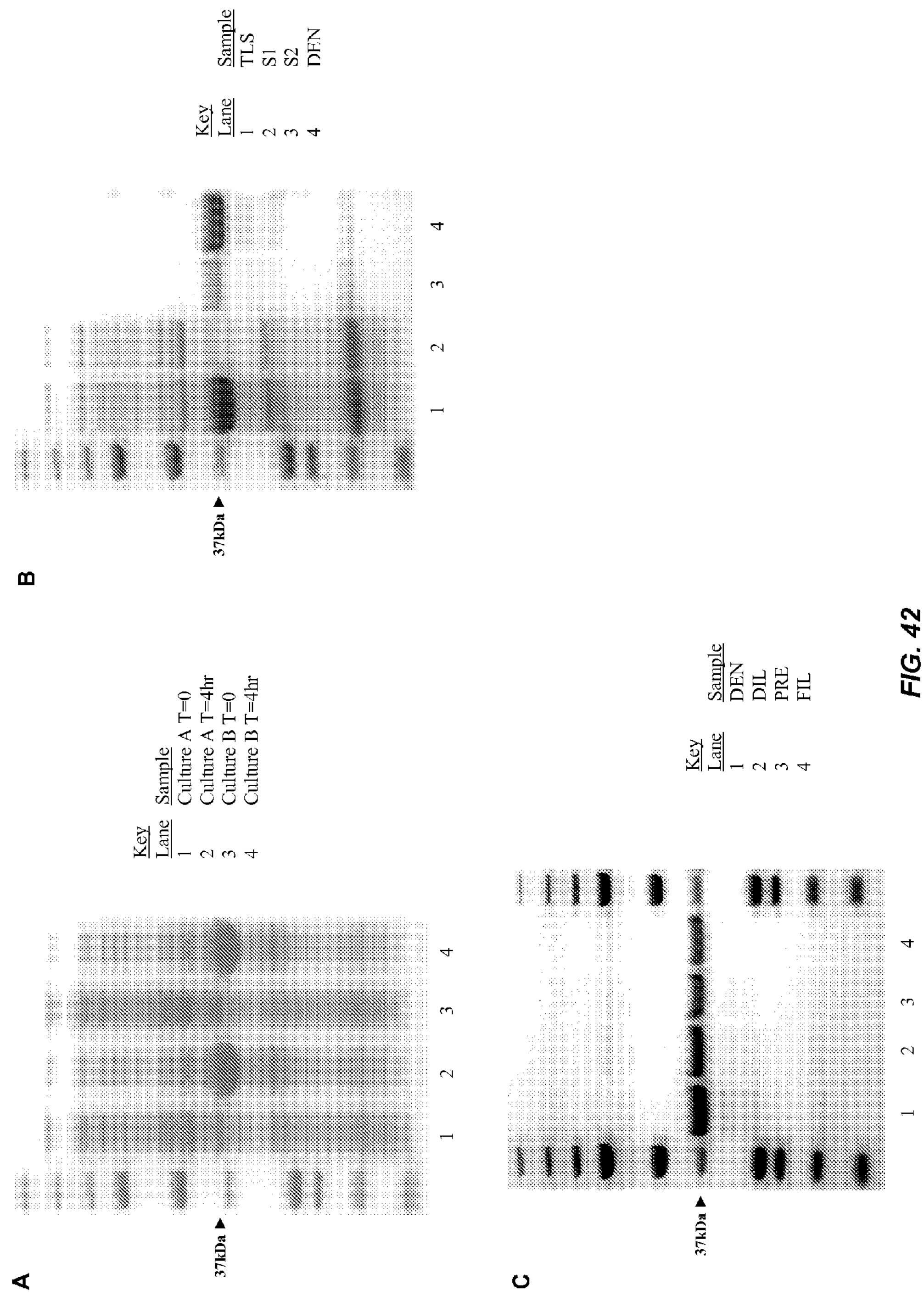
FIG. 42A illustrates a gel confirming the expression of the GST-I2 antigen.
FIG. 42B illustrates a gel confirming the presence of the GST-I2 antigen in the denatured sample (DEN).
FIG. 42C illustrates a gel confirming the presence of the GST-I2 antigen in the filtered sample (FIL).

3.8 Decant the Simply Blue Safe Stain and add 100 ml of Nanopure distilled $H_20$. Place the gel back on a rocker and incubate it for 1 hour. Within 10 mins of this incubation step you'll be able to confirm that the GST-I2 antigen was expressed (FIG. 42A). When the bands are confirmed move on to the next step.

3.9 Take this time to prepare 50 mls of I2 Buffer A—50 mM Tris-CL, 0.5 mM EDTA, 5% glycerol, 5 mM DTT, pH 8.0.

3.10 Take this time to prepare 50 mls of I2 Denaturing Buffer—10 mM Tris-C1, 0.1M $NaH_2PO_4$, 8M Urea, 5 mM DTT, pH 8.0 This solution is stored at room temperature until use.

3.11 Take this time to prepare 400 mls of I2 Refolding Buffer—25 mM Tris-C1, 100 mM NaCl, 10% glycerol, 0.2M Urea, 0.5 mM oxidized glutathione (GSSG), 1 mM reduced glutathione (GSH), pH 9.0. This solution is chilled in a 1 L beaker on wet ice until use. Place parafilm over the beaker to prevent contamination.

3.12 Prepare 20 mls of bacterial lysis buffer in a plastic 50 ml conical tube. Label the tube as "I2 Bacterial Lysis Buffer" (as follows in steps 3.13 through 3.16.).

3.13 Add 20 mls of I2 Buffer A to the 50 ml conical tube.

3.14 Add 20 mg of Lysozyme to the 50 ml conical tube (final concentration 1 mg/ml).

3.15 Add one Complete Protease Inhibitor Tablet (Roche) to the 50 ml conical tube.

3.16 Vortex mix the contents of the 50 ml conical tube until the Lysozyme and Protease Inhibitor Tablet are in solution. Then place this tube on wet ice until needed. It must be chilled before use.

3.17 Remove the I2 bacterial pellet(s) from the −70° C. freezer and place it on ice. The wet weight of the I2 bacterial pellet(s) must be between 3-5 g. Multiple pellets may need to be used to achieve the 3-5 g mass range. Thaw the pellet(s) out on ice for 15 minutes.

3.18 While the bacterial pellet is thawing prepare the 20 ml of 2% Deoxycholate (DOC) Reagent. Label a plastic 50 ml conical tube with "I2 2% DOC Reagent". Add the following to the 50 ml conical tube.

3.19 Add 20 ml of I2 Buffer A.

3.20 Add 400 mg of Sodium Deoxycholate (DOC).

3.21 Vortex the solution briefly then mix the components end over end until the DOC is completely dissolved. This solution is kept at room temperature until use.

3.22 Add 20 mls of I2 Bacterial Lysis Buffer to the bacterial pellet on ice. Suspend the pellet thoroughly on ice with a 10 ml serological pipet. The suspension is performed in the 500 ml centrifuge bottle and finished once there is no sign of visible particulates.

3.23 Incubate the suspension on ice for 30 mins.

3.24 Transfer the suspension to a 50 ml conical tube. Label this tube "I2 Total Lysate Sonicate" and today's date. Put this tube on ice.

3.25 Sonicate the suspension preparation on ice.

3.26 Adjust the Amplitude to 40%.

3.27 Push the recall button and select Program ID #1. Then press Enter. This program is set to perform 1 second pulses in one 10 sec cycle.

3.28 Insert the small-tipped probe in the 50 ml conical tube. Make sure the probe is inserted well into the lysate suspension. Make sure the tip is not touching the surface of the 50 ml conical tube.

3.29 Press start to send the suspension through one cycle of sonication. Then let the suspension sit for 15 seconds to prevent overheating of the sample.

3.30 Repeat step 3.29. five times. Then check the suspension with a 10 ml serological pipet. Run the suspension through the pipet several times. The suspension should run like a fluid out of the tip of the pipet with no visible changes in viscosity or stickiness. If the sample appears gooey that means the genomic DNA has not been sufficiently broken down. If this occurs, repeat step 3.29. until this trait disappears.

3.31 Transfer ~20 ml of the sonicated sample into a 50 ml Centrifuge Tube (Nalgene). After the transfer, save 50 µl of the sonicate for later gel analysis. This should be kept in the original 50 ml centrifuge tube labeled with "I2 Total Lysate Sonicate" until it is needed. Store the 50 µl aliquot at 4° C.

3.32 Place the sonicate suspension in the Beckmann J2-21 centrifuge and spin the sample at 12,000×g (12,400 rpm in JA-20 rotor) at 4° C. for 10 minutes.

3.33 After centrifugation, decant the supernatant into a 50 ml conical tube labeled with "51 Sonicate Supernatant" and today's date. This supernatant will be used for later gel analysis. Store it at 4° C. until it is needed. At this point the insoluble pellet will undergo further processing.

3.34 Suspend the insoluble pellet in 20 mls of I2 2% DOC Reagent in the 50 ml centrifuge tube. Suspend the pellet thoroughly at room temperature with a 10 ml serological pipet. The suspension is not finished until there is no visible sign of particulates. This step will take approximately 10 minutes to perform.

3.35 Incubate the 2% DOC suspension for 30 minutes at room temperature.

3.36 Place the 2% DOC suspension in the Beckmann J2-21 centrifuge and spin the sample at 12,000×g (12,400 rpm in JA-20 rotor) at 4° C. for 10 minutes.

3.37 After centrifugation, decant the supernatant into a 50 ml centrifuge tube labeled with "S2 DOC Wash Supernatant" and today's date. This supernatant will be used for later gel analysis. Store it at 4° C. until it is needed. At this point the insoluble pellet will undergo further processing.

3.38 Gently wash the insoluble pellet with 20 mls of 1×PBS pH 7.4. This will be performed twice with 10 ml increments of 1×PBS pH 7.4

3.39 Slowly add 10 mls of 1×PBS pH 7.4 to the 50 ml centrifuge bottle. Do not disturb the pellet. Cap the bottle and turn the bottle onto its side. Slowly rotate the bottle several times.

3.40 Decant the 1×PBS wash.

3.41 Repeat step 3.39.

3.42 Decant the 1×PBS wash.

3.43 Use a 1 ml pipette (P1000) to remove any residual liquid.

3.44 The pellet is then solubilized with 20 mls of I2 Denaturing Buffer in the 50 ml centrifuge tube. Suspend the pellet thoroughly at room temperature with a 10 ml serological pipet. This solubilization step will take approximately 15 minutes. To sufficiently solubilize this pellet, make sure the tip of the pipette is pressed firmly against the centrifuge tube wall while mixing. This will create a greater shearing force to further break down and solubilize the pellet. You will not completely solubilize the pellet but the particulates should be broken down to the point where their diameters are no larger than 1 millimeter.

3.45 This mixture is then incubated at room temperature for 30 minutes.

3.46 Place the solubilized mixture in the Beckmann J2-21 centrifuge and spin the sample at 12,000×g (12,400 rpm in JA-20 rotor) at 4° C. for 15 minutes.

3.47 Decant the supernatant into a 50 ml conical tube labeled with "Denatured GST-I2" and today's date. Save 50 μl of this solution in a 1.5 ml micro centrifuge tube for later gel analysis (Store at 4° C.). Discard the pellet. The ~20 ml of Denatured GST-I2 can be kept at room temperature until its need for the following step.

3.48 Dilute the Denatured GST-I2 20-fold slowly in ice cold I2 Refolding Buffer. The following steps are performed at 4° C. in a refrigerator. A peristaltic pump is used to slowly add the supernatant to the ice cold refolding buffer that is being stirred on a magnetic stir plate. The flow rate of the addition of the supernatant is approximately 0.5 ml/min. The flow rate may shift as long as the drop of supernatant is fully dissolved in the refolding solution before the addition of the subsequent drop. This is done to optimize the dilution of the GST-I2 and to prevent any steric hindrance that could occur during refolding due the GST-I2 molecules being too close together.

3.49 Priming the pump (priming can be performed during the 30 min incubation steps in 3.35. and 3.45. to conserve time).

3.49.1 Place the peristaltic pump with attached tygon tubing in the refrigerator. Next to the pump place a magnetic stir plate. Use a stir plate with an electronic read-out so you can accurately determine the rpm during the dilution step.

3.49.2 Prime the pump with 40 mls of Nanopure Distilled $H_20$. Place the tubing that is attached to the "in" connector into a 50 ml conical tube containing 40 ml of $H_20$. Make sure the tubing is at the bottom of the conical tube. Place the tubing that is attached to the "out" connector in a 250 ml beaker. This beaker is a waste basin for the priming process. Set the dial on the peristaltic pump to 10 and put the pump on its prime setting. Click the "forward" button to begin priming.

3.49.3 Once the water priming is finished, prime the tubing with 20 mls of Denaturing Buffer. Repeat the directions shown in step 3.49.2, except use 20 mls of I2 Denaturing Buffer instead of water. After this step the pump is ready for the loading of the denatured GST-I2.

3.50 Loading Denatured GST-I2 onto the pump and subsequent dilution in I2 Refolding Buffer.

3.50.1 Make sure the pump is turned off 3.50.2 Place the 50 ml conical tube containing the Denatured GST-I2 in the refrigerator next to the peristaltic pump. Insert the tubing that is attached to the "in" connector of the peristaltic pump. Make sure the tubing reaches the bottom of the 50 ml conical tube.

3.50.3 Place a magnetic stir bar in the 1 L beaker that contains the I2 Refolding Buffer. Remove the beaker from the wet ice and place it on the magnetic stir plate in the refrigerator. Turn on the stir plate and adjust the rpm setting to 120.

3.50.4 Insert the tubing that is attached to the "out" connector of the pump into the 1 L beaker. Do not insert the tube into the refolding buffer. You want to have a gap (6-7 cms) between the end of the tube and the surface of the refolding buffer. This will allow proper drop formation when the sample is being loaded into the refolded buffer. Make sure there is parafilm sealing the beaker.

3.50.5 Put the pump on its slow setting and then adjust the dial to 0. Click the "forward" button to begin loading of the Denatured GST-I2.

3.50.6 The start time of the dilution process begins when the sample reaches the end of the tube and begins dropping into the refolding buffer. At this point check to see that the drops are dissolving into solution before the next drop is added. If the drops are not dissolving quickly enough turn the stir bar speed up to 140 rpm.

3.50.7 Once all the Denatured GST-I2 has been loaded into the beaker turn off the peristaltic pump. Label the beaker with "Refolded GST-I2" and today's date. Reduce the speed of the stir plate to 100 rpm and let the dilution mixture incubate overnight at 4° C.

3.51 Prepare 10 Liters of 1×PBS pH 7.4 (2×5 Liter volumes).

3.51.1 Acquire two 5 Liter Beakers. Rinse them with 200 ml of Nanopure distilled $H_20$ before use. Label each beaker with "1×PBS pH 7.4" and today's date.

3.51.2 Add 250 ml of 20×PBS pH 7.4 to each 5 Liter Beaker.

3.51.3 Add 4.75 L of Nanopure Distilled H20 to each 5 Liter Beaker.

3.51.4 Mix each solution and cover each Beaker with aluminum foil. Store each solution in a 4° C. refrigerator overnight.

4. Day 4

4.1 Run a protein gel to determine if the GST-I2 has been processed properly up to the point where the GST-I2 is denatured in the Denaturing Buffer.

4.2 The following samples are run on this Gel:
4.2.1 I2 Total Lysate Sonicate, Step 3.31.—TLS
4.2.2 S1 Sonicate Supernatant, Step 3.33.—S1
4.2.3 S2 DOC Wash Supernatant, Step 3.37.—S2
4.2.4 Denatured GST-I2, Step 3.47.—DEN
4.3 Sample preparation: Label four micro centrifuge tubes with TLS, 51, S2 and DEN. Add the following to each tube:
4.3.1 1 µl of Sample
4.3.2 10 µl of 4× Sample Buffer
4.3.3 1 µl of 2.5% beta-mercaptoethanol
4.3.4 28 µl of Nanopure distilled $H_20$
4.4 Mix the samples and then incubate them in a heat block at 90° C. for 5 minutes. Repeat step 3.5. through 3.7. to prepare and process the gel.
4.5 Decant the Simply Blue Safe Stain and add 100 ml of Nanopure distilled $H_20$. Place the gel back on a rocker and incubate it for 1 hour. Within 10 mins of this incubation step you'll be able to confirm that the GST-I2 antigen is present in the denatured sample (DEN) (FIG. 42B). When the bands are confirmed move on to the next step.
4.6 Take three pieces of dialysis tubing (6-8 mwco) that have been pre-cut to 36 cm in length and submerge them in 500 ml of Nanopure distilled $H_20$. Let the dialysis tubing soak for 30 minutes.
4.7 Remove the "Refolded GST-I2" beaker from the refrigerator and place it on ice. The solution in the beaker will be clear with no visible precipitation. Remove a 50 µl sample of this solution for gel analysis. Label this sample "Diluted rGST-I2" and today's date.
4.8 Remove one beaker containing 5 Liters of cold 1×PBS pH 7.4 from refrigerator. Make sure this solution is mixed before placing it on ice. Label this beaker with "1$^{st}$ Exchange".
4.9 Take three 50 ml conical tubes and place them on ice. These conical tubes will be used to transfer the refolded GST-I2 into the dialysis tubing. Using a 25 ml serological pipet, transfer approximately 47 mls of refolded GST-I2 into each 50 ml conical tube.
4.10 Remove one of the pieces of dialysis tubing from the distilled water and place a clamp on the bottom of the tubing. Make sure the clamp is fastened and that it covers the width of the tubing to ensure a tight seal.
4.11 Insert a glass funnel into the open end of the dialysis tubing. Make sure that the funnel is inserted and that the inserted portion is held firmly against the dialysis tubing. It is important that this is done to prevent slippage of the tubing while it is being loaded. Due to the slippery nature of the sample that is being loaded, the tubing should be held firmly from the top at all times.
4.12 While the funnel is being held in position carefully load the refolded GST-I2 into the funnel. When each conical tube is emptied place it back on ice.
4.13 After the last conical tube of refolded GST-I2 is loaded place that empty conical tube on ice. With both hands, firmly grip the top of the dialysis tubing. Force all air bubbles out of the tubing, use a kim wipe to remove the bubbles. Make sure that there is no air left in the tubing before the top clamp is fastened.
4.14 Fasten the clamp on the top of the tubing. This tubing will expand after dialysis is finished so make sure that enough space is left in the tube for expansion. Leave 6 cm of space from the clamp to the surface of the sample. This will allow for that expansion. Once again there should be no air in the tube. Make sure that there are no leaks present.
4.15 Slowly place the full dialysis tube in the 5 Liter beaker of cold 1×PBS pH 7.4.
4.16 Repeat steps 4.9. through 4.15. two more times. Use the same three 50 ml conical tubes that were previously used. There will be a total of three filled dialysis tubes in the 5 Liter beaker at the end of this step.
4.17 Place the beaker on a magnetic stir plate in a 4° C. refrigerator. Place a magnetic stir bar in the beaker. Set the stir plate to mix at 100 rpm. Make sure the stir bar is not hitting any of the dialysis tubes. Incubate these dialysis tubes for 4 hrs at 4° C.
4.18 Slowly remove the dialysis tubes from the 5 liter beaker and place them in the other 5 liter beaker of 1×PBS pH 7.4 that has been stored in the 4° C. Make sure not to mix or agitate the solution inside of the dialysis tube. Place a magnetic stir bar in the beaker. Set the stir plate to mix at 100 rpm. Label this Beaker with "2$^{nd}$ Exchange". Incubate these dialysis tubes for overnight at 4° C.
4.19 Prepare 10 Liters of 1×PBS pH 7.4 (2×5 Liter volumes).
4.20 Acquire two 5 Liter Beakers. Rinse them with 200 ml of Nanopure distilled $H_20$ before use. Label each beaker with "1×PBS pH 7.4" and today's date.
4.21 Add 250 ml of 20×PBS pH 7.4 to each 5 Liter Beaker.
4.22 Add 4.75 L of Nanopure Distilled H20 to each 5 Liter Beaker.
4.23 Mix each solution and cover each Beaker with aluminum foil. Store each solution in a 4° C. refrigerator overnight.

5. Day 5
5.1 Slowly remove the dialysis tubes from the 5 liter beaker and place them in the other 5 liter beaker of 1×PBS pH 7.4 that has been stored in the 4° C. Make sure not to mix or agitate the solution inside of the dialysis tube. There may be some precipitation at this point. Place a magnetic stir bar in the beaker. Set the stir plate to mix at 100 rpm. Label this Beaker with "3$^{rd}$ Exchange". Incubate these dialysis tubes for four hours at 4° C.
5.2 Slowly remove the dialysis tubes from the 5 liter beaker and place them in the other 5 liter beaker of 1×PBS pH 7.4 that has been stored in the 4° C. Make sure not to mix or agitate the solution inside of the dialysis tube. There may be some precipitation at this point. Place a magnetic stir bar in the beaker. Set the stir plate to mix at 100 rpm. Label this Beaker with "4$^{th}$ Exchange". Incubate these dialysis tubes for four hours at 4° C.
5.3 Hook up a 1 Liter Filter System bottle to a vacuum pump. Remove the 5 liter beaker that contains the dialysis tubes from the refrigerator. One at a time, carefully empty the contents of the dialysis tube into the top of the filter system. Once all the dialysis tubes have been emptied into the top reservoir of the filter make sure to save a 50 µl aliquot of the solution for gel analysis. Label the aliquot "rGST-I2 dialyzed pre-filtered" and store it at 4° C. until needed.
5.4 Filter the solution into the 1 Liter System bottle. Once filtering is complete save a 50 µl aliquot of the solution for gel analysis. Label the aliquot "rGST-I2 dialyzed filtered" and store it at 4° C. until needed.

5.5 The volume of the filtered solution should be approximately 550 mls after dialysis. Label the bottle with "rGST-I2 dialyzed filtered-$1^{st}$ agarose incubation" and today's date. Place this bottle in the 4° C. while the immobilized glutathione agarose is being prepared.

5.6 Add immobilized glutathione agarose to the bottle of rGST-I2 as follows in steps 5.7 through 5.10—all steps.

5.7 Measure and equilibrate the immobilized glutathione agarose (resin).

5.8 Take a 20 ml chromatography column and place it in a clamp attached to a ring stand. Place a 250 ml beaker under the column to act as a waste basin.

5.9 Take the bottle of pre-made agarose and mix it well until the agarose is suspended evenly in the storage solution.

5.10 Using a 10 ml serological pipet load this mixed agarose into the column. Continue to load the mixture until a 6 ml bed of the agarose has settled at the bottom of the column. Let the solution in the column drain out until the top surface of the storage solution is 1 ml above the agarose bed. At that point cap the bottom of the column. (While working with this agarose do not let it dry out. Keep it wet at all times.)

5.10.1 Uncap the column. Wash the agarose with 60 ml of degassed 1×PBS pH 7.4. Cap the column.

5.10.2 Remove the 1 liter bottle containing the ~550 ml of rGST-I2 solution from the refrigerator.

5.10.3 Load 10 ml of degassed 1×PBS pH 7.4 into the column. Using a 10 ml serological pipet, suspend the agarose thoroughly and add it to the 1 liter bottle of rGST-I2 solution.

5.10.4 Add 10 ml of degassed 1×PBS pH 7.4 into the column. Mix this 10 ml volume to retrieve the residual agarose that is stuck to the column. Add that 10 ml volume to the 1 liter bottle of rGST-I2 solution.

5.10.5 Cap the bottle and slowly rotate the bottle by hand to mix the agarose thoroughly into solution.

5.10.6 Place the bottle in the 4° C. refrigerator and incubate it overnight.

6. Day 6

6.1 Run a protein gel to determine if the GST-I2 has been processed properly up to the point where the GST-I2 is filtered in 1×PBS pH 7.4.

6.2 The following samples are run on this gel:

6.2.1 Denatured GST-I2-, Step 3.47.—DEN 6.2.2 Diluted refolded GST-I2, Step 4.7.—DIL 6.2.3 Pre-filtered rGST-I2 in 1×PBS pH7.4, Step 5.3.—PRE 6.2.4 Filtered rGST-I2, Step 5.4.—FIL 6.3 Sample preparation: Label four micro centrifuge tubes with DEN, DIL, PRE and FIL.

6.4 To prepare the DEN sample, add the following to the tube:

6.4.1 1 μl of Sample 6.4.2 10 μl of 4× Sample Buffer 6.4.3 1 μl of 2.5% beta-mercaptoethanol 6.4.4 28 μl of Nanopure distilled $H_20$ 6.5 To prepare the DIL, PRE and FIL samples, add the following to each tube:

6.5.1 20 μl of Sample 6.5.2 10 μl of 4× Sample Buffer 6.5.3 1 μl of 2.5% beta-mercaptoethanol 6.5.4 9 μl of Nanopure distilled $H_20$ 6.6 Mix the samples and then incubate them in a heat block at 90° C. for 5 minutes. Repeat step 3.5. through 3.7. to prepare and process the gel.

6.7 Decant the Simply Blue Safe Stain and add 100 ml of Nanopure distilled $H_20$. Place the gel back on a rocker and incubate it for 1 hour. Within 10 mins of this incubation step you be able to confirm that the GST-I2 antigen is present in the filtered sample (FIL) (FIG. 42C). When the bands are confirmed move on to the next step.

6.8 First round of purification of the rGST-I2 antigen.

6.9 Set up two columns on a ring stand. Label each column with either #1 or #2. Under each column place a 250 ml beaker to act as a waste container. Snap the seal on the bottom of the column to open up the column. Pre-rinse each column with 50 ml of Nanopure Distilled $H_20$. Place a 1 L disposable sterile bottle below each column. Pull the "rGST-I2 dialyzed filtered-$1^{st}$ agarose incubation" bottle out of the refrigerator and slowly mix the bottle.

6.10 The mixture inside of the bottle will now be evenly split into two separate columns. The solution is split into two columns because larger volume beds decrease the flow rate. Splitting the column work will allow this purification procedure to be performed in approximately two hours.

6.11 Using a 25 ml serological pipet, begin to load each column with the agarose suspension. Fill the column to the top with the suspension. Then let the volume drop to the 15 ml mark on the column, at that point fill the column to the top again. You do not want to let the volume of the agarose suspension drop too low. If that occurs, the addition of your next agarose suspension could disturb the formation of the agarose bed. Make sure you are adding the suspension slowly to reduce the disturbance to the forming agarose bed.

6.12 Continue loading the column with the agarose suspension. When all of the agarose suspension is loaded on the column it should be capped. Cap them when the liquid phase in the column reaches the 10 ml mark on the column. Each bed volume will be approximately 3 mls in size. Take this time to prepare 1×PBS pH 7.4 (1 liter). Degas the PBS with argon for 5 minutes before using.

6.13 At this point remove each 1 liter bottle from underneath the column. Combine the flow through volumes of each bottle into one bottle. Label this bottle "rGST-I2 dialyzed filtered-$2^{nd}$ agarose incubation" with today's date and store it in the refrigerator until it is needed.

6.14 Place 250 ml Beakers under each column to act as waste containers.

6.15 Begin washing the bed with 60 ml of degassed 1×PBS pH 7.4 in 2×30 ml increments to each column. The PBS should be degassed for 5 mins with argon immediately before it is used. Be sure to load the wash buffer very slowly.

6.16 After the last wash is added, let the volume drop till the meniscus is 1-2 mm above the bed. Cap the column at this point. You will now degas the elution buffer (1×PBS pH 7.4 w/100 mM reduced glutathione). This elution buffer is degassed with argon for 2 minutes before using.

6.17 Load 1.5 ml of elution buffer to each capped column and let it stand for 5 minutes. Uncap the columns and collect the elutions in a 1.5 ml micro centrifuge tube. Collect the elution until the volume reaches approximately 1.2 mls. Cap the columns. These are the first elutions. Label each tube with "Elution#, column#" and today's date.

6.18 Monitoring of the elutions is done in parallel of this elution procedure using Bradford reagent. 5 ul of each elution is added to separate wells on a 96 well plate.

250 ul of Bradford reagent is then added to each well. The presence of protein will be identified in this procedure by the changing of the reagent color from brown to blue. If the elution gives off a blue color on the Bradford mark the respective micro centrifuge tube with a "B".

6.19 Repeat steps 6.17. through 6.18. three more times to collect elutions 2-4. At this point you should see the blue color of elution #4 disappearing on the 96-well plate. You will have a total of 8 micro centrifuge tubes at this point.

6.20 Store the elutions at 4° C. They will be used later when the elutions are pooled.

6.21 Wash each resin bed with 80 ml of degassed 1×PBS pH 7.4.

6.22 Using a 10 ml serological pipet suspend each bed in 10 ml of 1×PBS pH 7.4 and added it to the bottle labeled "rGST-I2 dialyzed filtered-2$^{nd}$ agarose incubation".

6.23 Add an additional 10 ml of degassed 1×PBS pH 7.4 to each column and mix the solution well to retrieve any residual agarose. Add this volume to the bottle labeled "rGST-I2 dialyzed filtered-2$^{nd}$ agarose incubation". Rotate this bottle slowly to mix the resin. Store the bottle overnight at 4° C.

7. Day 7

7.1 Repeat steps 6.9. through 6.23. This will generate a flow through bottle labeled as "rGST-I2 dialyzed filtered-3' agarose incubation" and produce a new set of 8 elutions that are stored overnight at 4° C.

8. Day 8

8.1 Repeat steps 6.9. through 6.23. This will generate a bottle labeled as "rGST-I2 dialyzed filtered-final flow through" and produce a new set of 8 elutions that are stored at 4° C.

8.2 Pool the elutions that were marked with a "B" into one final volume. Only pool the elutions that show a blue color on the Bradford assay.

8.2.1 Spin the elution tubes in a micro tube centrifuge for 1 minute at 5000×g to remove any precipitants.

8.2.2 Combine the elutions into one 15 ml conical tube. Label that tube "rGST-I2 pooled elutions".

8.3 Perform a Bradford Assay to determine the concentration of the protein using the Bradford Dye and a pre-made albumin standard.

8.3.1 Standard A comes in a sealed ampoule and acts as you stock solution. The standard diluent is 1×PBS pH 7.4 w/100 mM reduced glutathione.

8.3.2 Follow the table below for setting up the standard curve.

Preparation of Diluted Albumin (BSA) Standards

| Vial | Volume of Diluent | Volume and Source of BSA | Final BSA Concentration |
|---|---|---|---|
| A | 0 | 300 μl of Stock | 2,000 μg/ml |
| B | 125 μl | 375 μl of Stock | 1,500 μg/ml |
| C | 325 μl | 325 μl of Stock | 1,000 μg/ml |
| D | 175 μl | 175 μl of vial B dilution | 750 μg/ml |
| E | 325 μl | 325 μl of vial C dilution | 500 μg/ml |
| F | 325 μl | 325 μl of vial E dilution | 250 μg/ml |
| G | 325 μl | 325 μl of vial F dilution | 125 μg/ml |
| H | 400 μl | 100 μl of vial G dilution | 25 μg/ml |
| I | 400 μl | 0 | 0 μg/ml = Blank |

8.3.3 Load 5 ul of the standards and the pooled rGST-I2 sample into a 96 well plate. Load them in duplicate.

8.3.4 Add 250 ul of Bradford reagent into each well. Gently tap the plate to mix the samples. Incubate the plate for 5 mins then read the plate at 595 nm on micro plate reader. Do not over incubate the plate.

8.3.5 Graph the data on Excel. Graph the absorbance at 595 nm (x-axis) vs. concentration μg/ml (y-axis). Only graph from the range of 1,000 μg/ml through 25 μg/ml, because this is the linear part of the curve. Through linear regression determine the formula of the curve. It will be in y=mx+b format. Use this formula to determine the concentration of your sample.

8.4 Once the concentration has been determined, aliquot the antigen and freeze it in liquid nitrogen. Label the aliquots. Then store the antigen at −70. Save an aliquot for gel analysis.

8.5 Run a gel to determine that the GST-I2 has been purified.

8.5.1 Sample preparation: Label a micro centrifuge tubes with refolded GST-I2. Add the following to the tube. Load 2 ug of protein in the well. X=2.7 ug of GST-I2, where 30 μl of sample prep will be loaded from a total sample prep volume of 40 μl 8.5.1.1 X μl of Sample 8.5.1.2 10 μl of 4× Sample Buffer 8.5.1.3 1 μl of 2.5% beta-mercaptoethanol 8.5.1.4 29-X μl of Nanopure distilled $H_20$ 8.6 Mix the samples and then incubate them in a heat block at 90° C. for 5 minutes. Repeat steps 3.5. through 3.7. to prepare and process the gel.

8.7 Decant the Simply Blue Safe Stain and add 100 ml of Nanopure distilled $H_20$. Place the gel back on a rocker and incubate it for 1 hour.

Quality Control

Each lot of purified rGST-I2 antigen is compared to two previous lots to ensure the reproducibility of purification as shown in FIG. 23.

Analysis

Each lot of purified rGST-I2 antigen is compared to BSA standards to determine the concentration using the Bradford Assay and linear regression.

REFERENCES

"Purification and characterization of recombinant extraxellular domain of human HER2 from *Escherichia coli*" Protein Expression and Purification X. Liu et al. 2007 pages 247-254.

Example 20. Protocol for Performing Anti-I2 Immunoassays

Purpose

This anti-I2 Indirect Sandwich ELISA procedure details the steps necessary for the quantitative determination of Human IgA serum antibodies against I2.

Scope

The I2 Immunoassay test is used to detect serum concentrations of anti-I2 in patient samples.

Principle

The assay employs an indirect sandwich immunoassay format where capture antibodies are coated on the bottoms of the wells of a 96-well microplate. The plate is then blocked to minimize non-specific binding and high background. Antigen is added to the plate which binds to the capture antibody. Excess antigen is washed away after incubation.

The calibrators, controls, and patient samples are incubated in the appropriate wells and the biomarker binds to the antigen. Unbound biomarker is then washed away and the detection antibody labeled with alkaline phosphatase is incubated in the wells. The plate is washed again and a chemiluminescent substrate solution is added. The plate is read on Molecular Device's Spectramax M5$^e$ using luminescent detection.

Definitions

1. I2: *Pseudomonas fluorescens*-related peptide
2. ELISA: Enzyme-linked immunosorbant assay Sample Requirements Patient's whole blood is drawn into Serum Separator Tube (SST) and EDTA/Lavender Top tube. The tubes are shipped within 7 days to Prometheus Laboratories, under room temperature conditions or using Cold pack. Prior to shipment, the tubes are stored under refrigerated conditions.

Procedure

1. Prepare coating buffer by diluting 20×PBS to 1× with Nanopure Water.
2. Dilute Mouse α-GST mAb to 5 μg/mL in 1×PBS. Coat plates at 100 μL/well. Store overnight at 4° C.
3. Add 5% Mouse Serum to a volume of I2 Dilution Buffer (1×PBS+1% BSA+0.5% PVA+0.8% PVP) needed for 1° & 2° dilutions for the day to create I2 Working Buffer. [e.g., 2 mL Mouse Serum to 38 mL I2 Dilution Buffer]
4. Bring plates, Histidine Blocking Buffer (20 mM Histidine+0.5M NaCl+1% BSA) and I2 Working Buffer to room temperature prior to use. All other reagents, controls, standards, and samples should be kept on ice or at 4° C. prior to use.
5. Prepare Standard Curve by diluting Anti-His-I2 Rabbit Serum in I2 Working Buffer; standard curve is plated in duplicate.

Suggested Dilutions for Standard Curve (2 Plates):

| | Dilution | Add to | 12 Working Buffer |
|---|---|---|---|
| | 1:500 stock | 2 μL Rabbit Serum-Anti-His-I2 | 998 μL |
| 1 | 1:2000 | 163 μL 1:500 Stock | 489 μL |
| 2 | 1:3750 | 85 μL 1:500 Stock | 555 μL |
| 3 | 1:5000 | 65 μL 1:500 Stock | 585 μL |
| 4 | 1:10,000 | 32 μL 1:500 Stock | 608 μL |
| 5 | 1:20,000 | 16 μL 1:500 Stock | 624 μL |
| 6 | 1:80,000 | 160 μL 1:20,000 | 480 μL |
| 7 | 1:320,000 | 160 μL 1:80,000 | 480 μL |
| 8 | Blank | None | 480 μL |

6. Prepare wash buffer by diluting 20×PBS-Tween to 1× with $DIH_2O$.
7. Wash wells 3 times with 300 μL/well 1×PBS-Tween.
8. During blocking step, prepare dilution of each positive Control to be assayed; [e.g., 25 μL Control sample into 225 μL] of I2 Working Buffer for a 1:10 dilution; Negative control is a 1:100 dilution [e.g., 2.5 μL Stripped Serum into 250 μL Diluent]; all Control samples are plated in duplicate. Samples will be diluted 1:100 & 1:200 [e.g., 10 μL sample+90 μL I2 Working Buffer for 1:10; 25 μL of 1:10 into 225 μL I2 Working Buffer for 1:100; 15 μL of 1:10 into 285 μL I2 Working Buffer for 1:200]. All samples are plated in duplicate.

NOTE: Incubate diluted samples and standards on the bench for the duration of the antigen step.

9. Block wells with 300 μL/well of Histidine Blocking Buffer. Incubate for 1 hour at room temperature with shaking (approx 300 rpm).
10. Dump blocking solution. Do not wash plate.
11. Dilute rGST-I2 in 1×PBS (according to the formula below) immediately before coating on plates @ 5 μg/mL, 100 μL/well. [$V_F$=total volume needed; i.e., 11 mL total volume=one plate]

$$\text{Formula: } \frac{\text{Initial Concentration of Antigen Stock } (\mu g/\text{mL})}{5\ \mu g/\text{mL (final desired concentration)}} = D_F(\text{Dilution Factor}) = I_c/F_c$$

$V_F/D_F$=volume of Stock ($V_S$) needed to add to 1×PBS $V_F-(V_F/D_F)$=Volume of 1×PBS ($V_P$); $V_S+V_P=V_F$ @ 5 μg/mL conc. of Antigen e.g., If Antigen Stock is 1788 μg/mL, then 1788 μg/ml/5 μg/mL=357.6 ($D_F$); for one plate $V_F$=11 mL. 11 mL/357.6=0.031 mL of Stock antigen (i.e., 31 μL)

11 mL-0.031 mL=10.969 mL of 1×PBS 0.031 mL Antigen Stock+10.969 mL of 1×PBS=11 mL @ 5 μg/mL Incubate 1 hour with shaking.

12. Wash wells 3 times with 300 μL/well of 1×PBS-Tween.
13. Dilute Tropix Assay Buffer (10×) to 1× with $DDIH_2O$ for use in step 10.19. Keep buffer at 4° C. prior to use and use cold.
14. Add 100 μL/well calibrators and samples to plate in duplicate. Incubate 1 hour at room temperature on orbital shaker (approx. 300-700 rpm).
15. Wash wells 3 times with 300 μL/well of 1×PBS-Tween.
16. Add 100 μL/well of 1:5,000 secondary antibody diluted in I2 Working Buffer. [e.g., 1.24, Goat anti-Rabbit IgG to 6 mL I2 Working Buffer for Standard Curve; 2 μL Goat anti-Human IgA to 10 mL I2 Working Buffer for all patient and control samples.] Incubate 1 hour at room temperature with shaking.
17. Wash wells 3 times with 300 μL/well of 1×PBS-Tween.
18. Wash wells 2 times with 200 μL/well Tropix Assay Buffer (1χ).
19. Add 100 μL/well of the chemiluminescent substrate solution [10 mL for one plate]. Substrate should be kept at 4° C. prior to use and used cold. Incubate for 20 minutes, protected from light—with shaking.
20. Immediately read plates on Spectramax M5$^e$ using luminescence protocol, top read, opaque 96 well plate, with Integration set at 500.

Quality Control

Figure 43:
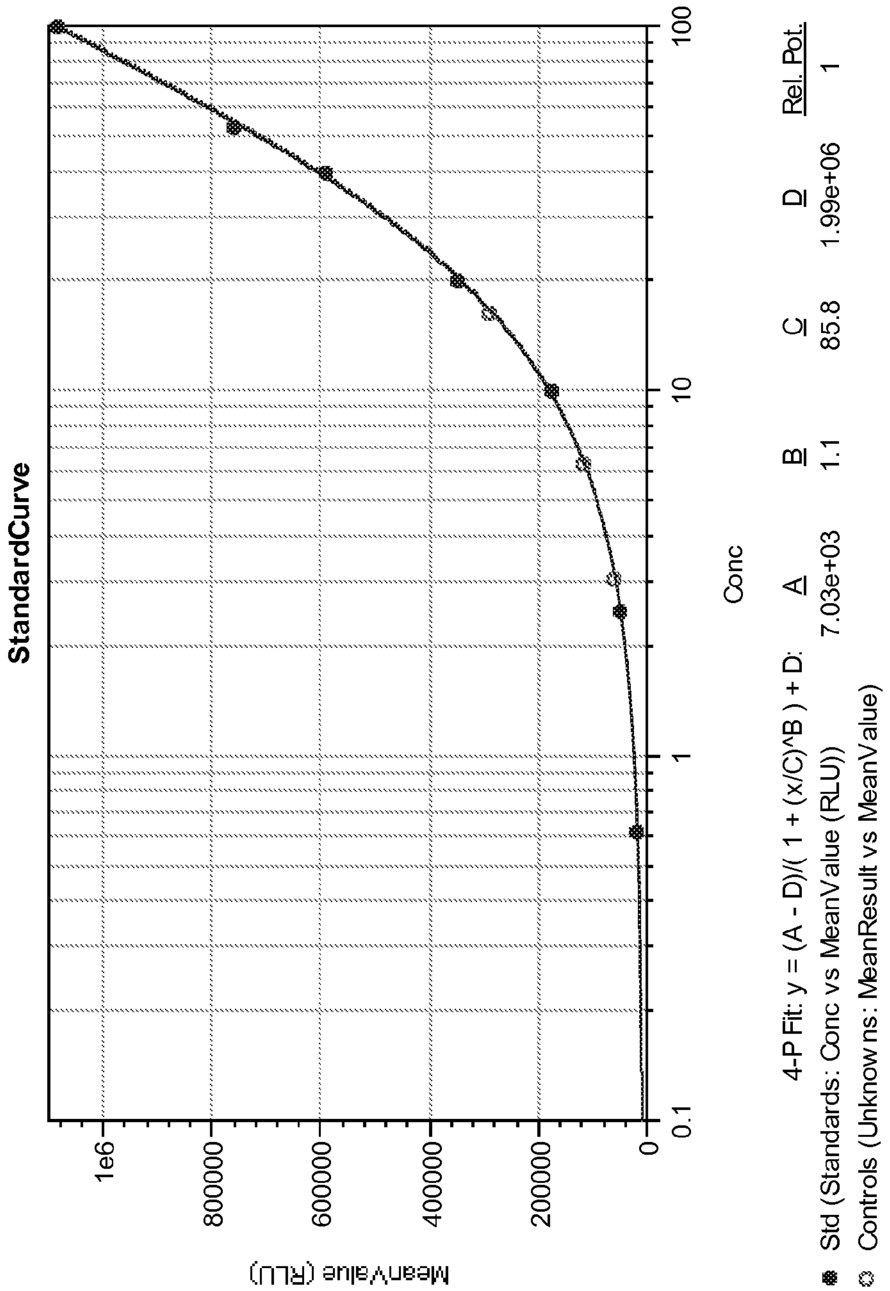
FIG. 43 illustrates a graph of a sample standard curve with controls as described in Example 20.

1. The Blank for each plate is determined by graphing of the standard curve.
2. The High, Medium, and Low Control values generated in the assay may be evaluated.
3. FIG. 43 shows a graph of a sample standard curve with controls. Standard and control data are evaluated and graphed using Softmax.

Analysis

1. The assay is measured in EU.
   1.1 Reference Range is 367.80 EU. Samples with values greater than 367.80 EU will be considered positive for anti-I2.
   1.2 Minimum Detectable Concentration (MDC) is 1.81 EU.

1.3 Reportable Range is 2.5 EU-100 EU.

1.4 Patient value less than 2.5 EU will be reported as <2.5 EU.

1.5 Patient value that exceeds 100 EU will be reported as >100 EU.

2. Testing must be repeated on samples with >15% CV between duplicates or if both duplicates are below the lower limit of the reportable range.

Calibration

A 7-point calibration curve is run with each assay and must meet expected criteria; each curve is compared to a reference set from 30 previous assays in order to determine acceptability.

Linearity

Assay linearity and reportable range are verified semiannually using the appropriate testing materials and statistical analysis.

Interference

This assay was tested for interference by Rheumatoid Factor, hemolysis and various substances (Bilirubin (400 ug/mL), Cholesterol (5 mg/mL), Heparin (80 U/mL), EDTA (1.8 mg/mL) and Hemoglobin (5 mg/mL). Anti-I2 detection was found within acceptable range following spiking with all of these substances.

Example 21. Protocol for Validating Anti-I2 Immunoassays

This example provides a protocol for the validation of human anti-I2 ELISA.

A. Reference Range

The reference range will be done by one analyst performing the assay on one day (two plates). Forty healthy control samples will be tested in duplicate. The reference range will be determined from anti-I2 concentration. Mean value, standard deviation, minimum value and maximum value will be calculated. 95% Confidence intervals (mean±1.96 standard deviation) will be considered as the normal range.

B. Validation

Performance of the assay will be done by 3 analysts performing the assay on five different days (total 15 assays). The validation will be performed using 3 lots antigen preparation. The study will distinguish operator and batch effects. Each of the three operators will use a different lot at least one time during the five days validation.

B.1. Standard Curve

The curve will be derived from 7 standards that range from 1:2000 to 1:320,000 dilutions and a blank. Serial dilution will be performed from a 1:500 stock. The stock 1:500 dilution will be prepared by adding 2 µl of anti-His rabbit serum to 998 µl assay diluent. To make the initial 1:2000 dilution, 163 µl of the stock will be added to a tube containing 489 µl of assay diluent. Subsequent dilution will be performed as described in the table below.

Suggested Dilutions for Standard Curve (2 Plates)

| | Dilution | Add to | Assay Diluent |
|---|---|---|---|
| | 1:500 stock | 2 µL Anti-His Rabbit Serum | 998 µL |
| 1 | 1:2000 | 163 µL 1:500 Stock | 489 µL |
| 2 | 1:3750 | 85 µL 1:500 Stock | 555 µL |
| 3 | 1:5000 | 65 µL 1:500 Stock | 585 µL |
| 4 | 1:10,000 | 32 µL 1:500 Stock | 608 µL |
| 5 | 1:20,000 | 16 µL 1:500 Stock | 624 µL |
| 6 | 1:80,000 | 4 µL 1:500 Stock | 636 µL |
| 7 | 1:320,000 | 1 µL 1:500 Stock | 639 µL |
| 8 | Blank | None | 640 µL |

Each standard will be assayed in duplicate. The reproducibility of the standard curve will be assessed by comparing for each lot the Expected value with the Mean Observed/Calculated, Standard Deviation and % CV. The analysis will show pair-wise comparison between multiple standard lots. Acceptable signal reproducibility for standard 1-7 will be defined as precision (% CV) less than 10%.

B.2. Sensitivity

The minimum detectable concentration (MDC) will be determined using a total of 20 replicates of the zero standards (blank). The Mean and Standard deviation will be used to calculate the MDC. MDC will be determined by adding two standard deviations to the mean optical density value of the 20 zero standard replicates.

B.3. Precision/Accuracy

The intra and inter-assay precision will be determined for high, medium and low positive controls. For intra-assay precision (precision within the assay), high, medium and positive controls will be tested in replicates of 16 on a single plate. For inter-assay precision (precision between assay), high, medium and positive controls will be tested in fifteen separate plates. Each sample will be assessed for each run. Assigned values, Mean, Standard Deviation and % CV will be calculated. Acceptable analytical precision for samples spanning the standard curve dynamic range will be defined as precision (% CV) less than 10%.

B.4. Reportable Range/Linearity

The dilution linearity will be evaluated using five serial two-fold dilution of the high positive, medium or low controls (Neat), starting from ½. Each will be assessed in duplicate. Yield of anti-I2 concentration will be obtained when multiplied by the dilution factor. Percent of recovery will be determined. Performance will be considered acceptable when the results are between 80% and 120% of the expected concentration. Linear regression ($R^2$) will be calculated to confirm that the sample dilution correlate linearly with the calculated ELISA units.

C. Stability Studies

Stability assays will be performed by 3 analysts the same day (3 plates). Each sample assay will be previously prepared and stored at −80° C.

C.1. Room Temperature Stability (RT)

High, Medium and Low controls will be incubated at room temperature for 1, 2, 4 or 7 days. The treated controls will be assayed and compared to the non-treated controls. Acceptable criteria: 80-120% of initial calculated I2 concentration.

C.2. 4° C. Temperature Stability (4° C.)

High, Medium and Low controls will be incubated at 2-8° C. for 1, 2, 4 or 7 days. The treated controls will be assayed and compared to the non-treated controls. Acceptable criteria: 80-120% of initial calculated anti-I2 concentration.

C.3. Freeze & Thaw (F/T) Purified GST-I2 Antigen Preparation and Samples

High, Medium and Low controls will be subjected to 5 freeze and thaw cycles. The treated controls will be assayed and compared to the non-treated controls. Acceptable criteria: 80-120% of zero freeze-thaw.

Aliquots of GST-I2 antigen will be subjected to 1-5 cycles (I2-FT0,1,2,3,4,5) of freeze-thaw and will be assayed and compared with samples kept frozen. Acceptable criteria: 80-120% of zero freeze-thaw C.4. Standard Stability For standard stability evaluation, standard stock solution will be divided into two aliquots and stored at 4° C. for 7 days and 14 days. The assay will be performed using high, medium and low controls. Acceptable criteria: 80-120% of zero freeze-thaw.

D. Interference/Specificity

Interference assays will be performed by 3 analysts the same day (3 plates).

D.1. Hemolyzed Serum

Hemolysed serum will be tested for anti-I2 assay interference. Whole blood will be collected from three healthy consented donors. The blood will be vortexed vigorously to cause severe hemolysis and then allowed to clot. Serum will be collected. High, Medium and Low controls will be diluted in duplicate with an equal volume of NHS or Hemolysed normal sample. Acceptable criteria: 80-120% of initial calculated anti-I2 concentration.

D.2. RF Serum

To determine if Rheumatoid Factor (RF) will interfere with the assay, High, Medium and Low controls will be diluted in duplicate with an equal volume of normal human Serum (NHS) or Rheumatoid factor (RF) positive serum (clinical sample purchased from Aalto Scientific). Anti-I2 recovery from controls spike with NHS will be compared with controls spiked with RF positive serum. Acceptable criteria: 80-120% of initial calculated anti-I2 concentration.

D.3. Specificity

The effect of various substances on the performance of anti-I2 assay will be determined. High, medium and low controls will be spiked with Bilirubin (400 ug/mL), Cholesterol (5 mg/mL), Heparin (80 U/mL), EDTA (1.8 mg/mL) and Hemoglobin (5 mg/mL). % I2 recovered in the spiked control will be calculated. Acceptable criteria: 80-120% of initial calculated anti-I2 concentration.

Example 22. Exemplary Anti-I2 Immunoassays Using Refolded GST-I2 Antigen

This example describes two anti-I2 immunoassays which utilize refolded GST-I2 antigen (see, Example 19) to detect anti-I2 antibodies in a biological sample. Both assays are performed on a 96-well microtiter plate with a refolded GST-tagged protein consisting of 100 amino acids of the I2 sequence. However, one of ordinary skill in the art will appreciate that a fragment of the I2 polypeptide that is immunoreactive with an anti-I2 antibody is suitable for use in the immunoassays described herein.

Figure 44:
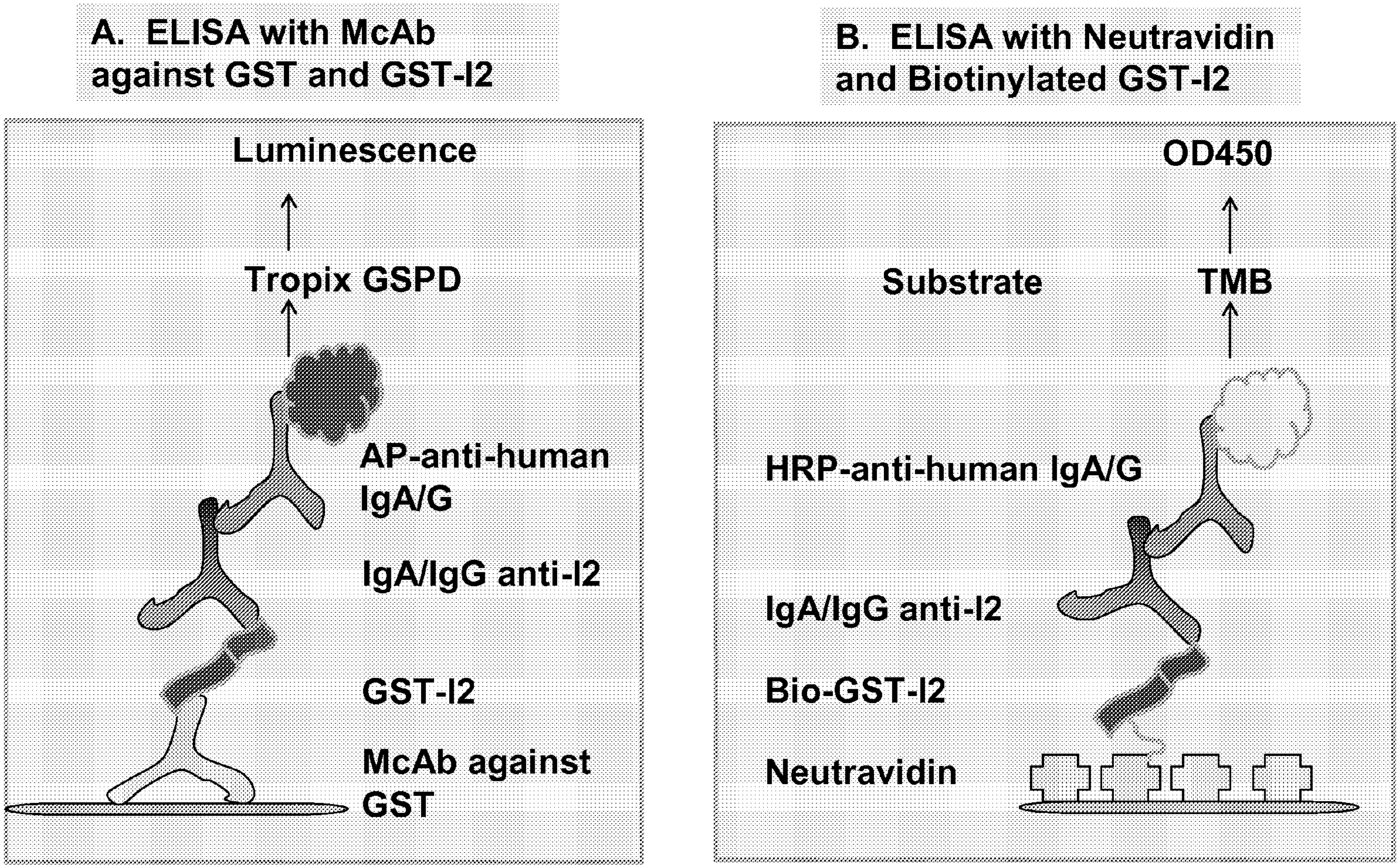
FIG. 44A illustrates an anti-I2 ELISA which utilizes a monoclonal antibody (McAb) against GST and a refolded GST-I2 antigen.
FIG. 44B illustrates an anti-I2 ELISA which utilizes neutravidin and a biotinylated refolded GST-I2 antigen.

In one embodiment, the anti-I2 assay is the ELISA depicted in FIG. 44A and described in Example 20. In particular, refolded GST-I2 antigen is captured on the plate using a monoclonal anti-GST antibody coated on the well surface. After incubation of patient serum samples in the wells, detection of anti-I2 IgA/IgG is accomplished using an alkaline phosphatase enzyme-conjugated anti-human IgA/G reagent. The reaction is then revealed using a cheminulescent substrate solution.

To assess the prognostic value of this assay, anti-I2 serum values were analyzed for patients with CD complications (e.g., penetrating or fibrostenosing) and CD patients having undergone a surgical procedure. The results showed that 64.6% of patients with high levels of anti-I2 (e.g., levels above a reference concentration level) experienced complicated disease behavior, compared to 52.2% of patients with low levels of anti-I2 ($p=0.002$). As such, the detection of anti-I2 using this robust assay finds utility in predicting possible disease behavior outcomes for CD patients.

In another embodiment, the anti-I2 assay is the ELISA depicted in FIG. 44B. In particular, the plate was coated with 100 μl/well of neutravidin in sodium carbonate buffer pH 9.5 at 4° C. overnight. After washing with PBST, the plate was blocked with SuperBlock for 30 minutes. After washing with PBST, half of the plate was incubated with 100 μl of biotinylated refolded GST-I2 (Bio-GST-I2; 100 μg/ml in SuperBlock), while the other half was incubated with 100 μl of SuperBlock (background) for 1 hour at room temperature (RT) with gentle agitation. Pooled IBD patient serum was used as a standard. The arbitrary unit of the standards was set as 160 U/ml for IgA GST-I2 and 146 U/ml for IgG GST-I2. Serial dilutions of the standard were made to generate the standard curve (3 U/ml and then 1:3 dilutions). 100 μl/well of the standards and samples (1:300 dilution in SuperBlock) were added to each well after washing with PBST. After incubating at RT for 1.5 hours with gentle agitation, the plate was washed and incubated with 100 μl of HRP-labeled anti-human IgA or IgG 2° antibody for 1 hour at RT with agitation. TMB substrate was added to each well after washing. The plate was incubated in the dark with agitation for 15 minutes and the reaction was stopped with 50 μl/well of 1M phosphoric acid. A SpectraMax plate reader was used to read the OD450. To analyze specific binding, the background OD450 from standards and samples were subtracted from the corresponding OD450 from Bio-GST-I2-containing wells. The values of IgA or IgG GST-I2 were calculated from the standard curve using the Prism graphPad program.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A method for determining the risk that an individual diagnosed with Crohn's disease (CD) develops a stricturing or penetrating disease presentation, said method comprising:

(a) detecting in a sample obtained from said individual the presence, absence, or level of a combination of serological markers by immunoassay and the genotype of a combination of genetic markers, wherein said serological markers comprise anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-CBir-1 antibody, an anti-I2 antibody, and a perinuclear anti-neutrophil cytoplasmic antibody (pANCA), and wherein said genetic markers comprise SNP8 (R702W), SNP12 (G908R), and SNP13 (3020InsC) in the NOD2 gene;

(b) applying a quartile analysis to each of said serological markers to obtain a quartile sum score (QSS) for said individual by:

(b1) converting the level of each of said serological markers ASCA-IgA, ASCA-IgG, anti-OmpC antibody, anti-CBir-1 antibody, and anti-I2 antibody into a quartile score for each of said serological markers;

(b2) converting the presence of said serological marker pANCA into a quartile score of 1 and the absence of said serological marker pANCA into a quartile score of 4; and (b3) summing said quartile scores for each of said serological markers from steps (b1) and (b2) to obtain the QSS;

(c) deriving a logistic regression model by applying logistic regression analysis to a set of parameters determined in a retrospective cohort of patients with a stricturing or penetrating disease presentation, the set of parameters comprising (1) the quartile sum scores obtained from the presence, absence, or level of said serological markers in the retrospective cohort, (2) the presence or absence of a SNP13 (3020InsC) genotype in the NOD2 gene in the retrospective cohort, and (3) the duration of CD in the retrospective cohort wherein said logistic regression model provides a cumulative probability of developing said stricturing or penetrating disease presentation over time;

(d) comparing said QSS and the genotype of said genetic markers for said individual to said logistic regression model; and (e) determining the risk that said individual develops said stricturing or penetrating disease presentation based on said comparison in step (d), wherein said individual has a risk of developing said stricturing or penetrating disease presentation at a rate of about 60% or more by the first year after diagnosis of CD when said QSS ranges from 6-24 and said SNP13 (3020InsC) genotype in the NOD2 gene is present.

2. The method of claim 1, wherein said serological markers further comprise an anti-neutrophil antibody, an anti-*Saccharomyces cerevisiae* antibody, an antimicrobial antibody, an acute phase protein, an apolipoprotein, a defensin, a growth factor, a cytokine, a cadherin, and a combination thereof.

3. The method of claim 2, wherein said anti-neutrophil antibody comprises an anti-neutrophil cytoplasmic antibody (ANCA).

4. The method of claim 2, wherein said antimicrobial antibody comprises an anti-flagellin antibody.

5. The method of claim 1, wherein the presence, absence, or level of each of said serological markers is detected with an enzyme immunoassay (EIA) or immunohistochemical assay.

6. The method of claim 1, wherein said genetic markers further comprise at least one of the genes set forth in Tables 1A-1E.

7. The method of claim 1, wherein the genotype of said genetic markers is detected by genotyping for the presence or absence of said single nucleotide polymorphism (SNP).

8. The method of claim 1, wherein said sample is selected from the group consisting of serum, plasma, whole blood, and stool.

9. The method of claim 1, wherein said logistic regression model comprises a look-up table or graph.

10. The method of claim 1, further comprising recommending a course of therapy for said individual based upon the risk that said individual develops said stricturing or penetrating disease presentation.

11. The method of claim 5, wherein said enzyme immunoassay (EIA) is an enzyme-linked immunosorbent assay (ELISA).

* * * * *